US007112674B2

(12) United States Patent
Richter et al.

(10) Patent No.: US 7,112,674 B2
(45) Date of Patent: Sep. 26, 2006

(54) ORGANIC ELECTROLUMINESCENT DEVICE BASED ON 2,5-DIAMINOTEREPHTHALIC ACID DERIVATIVES

(75) Inventors: Andreas Richter, Ploessnitz (DE); Jens Schoenewerk, Grimma (DE); Gerhard Diener, Koethen (DE)

(73) Assignee: Sensient Imaging Technologies GmbH, Wolfen (DE)

( * ) Notice: Subject to any disclaimer, the term of this patent is extended or adjusted under 35 U.S.C. 154(b) by 0 days.

(21) Appl. No.: 10/487,138

(22) PCT Filed: Aug. 21, 2002

(86) PCT No.: PCT/DE02/03110

§ 371 (c)(1),
(2), (4) Date: Feb. 20, 2004

(87) PCT Pub. No.: WO03/019697

PCT Pub. Date: Mar. 6, 2003

(65) Prior Publication Data

US 2005/0003230 A1 Jan. 6, 2005

(30) Foreign Application Priority Data

Aug. 21, 2001 (DE) ................................ 101 41 266

(51) Int. Cl.
*C09K 11/06* (2006.01)
*C07D 487/02* (2006.01)
*C07D 498/02* (2006.01)
*H05B 33/14* (2006.01)
*H01L 51/54* (2006.01)

(52) U.S. Cl. ............................ 544/73; 544/89; 544/95; 544/96; 544/250; 544/251; 544/296; 544/298; 544/319; 428/917; 313/504

(58) Field of Classification Search .................. 544/63, 544/72, 73, 89, 95, 224, 242, 249, 250, 251, 544/296, 298, 319
See application file for complete search history.

(56) References Cited

U.S. PATENT DOCUMENTS

| | | | | |
|---|---|---|---|---|
| 3,153,667 | A | 10/1964 | Smith | |
| 3,671,451 | A | 6/1972 | Butterfield | |
| 4,124,768 | A | 11/1978 | Kirsch et al. | 560/19 |
| 4,208,328 | A | 6/1980 | Lavallee et al. | 548/180 |
| 5,281,489 | A | 1/1994 | Mori et al. | |
| 5,409,783 | A | 4/1995 | Tang et al. | 428/690 |
| 5,616,779 | A | 4/1997 | Arndt | 560/48 |
| 6,288,232 | B1 | 9/2001 | Shershukov et al. | 546/52 |
| 6,329,086 | B1 | 12/2001 | Shi et al. | 428/690 |
| 6,458,476 | B1 | 10/2002 | Suzuki et al. | 428/690 |
| 6,534,201 | B1 | 3/2003 | Kim et al. | 428/690 |
| 6,579,633 | B1 | 6/2003 | Kim et al. | 428/690 |
| 6,613,458 | B1 | 9/2003 | Lee et al. | 428/690 |
| 2001/0012905 | A1 | 8/2001 | Shershukov et al. | 562/446 |
| 2002/0028351 | A1 | 3/2002 | Wang et al. | 428/690 |
| 2002/0043656 | A1 | 4/2002 | Shershukov et al. | 252/586 |
| 2002/0045065 | A1 | 4/2002 | Kim et al. | 428/690 |
| 2002/0114973 | A1 | 8/2002 | Hotta et al. | 428/690 |
| 2003/0082403 | A1 | 5/2003 | Lee et al. | 428/690 |
| 2003/0096137 | A1 | 5/2003 | Son et al. | 428/690 |
| 2003/0099861 | A1 | 5/2003 | Lee et al. | 428/690 |
| 2003/0165711 | A1 | 9/2003 | Kim et al. | 428/690 |

FOREIGN PATENT DOCUMENTS

GB 868361 5/1961

(Continued)

OTHER PUBLICATIONS

Moore et al., "Poly(amine esters) Derived from Diethyl 1,4-Cyclohexanedione-2,5-dicarboxylate", *Macromolecules*, vol. 8, 1975, (pp. 121-127).

(Continued)

*Primary Examiner*—Marie Yamnitzky
(74) *Attorney, Agent, or Firm*—Michael Best & Friedrich LLP

(57) ABSTRACT

The invention relates to an organic electroluminescent device which contains 2,5-diaminoterephthalic acid derivatives of formula 1a as emitter substances in one or several emitter layers in a pure or doped manner. The ring A is a triple unsaturated benzene ring wherein $R^{4'}$ and $R^{8'}$ are zero or ring A is a double unsaturated ring respectively provided with a double bond in the 1,2 position and 4,5 position, and wherein $R^{10}$ is a nitrile radical —CN or a radical $C({=}X^1)—X^2R^1$, $R^{11}$ is a nitrile radical —CN or a radical $—C({=}X^3)—X^4R^5$, $X^1$ and $X^3$ are oxygen, sulfur or imino, $X^2$ and $X^4$ are oxygen, sulfur or optionally substituted amino, $R^1$–$R^8$, $R^{4'}$ and $R^{8'}$ are H, C1–20-alkyl, aryl, heteroaryl, $R^4$ and $R^8$ can be halogen, nitro, cyanogen or amino, $R^2$–$R^4$, $R^6$–$R^8$, $R^{4'}$ and $R^{8'}$ can be trifluoromethyl or pentafluorophenyl, and wherein certain radicals can form a saturated or unsaturated ring. The devices are characterized by narrow emission bands, low driver voltages, high photometric efficiency and high thermal stability within a broad spectral range (Ia)

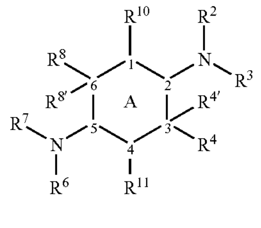

33 Claims, 1 Drawing Sheet

FOREIGN PATENT DOCUMENTS

| | | | |
|---|---|---|---|
| GB | 918511 | | 2/1963 |
| JP | 10-284250 | | 10/1998 |
| JP | 10284250 | | 10/1998 |
| JP | 10-294178 | | 11/1998 |
| WO | WO 03/076390 | A1 | 9/2003 |
| WO | WO 2004/026809 | A1 | 4/2004 |

OTHER PUBLICATIONS

Ulbricht et al., "Synthese und π-Elektronenstruktur von 2,5-Bis-alkylamino-terephthalsäurediethylestern", *Journal f. prakt. Chemie. Band 321, Heft 6*, 1979, (S. 905-912).

ORGANIC ELECTROLUMINESCENT DEVICE BASED ON 2,5-DIAMINOTEREPHTHALIC ACID DERIVATIVES

CROSS REFERENCE TO RELATED APPLICATION

This application is a national stage of PCT/DE02/03110 filed Aug. 21, 2002, and based upon DE 101 41 266.5 filed Aug. 21, 2001 under the International Convention.

FIELD OF THE INVENTION

The present invention relates to a new organic electroluminescent device based on 2,5-diaminoterephthalic acid derivatives. Said derivatives are emitter substances for organic light-emitting diodes (OLED).

BACKGROUND TO THE INVENTION

Organic light-emitting diodes, which have long been known, use the electroluminescence of certain organic compounds. An OLED's structure and the tasks of its individual layers are exemplified in FIG. 1:

A layer sequence of organic substances is arranged between two electrodes, of which at least one must be translucent, each organic substance having a specific function within the device.

1. The cathode consists of a base metal or an alloy (e.g. aluminium or calcium) and has the function of injecting electrons;
2. The buffer layer consists of certain metal salts or the oxides thereof, e.g. LiF, and has the function of improving the electron injection into the layer 3;
3. The electron conductor can e.g. consist of Alq3 (tris-(8-hydroxychinolinato)-aluminium) and conducts the electrons from the cathode to the emitting layer or the hole conductor inside the device;
4. The hole conductor mainly consists of triphenylamine derivatives; several hole conductor layers can be provided whose characteristics are adapted to the device and whose function is to transport the holes to the emitting layer;
5. The anode consists of ITO which injects the holes into the hole transport layer;
6. The substrate consists of a transparent material, e.g. glass.

An arrangement of the type described above emits green light generated due to the excitation of Alq3 by the excitons formed from the holes and electrons.

However, such a simple arrangement has several drawbacks:

1. Alq3 only emits light in the green spectral range;
2. The emission band of Alq3 is too broad.

Said drawbacks can in part be eliminated by doping. This means that one or more substances are co-evaporated during the diode's production process. In general, these substances are contained in the Alq3 layer in an amount ranging up to a few percent. Said co-evaporation process is difficult to control.

SUMMARY AND DETAILED DESCRIPTION OF THE INVENTION

The invention relates to new emitter substances which eliminate the known drawbacks of Alq3 both as an emitter substance and a host material for dopants. As a consequence, Alq3 is generally required as an electron conductor only. The new emitter substances are characterized by:

1. narrower emission bands;
2. the devices cover a broad spectral range due to the fact that different substances are used, either in layers separated from one another or in mixed layers;
3. low driver voltages;
4. high photometric efficiency (low power consumption);
5. high luminance (emission intensity);
6. high thermal stability.

Figure 1:
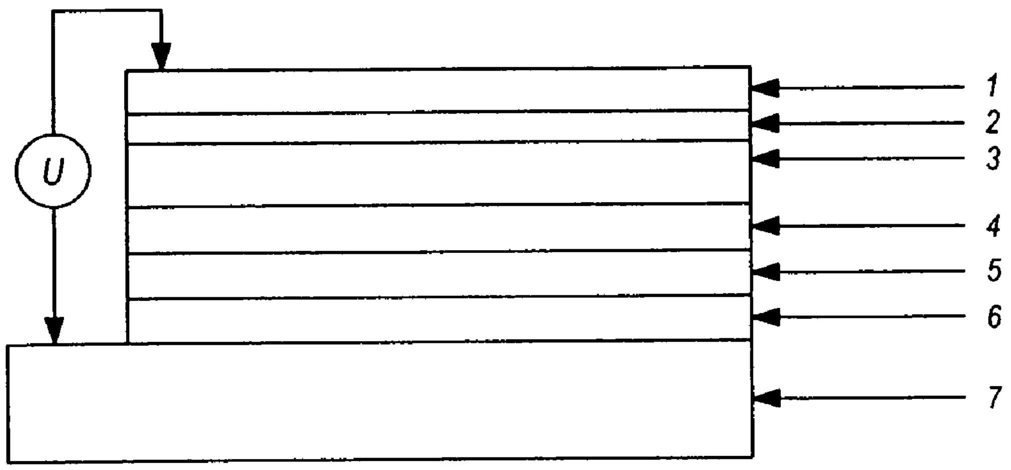
FIG. 1 shows the layered structure of an organic light-emitting diode.
Figure 2:
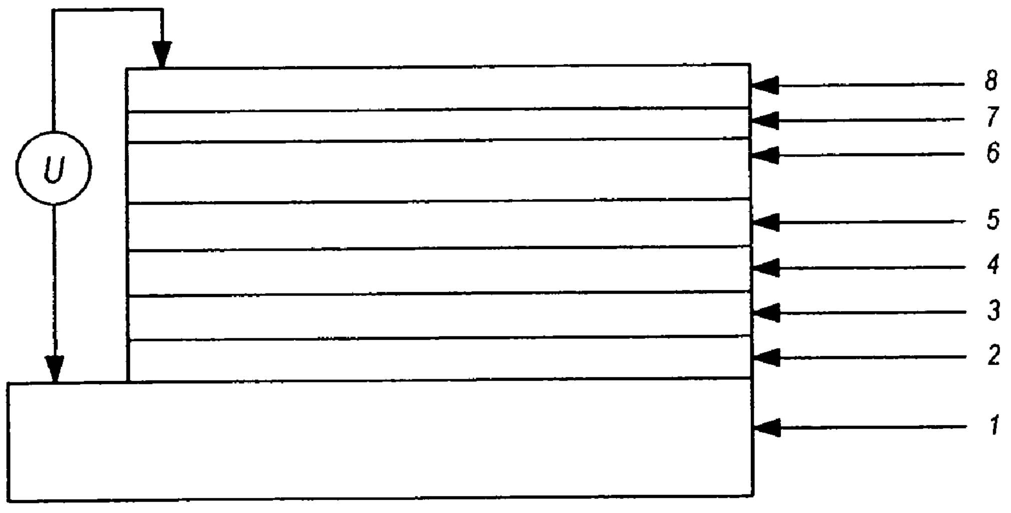
FIG. 2 shows an embodiment of the layered structure of an organic light-emitting diode of the present invention.

For the purposes of the invention, the term "device" relates to an arrangement in which the substrate and layers are arranged on top of one another according to FIG. 1 or 2, but which has not yet been incorporated into a light-emitting diode. Such an inventive device can in principle have the structure shown in FIG. 1 or 2. In said devices, the 2,5-diaminoterephthalic acid derivatives can be co-evaporated either alone or conjointly with other compounds, optionally even with known compounds, to obtain emitters. These emitters are used in combination with known hole conductors.

The object of the invention is to provide new organic electroluminescent devices using improved emitter substances.

According to the invention, the organic electroluminescent device contains 2,5-diaminoterephthalic acid derivatives of the following formula 1a in one or several emitter layers in a pure or doped form in a device 1a

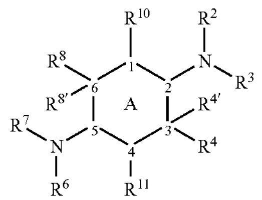

wherein the ring A is a triply unsaturated benzene ring wherein $R^{4'}$ and $R^{8'}$ are omitted, or the ring A is a doubly unsaturated ring having a double bond in the 1,2-position and in the 4,5-position, and wherein $R^{10}$ represents a nitrile radical —CN or a radical —C(=$X^1$)—$X^2R^1$, $R^{11}$ is a nitrile radical —CN or a radical —C(=$X^3$)—$X^4R^5$, wherein $X^1$ and $X^3$ can be the same or different atoms or groups, such as oxygen, sulphur, imino, preferably oxygen;

$X^2$ and $X^4$ can be the same or different atoms or groups, such as oxygen, sulphur, amino, wherein the amino nitrogen can be substituted with alkyl having 1 to 20 C-atoms, preferably C1 to C8, or with aryl, e.g. phenyl, naphthyl, or with heteroaryl, e.g. cumaryl, pyridyl, chinolyl, indolyl, carbazolyl, imidazolyl, thienyl, thiazolyl, furyl, oxazolyl;

$R^1$ to $R^8$, $R^{4'}$ and $R^{8'}$ can be the same or different substituents, such as hydrogen, alkyl having 1 to 20 atoms, preferably C1 to C8; aryl, e.g. phenyl, naphthyl, as well as heteroaryl, e.g. cumaryl, pyridyl, chinolyl, indolyl, carbazolyl, imidazolyl, thienyl, thiazolyl, furyl, oxazolyl, and the aforesaid radicals can be substituted singly or doubly with atoms or groups, e.g. di-C1–C3-amino or alkoxy with alkyl radicals C1 to C10, preferably C1–C4; C1–C4 alkyl, cyano, fluorine, chlorine, bromine or iodine as well as phenyl;

$R^4$ and $R^8$ can also be the same or different substituents, such as halogen, nitro, cyano or amino;

$R^2$ to $R^4$, $R^6$ to $R^8$, $R^{4'}$ and $R^{8'}$ can also be trifluoromethyl or pentafluorophenyl, and wherein the following radicals can form a saturated or unsaturated ring $X^1$ and $X^2$, $R^1$ and $R^2$, $R^2$ and $X^2$, $R^2$ and $R^3$, $R^3$ and $R^4$, $R^4$ and $X^3$, $X^3$ and $X^4$, $R^5$ and $X^4$, $R^6$ and $X^4$, $R^6$ and $R^7$, $R^7$ and $R^8$, $R^8$ and $X^1$, $R^3$ and $R^{4'}$, $R^7$ and $R^{8'}$, $R^4$ and $R^{4'}$, and $R^8$ and $R^{8'}$, to which rings further rings can be fused.

It is preferred that $R^2$, $R^3$, $R^6$ and $R^7$ be trifluoromethyl or pentafluorophenyl, $R^4$ and $R^8$ be halogen, nitro, cyano or amino, and the other substituents have the meaning indicated above.

It is particularly preferred that $R^4$ and $R^8$ be trifluoromethyl or pentafluorophenyl, and the other substituents have the meaning indicated above.

As regards spelling in the following text, $R^{1-8}$ means $R^1$ to $R^8$; $X^{2,4}$ means $X^2$ and $X^4$; $R^{4',8'}$ means $R^{4'}$ and $R^{8'}$.

The invention also relates to new 2,5-diaminoterephthalic acid derivatives of the formula 19

19

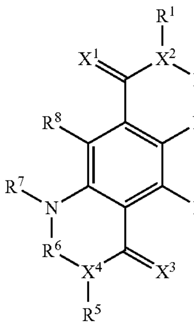

wherein $X^1$ is O and $X^2$ is O or N; $R^2$ and $R^6$ are methylene (—$CH_2$—) which can be substituted with trifluoromethyl, $R^3$ and $R^7$ are the same or different, H, C1–C8 alkyl, aryl or heteroaryl, and $R^4$ and $R^8$ are the same or different, H, alkyl, aryl or trifluoromethyl. It is particularly preferred that alkyl be C1–C4 alkyl, aryl be phenyl or naphthyl, and heteroaryl be pyridyl, thienyl or furyl.

In general, it is preferred that substituents arranged opposite one another, such as $X^1$ and $X^3$, $X^2$ and $X^4$, $R^1$ and $R^5$, $R^2$ and $R^6$, $R^3$ and $R^7$, $R^4$ and $R^8$, $R^{4'}$ and $R^{8'}$, and $R^{10}$ and $R^{11}$, are the same, i.e. not different, in all structures according to the invention.

The electroluminescent devices according to the invention preferably contain 2 to 3 different substances which are mixed with one another in one device.

Now, preferred structures will be listed, wherein in the structures 1

1

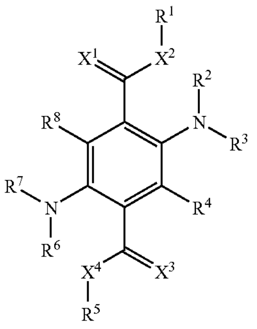

$X^1$ and $X^2$ can be members of a ring provided $X^1$=N and there is no substituent $R^1$ in case $X^2$≠N;

5

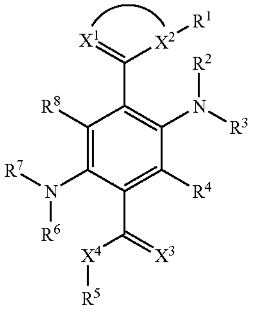

$X^2$ and $R^1$ can be members of a ring provided $X^2$=N;

6

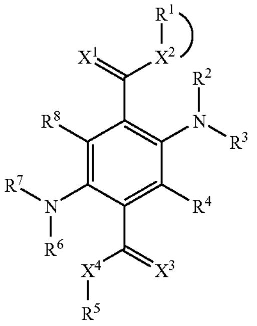

$X^2$ and $R^2$ can be members of a ring provided $X^2$=N;

7

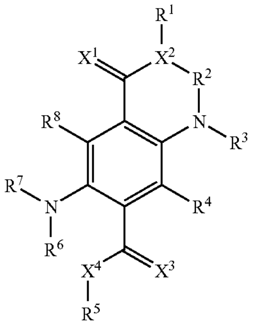

$R^2$ and $R^3$ can be members of a ring;

8

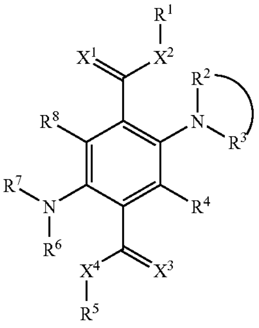

$R^3$ and $R^4$ can be members of a ring;

9

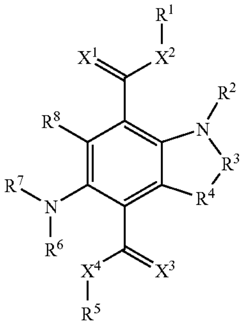

$R^4$ and $X^3$ can be members of a ring provided $X^3$=N;

10

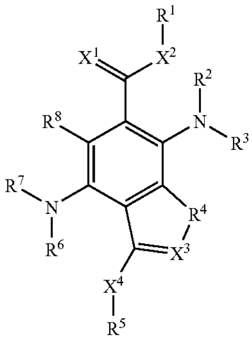

$X^3$ and $X^4$ can be members of a ring provided $X^3$=N and there is no substituent $R^1$ in case $X^4 \neq N$;

11

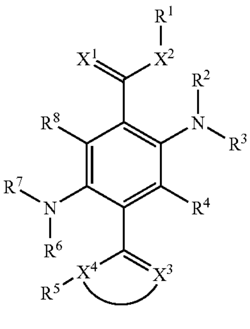

$X^4$ and $R^5$ can be members of a ring provided $X^4$=N;

12

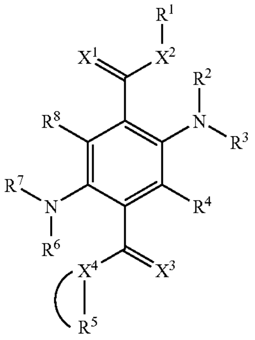

$X^4$ and $R^6$ can be members of a ring provided $X^4$=N;

13

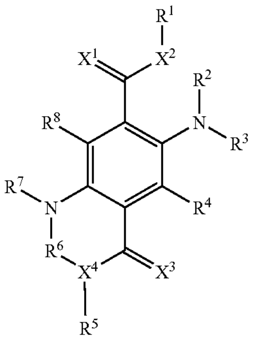

$R^6$ and $R^7$ can be members of a ring;

14

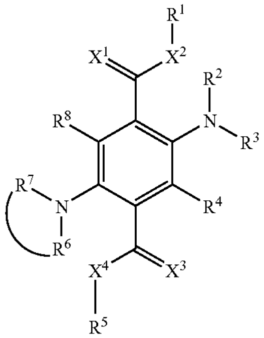

$R^7$ and $R^8$ can be members of a ring;

15

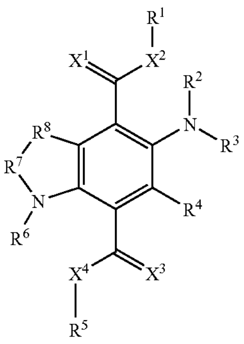

$R^8$ and $X^1$ can be members of a ring provided $X^1$=N;

16

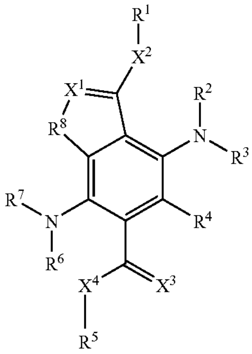

wherein symmetric combinations of the aforesaid structural types are preferred $X^1$ and $X^2$ as well as $X^3$ and $X^4$ can be members of a ring provided $X^{1,3}$=N and there is no substituent $R^{1,5}$ in case $X^{2,4}\neq$N;

17

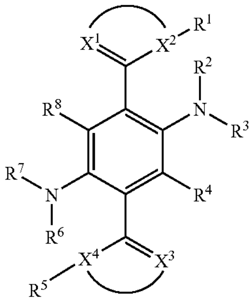

$X^2$ and $R^1$ can be members of a ring provided $X^{2,4}$=N;

18

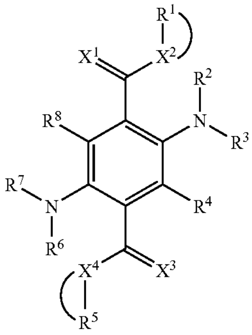

$X^2$ and $R^2$ as well as $X^4$ and $R^6$ can be members of a ring provided $X^{2,4}$=N;

19

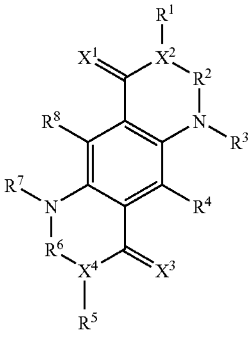

$R^2$ and $R^3$ as well as $R^6$ and $R^7$ can be members of a ring;

20

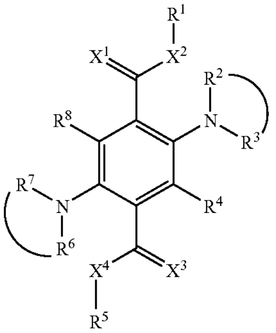

$R^3$ and $R^4$ as well as $R^7$ and $R^8$ can be members of a ring;

21

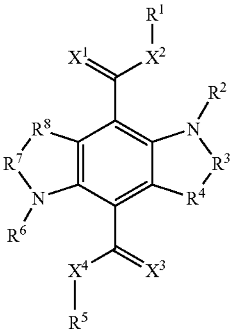

$R^4$ and $X^3$ as well as $R^8$ and $X^1$ can be members of a ring provided $X^{1,3}$=N;

22

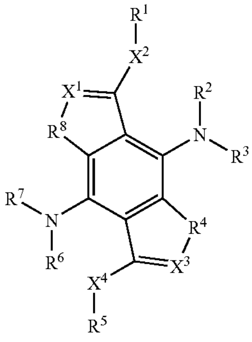

and wherein in the structure 2

2

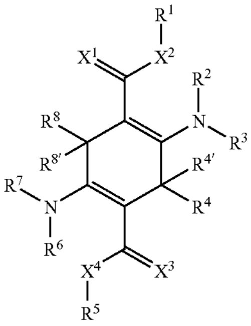

$X^1$ and $X^2$ can be members of a ring provided $X^1$=N and there is no substituent $R^1$ in case $X^2 \neq N$;

23

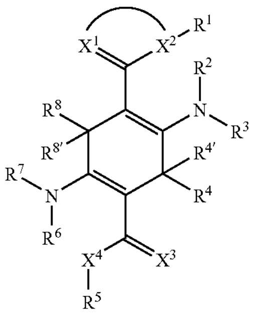

$X^2$ and $R^1$ can be members of a ring provided $X^2$=N;

24

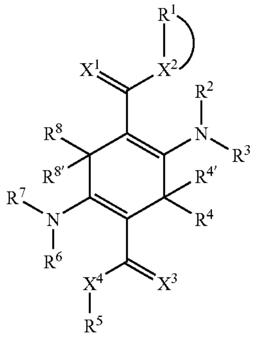

$X^2$ and $R^2$ can be members of a ring provided $X^2$=N;

25

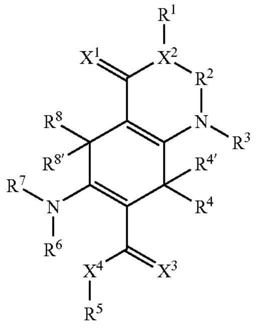

$R^2$ and $R^3$ can be members of a ring;

26

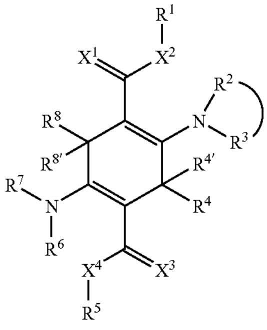

$R^3$ and $R^4$ can be members of a ring;

27

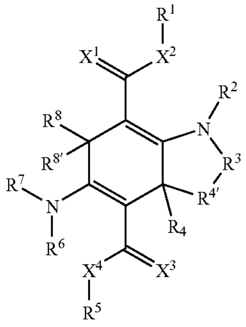

$R^4$ and $R^{4'}$ can be members of a ring;
28
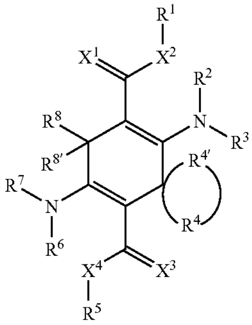
$R^4$ and $X^3$ can be members of a ring provided $X^3$=N;
29
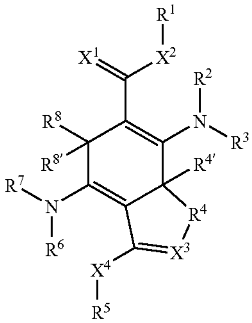
$X^3$ and $X^4$ can be members of a ring provided $X^3$=N and there is no substituent $R^5$ in case $X^4$≠N;
30
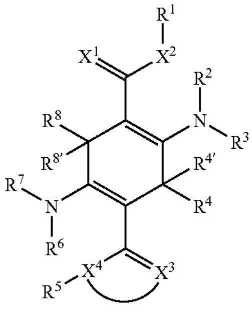
$X^4$ and $R^5$ can be members of a ring provided $X^4$=N;
31
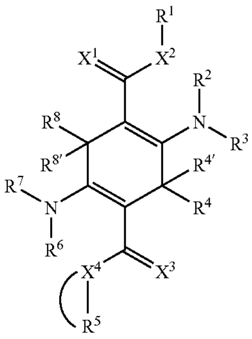
$X^4$ and $R^6$ can be members of a ring provided $X^4$=N;
32
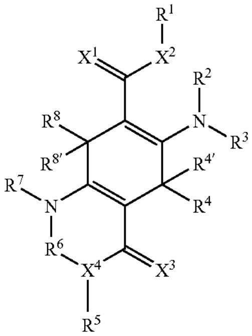
$R^6$ and $R^7$ can be members of a ring;
33
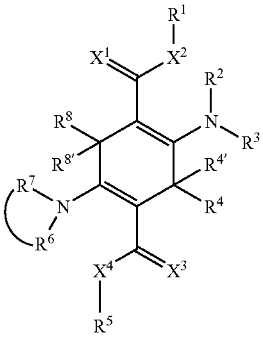

$R^7$ and $R^8$ can be members of a ring;

34

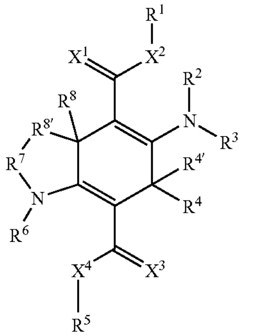

$R^8$ and $R^{8'}$ can be members of a ring;

35

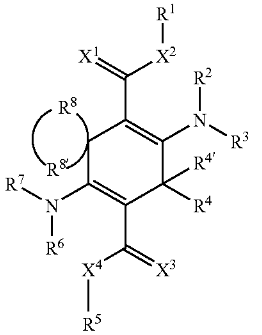

$R^8$ and $X^1$ can be members of a ring provided $X^1$=N;

36

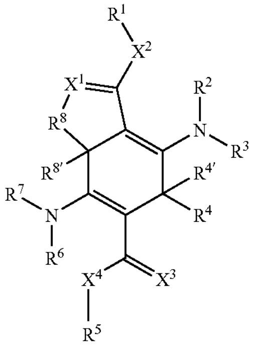

wherein symmetric combinations of the aforesaid structural types are preferred $X^1$ and $R^2$ as well as $X^3$ and $X^4$ can be members of a ring provided $X^{1,3}$=N and there is no substituent $R^{1,5}$ in case $X^{2,4}\neq$N;

37

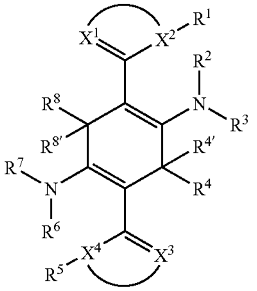

$X^2$ and $R^1$ can be members of a ring provided $X^{2,4}$=N;

38

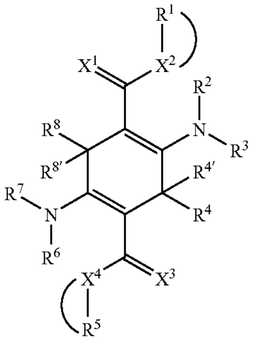

$X^2$ and $R^2$ as well as $X^4$ and $R^6$ can be members of a ring provided there is no substituent $R^{1,5}$ in case $X^{2,4}\neq$N;

39

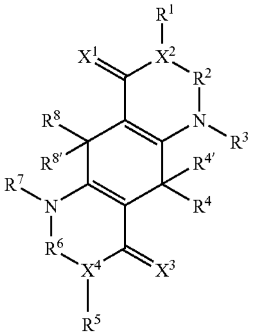

$R^2$ and $R^3$ as well as $R^6$ and $R^7$ can be members of a ring;

40

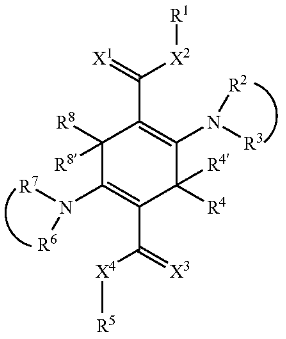

$R^3$ and $R^{4'}$ as well as $R^7$ and $R^{8'}$ can be members of a ring;

41

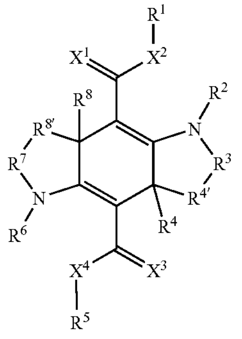

$R^4$ and $R^{4'}$ as well as $R^8$ and $R^{8'}$ can be members of a ring;

42

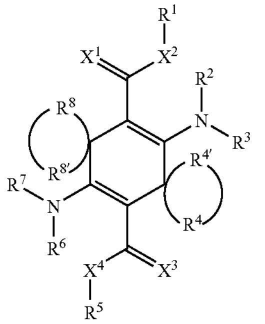

$R^4$ and $X^3$ as well as $R^8$ and $X^1$ can be members of a ring provided $X^{1,3}$=N;

43

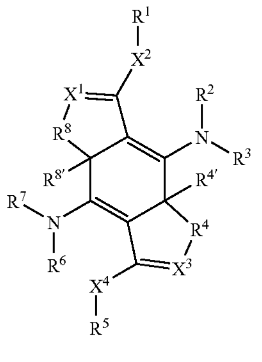

and wherein in the structures 3

3

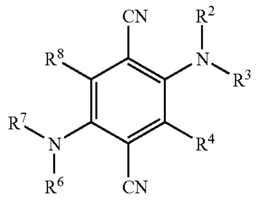

$R^2$ and $R^3$ can be members of a ring;

44

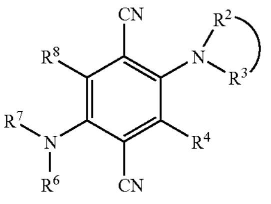

$R^3$ and $R^4$ can be members of a ring;

45

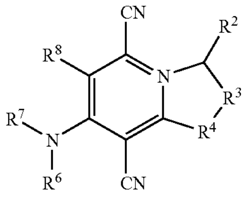

$R^6$ and $R^7$ can be members of a ring;

46

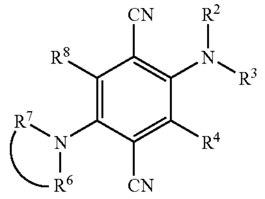

$R^7$ and $R^8$ can be members of a ring;

47

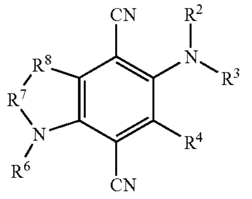

$R^2$ and $R^3$ as well as $R^6$ and $R^7$ can be members of a ring;

48

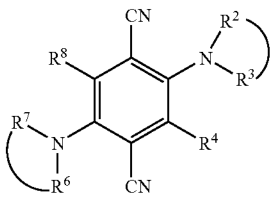

$R^3$ and $R^4$ as well as $R^7$ and $R^8$ can be members of a ring;

49

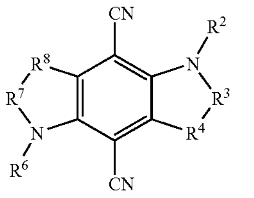

and wherein in the structures 4

4

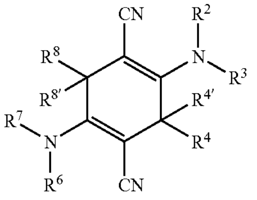

$R^2$ and $R^3$ can be members of a ring;

50

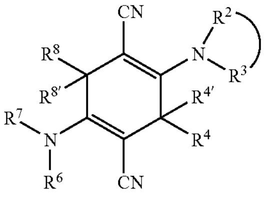

$R^3$ and $R^{4'}$ can be members of a ring;

51

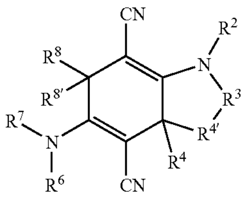

$R^4$ and $R^{4'}$ can be members of a ring;

52

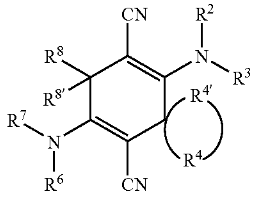

$R^6$ and $R^7$ can be members of a ring;

53

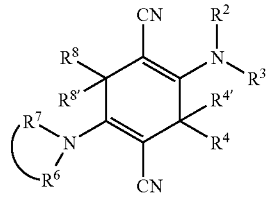

$R^7$ and $R^{8'}$ can be members of a ring;

54

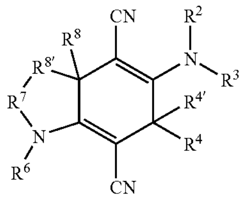

$R^8$ and $R^{8'}$ can be members of a ring;

55

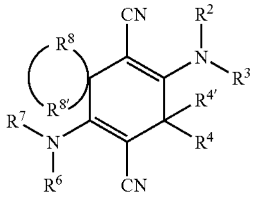

$R^2$ and $R^3$ as well as $R^6$ and $R^7$ can be members of a ring;

56

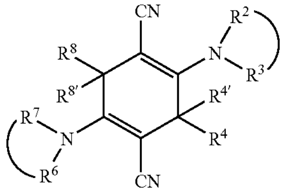

$R^3$ and $R^{4'}$ as well as $R^7$ and $R^{8'}$ can be members of a ring;

57

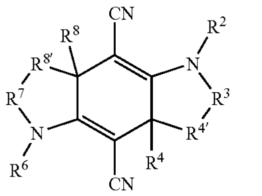

$R^4$ and $R^{4'}$ as well as $R^8$ and $R^{8'}$ can be members of a ring;

58

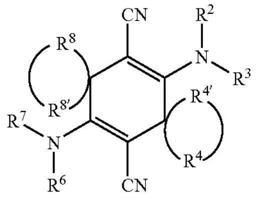

The emitter substances of formula 1, i.e. derivatives of 2,5-diaminoterephthalic acid, can be obtained by reacting esters of cyclohexane-2,5-dione-1,4-dicarboxylic acid with primary anilines or amines, subsequent oxidation and, optionally, further modification. Said derivatives can be processed into cyclized derivatives in a manner known per se, as shown e.g. in Formula Diagrams I and II.

Formula Diagram I: Synthesis of the open compounds

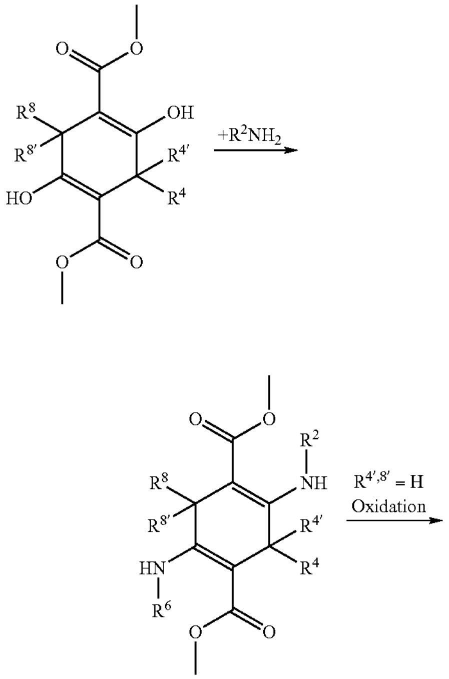

-continued

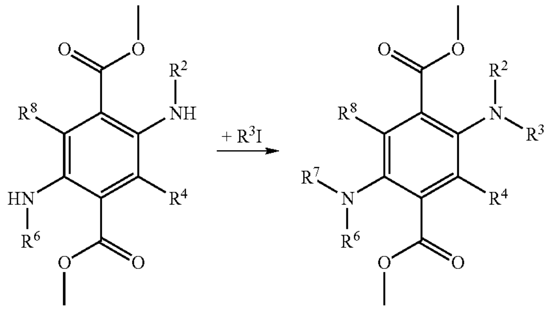

Formula Diagram II: Synthesis of the cyclized compounds

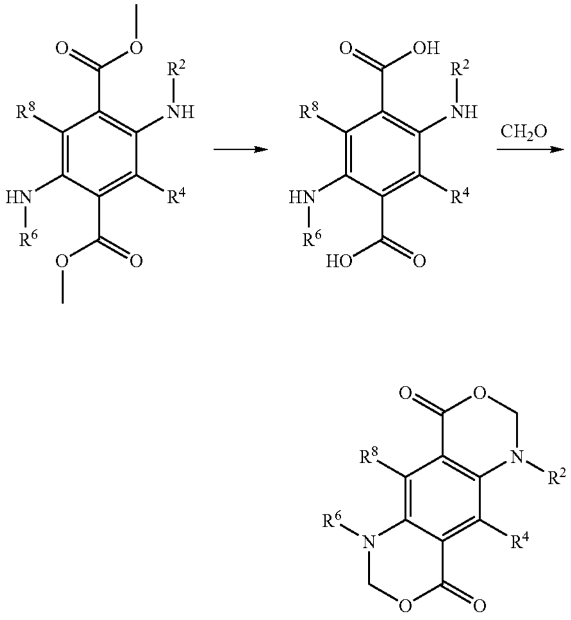

The compounds of formula 3 can be produced by reacting the respective 2,5-diaminoterephthalic acid amides with dehydrating agents.

In order to produce the compounds of formula 4, wherein $R^4$ and $R^8$ as well as $R^{4'}$ and $R^{8'}$ are not H, the esters of 2,5-diaminocyclohexane-1,4-dicarboxylic acid are converted into hydrazides and reacted with potassium hexacyanoferrate(III) in order to obtain aldehydes. These 2,5-diaminocyclohexane-1,4-dicarbaldehydes can be converted into oximes which are reacted with formic acid in order to obtain the compounds of formula 4.

Examples of the new emitters according to formula 1 are listed in Table 1:

TABLE 1
| 2,5-diaminoterephthalic acid derivatives | | | | |
|---|---|---|---|---|
| Substance | $X^1$ | $X^2$ | $R^3$ | $R^1$ |
| 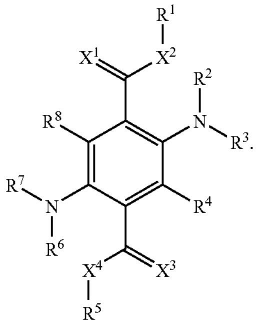 1.0 | | | | |
| 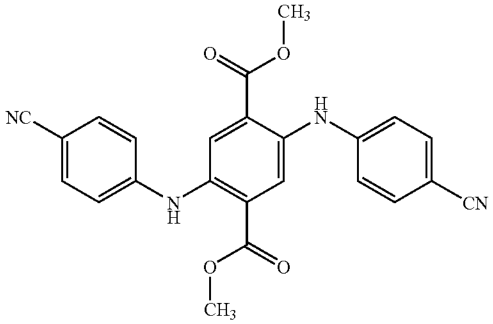 1.1 | O | O | 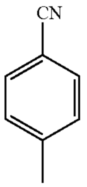 | —$CH_3$ |
| 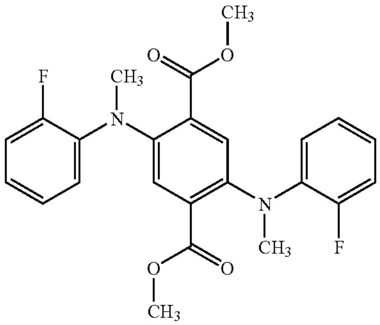 1.2 | O | O | 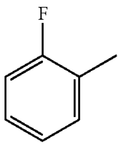 | —$CH_3$ |
| 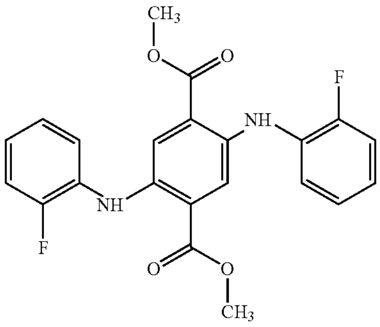 1.3 | O | O | 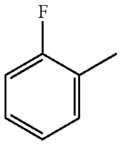 | —$CH_3$ |

TABLE 1-continued
| 2,5-diaminoterephthalic acid derivatives | | | | |
|---|---|---|---|---|
| 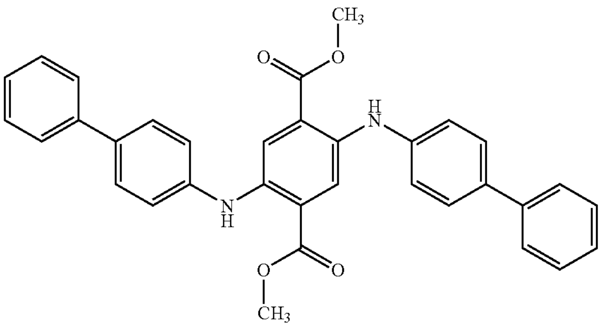 1.4 | O | O | 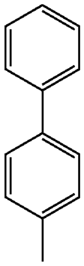 | $—CH_3$ |
| 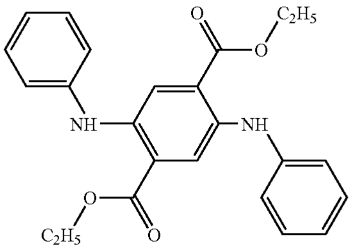 1.5 | O | O | 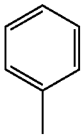 | $—C_2H_5$ |
| 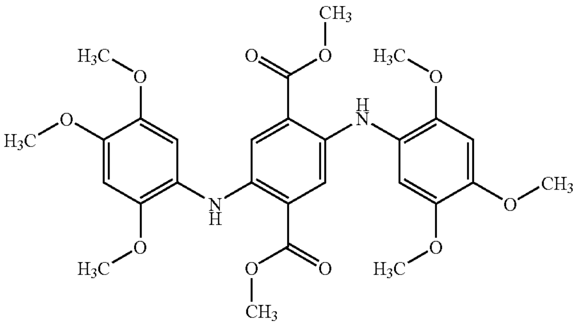 1.6 | O | O | 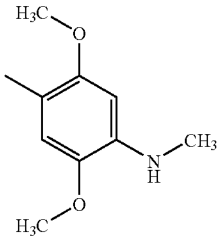 | $—CH_3$ |
| 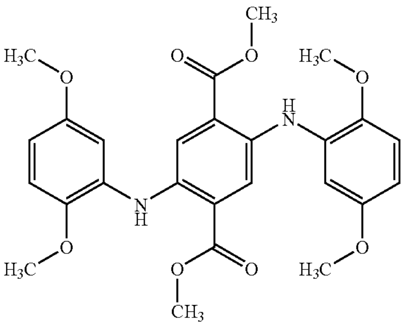 1.7 | O | O | 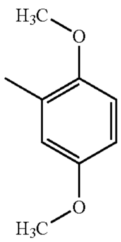 | $—CH_3$ |

TABLE 1-continued
2,5-diaminoterephthalic acid derivatives
| | | | | | |
|---|---|---|---|---|---|
| 1.8 | 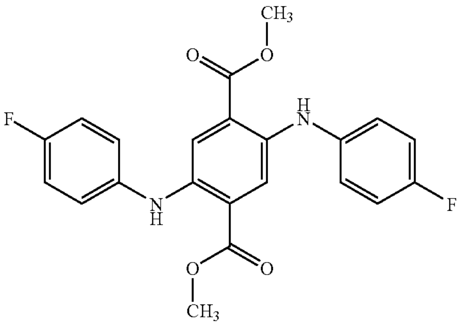 | O | O | 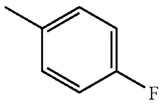 | —$CH_3$ |
| 1.9 | 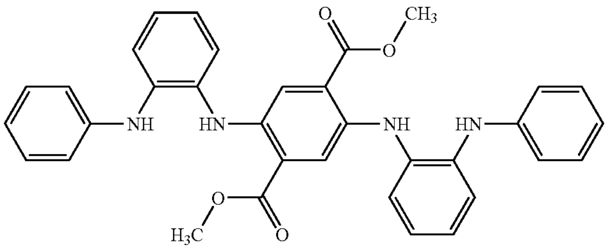 | O | O | 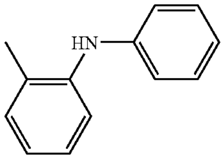 | —$CH_3$ |
| 1.10 | 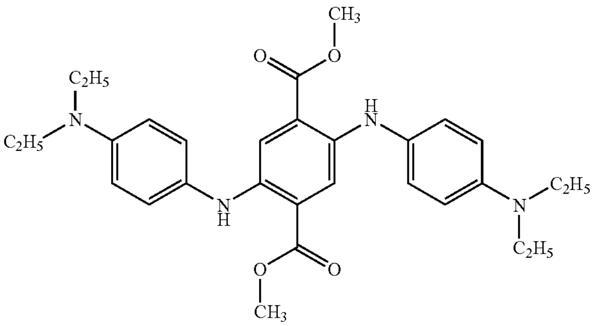 | O | O | 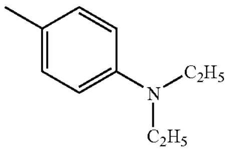 | —$CH_3$ |
| 1.11 | 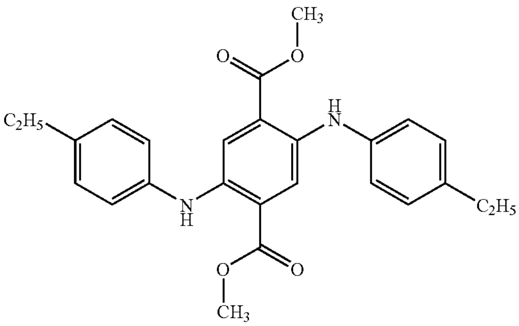 | O | O | 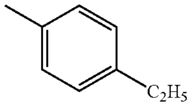 | —$CH_3$ |

TABLE 1-continued
| 2,5-diaminoterephthalic acid derivatives | | | | |
|---|---|---|---|---|
| 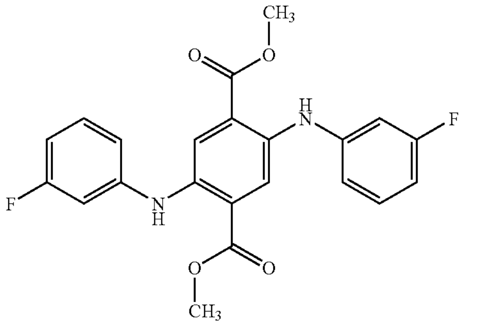 1.12 | O | O | 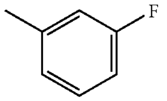 | —$CH_3$ |
| 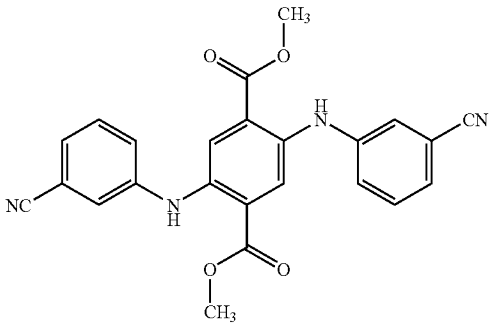 1.13 | O | O | 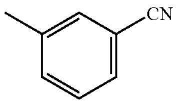 | —$CH_3$ |
| 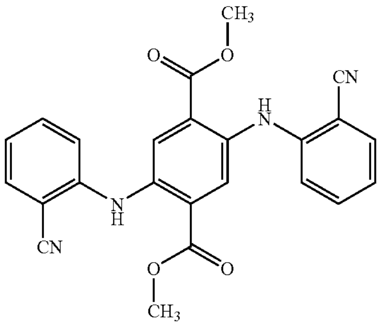 1.14 | O | O | 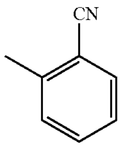 | —$CH_3$ |
| 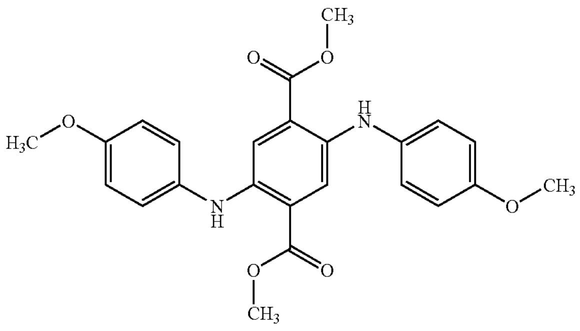 1.15 | O | O | 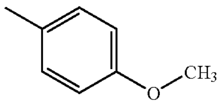 | —$CH_3$ |

TABLE 1-continued
| 2,5-diaminoterephthalic acid derivatives | | | | |
|---|---|---|---|---|
| 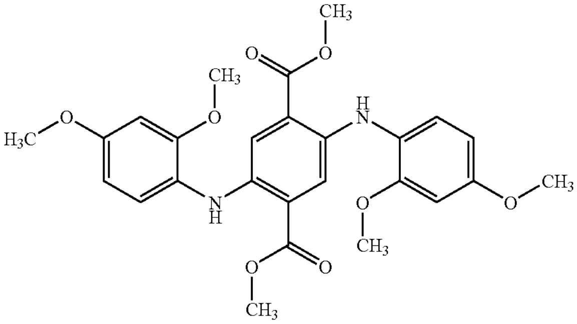 1.16 | O | O | 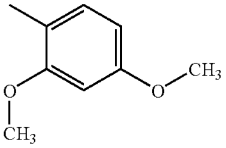 | —$CH_3$ |
| 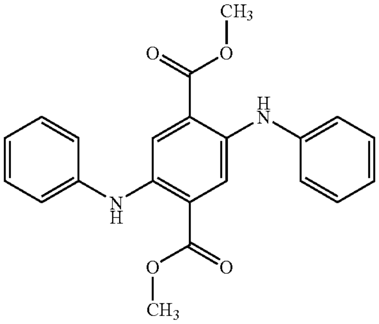 1.17 | O | O | 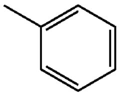 | —$CH_3$ |
| 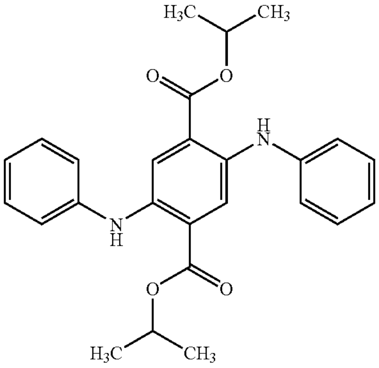 1.18 | O | O | 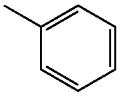 | —$CH_3$ |
| 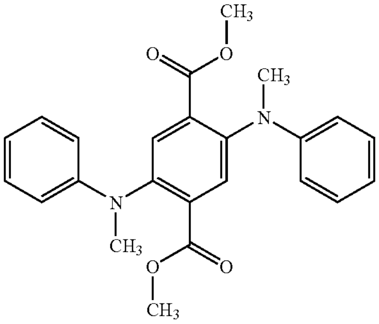 1.19 | O | O | 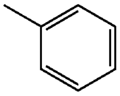 | —$CH_3$ |

TABLE 1-continued
| 2,5-diaminoterephthalic acid derivatives | | | | |
|---|---|---|---|---|
| 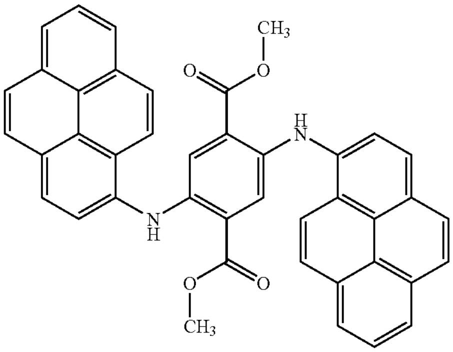 1.20 | O | O | 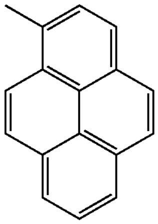 | —$CH_3$ |
| 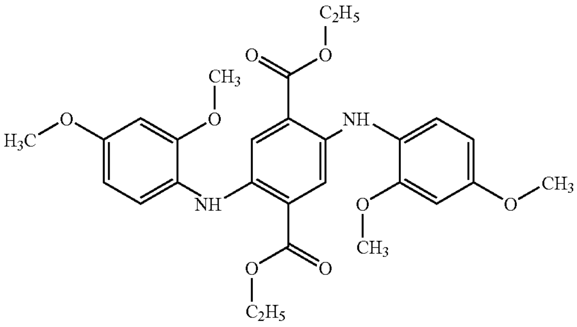 1.21 | O | O | 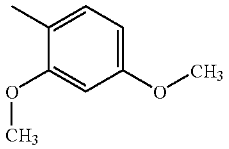 | —$CH_3$ |
| 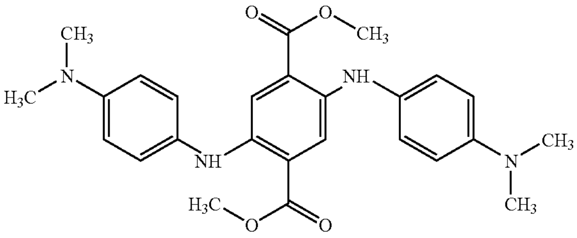 1.22 | O | O | 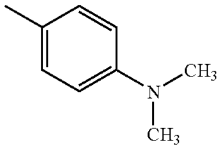 | —$CH_3$ |
| 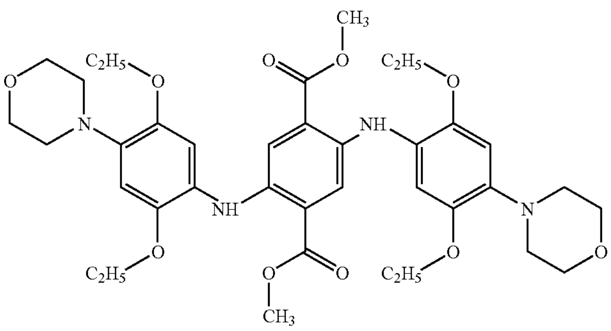 1.23 | O | O | 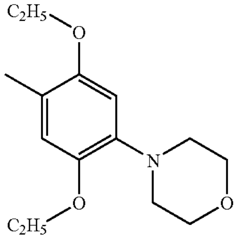 | —$CH_3$ |

TABLE 1-continued
| 2,5-diaminoterephthalic acid derivatives | | | | |
|---|---|---|---|---|
| 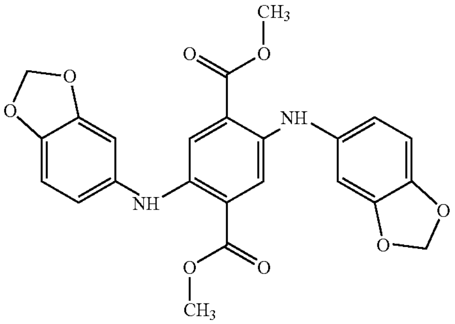<br>1.24 | O | O | 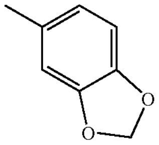 | —$CH_3$ |
| 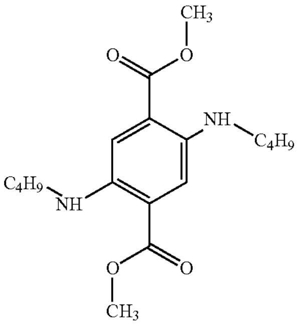<br>1.25 | O | O | —$C_4H_9$ | —$CH_3$ |
| 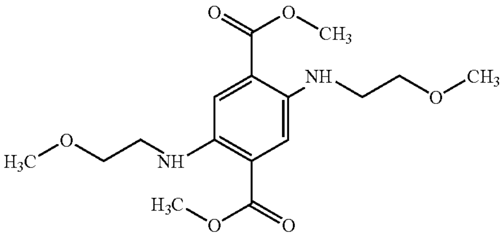<br>1.26 | O | O | 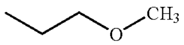 | —$CH_3$ |
| 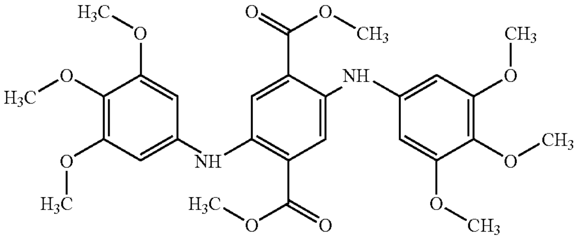<br>1.27 | O | O | 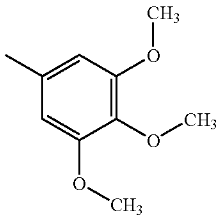 | —$CH_3$ |

TABLE 1-continued
| 2,5-diaminoterephthalic acid derivatives | | | | |
|---|---|---|---|---|
| 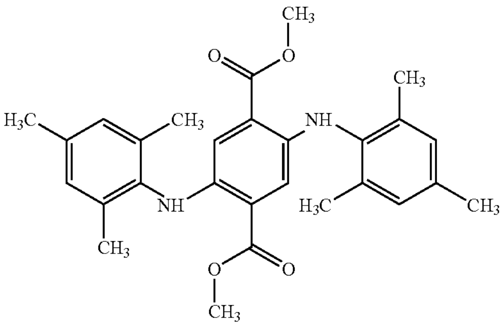 1.28 | O | O | 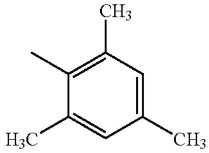 | $—CH_3$ |
| 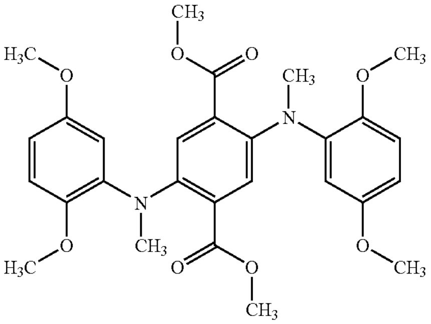 1.29 | O | O | 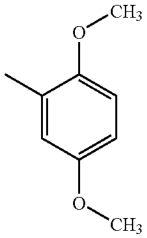 | $—CH_3$ |
| 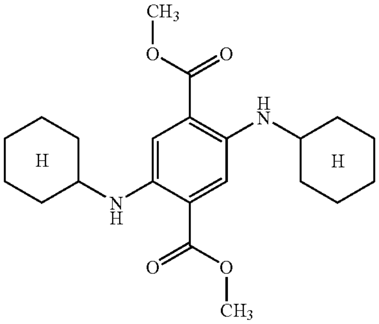 1.30 | O | O | 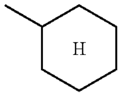 | $—CH_3$ |
| 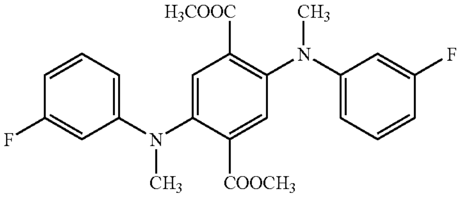 1.31 | O | O | 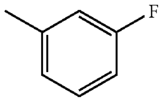 | $—CH_3$ |

TABLE 1-continued
| 2,5-diaminoterephthalic acid derivatives | | | | |
|---|---|---|---|---|
| 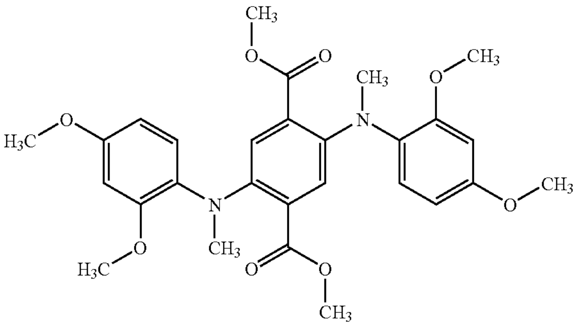<br>1.32 | O | O | 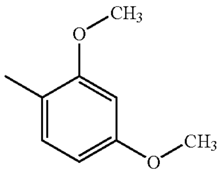 | —$CH_3$ |
| 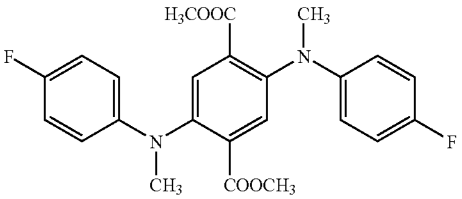<br>1.33 | O | O | 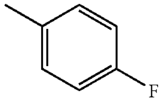 | —$CH_3$ |
| 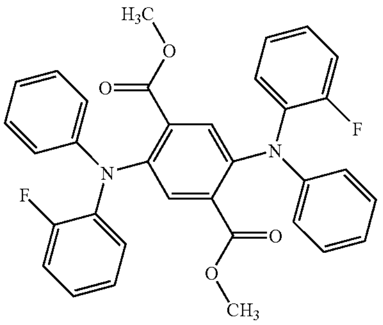<br>1.34 | O | O | 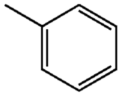 | —$CH_3$ |
| 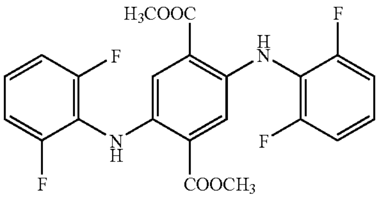<br>1.35 | O | O | 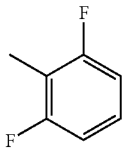 | —$CH_3$ |
| 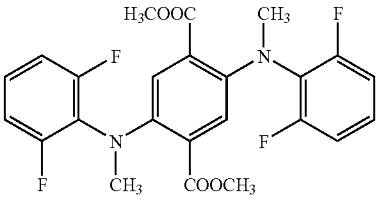<br>1.36 | O | O | 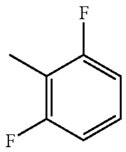 | —$CH_3$ |

TABLE 1-continued
| 2,5-diaminoterephthalic acid derivatives | | | | |
|---|---|---|---|---|
| 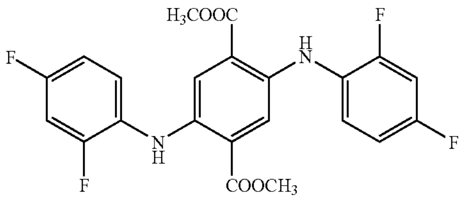 1.37 | O | O | 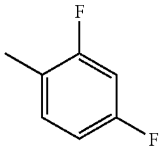 | —$CH_3$ |
| 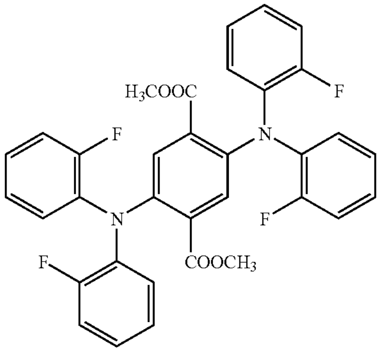 1.38 | O | O | 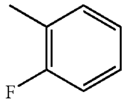 | —$CH_3$ |
| 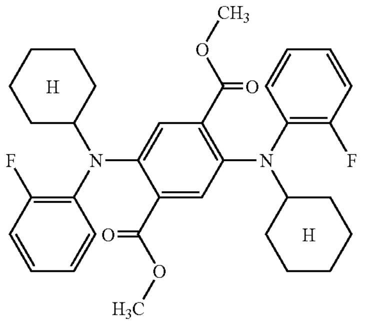 1.39 | O | O | 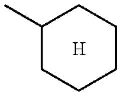 | —$CH_3$ |
| 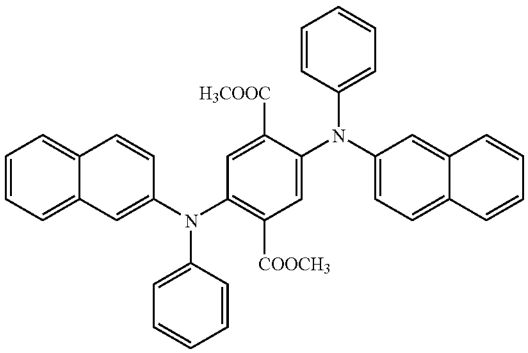 1.40 | O | O | 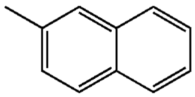 | —$CH_3$ |

TABLE 1-continued
2,5-diaminoterephthalic acid derivatives
| | | | | |
|---|---|---|---|---|
| 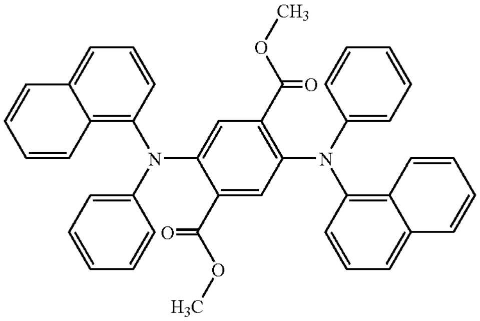 1.41 | O | O | 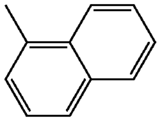 | —$CH_3$ |
| 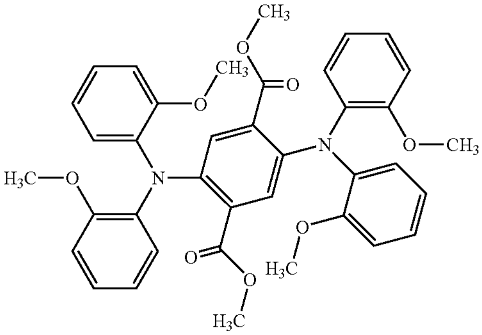 1.42 | O | O | 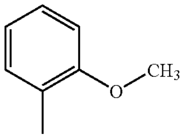 | —$CH_3$ |
| 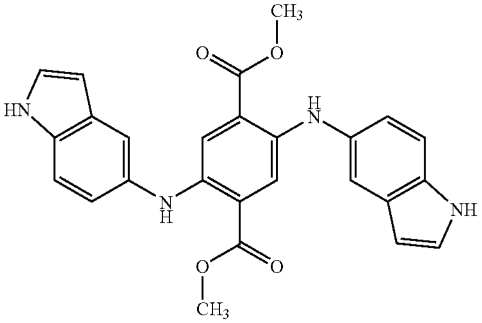 1.43 | O | O | 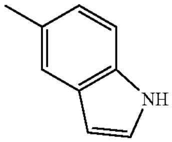 | —$CH_3$ |
| 1.44 | O | O | 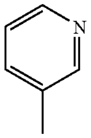 | —$CH_3$ |
| 1.45 | O | O | 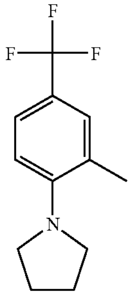 | —$CH_3$ |

TABLE 1-continued
| 2,5-diaminoterephthalic acid derivatives | | | | |
|---|---|---|---|---|
| 1.46 | O | O | 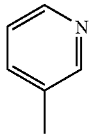 | —$CH_3$ |
| 1.47 | O | O | 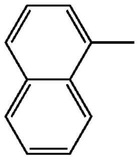 | —$CH_3$ |
| 1.48 | O | O | 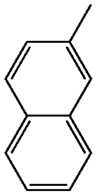 | —$CH_3$ |
| 1.49 | O | O | 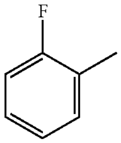 | —$CH_3$ |
| 1.50 | O | O | 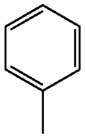 | —$CH_3$ |
| 1.51 | O | O | 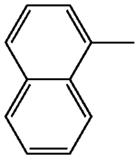 | —$CH_3$ |
| 1.52 | O | O | 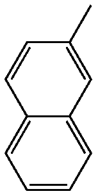 | —$CH_3$ |
| 1.53 | O | O | 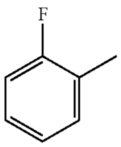 | —$CH_3$ |
| 1.54 | O | O | 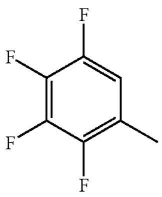 | —$CH_3$ |

TABLE 1-continued
| 2,5-diaminoterephthalic acid derivatives | | | | |
|---|---|---|---|---|
| 1.55 | O | O | | —$CH_3$ |
| 1.56 | O | O | 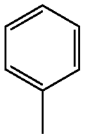 | —$CH_3$ |
| 1.57 | O | O | 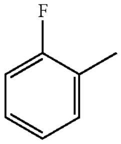 | —$CH_3$ |
| 1.58 | O | O | 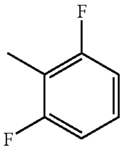 | —$CH_3$ |
| 1.59 | O | O | 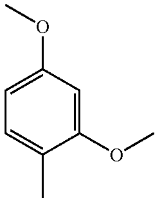 | —$CH_3$ |
| 1.60 | O | O | 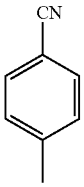 | —$CH_3$ |
| 1.61 | O | O | 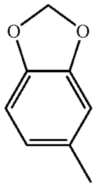 | —$CH_3$ |
| 1.62 | O | O | 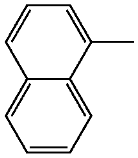 | —$CH_3$ |
| 1.63 | O | O | 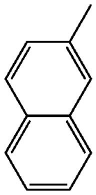 | —$CH_3$ |

TABLE 1-continued
| 2,5-diaminoterephthalic acid derivatives | | | | |
|---|---|---|---|---|
| 1.64 | O | O | 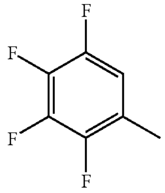 | —$CH_3$ |
| 1.65 | O | O | 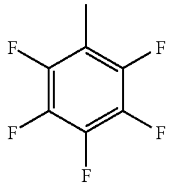 | —$CH_3$ |
| 1.67 | O | O | 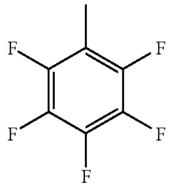 | —$CH_3$ |
| 1.68 | O | O | 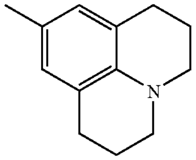 | —$CH_3$ |
| 1.69 | O | O | 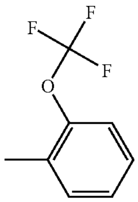 | —$CH_3$ |
| 1.70 | | | 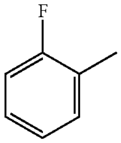 | —$CH_3$ |
| 1.71 | O | N | 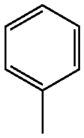 | 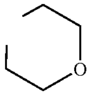 |
| 1.72 | O | N | 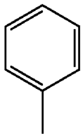 | 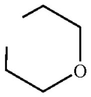 |

TABLE 1-continued
| 2,5-diaminoterephthalic acid derivatives | | | | |
| --- | --- | --- | --- | --- |
| 1.73 | O | O | 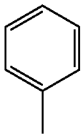 | —$CH_3$ |
| 1.74 | O | O | 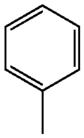 | —$CH_3$ |
| 1.75 | O | O | 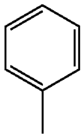 | —$CH_3$ |
| 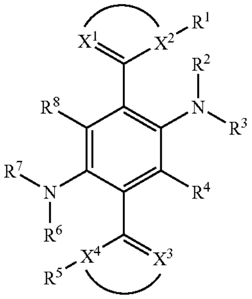 17.0 | | | | |
| 17.1 | 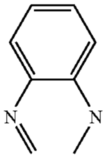 | | 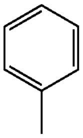 | —$CH_3$ |
| 17.2 | 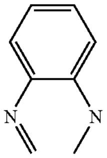 | | 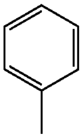 | —$CH_3$ |
| 17.3 | 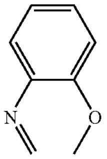 | | 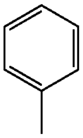 | — |
| 17.4 | 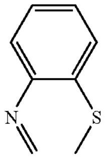 | | 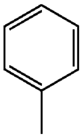 | — |

TABLE 1-continued
| 2,5-diaminoterephthalic acid derivatives | | | | |
|---|---|---|---|---|
| 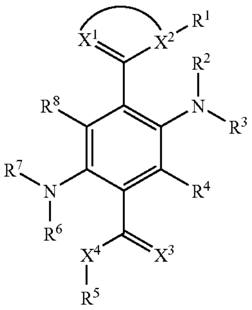 | | | | |
| 5.0 | | | | |
| 5.1 | 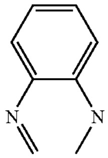 | | 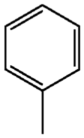 | 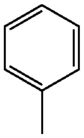 |
| 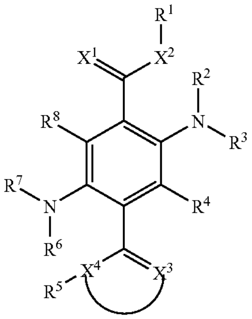 | | | | |
| 11.0 | | | | |
| 11.1 | O | O | 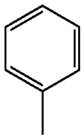 | —$CH_3$ |
| Substance | $R^2$ | $R^4$ | $X^4$ | $X^3$ |
|---|---|---|---|---|
| 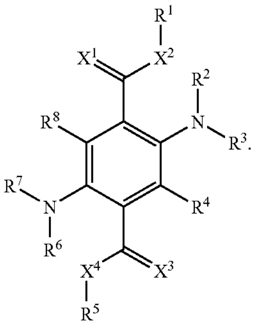 | | | | |
| 1.0 | | | | |

TABLE 1-continued
| 2,5-diaminoterephthalic acid derivatives | | | | |
|---|---|---|---|---|
| 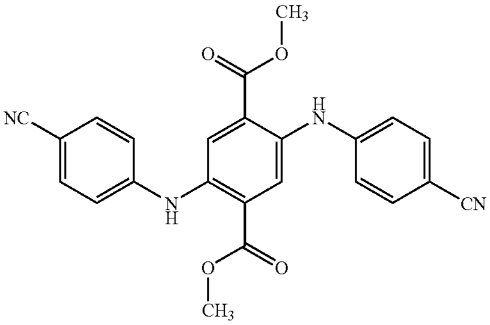 1.1 | H | H | O | O |
| 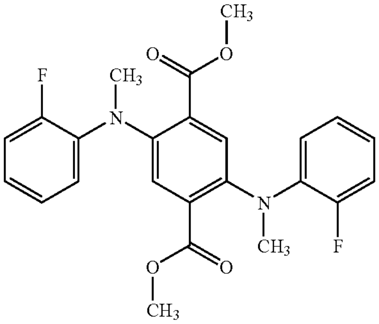 1.2 | —$CH_3$ | H | O | O |
| 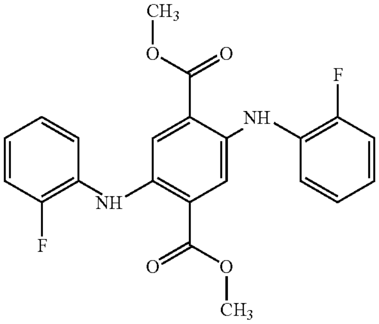 1.3 | H | H | O | O |
| 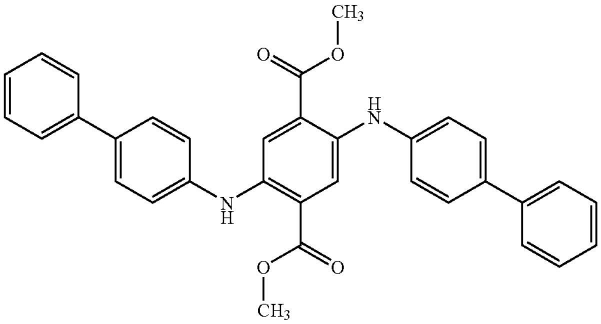 1.4 | H | H | O | O |

TABLE 1-continued
| 2,5-diaminoterephthalic acid derivatives | | | | |
|---|---|---|---|---|
| 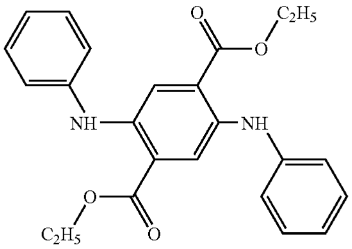 1.5 | H | H | O | O |
| 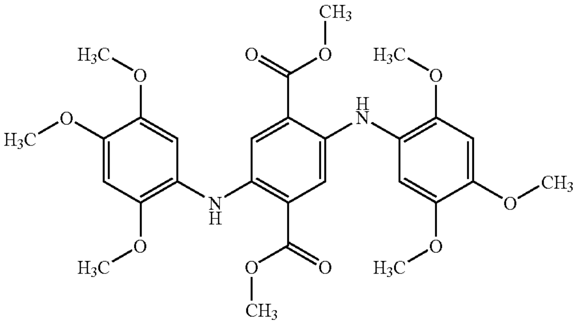 1.6 | H | H | O | O |
| 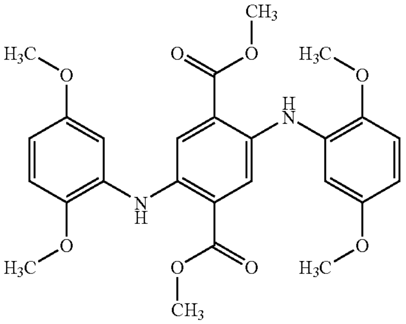 1.7 | H | H | O | O |
| 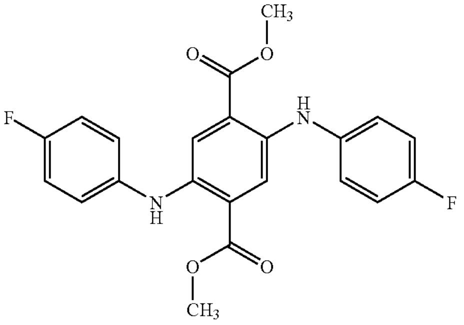 1.8 | H | H | O | O |

TABLE 1-continued
| 2,5-diaminoterephthalic acid derivatives | | | | |
|---|---|---|---|---|
| 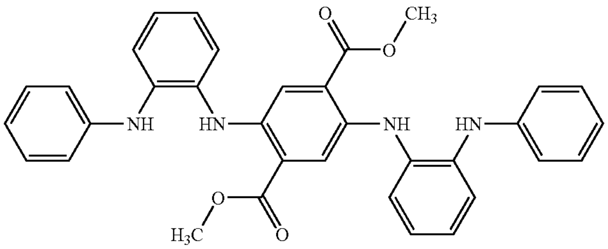 1.9 | H | H | O | O |
| 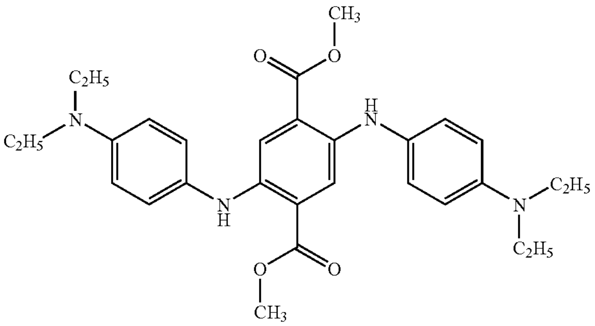 1.10 | H | H | O | O |
| 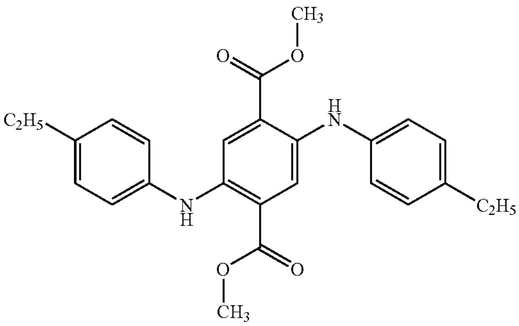 1.11 | H | H | O | O |
| 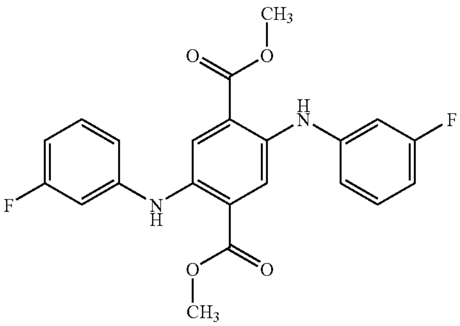 1.12 | H | H | O | O |

TABLE 1-continued
| 2,5-diaminoterephthalic acid derivatives | | | | |
|---|---|---|---|---|
| 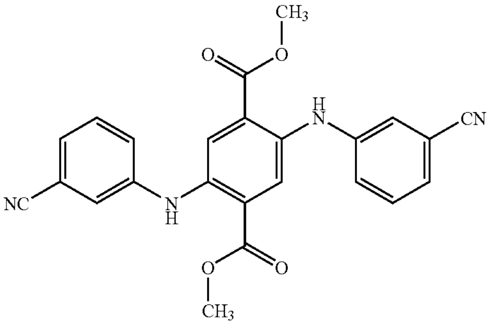 1.13 | H | H | O | O |
| 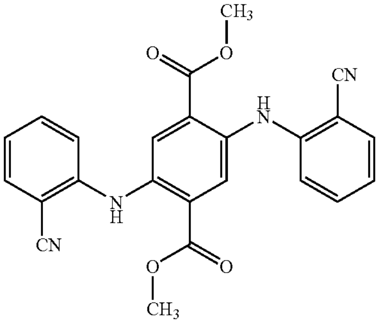 1.14 | H | H | O | O |
| 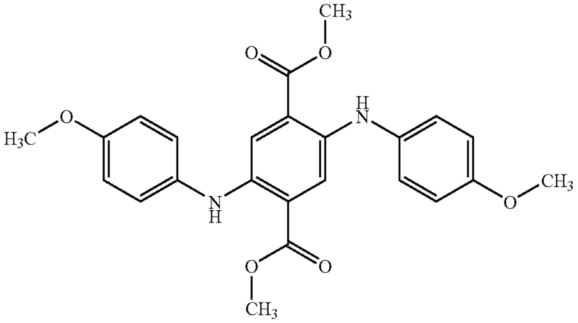 1.15 | H | H | O | O |
| 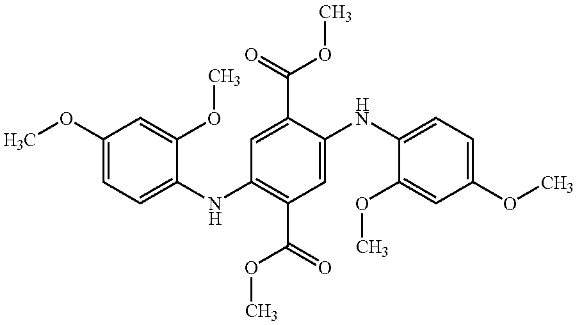 1.16 | H | H | O | O |

TABLE 1-continued
| 2,5-diaminoterephthalic acid derivatives | | | | |
|---|---|---|---|---|
| 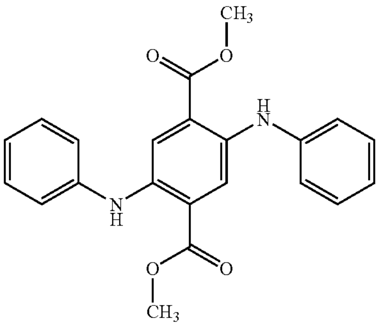 1.17 | H | H | O | O |
| 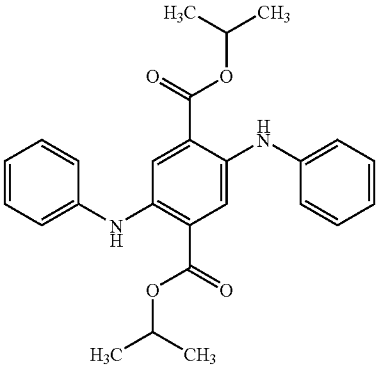 1.18 | H | H | O | O |
| 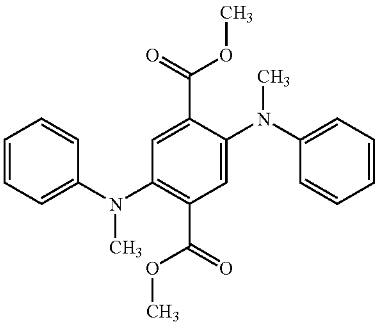 1.19 | —$CH_3$ | H | O | O |
| 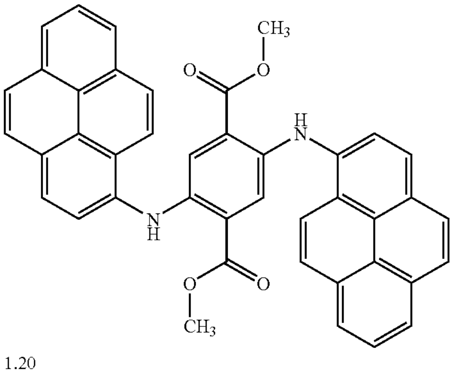 1.20 | H | H | O | O |

TABLE 1-continued
| 2,5-diaminoterephthalic acid derivatives | | | | |
|---|---|---|---|---|
| 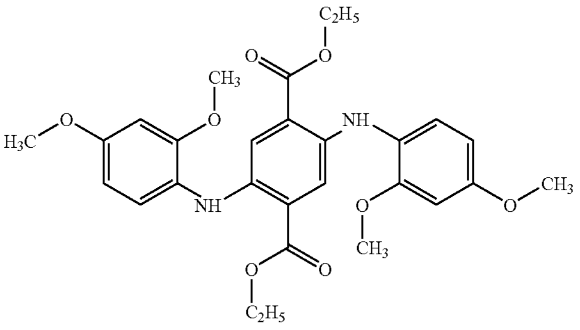 1.21 | H | H | O | O |
| 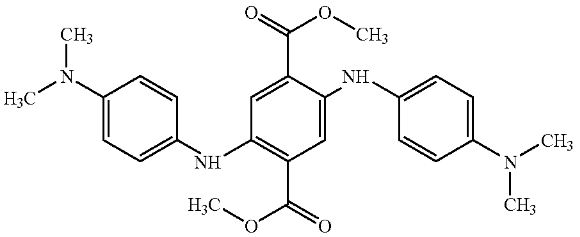 1.22 | H | H | O | O |
| 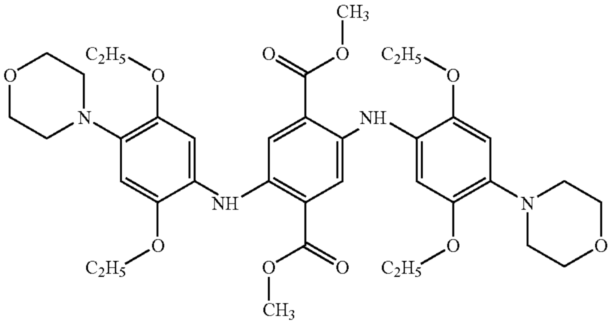 1.23 | H | H | O | O |
| 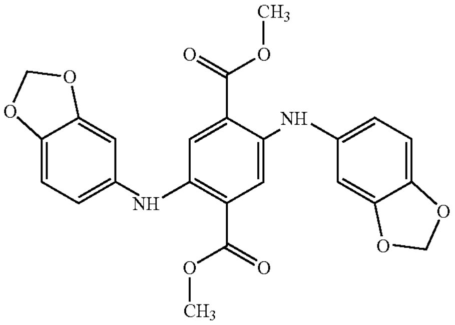 1.24 | H | H | O | O |

TABLE 1-continued
| 2,5-diaminoterephthalic acid derivatives | | | | |
|---|---|---|---|---|
| 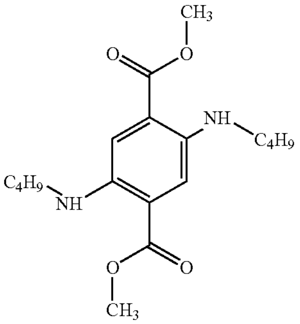 1.25 | H | H | O | O |
| 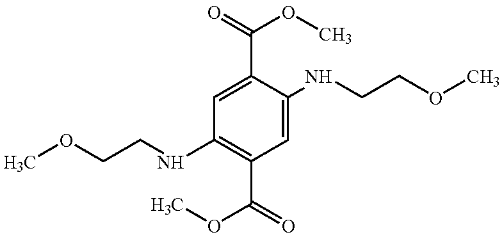 1.26 | H | H | O | O |
| 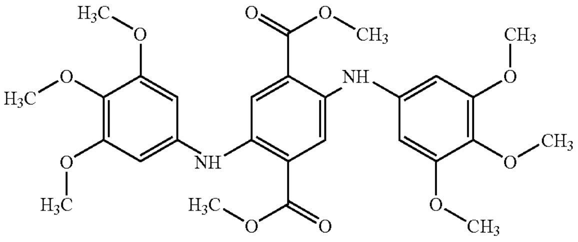 1.27 | H | H | O | O |
| 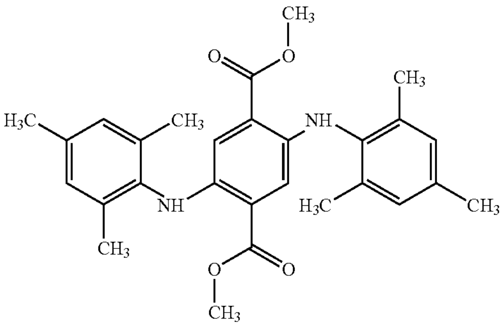 1.28 | H | H | O | O |

TABLE 1-continued
| 2,5-diaminoterephthalic acid derivatives | | | | |
|---|---|---|---|---|
| 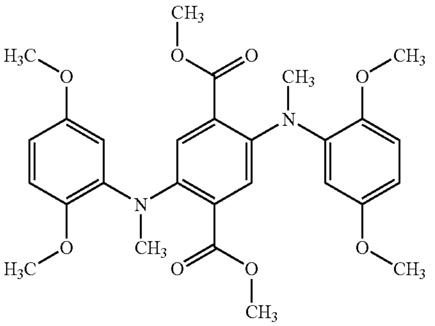 1.29 | —$CH_3$ | H | O | O |
| 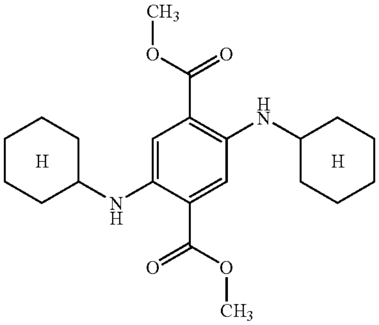 1.30 | H | H | O | O |
| 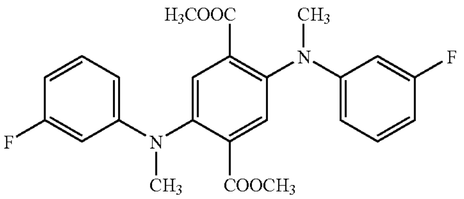 1.31 | —$CH_3$ | H | O | O |
| 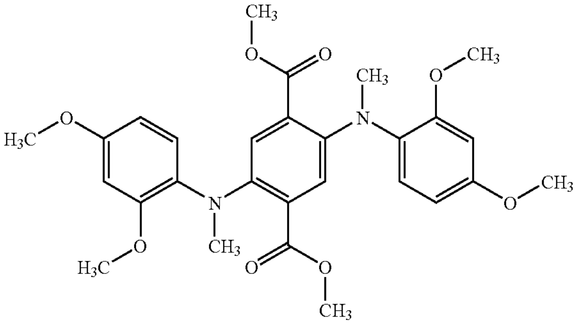 1.32 | —$CH_3$ | H | O | O |
| 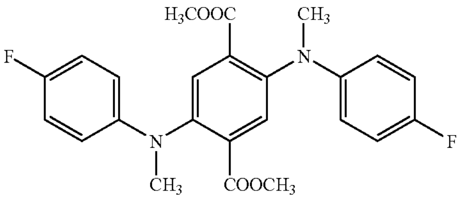 1.33 | —$CH_3$ | H | O | O |

TABLE 1-continued
| 2,5-diaminoterephthalic acid derivatives | | | | |
|---|---|---|---|---|
| 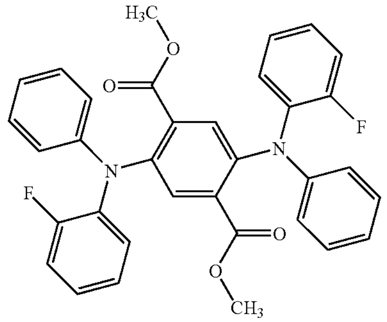 1.34 | 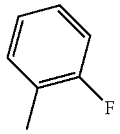 | H | O | O |
| 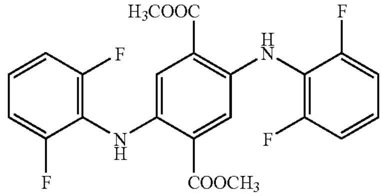 1.35 | H | H | O | O |
| 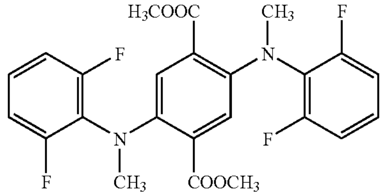 1.36 | $-CH_3$ | H | O | O |
| 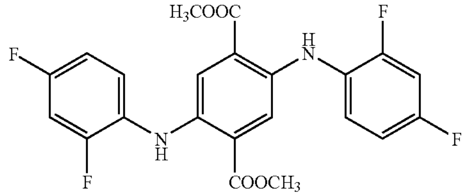 1.37 | H | H | O | O |
| 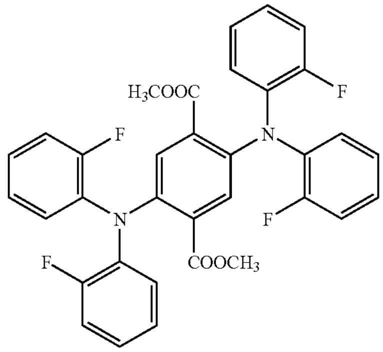 1.38 | 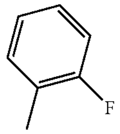 | H | O | O |

TABLE 1-continued
| 2,5-diaminoterephthalic acid derivatives | | | | |
|---|---|---|---|---|
| 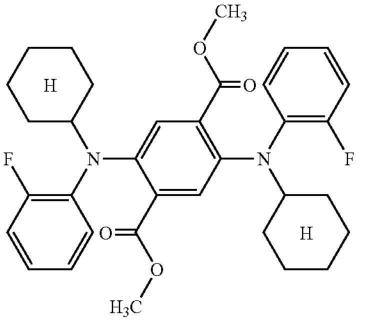 1.39 | 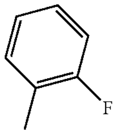 | H | O | O |
| 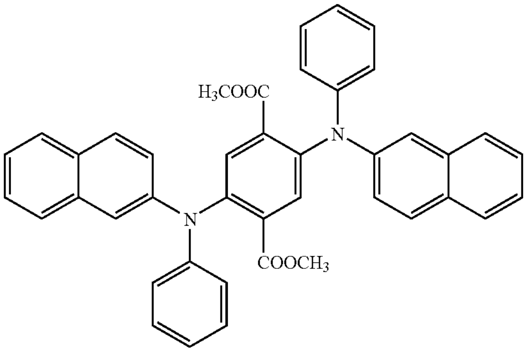 1.40 | 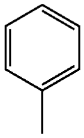 | H | O | O |
| 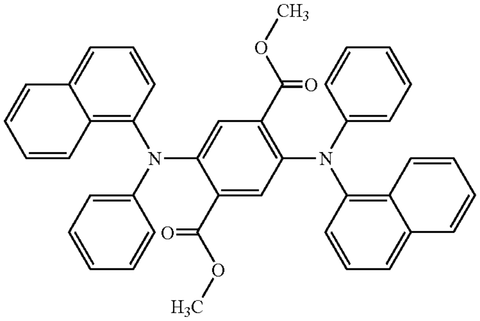 1.41 | 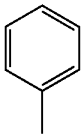 | H | O | O |
| 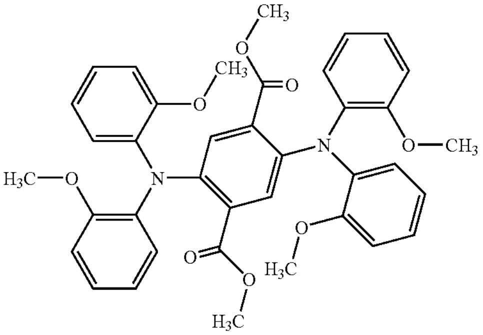 1.42 | 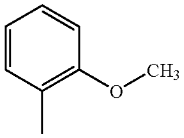 | H | O | O |

TABLE 1-continued
| 2,5-diaminoterephthalic acid derivatives | | | | | |
|---|---|---|---|---|---|
| 1.43 | 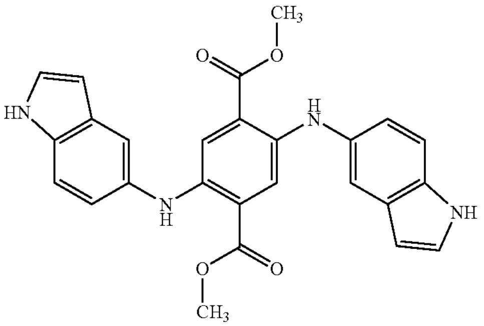 | H | H | O | O |
| 1.44 | | —$CH_3$ | H | O | O |
| 1.45 | | —$CH_3$ | H | O | O |
| 1.46 | | —$CH_3$ | H | O | O |
| 1.47 | | —$CH_3$ | H | O | O |
| 1.48 | | —$CH_3$ | H | O | O |
| 1.49 | | —$CH_3$ | H | O | O |
| 1.50 | | —$CF_3$ | H | O | O |
| 1.51 | | —$CF_3$ | H | O | O |
| 1.52 | | —$CF_3$ | H | O | O |
| 1.53 | | —$CF_3$ | H | O | O |
| 1.54 | | —$CF_3$ | H | O | O |
| 1.55 | | —$CF_3$ | H | O | O |
| 1.56 | | 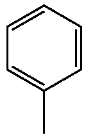 | H | O | O |
| 1.57 | | 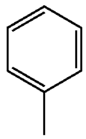 | H | O | O |
| 1.58 | | 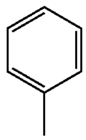 | H | O | O |
| 1.59 | | 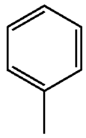 | H | O | O |

TABLE 1-continued
| 2,5-diaminoterephthalic acid derivatives | | | | |
|---|---|---|---|---|
| 1.60 | 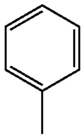 | H | O | O |
| 1.61 | 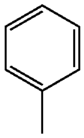 | H | O | O |
| 1.62 | 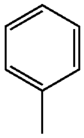 | H | O | O |
| 1.63 | 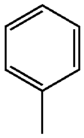 | H | O | O |
| 1.64 | 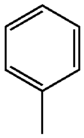 | H | O | O |
| 1.65 | $—CH_3$ | H | O | O |
| 1.67 | 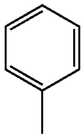 | H | O | O |
| 1.68 | 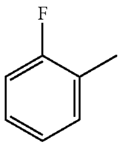 | H | O | O |
| 1.69 | 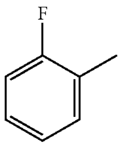 | H | O | O |
| 1.70 | 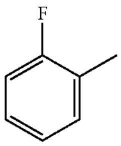 | H | O | O |
| 1.71 | H | H | N | O |

TABLE 1-continued
| 2,5-diaminoterephthalic acid derivatives | | | | | |
|---|---|---|---|---|---|
| 1.72 | | 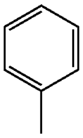 | H | N | O |
| 1.73 | | —$CH_3$ | 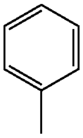 | O | O |
| 1.74 | | 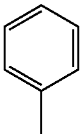 | 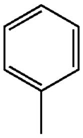 | O | O |
| 1.75 | | 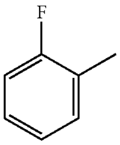 | 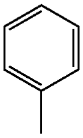 | O | O |
| 17.0 | 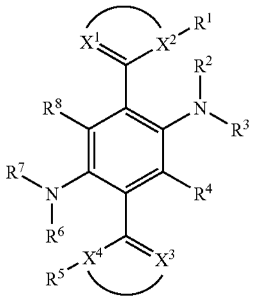 | | | | |
| 17.1 | | —$CH_3$ | H | 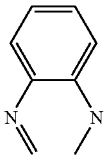 | |
| 17.2 | | —$CH_3$ | H | 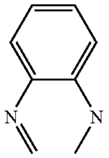 | |
| 17.3 | | —$CH_3$ | H | 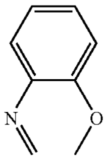 | |

TABLE 1-continued
| 2,5-diaminoterephthalic acid derivatives | | | | |
|---|---|---|---|---|
| 17.4 | $-CH_3$ | H | 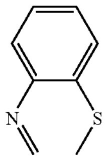 | |
| 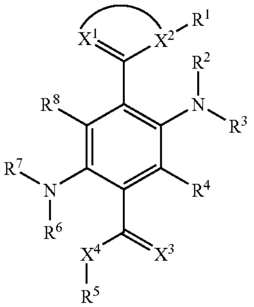<br>5.0 | | | | |
| 5.1 | $-CH_3$ | H | O | O |
| 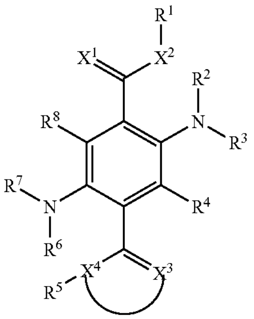<br>11.0 | | | | |
| 11.1 | $-CH_3$ | H | 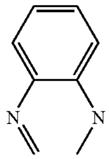 | |
| Substance | $R^8$ | $R^5$ | $R^6$ |
|---|---|---|---|
| 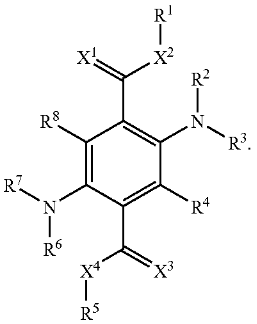<br>1.0 | | | |

TABLE 1-continued
| 2,5-diaminoterephthalic acid derivatives | | | |
|---|---|---|---|
| 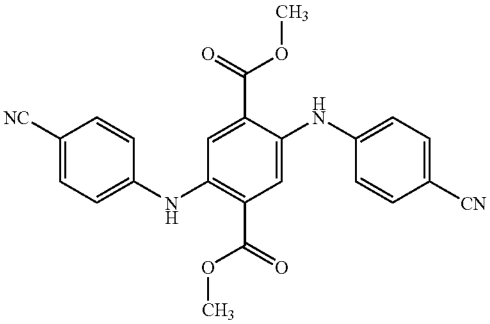 1.1 | H | —$CH_3$ | H |
| 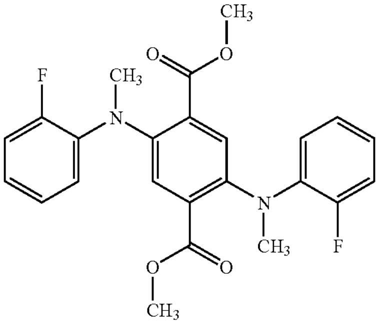 1.2 | H | —$CH_3$ | —$CH_3$ |
| 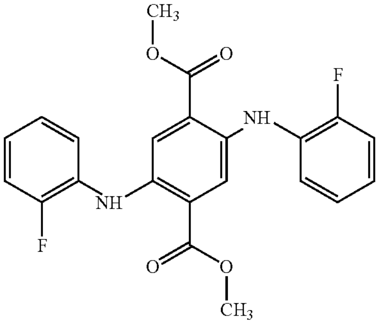 1.3 | H | —$CH_3$ | H |
| 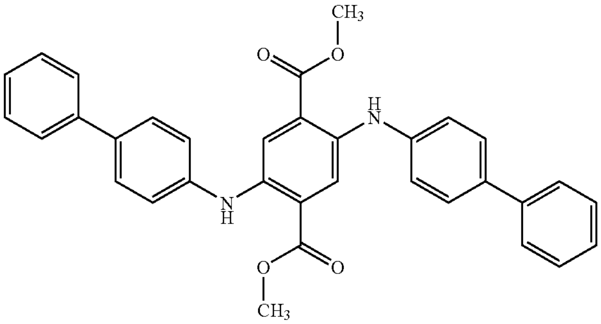 1.4 | H | —$CH_3$ | H |

TABLE 1-continued
2,5-diaminoterephthalic acid derivatives
| | | | |
|---|---|---|---|
| 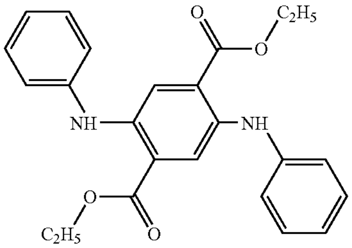 1.5 | H | $-C_2H_5$ | H |
| 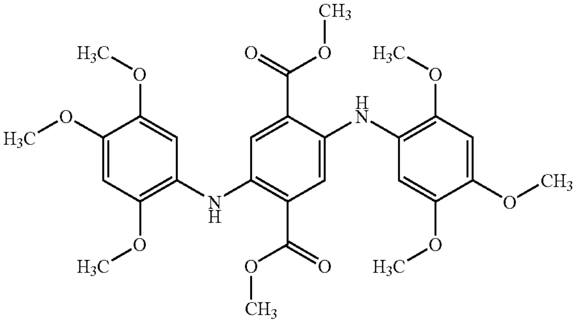 1.6 | H | $-CH_3$ | H |
| 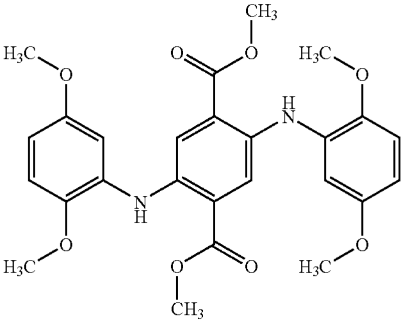 1.7 | H | $-CH_3$ | H |
| 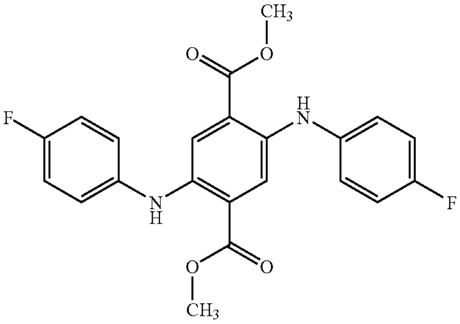 1.8 | H | $-CH_3$ | H |

TABLE 1-continued
| 2,5-diaminoterephthalic acid derivatives | | | |
|---|---|---|---|
| 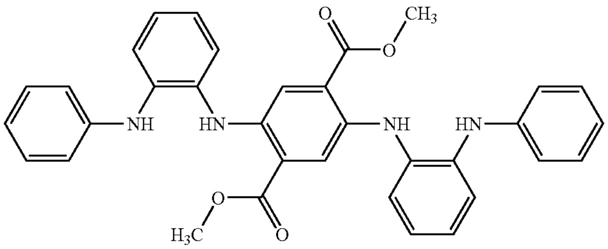 1.9 | H | $—CH_3$ | H |
| 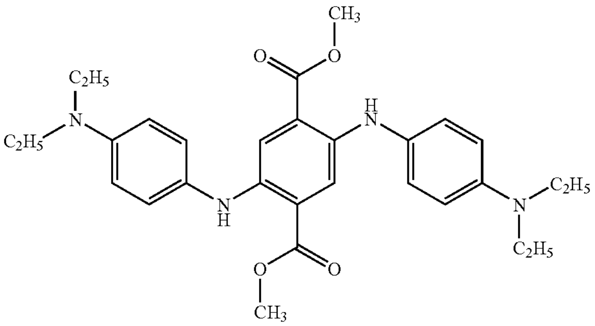 1.10 | H | $—CH_3$ | H |
| 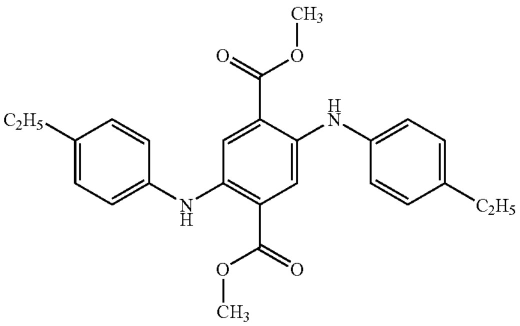 1.11 | H | $—CH_3$ | H |
| 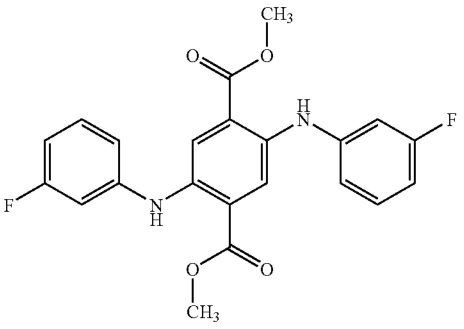 1.12 | H | $—CH_3$ | H |

TABLE 1-continued
| 2,5-diaminoterephthalic acid derivatives | | | |
|---|---|---|---|
| 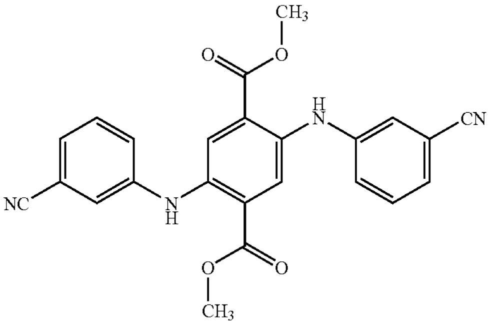 1.13 | H | —$CH_3$ | H |
| 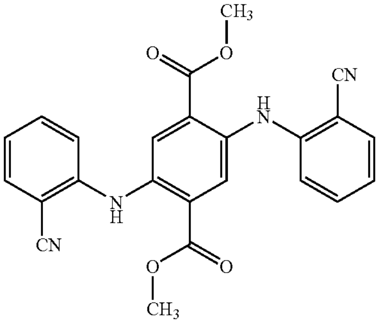 1.14 | H | —$CH_3$ | H |
| 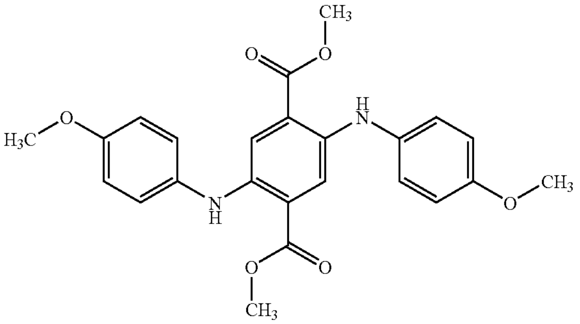 1.15 | H | —$CH_3$ | H |
| 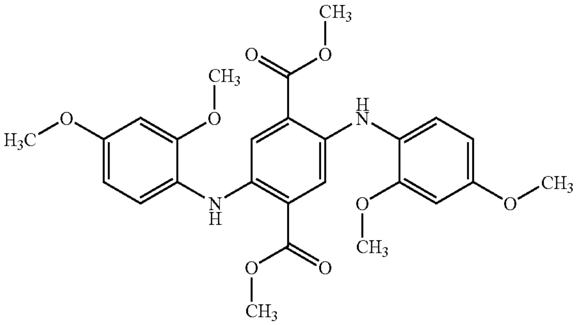 1.16 | H | —$CH_3$ | H |

TABLE 1-continued
| 2,5-diaminoterephthalic acid derivatives | | | |
|---|---|---|---|
| 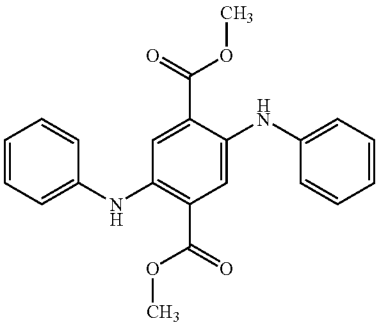 1.17 | H | —$CH_3$ | H |
| 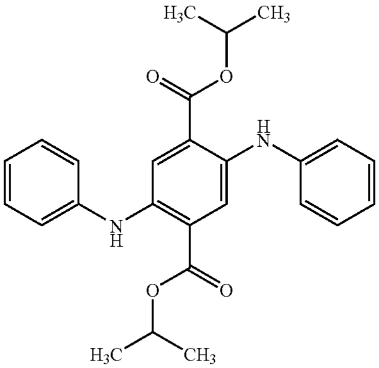 1.18 | H | —$CH_3$ | H |
| 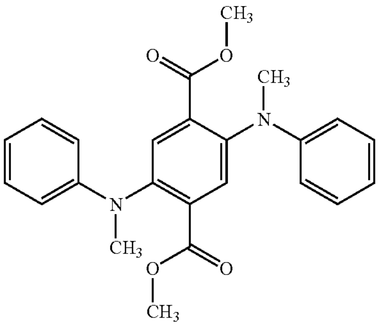 1.19 | H | —$CH_3$ | —$CH_3$ |
| 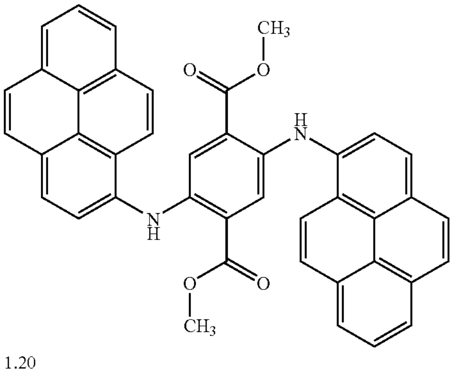 1.20 | H | —$CH_3$ | H |

TABLE 1-continued
2,5-diaminoterephthalic acid derivatives
| | | | |
|---|---|---|---|
| 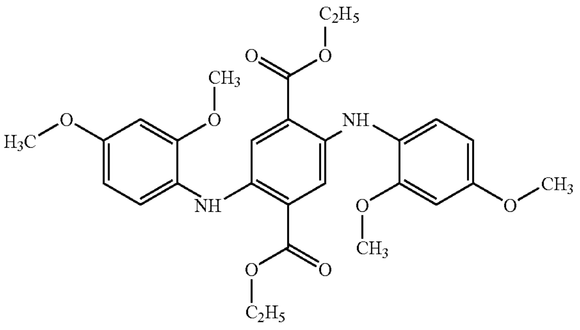 1.21 | H | —$CH_3$ | H |
| 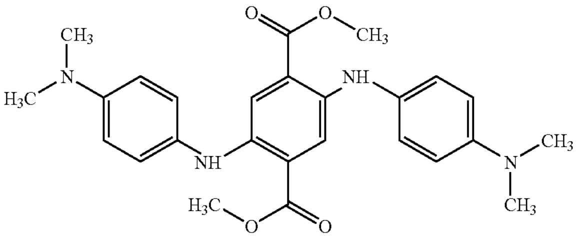 1.22 | H | —$CH_3$ | H |
| 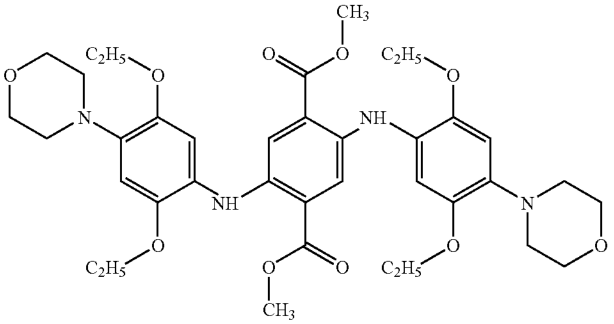 1.23 | H | —$CH_3$ | H |
| 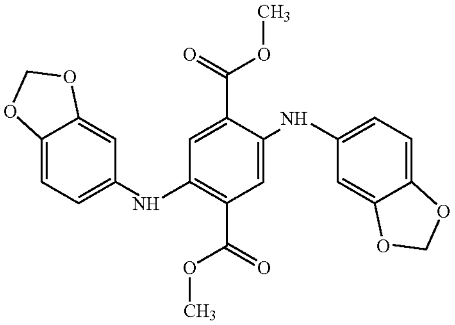 1.24 | H | —$CH_3$ | H |

TABLE 1-continued
| 2,5-diaminoterephthalic acid derivatives | | | |
|---|---|---|---|
| 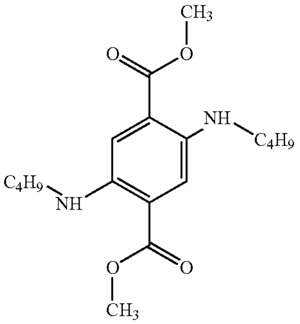 1.25 | H | $—CH_3$ | H |
| 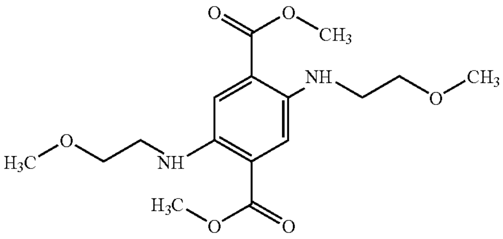 1.26 | H | $—CH_3$ | H |
| 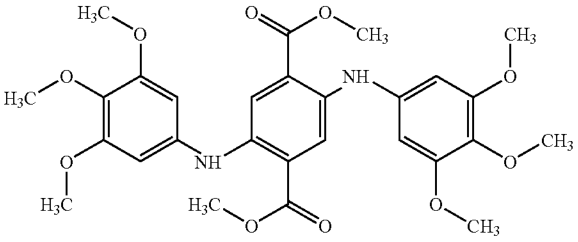 1.27 | H | $—CH_3$ | H |
| 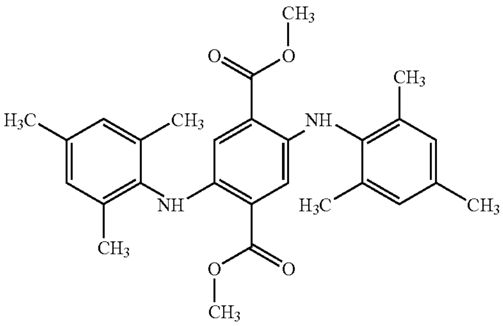 1.28 | H | $—CH_3$ | H |

TABLE 1-continued
| 2,5-diaminoterephthalic acid derivatives | | | |
|---|---|---|---|
| 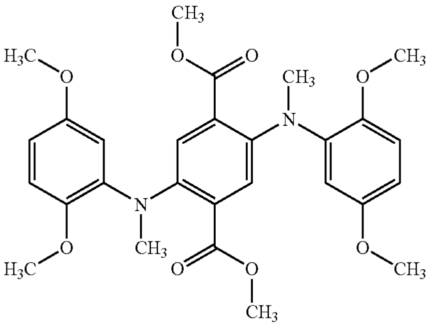 1.29 | H | —$CH_3$ | —$CH_3$ |
| 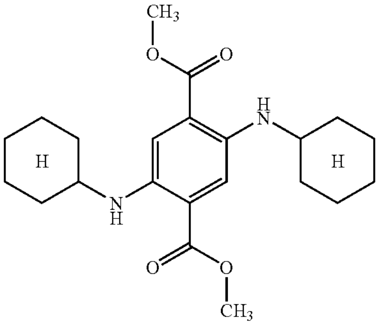 1.30 | H | —$CH_3$ | H |
| 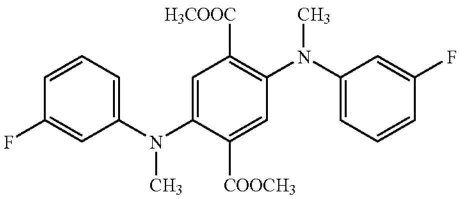 1.31 | H | —$CH_3$ | —$CH_3$ |
| 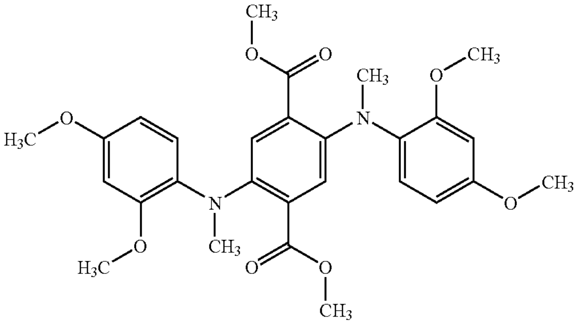 1.32 | H | —$CH_3$ | —$CH_3$ |
| 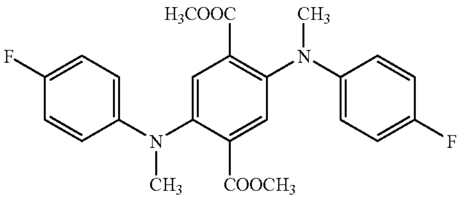 1.33 | H | —$CH_3$ | —$CH_3$ |

TABLE 1-continued
| 2,5-diaminoterephthalic acid derivatives | | | |
|---|---|---|---|
| 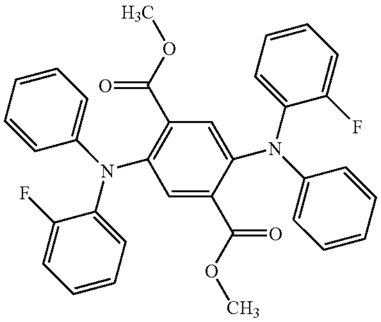 1.34 | H | $—CH_3$ | 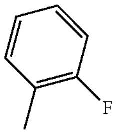 |
| 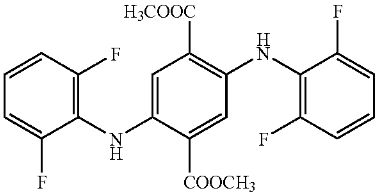 1.35 | H | $—CH_3$ | H |
| 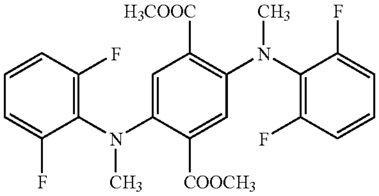 1.36 | H | $—CH_3$ | $—CH_3$ |
| 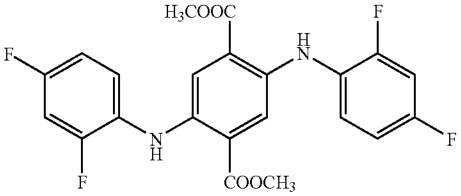 1.37 | H | $—CH_3$ | H |
| 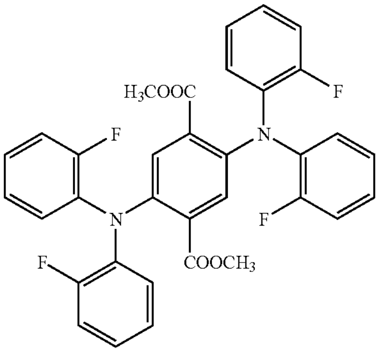 1.38 | H | $—CH_3$ | 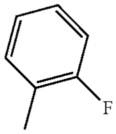 |

TABLE 1-continued
| 2,5-diaminoterephthalic acid derivatives | | | |
|---|---|---|---|
| 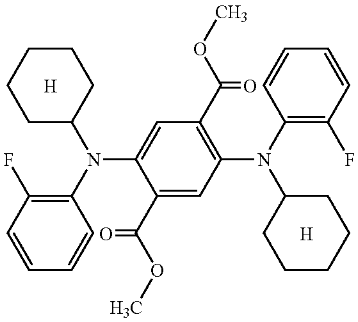 1.39 | H | —$CH_3$ | 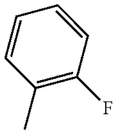 |
| 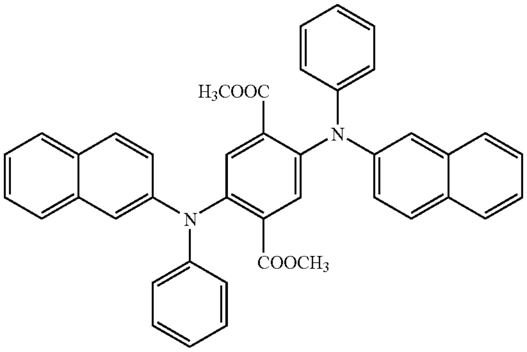 1.40 | H | —$CH_3$ | 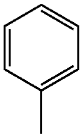 |
| 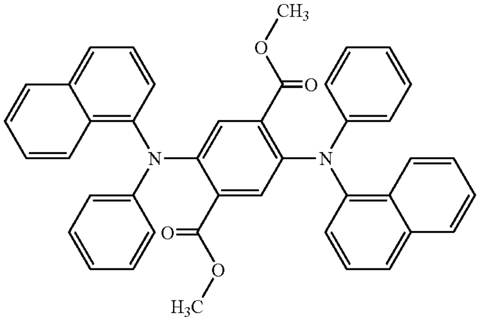 1.41 | H | —$CH_3$ | 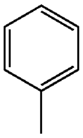 |
| 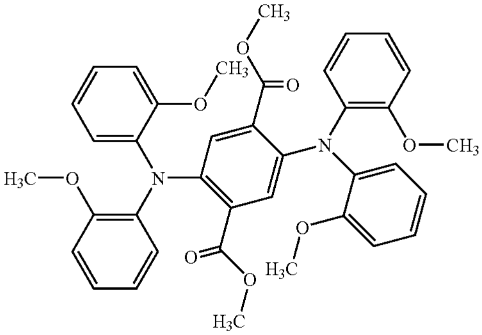 1.42 | H | —$CH_3$ | 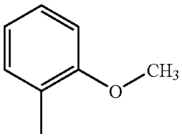 |

TABLE 1-continued
| 2,5-diaminoterephthalic acid derivatives | | | | |
|---|---|---|---|---|
| 1.43 | 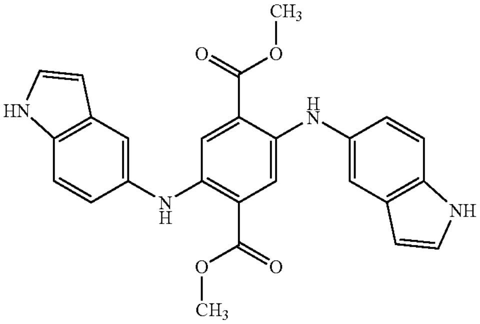 | H | —$CH_3$ | H |
| 1.44 | | H | —$CH_3$ | —$CH_3$ |
| 1.45 | | H | —$CH_3$ | —$CH_3$ |
| 1.46 | | H | —$CH_3$ | —$CH_3$ |
| 1.47 | | H | —$CH_3$ | —$CH_3$ |
| 1.48 | | H | —$CH_3$ | —$CH_3$ |
| 1.49 | | H | —$CH_3$ | —$CH_3$ |
| 1.50 | | H | —$CH_3$ | —$CF_3$ |
| 1.51 | | H | —$CH_3$ | —$CF_3$ |
| 1.52 | | H | —$CH_3$ | —$CF_3$ |
| 1.53 | | H | —$CH_3$ | —$CF_3$ |
| 1.54 | | H | —$CH_3$ | —$CF_3$ |
| 1.55 | | H | —$CH_3$ | —$CF_3$ |
| 1.56 | | H | —$CH_3$ | 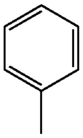 |
| 1.57 | | H | —$CH_3$ | 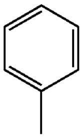 |
| 1.58 | | H | —$CH_3$ | 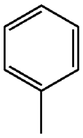 |
| 1.59 | | H | —$CH_3$ | 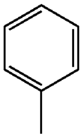 |

TABLE 1-continued
| 2,5-diaminoterephthalic acid derivatives | | | |
|---|---|---|---|
| 1.60 | H | —$CH_3$ | 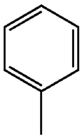 |
| 1.61 | H | —$CH_3$ | 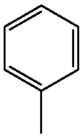 |
| 1.62 | H | —$CH_3$ | 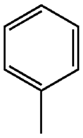 |
| 1.63 | H | —$CH_3$ | 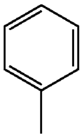 |
| 1.64 | H | —$CH_3$ | 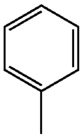 |
| 1.65 | H | —$CH_3$ | —$CH_3$ |
| 1.67 | H | —$CH_3$ | 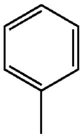 |
| 1.68 | H | —$CH_3$ | 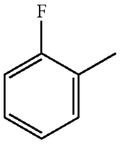 |
| 1.69 | H | —$CH_3$ | 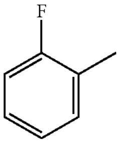 |
| 1.70 | H | —$CH_3$ | 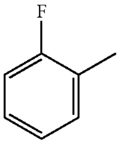 |
| 1.71 | H | 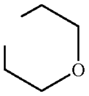 | H |

TABLE 1-continued
| 2,5-diaminoterephthalic acid derivatives | | | |
|---|---|---|---|
| 1.72 | H | 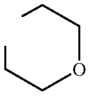 | 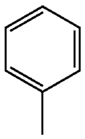 |
| 1.73 | 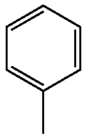 | $—CH_3$ | $—CH_3$ |
| 1.74 | 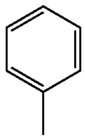 | $—CH_3$ | 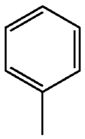 |
| 1.75 | 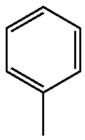 | $—CH_3$ | 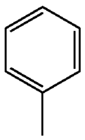 |
| 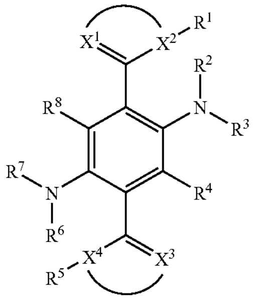 17.0 | | | |
| 17.1 | H | $—CH_3$ | $—CH_3$ |
| 17.2 | H | $—CH_3$ | $—CH_3$ |
| 17.3 | H | — | $—CH_3$ |
| 17.4 | H | — | $—CH_3$ |
| 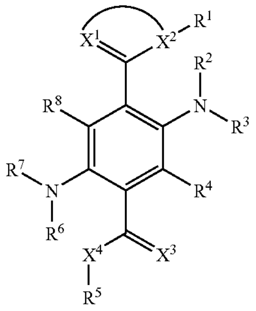 5.0 | | | |
| 5.1 | H | $—CH_3$ | $—CH_3$ |

TABLE 1-continued
| 2,5-diaminoterephthalic acid derivatives | | | |
|---|---|---|---|
| 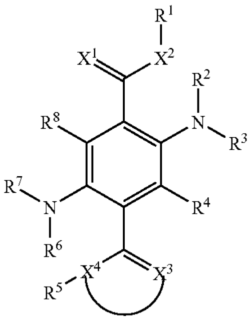 11.0 | | | |
| 11.1 | 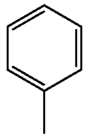 | —$CH_3$ | —$CH_3$ |
| Substance | $R^7$ |
|---|---|
| 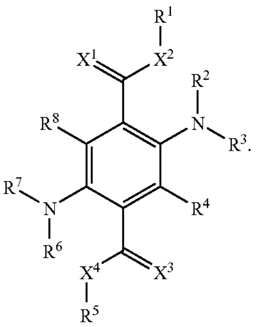 1.0 | |
| 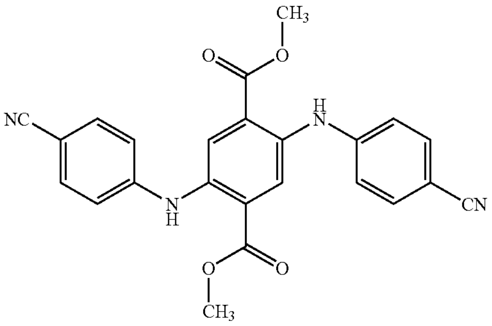 1.1 | 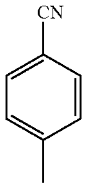 |

TABLE 1-continued
| 2,5-diaminoterephthalic acid derivatives | | |
|---|---|---|
| 1.2 | 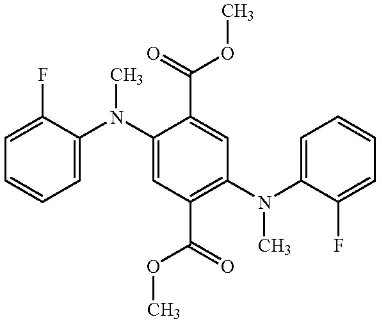 | 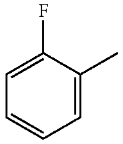 |
| 1.3 | 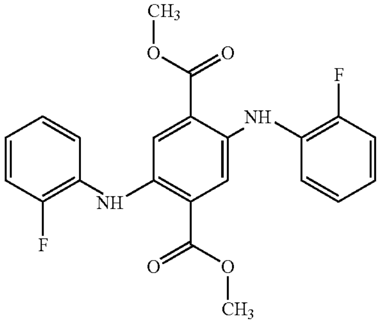 | 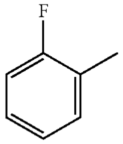 |
| 1.4 | 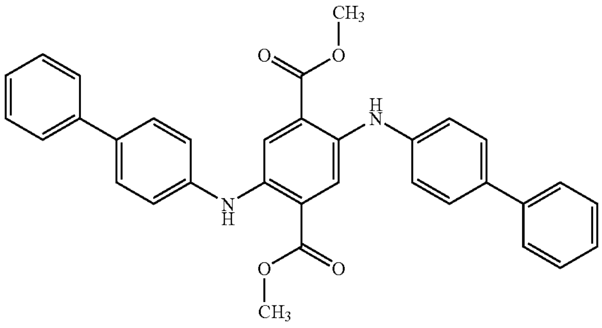 | 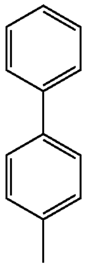 |
| 1.5 | 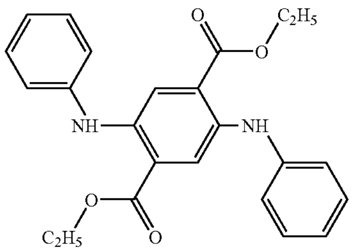 | 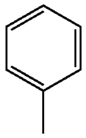 |

TABLE 1-continued
| 2,5-diaminoterephthalic acid derivatives | |
|---|---|
| 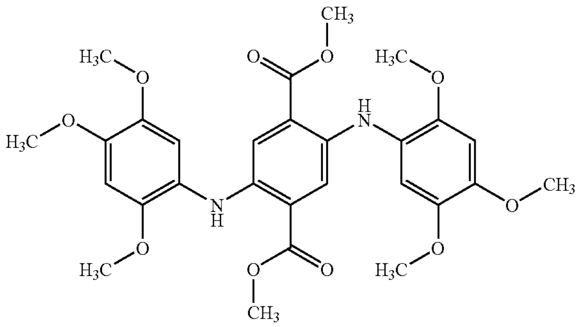 1.6 | 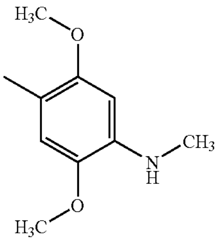 |
| 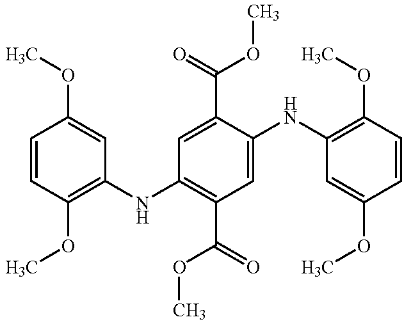 1.7 | 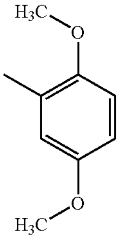 |
| 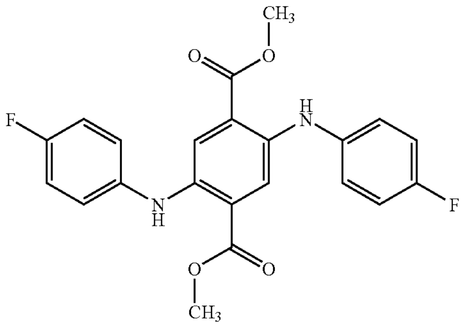 1.8 | 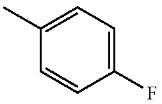 |
| 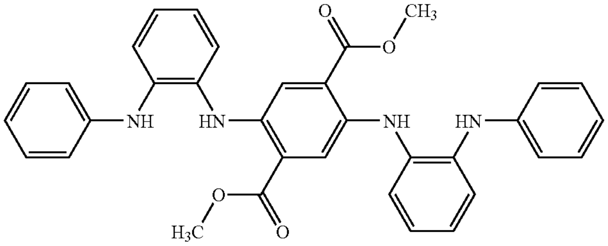 1.9 | 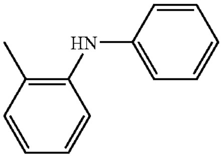 |

TABLE 1-continued
| 2,5-diaminoterephthalic acid derivatives | |
|---|---|
| 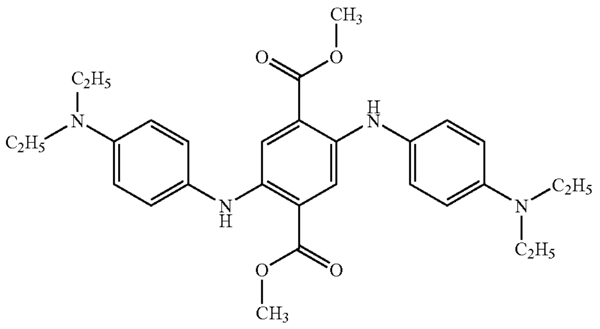 | 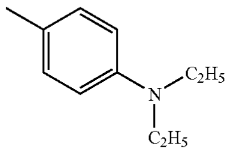 |
| 1.10 | |
| 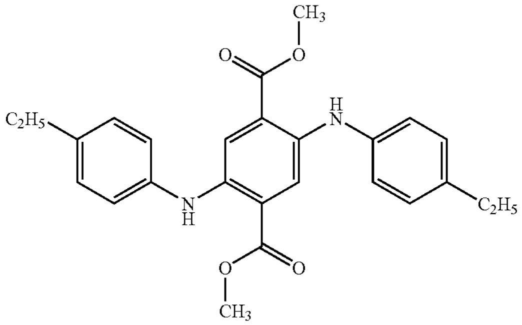 | 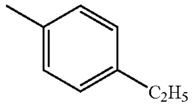 |
| 1.11 | |
| 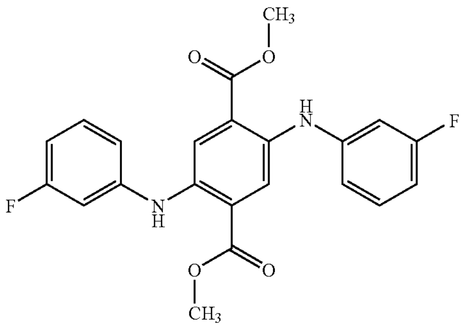 | 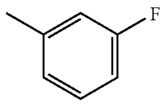 |
| 1.12 | |
| 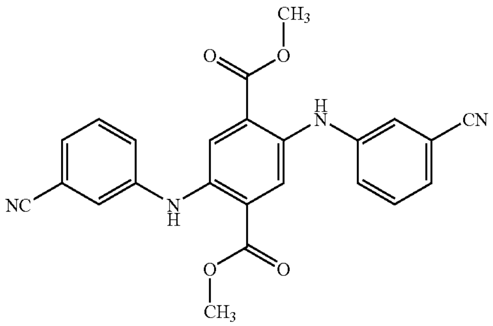 | 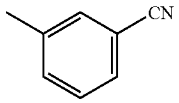 |
| 1.13 | |

TABLE 1-continued
| 2,5-diaminoterephthalic acid derivatives | |
|---|---|
| 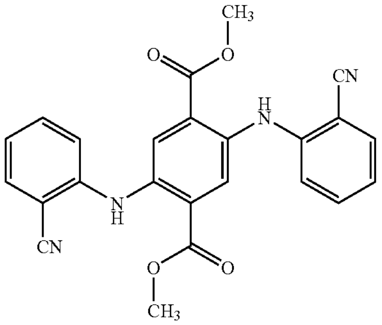 1.14 | 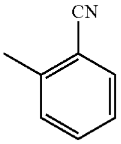 |
| 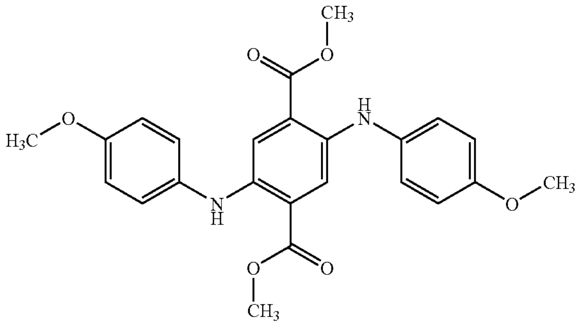 1.15 | 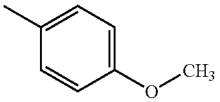 |
| 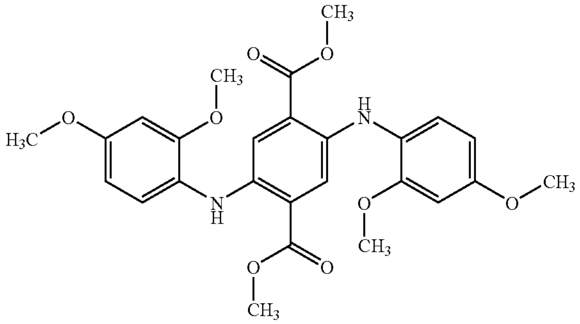 1.16 | 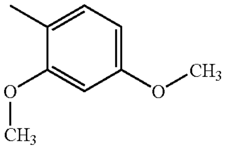 |
| 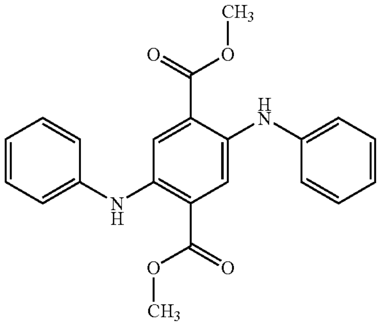 1.17 | 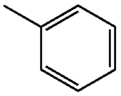 |

TABLE 1-continued
| 2,5-diaminoterephthalic acid derivatives | |
|---|---|
| 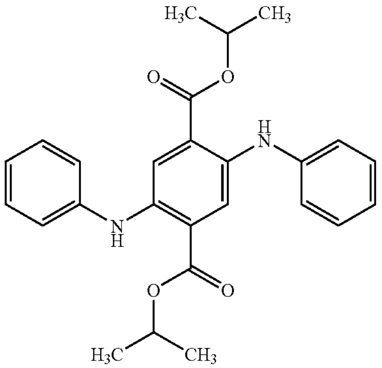 1.18 | 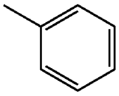 |
| 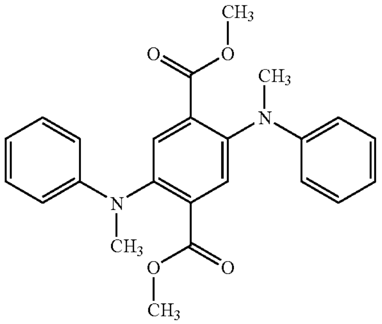 1.19 | 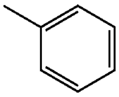 |
| 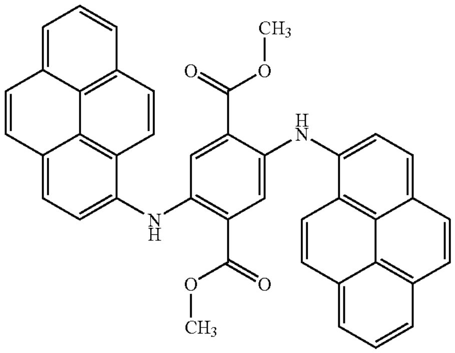 1.20 | 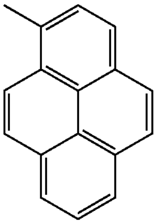 |
| 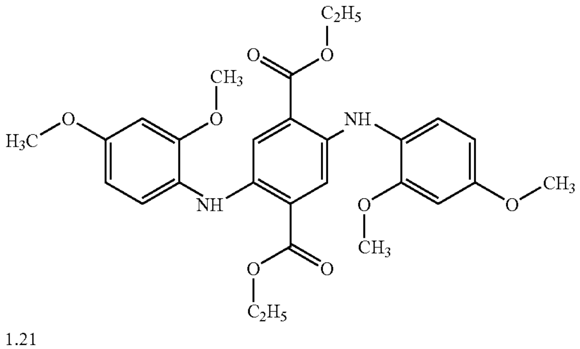 1.21 | 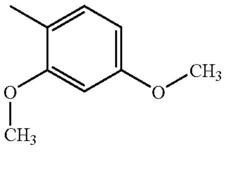 |

TABLE 1-continued
2,5-diaminoterephthalic acid derivatives
| | |
|---|---|
| 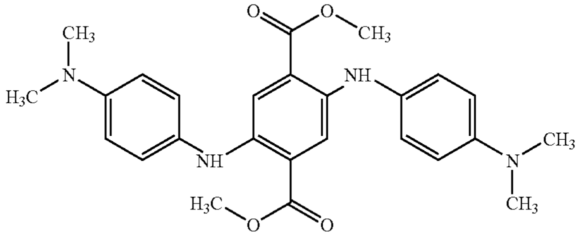 1.22 | 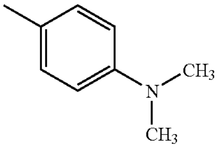 |
| 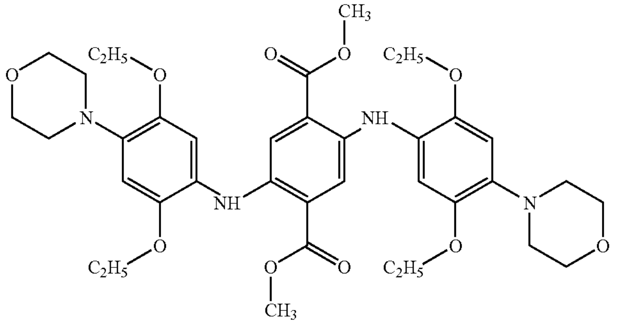 1.23 | |
| 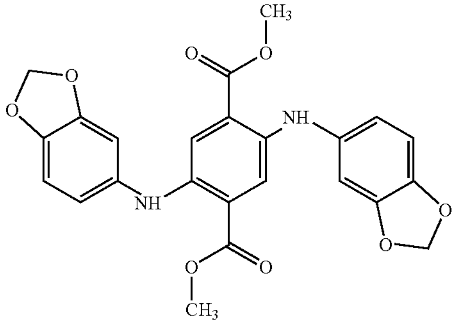 1.24 | 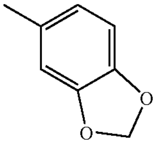 |
| 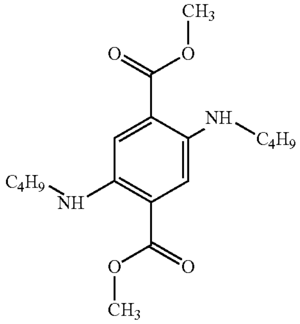 1.25 | $—C_4H_9$ |
| 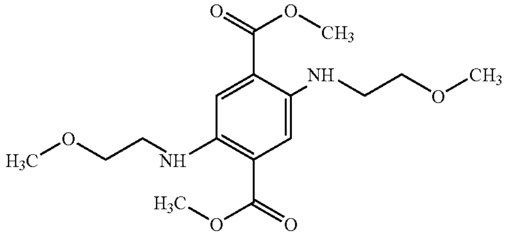 1.26 | 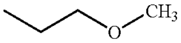 |

TABLE 1-continued
2,5-diaminoterephthalic acid derivatives
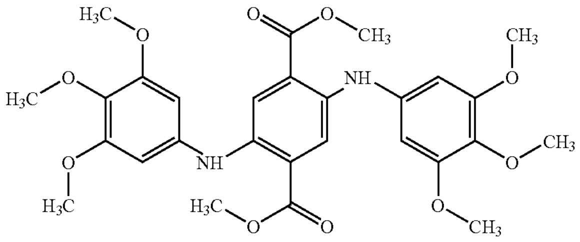
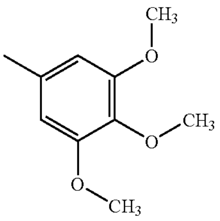
1.27
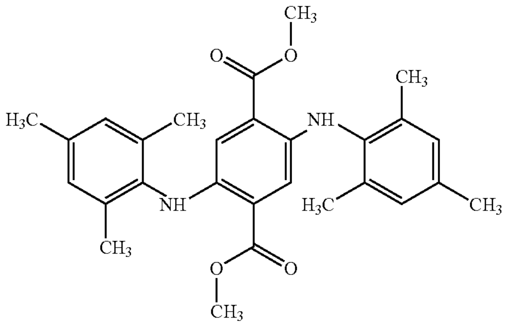
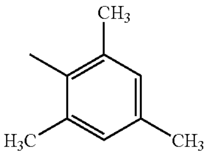
1.28
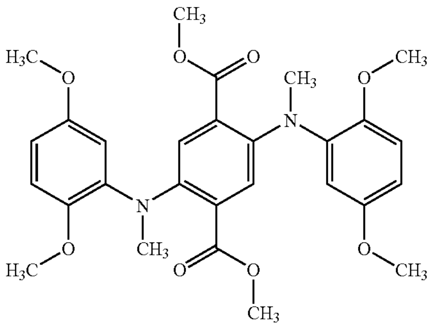
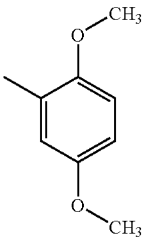
1.29
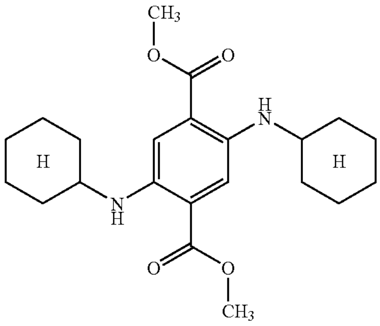
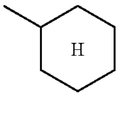
1.30
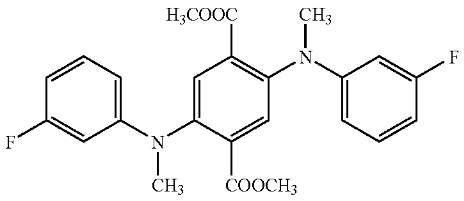
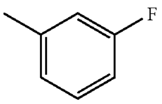
1.31

TABLE 1-continued
| 2,5-diaminoterephthalic acid derivatives | | |
|---|---|---|
| 1.32 | 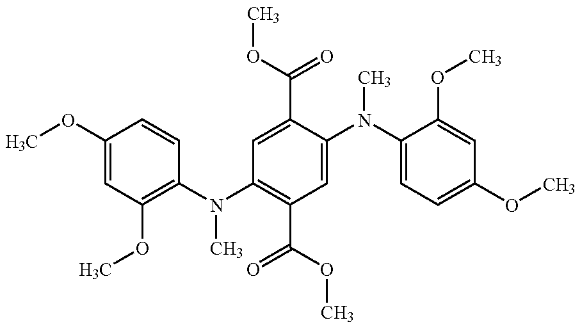 | 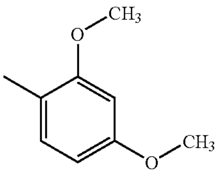 |
| 1.33 | 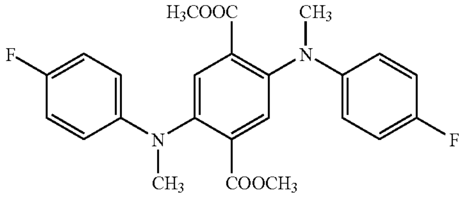 | 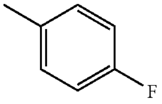 |
| 1.34 | 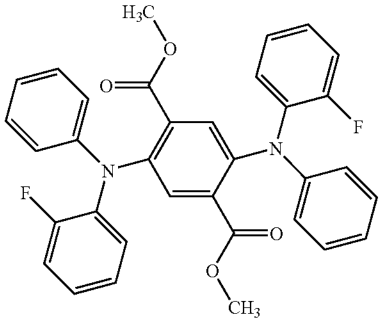 | 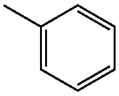 |
| 1.35 | 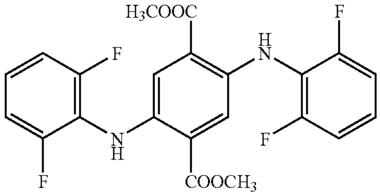 | 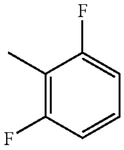 |
| 1.36 | 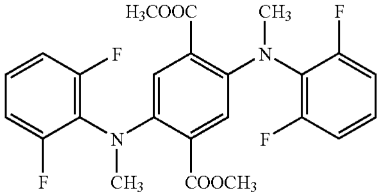 | 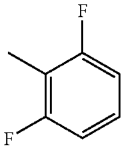 |

TABLE 1-continued
| 2,5-diaminoterephthalic acid derivatives | |
|---|---|
| 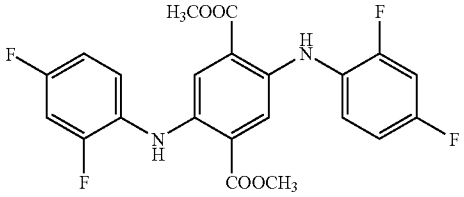 1.37 | 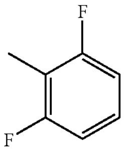 |
| 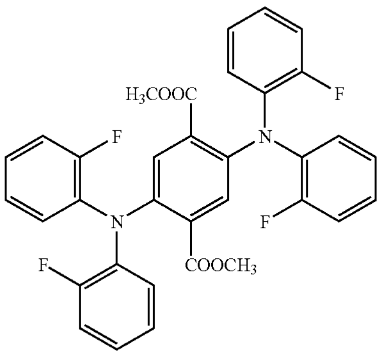 1.38 | 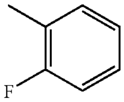 |
| 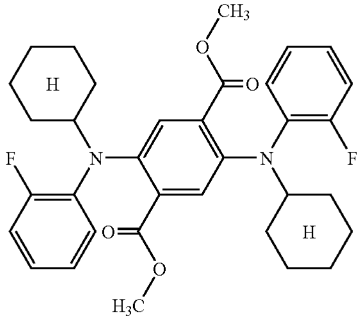 1.39 | 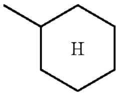 |
| 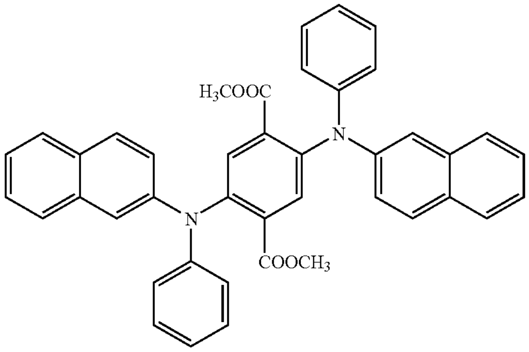 1.40 | 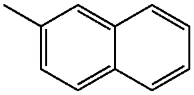 |

TABLE 1-continued
| 2,5-diaminoterephthalic acid derivatives | |
|---|---|
| 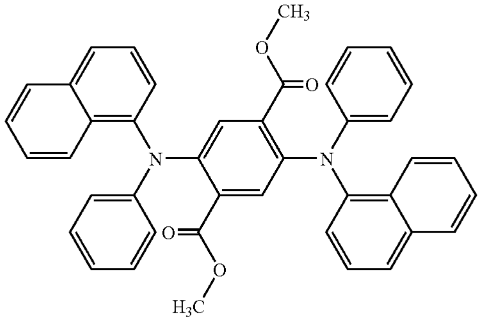<br>1.41 | 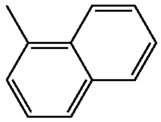 |
| 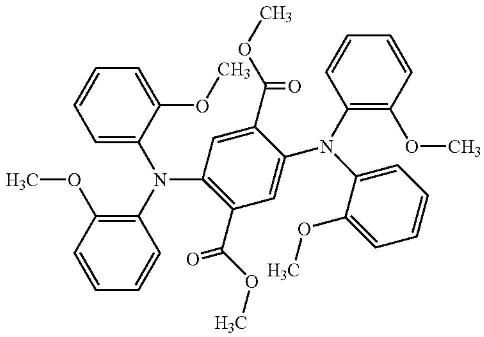<br>1.42 | 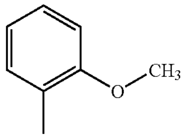 |
| 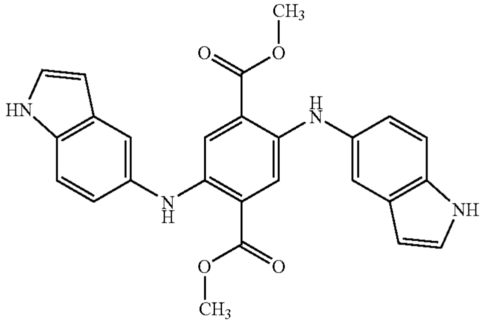<br>1.43 | 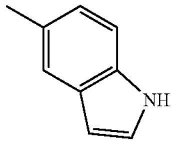 |
| 1.44 | 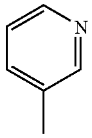 |
| 1.45 | 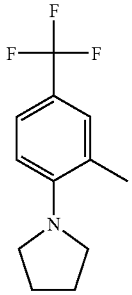 |

TABLE 1-continued
| 2,5-diaminoterephthalic acid derivatives | |
|---|---|
| 1.46 | 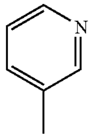 |
| 1.47 | 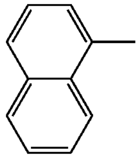 |
| 1.48 | 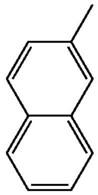 |
| 1.49 | 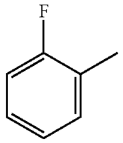 |
| 1.50 | 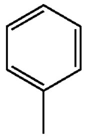 |
| 1.51 | 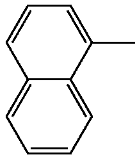 |
| 1.52 | 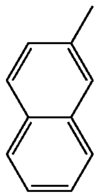 |
| 1.53 | 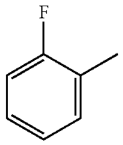 |
| 1.54 | 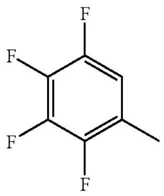 |

TABLE 1-continued
| 2,5-diaminoterephthalic acid derivatives | |
|---|---|
| 1.55 | |
| 1.56 | 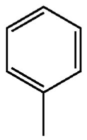 |
| 1.57 | 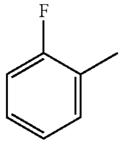 |
| 1.58 | 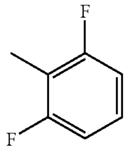 |
| 1.59 | 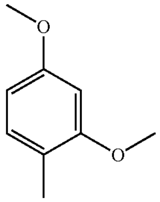 |
| 1.60 | 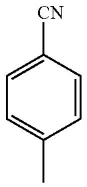 |
| 1.61 | 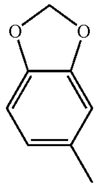 |
| 1.62 | 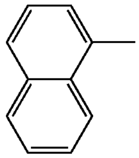 |
| 1.63 | 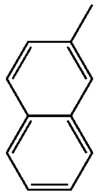 |

TABLE 1-continued
| 2,5-diaminoterephthalic acid derivatives | |
|---|---|
| 1.64 | 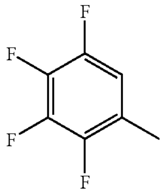 |
| 1.65 | 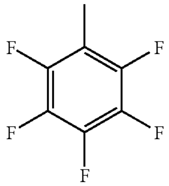 |
| 1.67 | 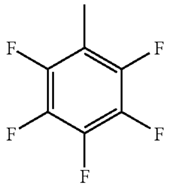 |
| 1.68 | 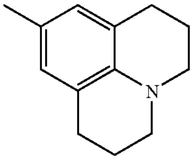 |
| 1.69 | 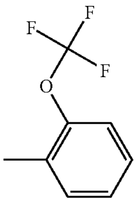 |
| 1.70 | 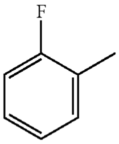 |
| 1.71 | 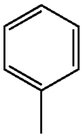 |
| 1.72 | 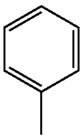 |

TABLE 1-continued
| 2,5-diaminoterephthalic acid derivatives | |
|---|---|
| 1.73 | 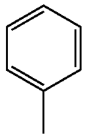 |
| 1.74 | 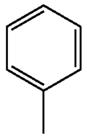 |
| 1.75 | 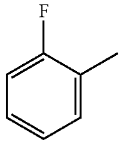 |
| 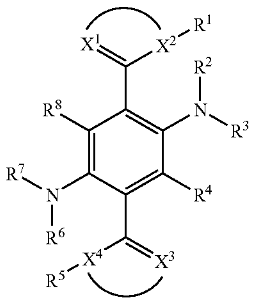 17.0 | |
| 17.1 | 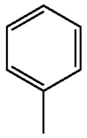 |
| 17.2 | 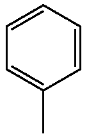 |
| 17.3 | 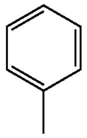 |
| 17.4 | 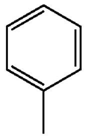 |

TABLE 1-continued
| 2,5-diaminoterephthalic acid derivatives | |
|---|---|
| 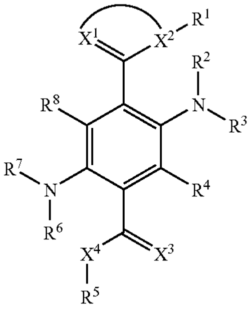<br>5.0 | |
| 5.1 | 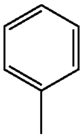 |
| 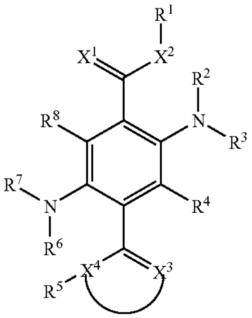<br>11.0 | |
| 11.1 | 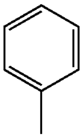 |
| Substance | $X^1$ | $X^2$ | $R^3$ |
|---|---|---|---|
| 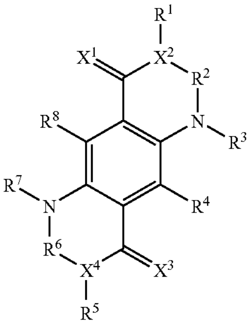<br>19.0 | | | |

TABLE 1-continued
| 2,5-diaminoterephthalic acid derivatives | | | |
| --- | --- | --- | --- |
| 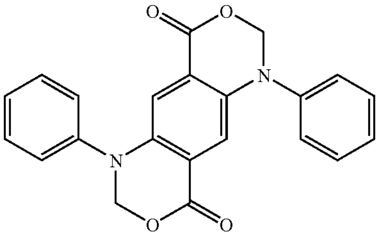 19.1 | O | O | 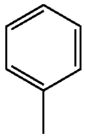 |
| 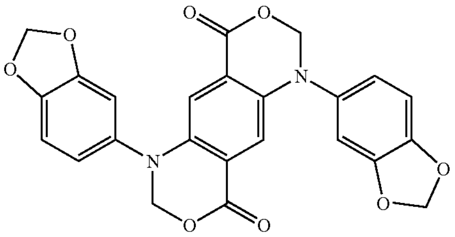 19.2 | O | O | 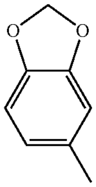 |
| 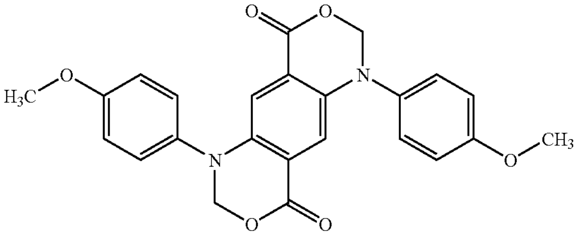 19.3 | O | O | 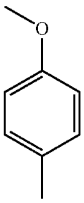 |
| 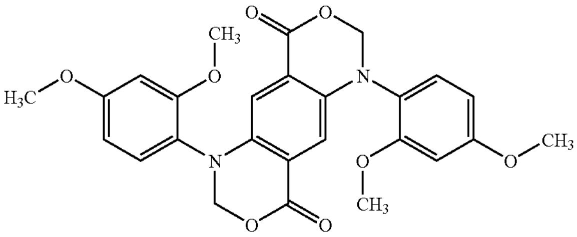 19.4 | O | O | 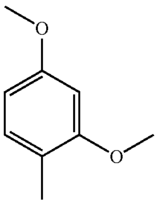 |
| 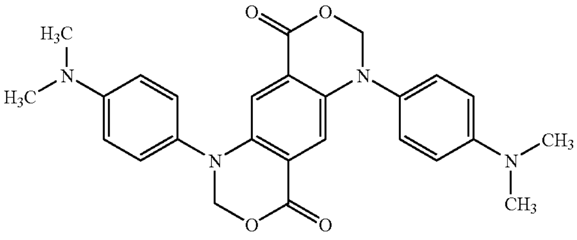 19.5 | O | O | 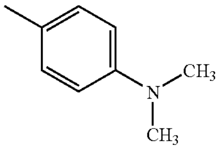 |

TABLE 1-continued
| 2,5-diaminoterephthalic acid derivatives | | | |
|---|---|---|---|
| 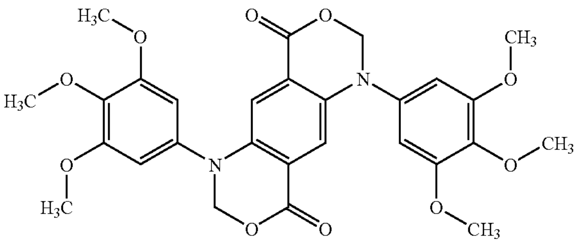 19.6 | O | O | 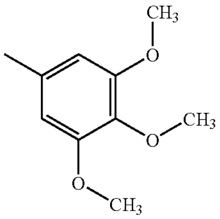 |
| 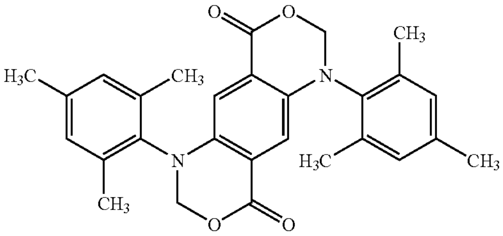 19.7 | O | O | 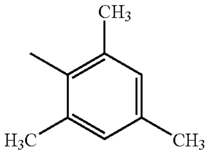 |
| 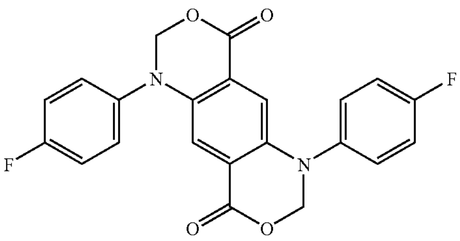 19.8 | O | O | 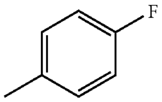 |
| 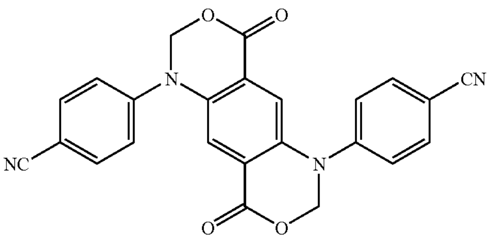 19.9 | O | O | 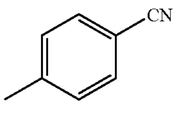 |
| 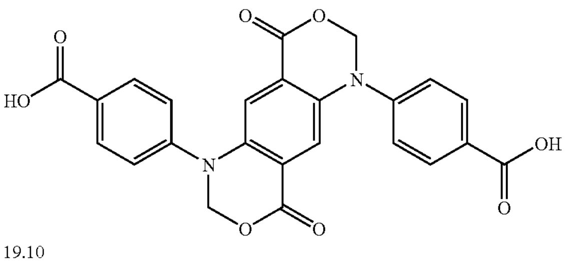 19.10 | O | O | 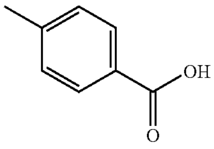 |

TABLE 1-continued
| | | | | |
|---|---|---|---|---|
| 2,5-diaminoterephthalic acid derivatives | | | | |
| 19.11 | 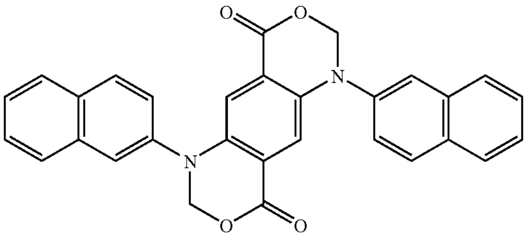 | O | O | 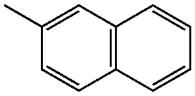 |
| 19.12 | 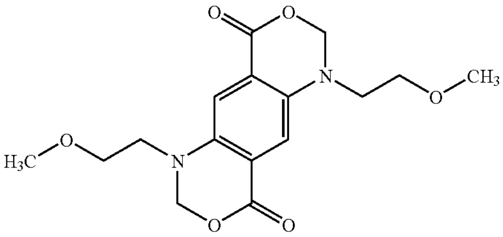 | O | O | 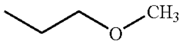 |
| 19.13 | | O | O | 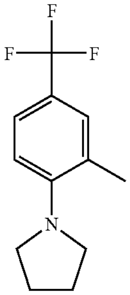 |
| 19.14 | | O | O | 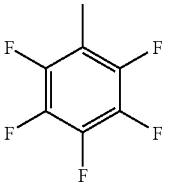 |
| 19.15 | | O | O | 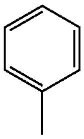 |
| 19.16 | | O | O | 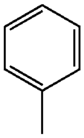 |
| 19.17 | | O | O | 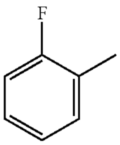 |

TABLE 1-continued
| 2,5-diaminoterephthalic acid derivatives | | | |
|---|---|---|---|
| 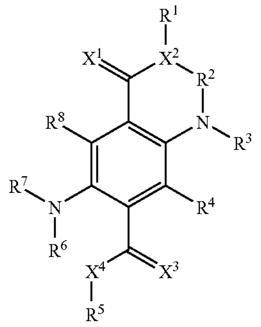 7.0 | | | |
| 7.1 | O | O | 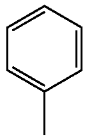 |
| 7.2 | O | O | 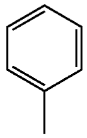 |
| 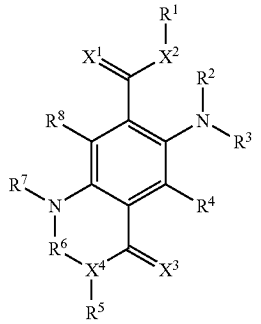 13.0 | | | |
| 13.1 | O | O | 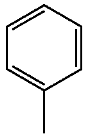 |
| 13.2 | O | O | 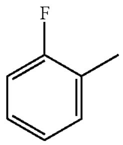 |

TABLE 1-continued
2,5-diaminoterephthalic acid derivatives
| Substance | $R^2$ | $R^1$ | $R^4$ | $X^4$ | $X^3$ | $R^8$ |
|---|---|---|---|---|---|---|
| 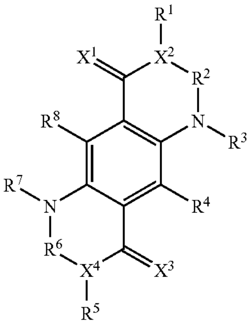 19.0 | | | | | | |
| 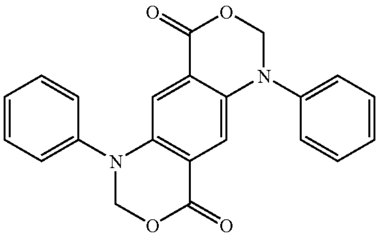 19.1 | —$CH_2$— | — | H | O | O | H |
| 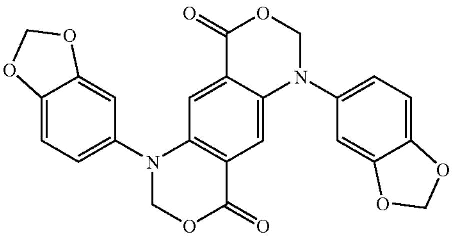 19.2 | —$CH_2$— | — | H | O | O | H |
| 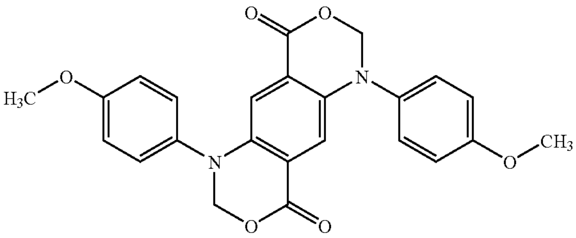 19.3 | —$CH_2$— | — | H | O | O | H |
| 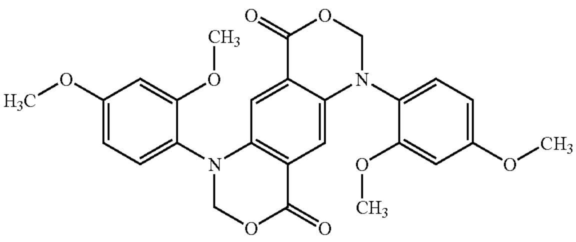 19.4 | —$CH_2$— | — | H | O | O | H |

TABLE 1-continued
2,5-diaminoterephthalic acid derivatives
| | | | | | | | |
|---|---|---|---|---|---|---|---|
| 19.5 | 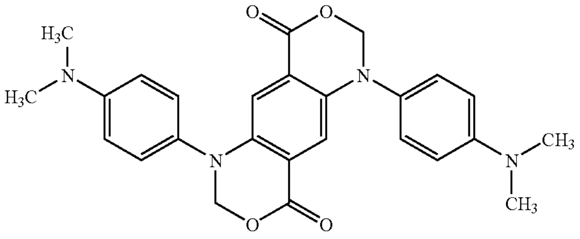 | —$CH_2$— | — | H | O | O | H |
| 19.6 | 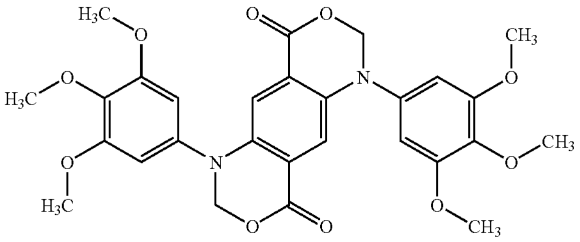 | —$CH_2$— | — | H | O | O | H |
| 19.7 | 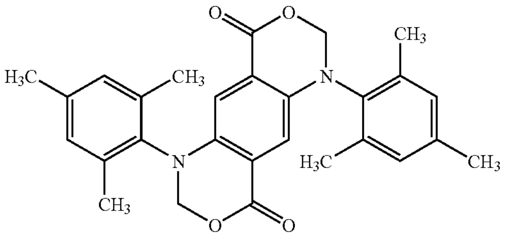 | —$CH_2$— | — | H | O | O | H |
| 19.8 | 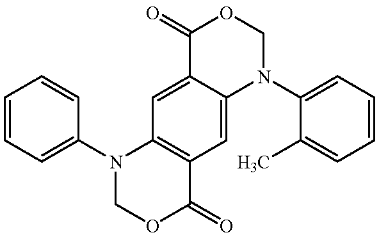 | —$CH_2$— | — | H | O | O | H |
| 19.9 | 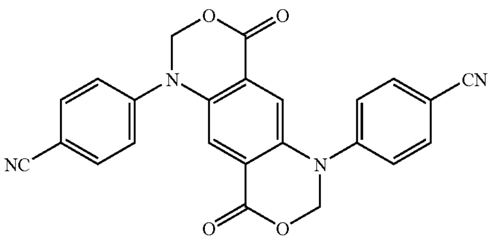 | —$CH_2$— | — | H | O | O | H |

TABLE 1-continued
2,5-diaminoterephthalic acid derivatives
| | | | | | | | |
|---|---|---|---|---|---|---|---|
| 19.10 | 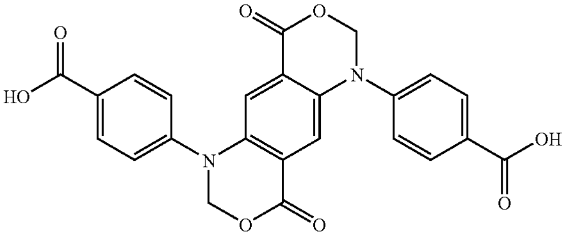 | —$CH_2$— | — | H | O | O | H |
| 19.11 | 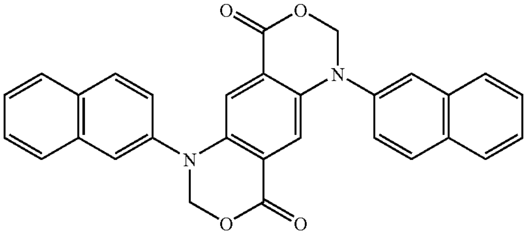 | —$CH_2$— | — | H | O | O | H |
| 19.12 | 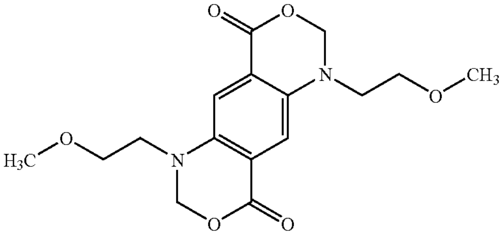 | —$CH_2$— | — | H | O | O | H |
| 19.13 | | —$CH_2$— | — | H | O | O | H |
| 19.14 | | —$CH_2$— | — | H | O | O | H |
| 19.15 | | —$CF_2$— | — | H | O | O | H |
| 19.16 | | 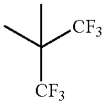 | — | H | O | O | H |
| 19.17 | | 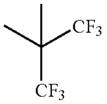 | — | H | O | O | H |
| | | | | | | |
|---|---|---|---|---|---|---|
| 7.0 | 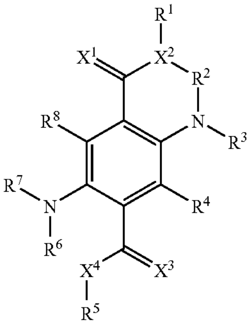 | | | | | |
| 7.1 | | —$CH_2$— | H | O | O | H |

TABLE 1-continued
2,5-diaminoterephthalic acid derivatives
| | | | | | | |
|---|---|---|---|---|---|---|
| 7.2 | | —$CH_2$— | H | N | O | H |
| 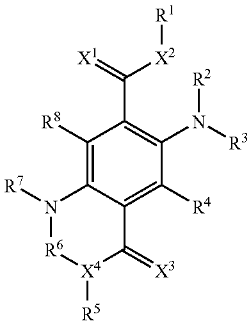 13.0 | | | | | | |
| 13.1 | 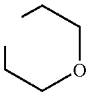 | —$CH_3$ | H | N | O | H |
| 13.2 | 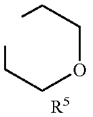 | —$CH_3$ | H | N | O | H |
| Substance | $R^6$ | $R^5$ | $R^7$ |
|---|---|---|---|
| 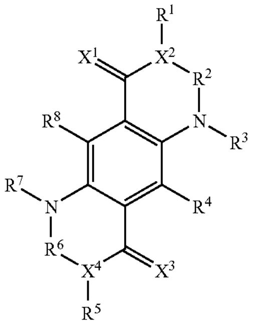 19.0 | | | |
| 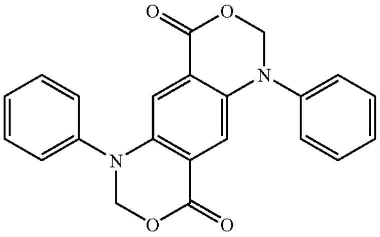 19.1 | —$CH_2$— | — | 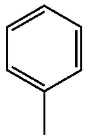 |
| 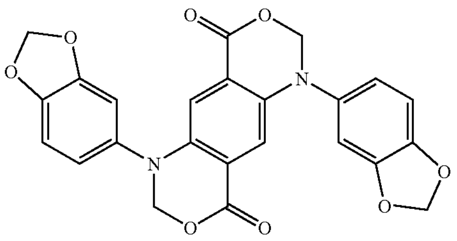 19.2 | —$CH_2$— | — | 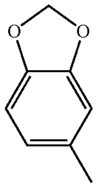 |

TABLE 1-continued
| 2,5-diaminoterephthalic acid derivatives | | | |
|---|---|---|---|
| 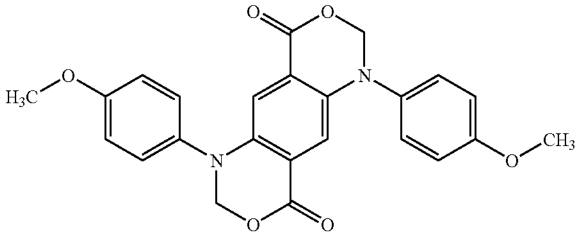 19.3 | $-CH_2-$ | — | 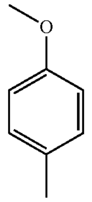 |
| 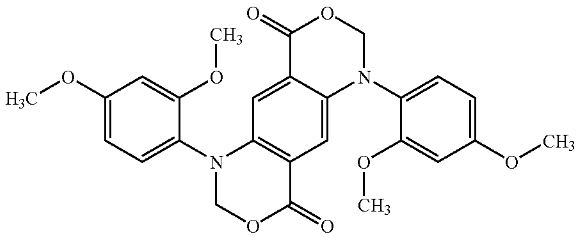 19.4 | $-CH_2-$ | — | 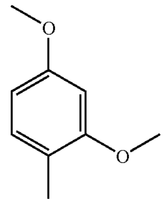 |
| 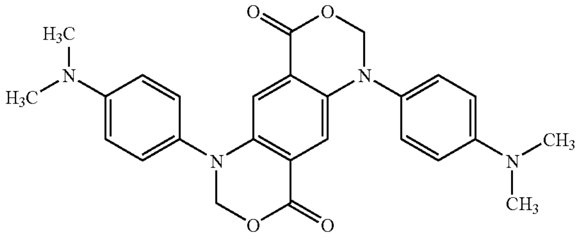 19.5 | $-CH_2-$ | — | 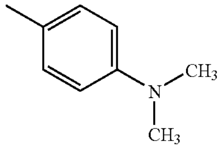 |
| 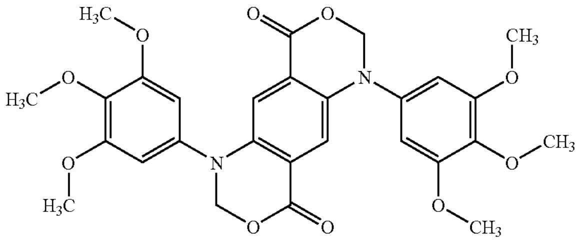 19.6 | $-CH_2-$ | — | 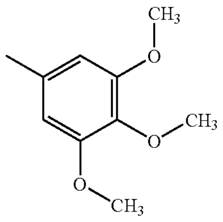 |
| 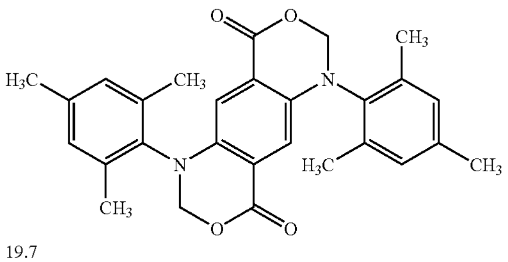 19.7 | $-CH_2-$ | — | 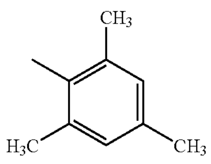 |

TABLE 1-continued
| 2,5-diaminoterephthalic acid derivatives | | | |
|---|---|---|---|
| 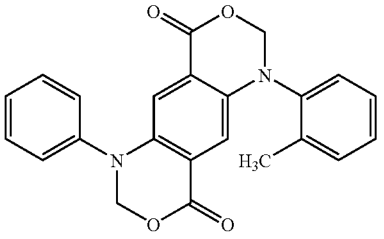 19.8 | —$CH_2$— | — | 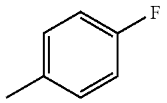 |
| 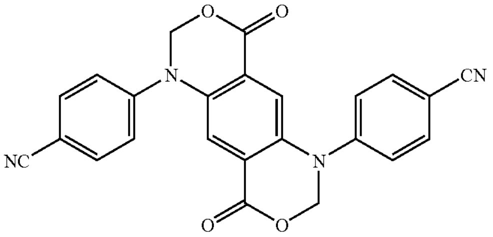 19.9 | —$CH_2$— | — | 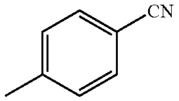 |
| 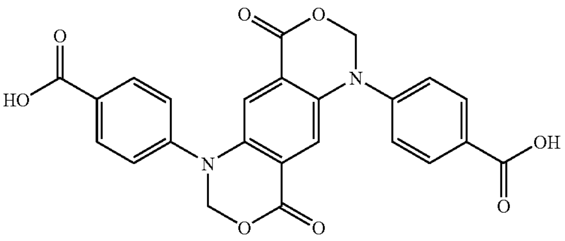 19.10 | —$CH_2$— | — | 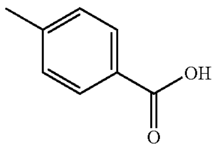 |
| 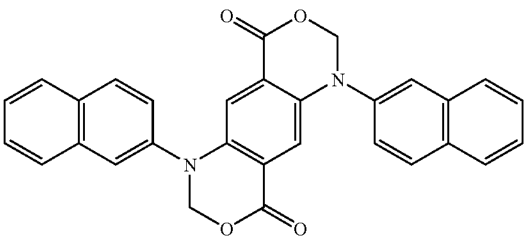 19.11 | —$CH_2$— | — | 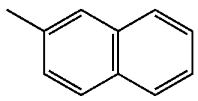 |
| 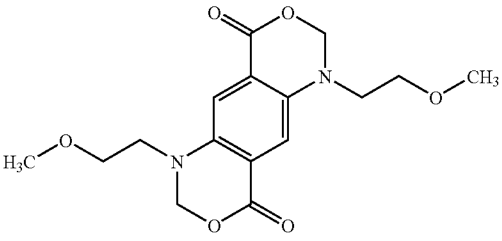 19.12 | —$CH_2$— | — | 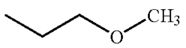 |

TABLE 1-continued
2,5-diaminoterephthalic acid derivatives
| | | | |
|---|---|---|---|
| 19.13 | $—CH_2—$ | — | 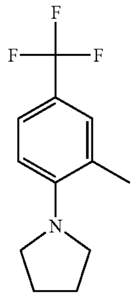 |
| 19.14 | $—CH_2—$ | — | 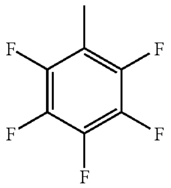 |
| 19.15 | $—CF_2—$ | — | 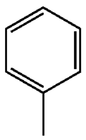 |
| 19.16 | 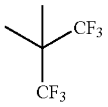 | — | 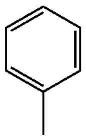 |
| 19.17 | 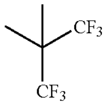 | — | 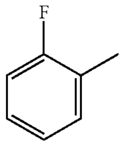 |
| 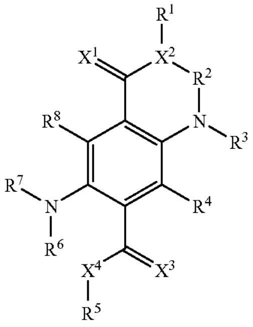 7.0 | | | |
| 7.1 | $—CH_3$ | $—CH_3$ | 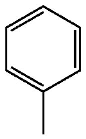 |

TABLE 1-continued
2,5-diaminoterephthalic acid derivatives
| | | | |
|---|---|---|---|
| 7.2 | 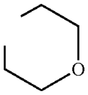 | —$CH_3$ | 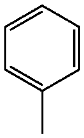 |
| 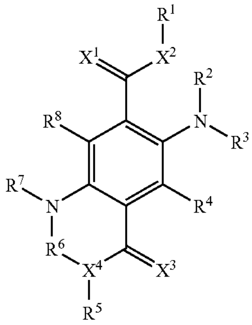 13.0 | | | |
| 13.1 | —$CH_2$— | 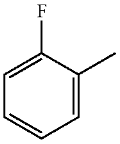 | |
| 13.2 | —$CH_2$— | 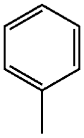 | |
| Substance | $X^1$ | $R^1$ | $X^2$ | $R^2$ | $R^3$ | $R^4$ | $R^5$ | $X^3$ | $X^4$ | $R^6$ | $R^7$ |
|---|---|---|---|---|---|---|---|---|---|---|---|
| 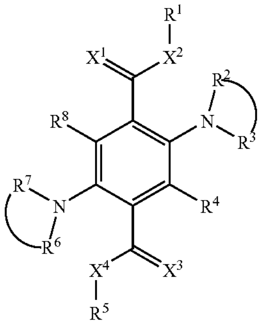 20.0 | | | | | | | | | | | |
| 20.1 | O | —$CH_3$ | O | 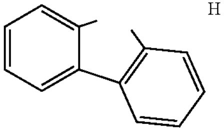 | | H | —$CH_3$ | O | O | 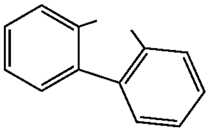 | |
| 20.2 | O | —$CH_3$ | O | 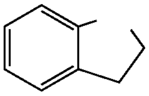 | | H | —$CH_3$ | O | O | 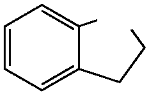 | |
| 20.3 | O | —$CH_3$ | O | 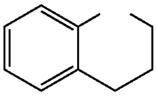 | | H | —$CH_3$ | O | O | 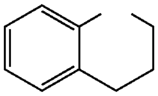 | |

TABLE 1-continued
2,5-diaminoterephthalic acid derivatives
| | | | | | | | | | | |
|---|---|---|---|---|---|---|---|---|---|---|
| 20.4 | O | —$CH_3$ | O | 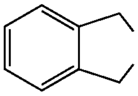 | H | —$CH_3$ | O | O | 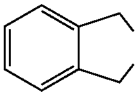 | |
| 8.0 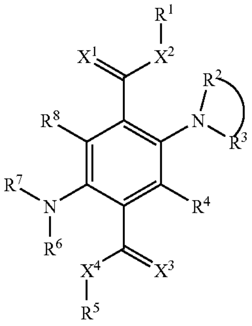 | | | | | | | | | | |
| 8.1 | O | —$CH_3$ | O | 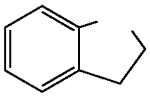 | H | —$CH_3$ | O | O | —$CH_3$ | 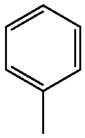 |
| 8.2 | O | —$CH_3$ | O | 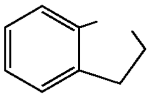 | H | —$CH_3$ | O | O | 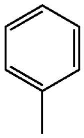 | 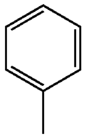 |
| 8.3 | O | —$CH_3$ | O | 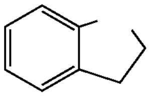 | 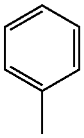 | —$CH_3$ | O | O | 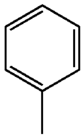 | 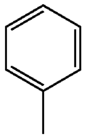 |
| Substance | $R^8$ |
|---|---|
| 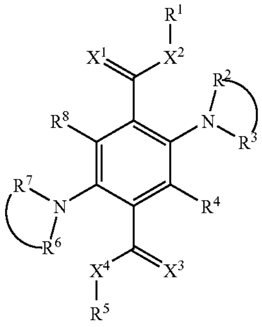 20.0 | |
| 20.1 | H |
| 20.2 | H |
| 20.3 | H |
| 20.4 | H |

TABLE 1-continued
2,5-diaminoterephthalic acid derivatives
| | |
|---|---|
| 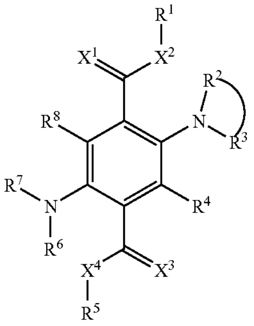 8.0 | |
| 8.1 | H |
| 8.2 | H |
| 8.3 | H |
| Substance | $X^1$ | $X^2$ | $R^3$ | $R^2$ | $R^1$ | $R^4$ | $X^4$ | $X^3$ | $R^8$ | $R^6$ | $R^5$ | $R^7$ |
|---|---|---|---|---|---|---|---|---|---|---|---|---|
| 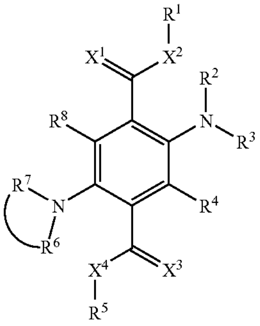 14.0 | | | | | | | | | | | | |
| 14.1 | O | —$CH_3$ | O | —$CH_3$ | 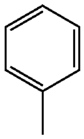 | 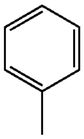 | —$CH_3$ | O | O | 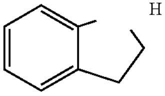 | | H |
| 14.2 | O | —$CH_3$ | O | 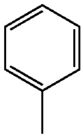 | 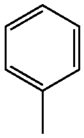 | 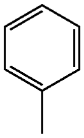 | —$CH_3$ | O | O | 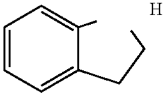 | | H |
| Substance | $R^1$ | $X^2$ | $X^1$ | $R^4$ | $R^3$ | $R^2$ | $R^5$ | $X^4$ | $X^3$ |
|---|---|---|---|---|---|---|---|---|---|
| 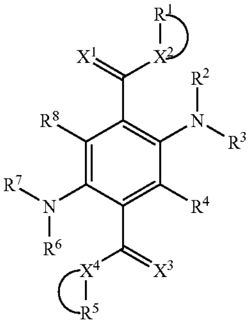 18.0 | | | | | | | | | |

TABLE 1-continued
2,5-diaminoterephthalic acid derivatives
| | | | | | | | | |
|---|---|---|---|---|---|---|---|---|
| 18.1 | 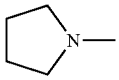 | O | H | 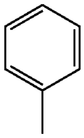 | —$CH_3$ | 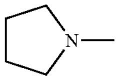 | | O |
| 18.2 | 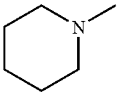 | O | H | 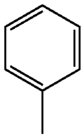 | —$CH_3$ | 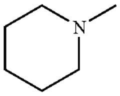 | | O |
| 18.3 | 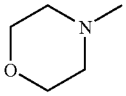 | O | H | 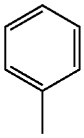 | —$CH_3$ | 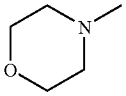 | | O |
| 18.4 | 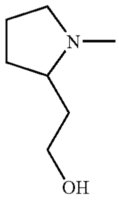 | O | H | 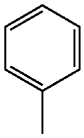 | —$CH_3$ | 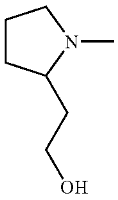 | | O |
| 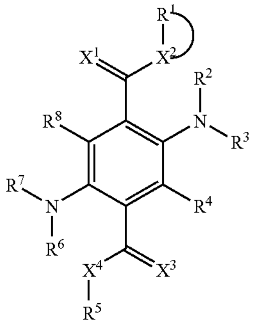 6.0 | | | | | | | | |
| 6.1 | 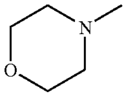 | O | H | 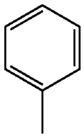 | —$CH_3$ | —$CH_3$ | O | O |
| 6.2 | 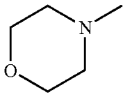 | O | H | 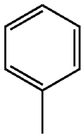 | 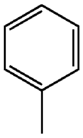 | —$CH_3$ | O | O |

TABLE 1-continued
| 2,5-diaminoterephthalic acid derivatives | | | | | | | | |
|---|---|---|---|---|---|---|---|---|
| 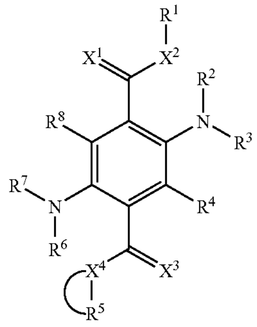 12.0 | | | | | | | | |
| 12.1 | —$CH_3$ | O | O | H | 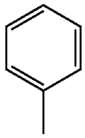 | —$CH_3$ | 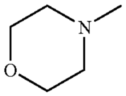 | O |
| 12.2 | —$CH_3$ | O | O | H | 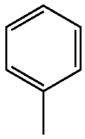 | 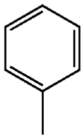 | 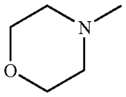 | O |
| 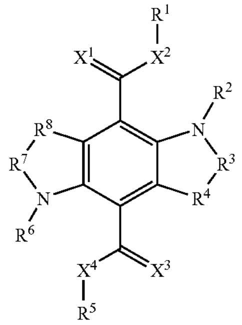 21.0 | | | | | | | | |
| 21.1 | —$CH_3$ | O | O | 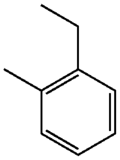 | 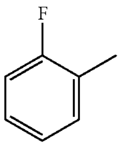 | —$CH_3$ | O | O |
| 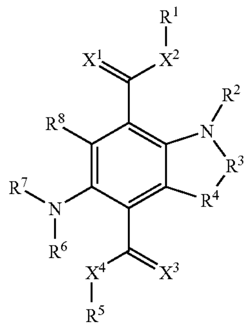 9.0 | | | | | | | | |

TABLE 1-continued
| 2,5-diaminoterephthalic acid derivatives | | | | | | | | |
|---|---|---|---|---|---|---|---|---|
| 9.1 | —$CH_3$ | O | O | 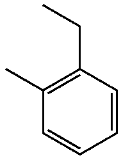 | 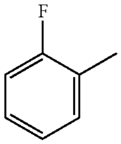 | —$CH_3$ | O | O |
| 9.2 | —$CH_3$ | O | O | 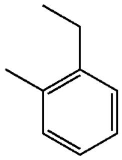 | 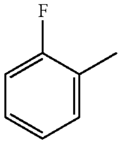 | 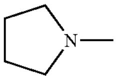 | | O |
| 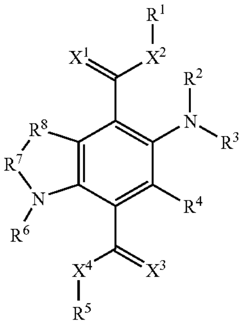 15.0 | | | | | | | | |
| 15.1 | 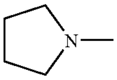 | | O | H | 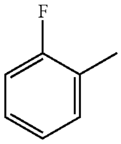 | —$CH_3$ | O | O |
| | Substance | $R^8$ | $R^7$ | $R^6$ |
|---|---|---|---|---|
| | 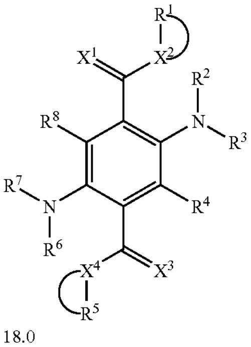 18.0 | | | |
| | 18.1 | H | 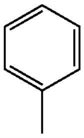 | —$CH_3$ |
| | 18.2 | H | 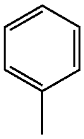 | —$CH_3$ |

TABLE 1-continued
| 2,5-diaminoterephthalic acid derivatives | | | |
|---|---|---|---|
| 18.3 | H | 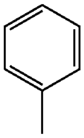 | —$CH_3$ |
| 18.4 | H | 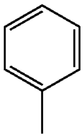 | —$CH_3$ |
| 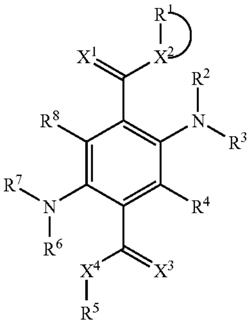 6.0 | | | |
| 6.1 | H | 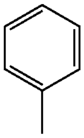 | —$CH_3$ |
| 6.2 | H | 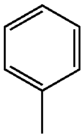 | 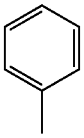 |
| 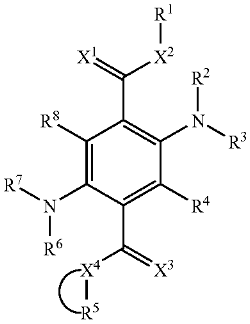 12.0 | | | |
| 12.1 | H | 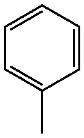 | H |

TABLE 1-continued
| 2,5-diaminoterephthalic acid derivatives | | | |
|---|---|---|---|
| 12.2 | H | 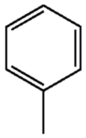 | —$CH_3$ |
| 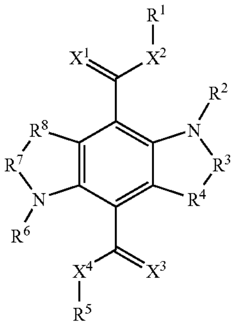 21.0 | | | |
| 21.1 | | 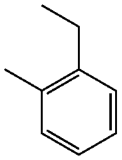 | 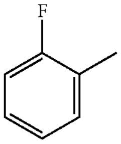 |
| 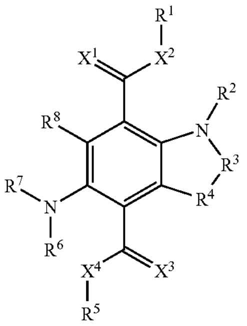 9.0 | | | |
| 9.1 | H | 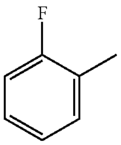 | 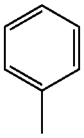 |
| 9.2 | H | 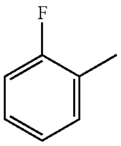 | 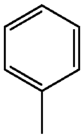 |

TABLE 1-continued
| 2,5-diaminoterephthalic acid derivatives | | |
|---|---|---|
| 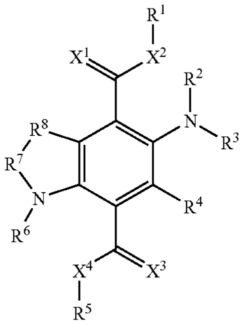<br>15.0 | | |
| 15.1 | 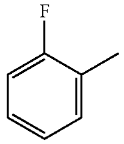 | 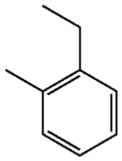 |
| Substance | $X^2$ | $R^2$ | $R^3$ | $R^4$ | $X^3$ | $R^5$ | $R^6$ | $X^4$ | $R^7$ |
|---|---|---|---|---|---|---|---|---|---|
| 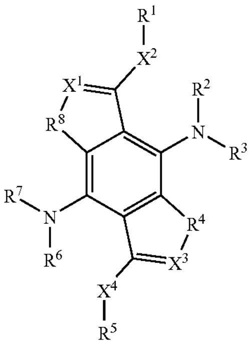<br>22.0 | | | | | | | | | |
| 22.1 | O | $—CH_3$ | 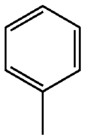 | 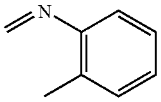 | | $—CH_3$ | $—CH_3$ | O | 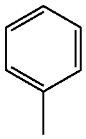 |
| 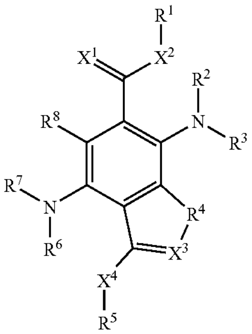<br>10.0 | | | | | | | | | |

TABLE 1-continued
2,5-diaminoterephthalic acid derivatives
| | | | | | | | | | |
|---|---|---|---|---|---|---|---|---|---|
| 10.1 | O | —$CH_3$ | 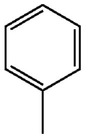 | 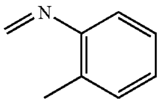 | | —$CH_3$ | —$CH_3$ | O | 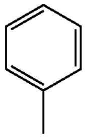 |
| 10.2 | O | | 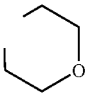 | 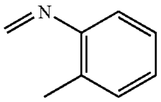 | | —$CH_3$ | —$CH_3$ | O | |
| 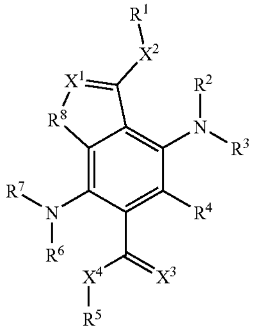 16.0 | | | | | | | | | |
| 16.1 | O | | 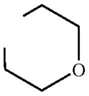 | H | O | —$CH_3$ | —$CH_3$ | O | 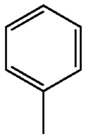 |
| Substance | $R^8$ | $X^1$ | $R^1$ |
|---|---|---|---|
| 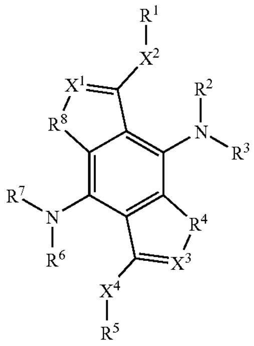 22.0 | | | |
| 22.1 | 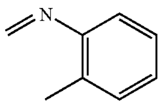 | | —$CH_3$ |

TABLE 1-continued
| 2,5-diaminoterephthalic acid derivatives | | | |
|---|---|---|---|
| 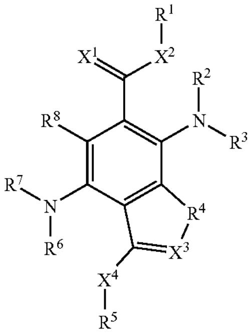 10.0 | | | |
| 10.1 | H | O | —$CH_3$ |
| 10.2 | H | O | —$CH_3$ |
| 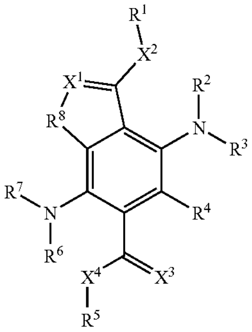 16.0 | | | |
| 16.1 | 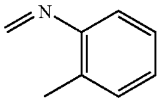 | | —$CH_3$ |
TABLE 2
| Substance | $X^1$ | $X^2$ | $R^3$ | $R^1$ | $R^2$ |
|---|---|---|---|---|---|
| 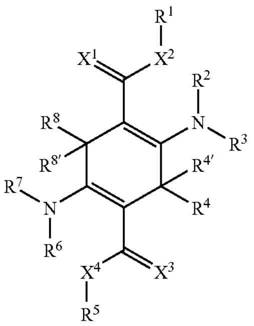 2.0 | | | | | |

TABLE 2-continued
| 2,5-diamino-3,6-dihydroterephthalic acid derivatives | | | | | |
|---|---|---|---|---|---|
| 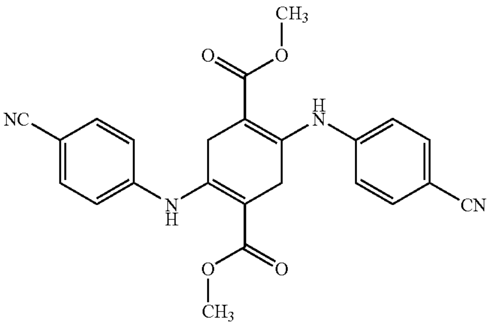 2.1 | O | O | 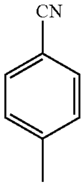 | —$CH_3$ | H |
| 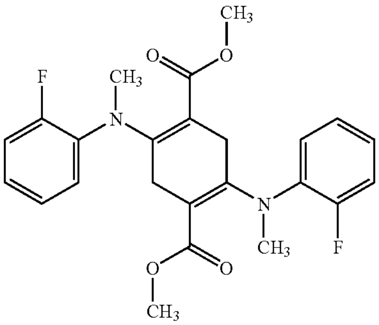 2.2 | O | O | 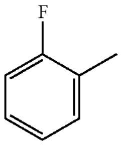 | —$CH_3$ | —$CH_3$ |
| 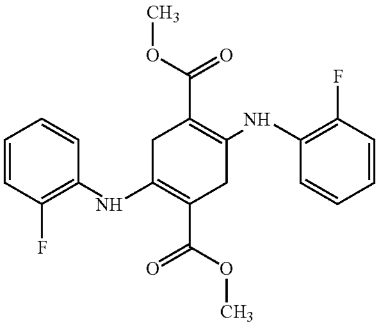 2.3 | O | O | 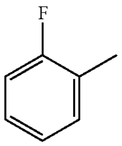 | —$CH_3$ | H |
| 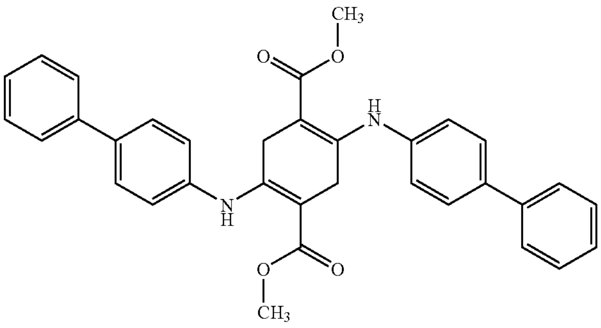 2.4 | O | O | 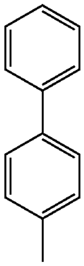 | —$CH_3$ | H |

TABLE 2-continued
2,5-diamino-3,6-dihydroterephthalic acid derivatives
| | | | | | |
|---|---|---|---|---|---|
| 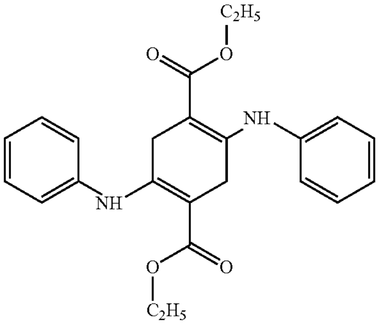 2.5 | O | O | 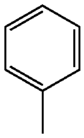 | $—C_2H_5$ | H |
| 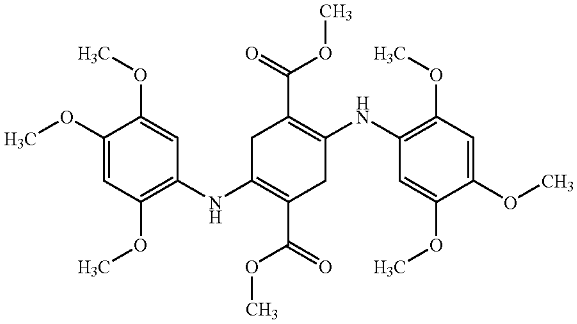 2.6 | O | O | 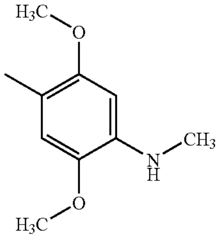 | $—CH_3$ | H |
| 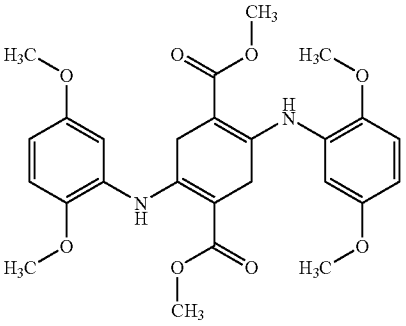 2.7 | O | O | 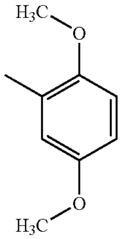 | $—CH_3$ | H |
| 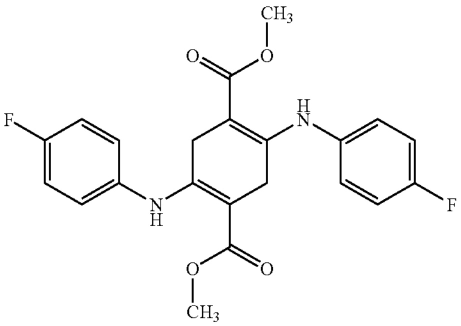 2.8 | O | O | 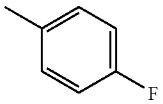 | $—CH_3$ | H |

TABLE 2-continued
| 2,5-diamino-3,6-dihydroterephthalic acid derivatives | | | | | |
|---|---|---|---|---|---|
| 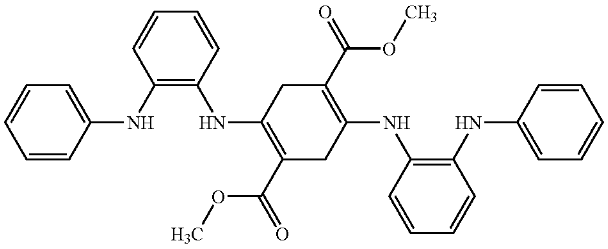 2.9 | O | O | 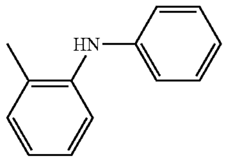 | —$CH_3$ | H |
| 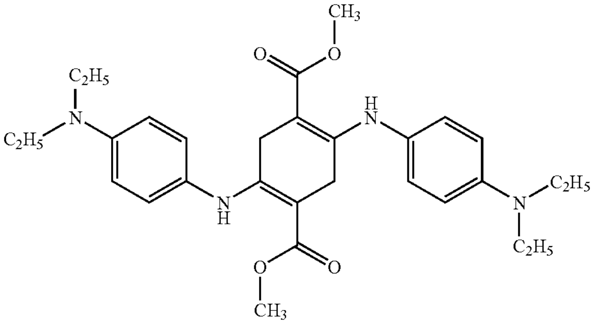 2.10 | O | O | 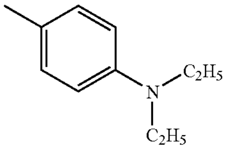 | —$CH_3$ | H |
| 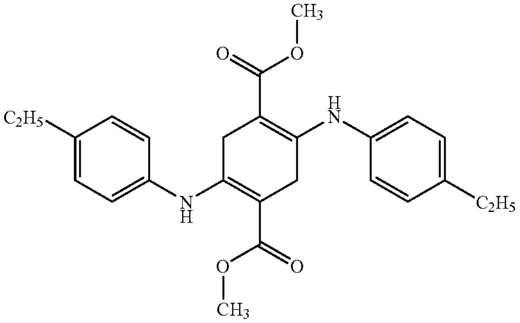 2.11 | O | O | 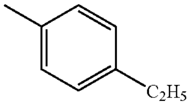 | —$CH_3$ | H |
| 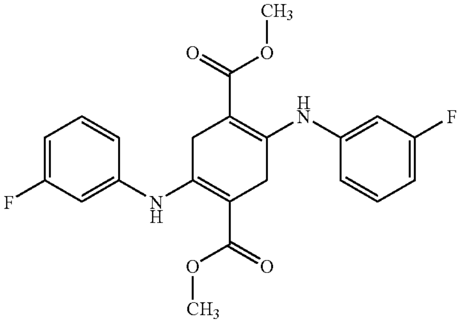 2.12 | O | O | 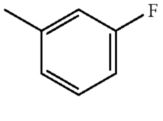 | —$CH_3$ | H |

TABLE 2-continued
| 2,5-diamino-3,6-dihydroterephthalic acid derivatives | | | | | |
|---|---|---|---|---|---|
| 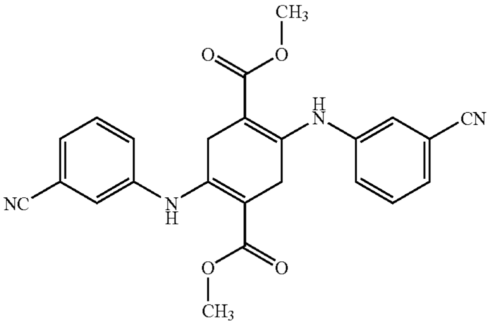 2.13 | O | O | 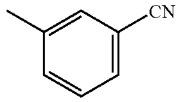 | —$CH_3$ | H |
| 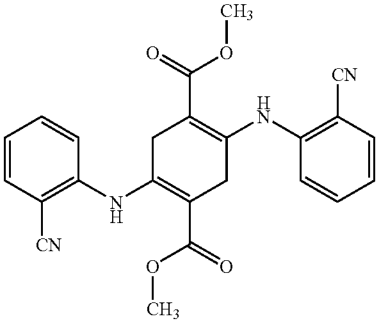 2.14 | O | O | 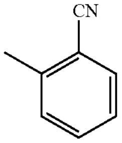 | —$CH_3$ | H |
| 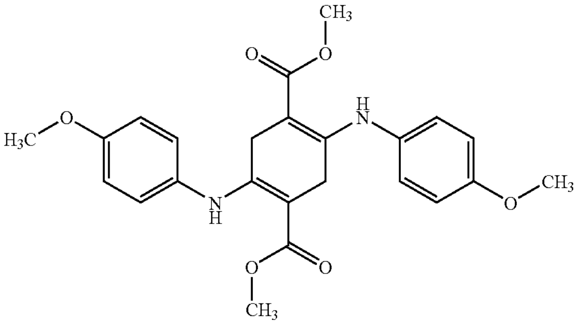 2.15 | O | O | 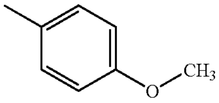 | —$CH_3$ | H |
| 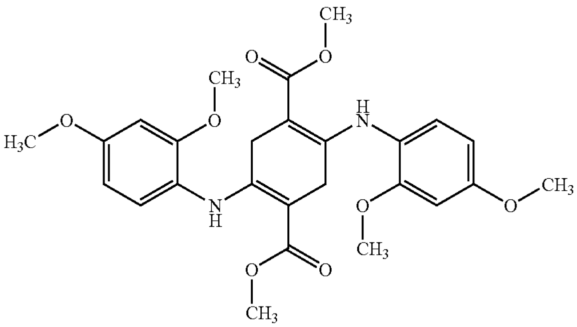 2.16 | O | O | 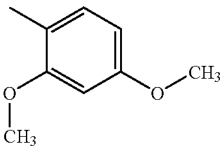 | —$CH_3$ | H |

TABLE 2-continued
| 2,5-diamino-3,6-dihydroterephthalic acid derivatives | | | | | |
|---|---|---|---|---|---|
| 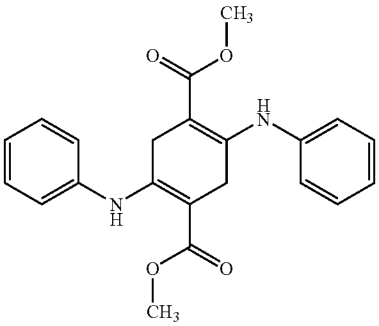<br>2.17 | O | O | 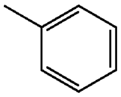 | —$CH_3$ | H |
| 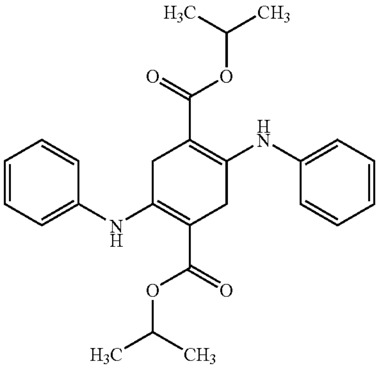<br>2.18 | O | O | 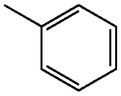 | —$CH_3$ | H |
| 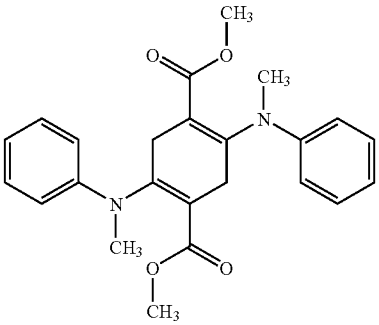<br>2.19 | O | O | 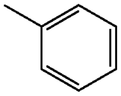 | —$CH_3$ | —$CH_3$ |
| 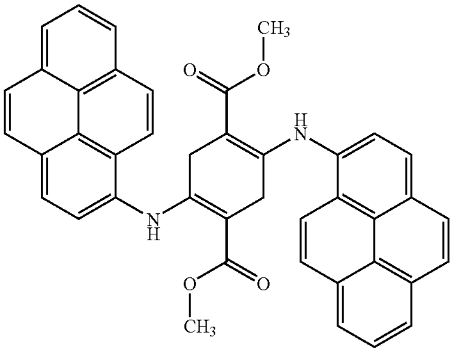<br>2.20 | O | O | 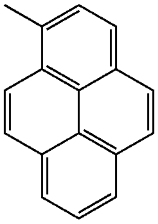 | —$CH_3$ | H |

TABLE 2-continued
2,5-diamino-3,6-dihydroterephthalic acid derivatives
| | | | | | |
|---|---|---|---|---|---|
| 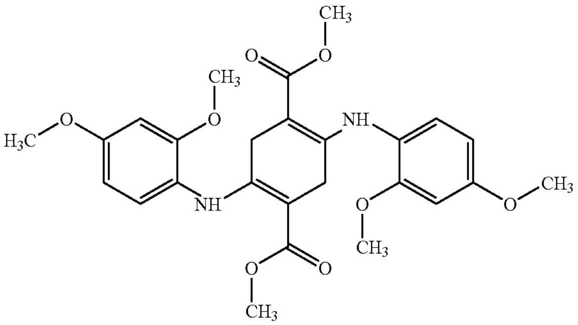 2.21 | O | O | 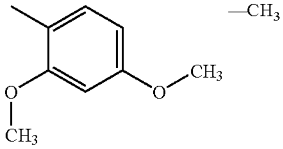 | $—CH_3$ | H |
| 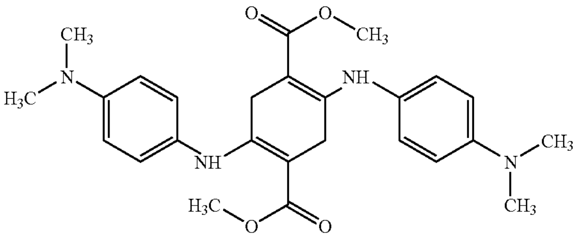 2.22 | O | O | 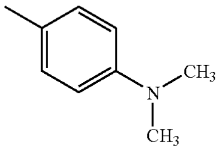 | $—CH_3$ | H |
| 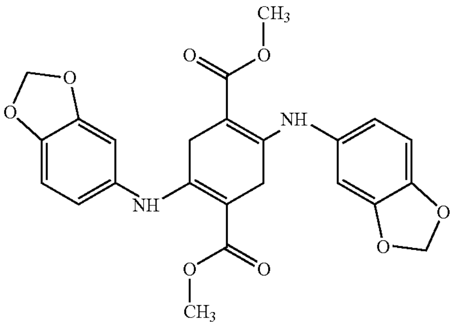 2.24 | O | O | 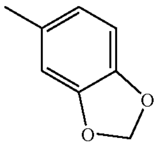 | $—CH_3$ | H |
| 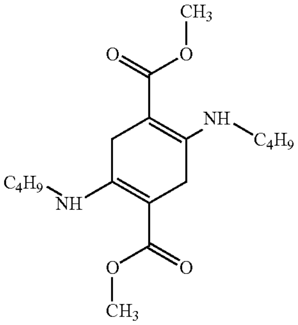 2.25 | O | O | $—C_4H_9$ | $—CH_3$ | H |
| 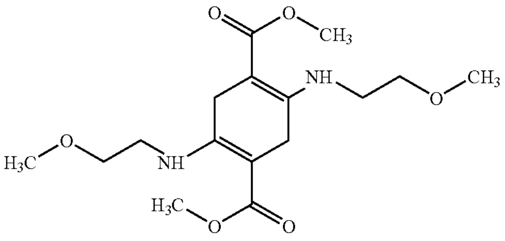 2.26 | O | O | 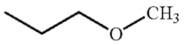 | $—CH_3$ | H |

TABLE 2-continued
2,5-diamino-3,6-dihydroterephthalic acid derivatives
| | | | | | |
|---|---|---|---|---|---|
| 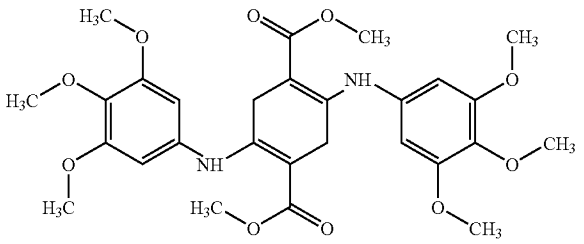<br>2.27 | O | O | 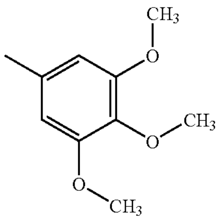 | —$CH_3$ | H |
| 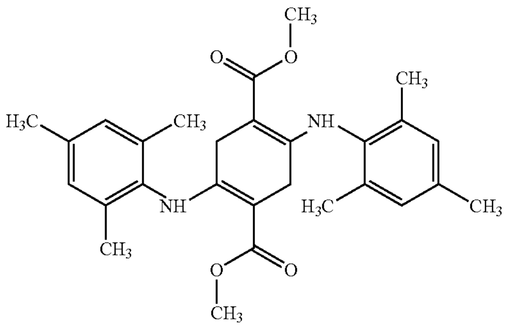<br>2.28 | O | O | 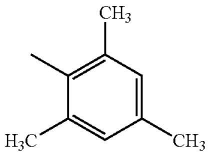 | —$CH_3$ | H |
| 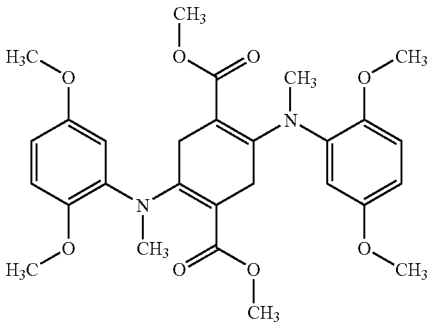<br>2.29 | O | O | 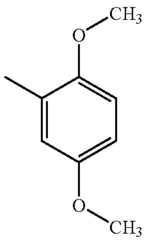 | —$CH_3$ | —$CH_3$ |
| 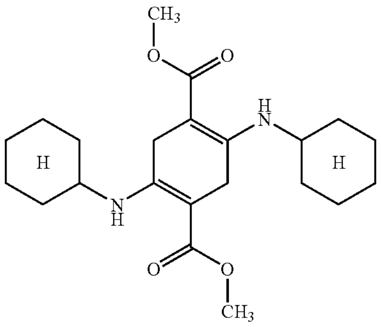<br>2.30 | O | O | 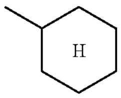 | —$CH_3$ | H |
| 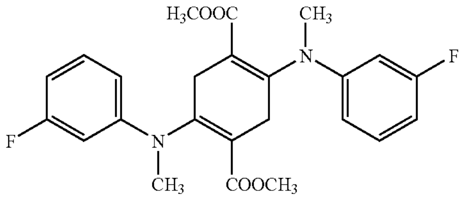<br>2.31 | O | O | 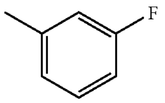 | —$CH_3$ | —$CH_3$ |

TABLE 2-continued
2,5-diamino-3,6-dihydroterephthalic acid derivatives
| | | | | | |
|---|---|---|---|---|---|
| 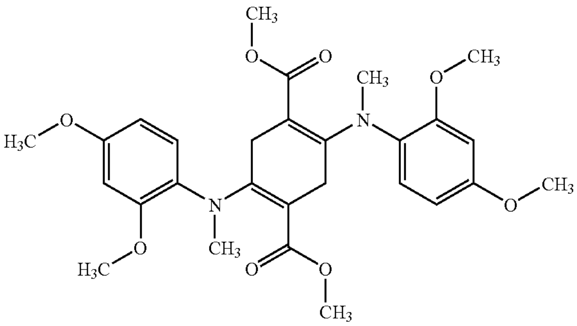 2.32 | O | O | 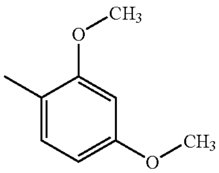 | —$CH_3$ | —$CH_3$ |
| 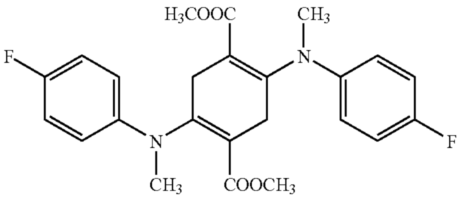 2.33 | O | O | 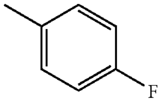 | —$CH_3$ | —$CH_3$ |
| 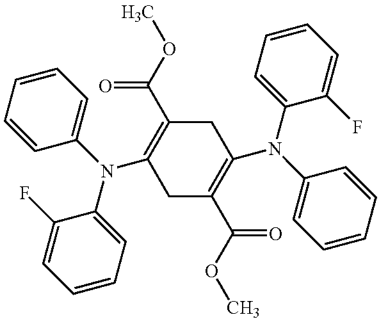 2.34 | O | O | 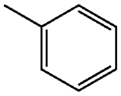 | —$CH_3$ | 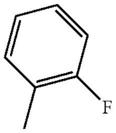 |
| 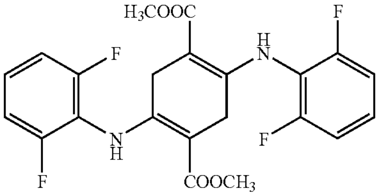 2.35 | O | O | 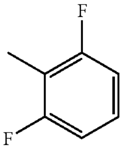 | —$CH_3$ | H |
| 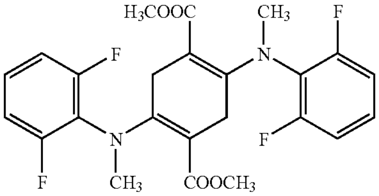 2.36 | O | O | 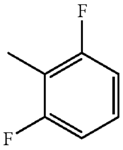 | —$CH_3$ | —$CH_3$ |

TABLE 2-continued
2,5-diamino-3,6-dihydroterephthalic acid derivatives
| | | | | | |
|---|---|---|---|---|---|
| 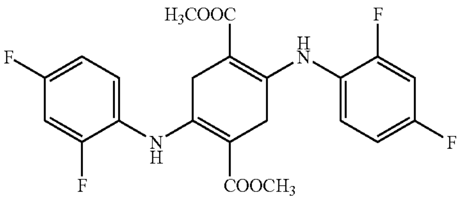 2.37 | O | O | 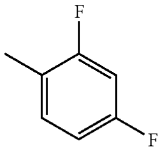 | —$CH_3$ | H |
| 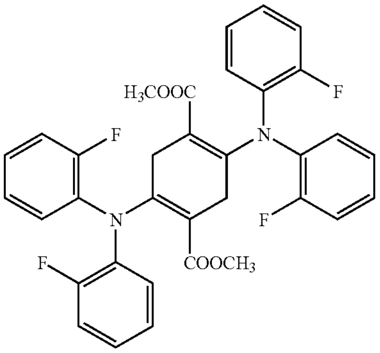 2.38 | O | O | 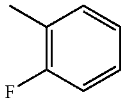 | —$CH_3$ | 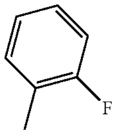 |
| 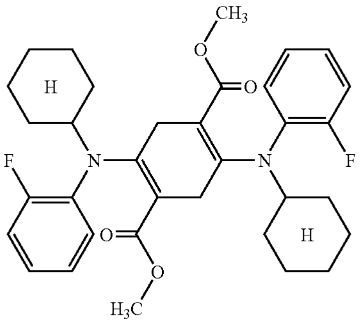 2.39 | O | O | 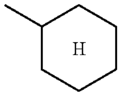 | —$CH_3$ | 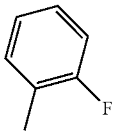 |
| 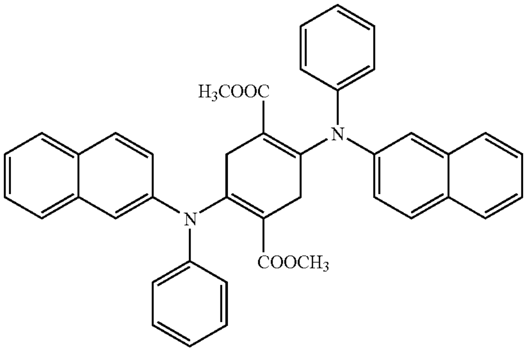 2.40 | O | O | 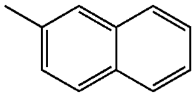 | —$CH_3$ | 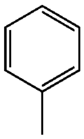 |

TABLE 2-continued
| 2,5-diamino-3,6-dihydroterephthalic acid derivatives | | | | | |
|---|---|---|---|---|---|
| 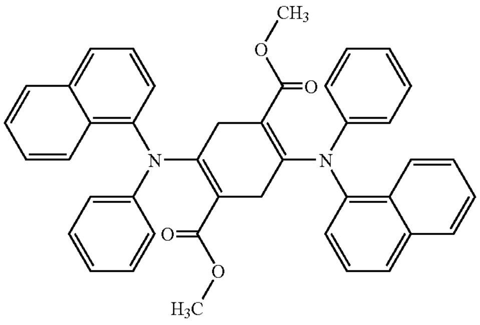 2.41 | O | O | 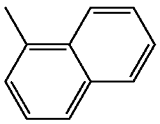 | —$CH_3$ | 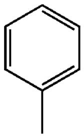 |
| 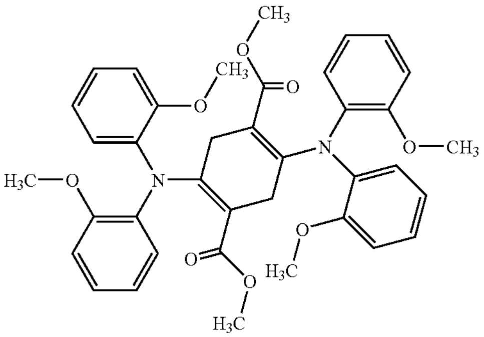 2.42 | O | O | 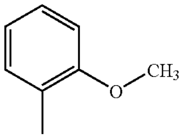 | —$CH_3$ | 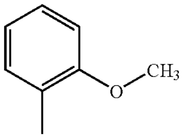 |
| 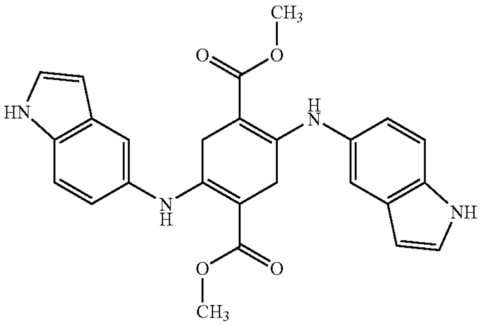 2.43 | O | O | 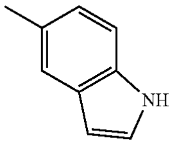 | —$CH_3$ | H |
| 2.44 | O | O | 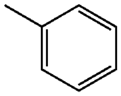 | —$CH_3$ | —$CH_3$ |
| 2.45 | O | O | 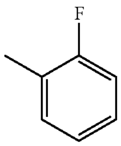 | —$CH_3$ | —$CH_3$ |
| 2.46 | O | O | 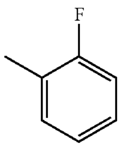 | —$CH_3$ | 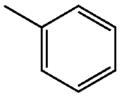 |

TABLE 2-continued
| 2,5-diamino-3,6-dihydroterephthalic acid derivatives | | | | | |
|---|---|---|---|---|---|
| 2.47 | O | O | 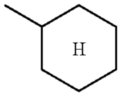 | —$CH_3$ | 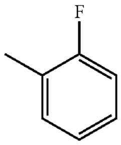 |
| 2.48 | O | O | 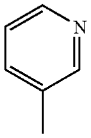 | —$CH_3$ | —$CH_3$ |
| 2.49 | O | O | 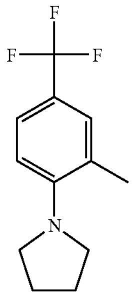 | —$CH_3$ | —$CH_3$ |
| 2.50 | O | O | 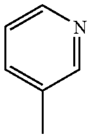 | —$CH_3$ | —$CH_3$ |
| 2.51 | O | O | 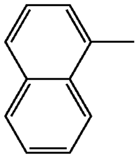 | —$CH_3$ | —$CH_3$ |
| 2.52 | O | O | 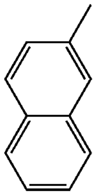 | —$CH_3$ | —$CH_3$ |
| 2.53 | O | O | 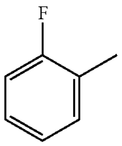 | —$CH_3$ | —$CH_3$ |
| 2.54 | O | O | 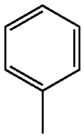 | —$CH_3$ | —$CF_3$ |

TABLE 2-continued
| 2,5-diamino-3,6-dihydroterephthalic acid derivatives | | | | | |
|---|---|---|---|---|---|
| 2.55 | O | O | 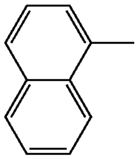 | —$CH_3$ | —$CF_3$ |
| 2.56 | O | O | 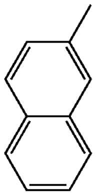 | —$CH_3$ | —$CF_3$ |
| 2.57 | O | O | 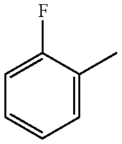 | —$CH_3$ | —$CF_3$ |
| 2.58 | O | O | 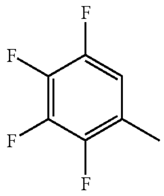 | —$CH_3$ | —$CF_3$ |
| 2.59 | O | O | 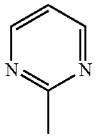 | —$CH_3$ | —$CF_3$ |
| 2.60 | O | O | 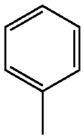 | —$CH_3$ | 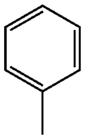 |
| 2.61 | O | O | 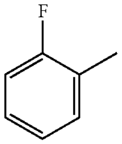 | —$CH_3$ | 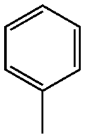 |
| 2.62 | O | O | 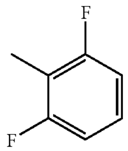 | —$CH_3$ | 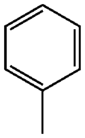 |
| 2.63 | O | O | 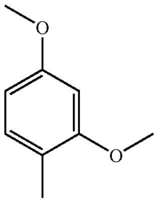 | —$CH_3$ | 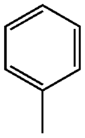 |

TABLE 2-continued
| 2,5-diamino-3,6-dihydroterephthalic acid derivatives | | | | | |
|---|---|---|---|---|---|
| 2.64 | O | O | 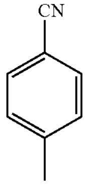 | —$CH_3$ | 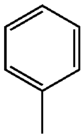 |
| 2.65 | O | O | 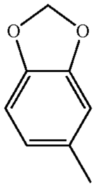 | —$CH_3$ | 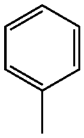 |
| 2.66 | O | O | 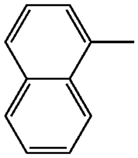 | —$CH_3$ | 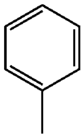 |
| 2.67 | O | O | 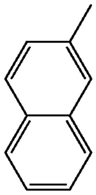 | —$CH_3$ | 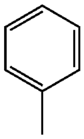 |
| 2.68 | O | O | 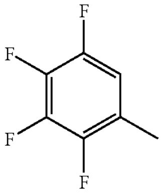 | —$CH_3$ | 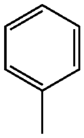 |
| 2.69 | O | O | 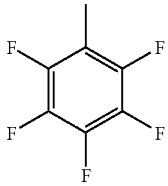 | —$CH_3$ | —$CH_3$ |
| 2.70 | O | O | 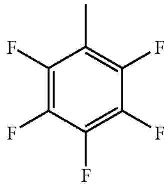 | —$CH_3$ | 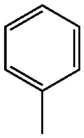 |
| 2.71 | O | O | 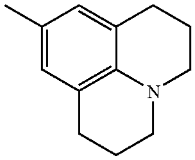 | —$CH_3$ | 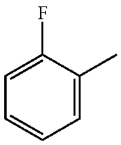 |

TABLE 2-continued
2,5-diamino-3,6-dihydroterephthalic acid derivatives
| | | | | | |
|---|---|---|---|---|---|
| 2.72 | O | O | 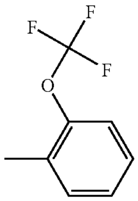 | —$CH_3$ | 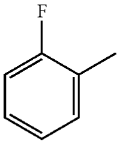 |
| 2.73 | | | 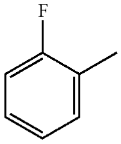 | —$CH_3$ | 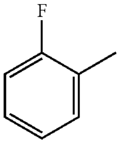 |
| 2.74 | O | N | 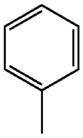 | 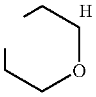 | |
| 2.75 | O | N | 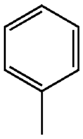 | 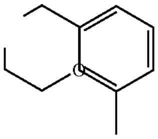 | |
| 2.76 | O | O | 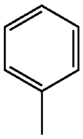 | —$CH_3$ | —$CH_3$ |
| 2.78 | O | O | 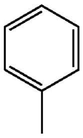 | —$CH_3$ | 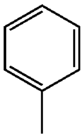 |
| 2.79 | O | O | 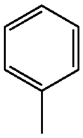 | —$CH_3$ | 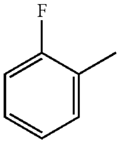 |
| Substance | $R^{4'}$ | $R^{4'}$ | $X^4$ | $X^3$ | $R^8$ | $R^{8'}$ | $R^5$ |
|---|---|---|---|---|---|---|---|
| 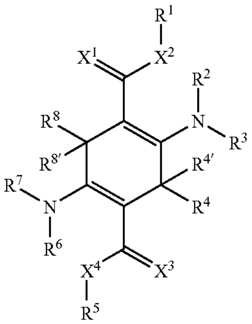 2.0 | | | | | | | |

TABLE 2-continued
| 2,5-diamino-3,6-dihydroterephthalic acid derivatives | | | | | | | |
|---|---|---|---|---|---|---|---|
| 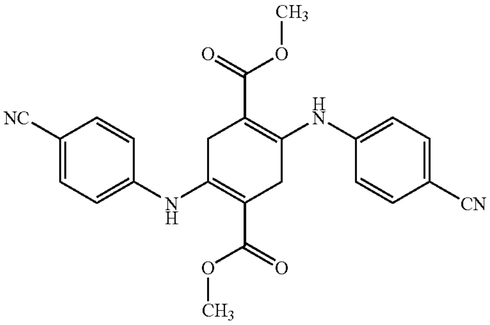 2.1 | H | H | O | O | H | H | —$CH_3$ |
| 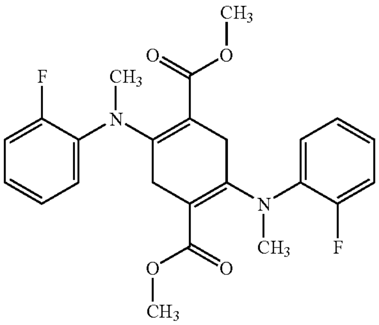 2.2 | H | H | O | O | H | H | —$CH_3$ |
| 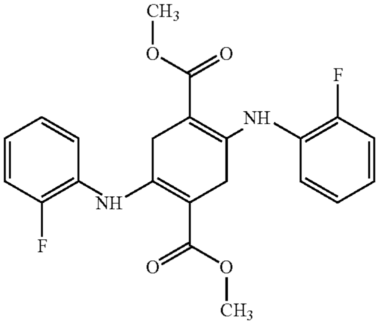 2.3 | H | H | O | O | H | H | —$CH_3$ |
| 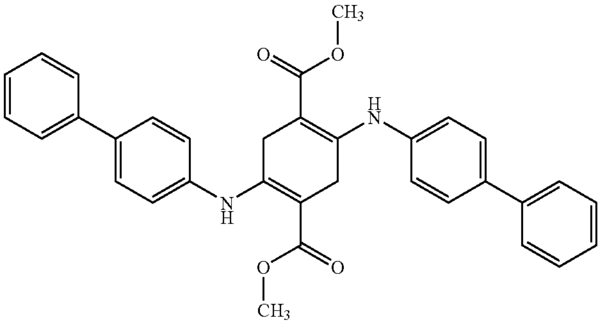 2.4 | H | H | O | O | H | H | —$CH_3$ |

TABLE 2-continued
| 2,5-diamino-3,6-dihydroterephthalic acid derivatives | | | | | | | |
|---|---|---|---|---|---|---|---|
| 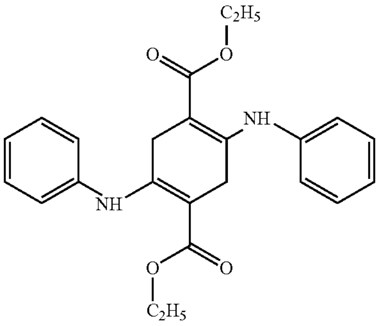 2.5 | H | H | O | O | H | H | —$CH_3$ |
| 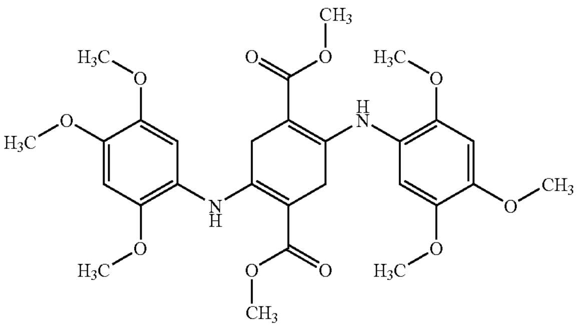 2.6 | H | H | O | O | H | H | —$CH_3$ |
| 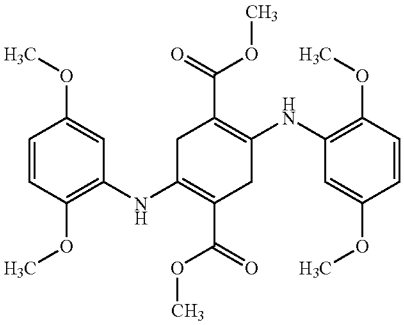 2.7 | H | H | O | O | H | H | —$CH_3$ |
| 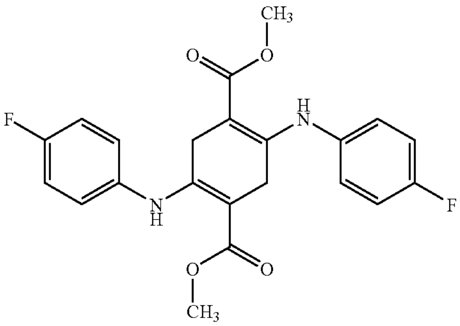 2.8 | H | H | O | O | H | H | —$CH_3$ |

TABLE 2-continued
2,5-diamino-3,6-dihydroterephthalic acid derivatives
| | | | | | | | | |
|---|---|---|---|---|---|---|---|---|
| 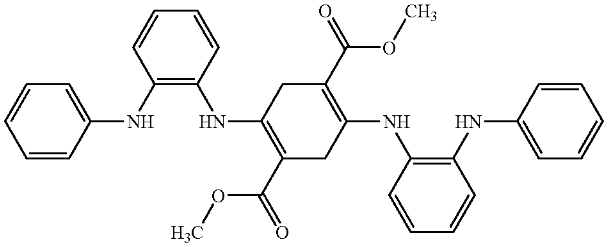 2.9 | H | H | O | O | H | H | —$CH_3$ |
| 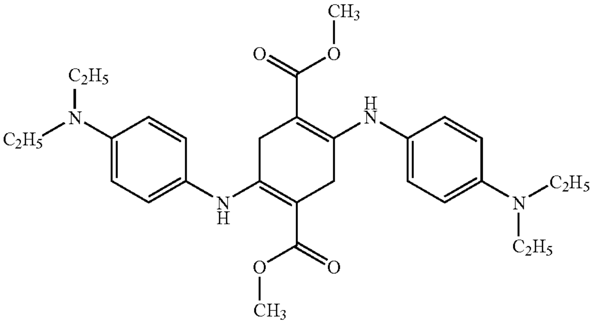 2.10 | H | H | O | O | H | H | —$CH_3$ |
| 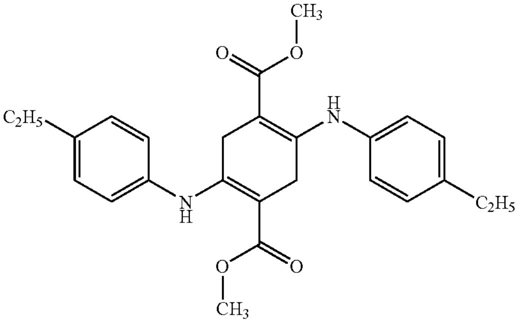 2.11 | H | H | O | O | H | H | —$CH_3$ |
| 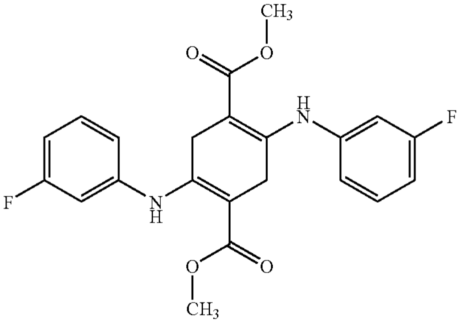 2.12 | H | H | O | O | H | H | —$CH_3$ |

TABLE 2-continued
| 2,5-diamino-3,6-dihydroterephthalic acid derivatives | | | | | | | |
|---|---|---|---|---|---|---|---|
| 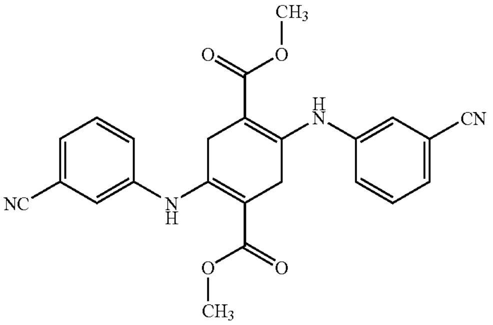 2.13 | H | H | O | O | H | H | —$CH_3$ |
| 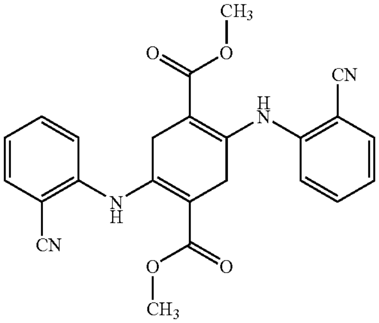 2.14 | H | H | O | O | H | H | —$CH_3$ |
| 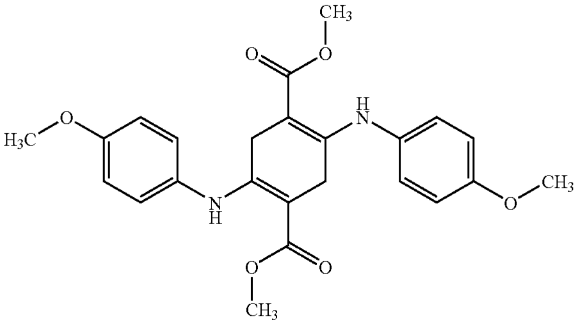 2.15 | H | H | O | O | H | H | —$CH_3$ |
| 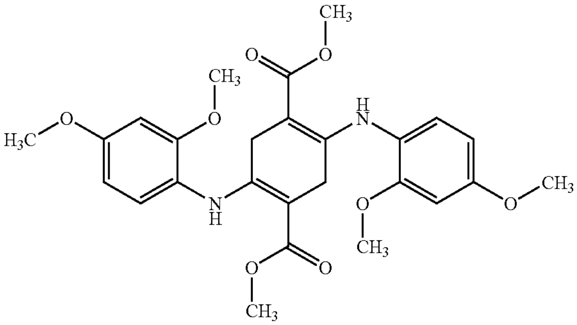 2.16 | H | H | O | O | H | H | —$CH_3$ |

TABLE 2-continued
2,5-diamino-3,6-dihydroterephthalic acid derivatives
| | | | | | | | |
|---|---|---|---|---|---|---|---|
| 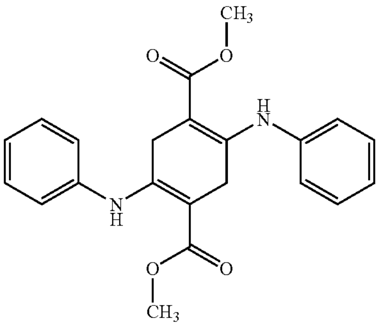 2.17 | H | H | O | O | H | H | —$CH_3$ |
| 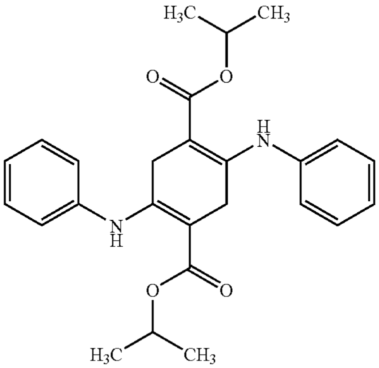 2.18 | H | H | O | O | H | H | —$CH_3$ |
| 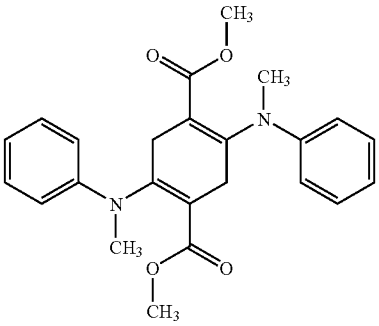 2.19 | H | H | O | O | H | H | —$CH_3$ |
| 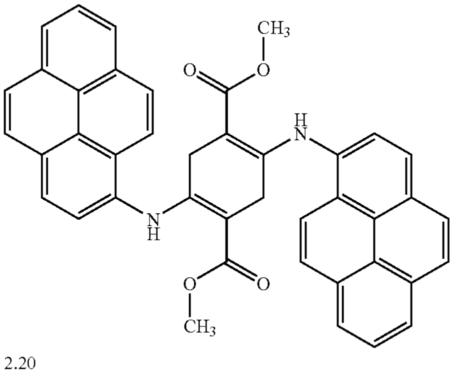 2.20 | H | H | O | O | H | H | —$CH_3$ |

TABLE 2-continued
2,5-diamino-3,6-dihydroterephthalic acid derivatives
| | | | | | | | |
|---|---|---|---|---|---|---|---|
| 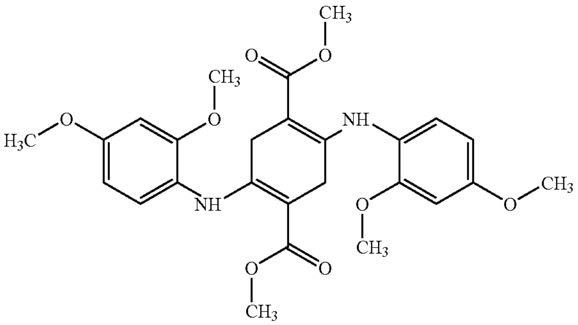 2.21 | H | H | O | O | H | H | —$CH_3$ |
| 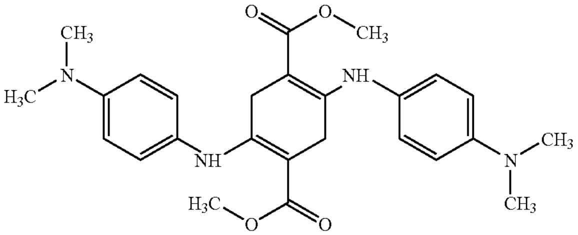 2.22 | H | H | O | O | H | H | —$CH_3$ |
| 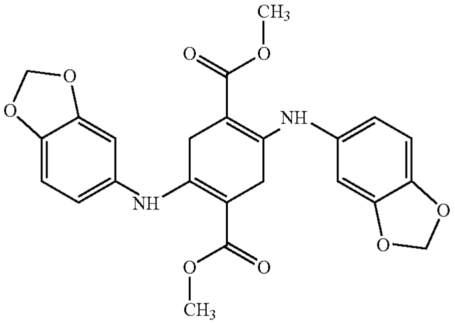 2.24 | H | H | O | O | H | H | —$CH_3$ |
| 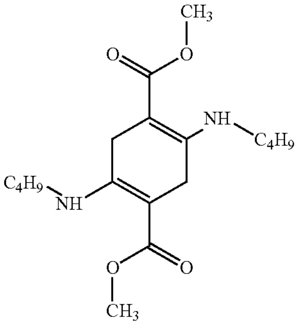 2.25 | H | H | O | O | H | H | —$CH_3$ |
| 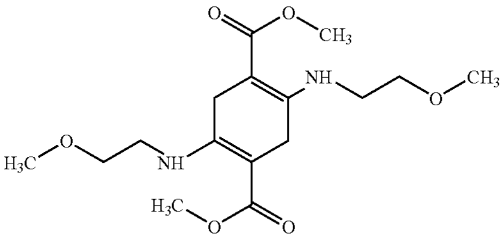 2.26 | H | H | O | O | H | H | —$CH_3$ |

TABLE 2-continued
2,5-diamino-3,6-dihydroterephthalic acid derivatives
| | | | | | | | |
|---|---|---|---|---|---|---|---|
| 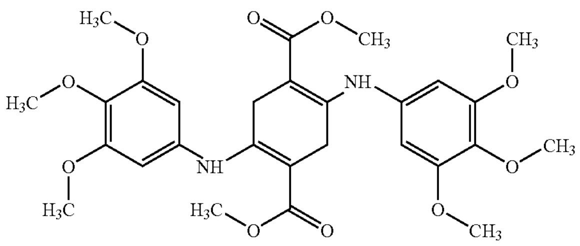 2.27 | H | H | O | O | H | H | —$CH_3$ |
| 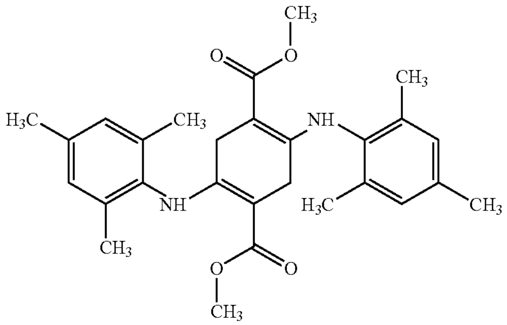 2.28 | H | H | O | O | H | H | —$CH_3$ |
| 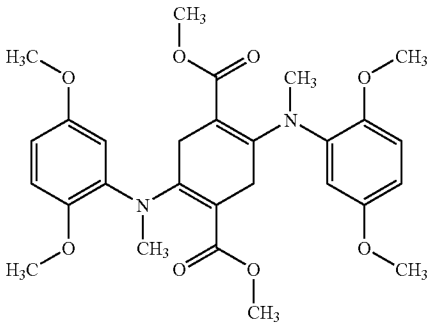 2.29 | H | H | O | O | H | H | —$CH_3$ |
| 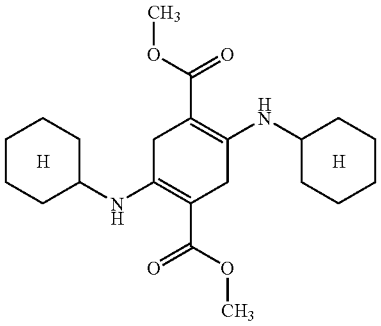 2.30 | H | H | O | O | H | H | —$CH_3$ |
| 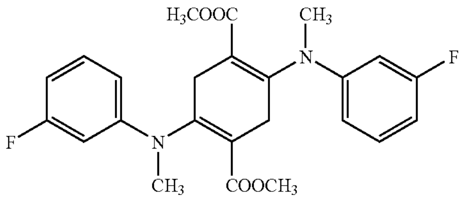 2.31 | H | H | O | O | H | H | —$CH_3$ |

TABLE 2-continued
| 2,5-diamino-3,6-dihydroterephthalic acid derivatives | | | | | | | |
|---|---|---|---|---|---|---|---|
| 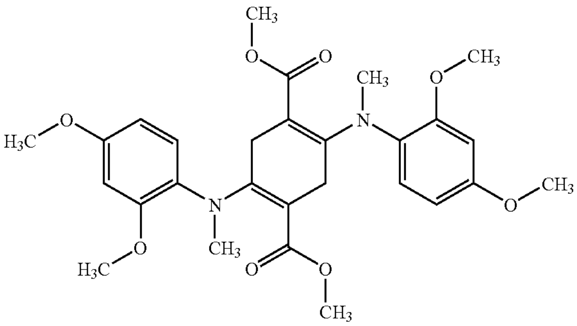 2.32 | H | H | O | O | H | H | —$CH_3$ |
| 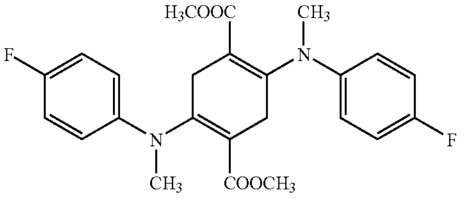 2.33 | H | H | O | O | H | H | —$CH_3$ |
| 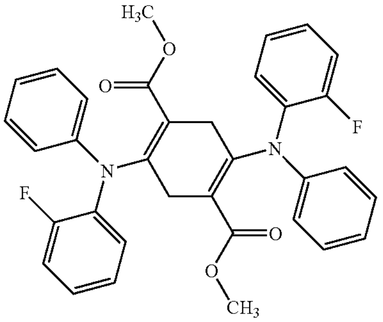 2.34 | H | H | O | O | H | H | —$CH_3$ |
| 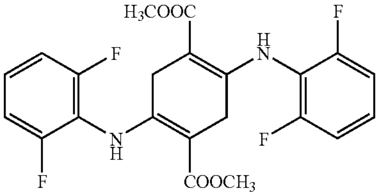 2.35 | H | H | O | O | H | H | —$CH_3$ |
| 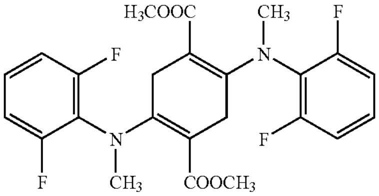 2.36 | H | H | O | O | H | H | —$CH_3$ |

TABLE 2-continued
2,5-diamino-3,6-dihydroterephthalic acid derivatives
| | | | | | | | |
|---|---|---|---|---|---|---|---|
| 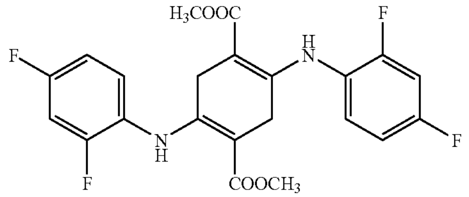 2.37 | H | H | O | O | H | H | —$CH_3$ |
| 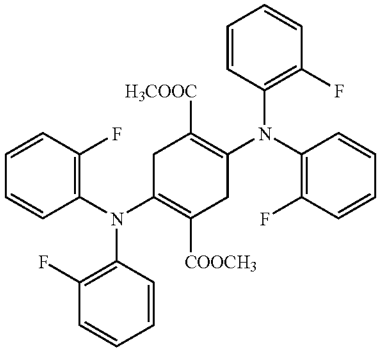 2.38 | H | H | O | O | H | H | —$CH_3$ |
| 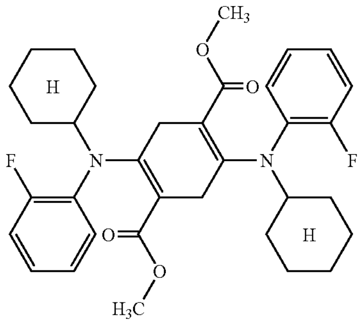 2.39 | H | H | O | O | H | H | —$CH_3$ |
| 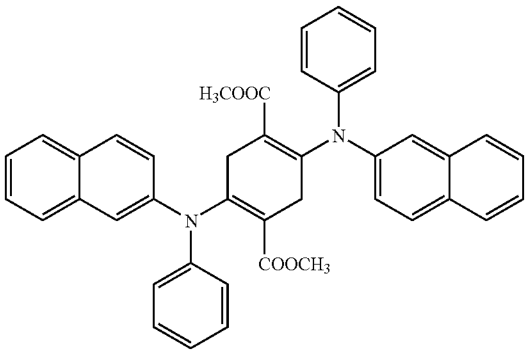 2.40 | H | H | O | O | H | H | —$CH_3$ |

TABLE 2-continued
| 2,5-diamino-3,6-dihydroterephthalic acid derivatives | | | | | | | |
|---|---|---|---|---|---|---|---|
| 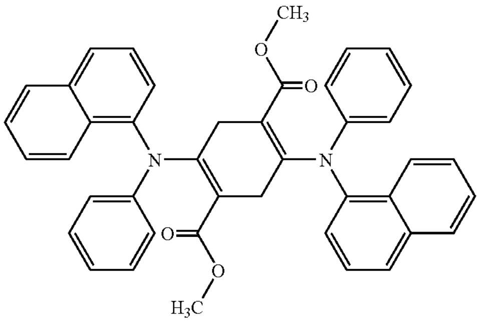 2.41 | H | H | O | O | H | H | —$CH_3$ |
| 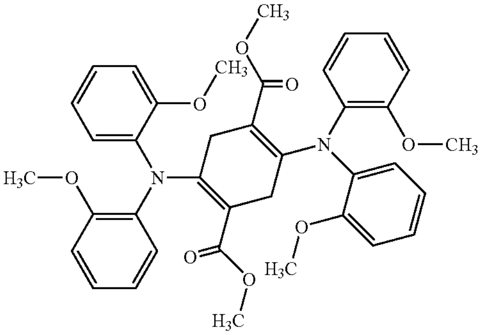 2.42 | H | H | O | O | H | H | —$CH_3$ |
| 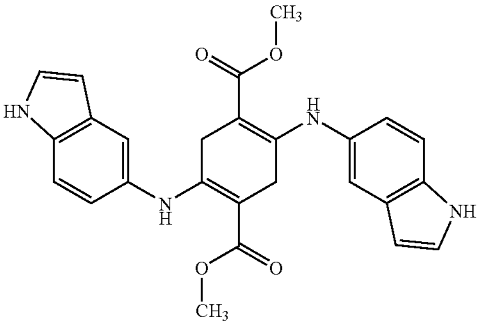 2.43 | H | H | O | O | H | H | —$CH_3$ |
| 2.44 | F | F | O | O | F | F | —$CH_3$ |
| 2.45 | F | F | O | O | F | F | —$CH_3$ |
| 2.46 | F | F | O | O | F | F | —$CH_3$ |
| 2.47 | F | F | O | O | F | F | —$CH_3$ |
| 2.48 | H | H | O | O | H | H | —$CH_3$ |
| 2.49 | H | H | O | O | H | H | —$CH_3$ |
| 2.50 | H | H | O | O | H | H | —$CH_3$ |
| 2.51 | H | H | O | O | H | H | —$CH_3$ |
| 2.52 | H | H | O | O | H | H | —$CH_3$ |
| 2.53 | H | H | O | O | H | H | —$CH_3$ |

TABLE 2-continued
2,5-diamino-3,6-dihydroterephthalic acid derivatives
| | | | | | | | |
|---|---|---|---|---|---|---|---|
| 2.54 | H | H | O | O | H | H | —$CH_3$ |
| 2.55 | H | H | O | O | H | H | —$CH_3$ |
| 2.56 | H | H | O | O | H | H | —$CH_3$ |
| 2.57 | H | H | O | O | H | H | —$CH_3$ |
| 2.58 | H | H | O | O | H | H | —$CH_3$ |
| 2.59 | H | H | O | O | H | H | —$CH_3$ |
| 2.60 | H | H | O | O | H | H | —$CH_3$ |
| 2.61 | H | H | O | O | H | H | —$CH_3$ |
| 2.62 | H | H | O | O | H | H | —$CH_3$ |
| 2.63 | H | H | O | O | H | H | —$CH_3$ |
| 2.64 | H | H | O | O | H | H | —$CH_3$ |
| 2.65 | H | H | O | O | H | H | —$CH_3$ |
| 2.66 | H | H | O | O | H | H | —$CH_3$ |
| 2.67 | H | H | O | O | H | H | —$CH_3$ |
| 2.68 | H | H | O | O | H | H | —$CH_3$ |
| 2.69 | H | H | O | O | H | H | —$CH_3$ |
| 2.70 | H | H | O | O | H | H | —$CH_3$ |
| 2.71 | H | H | O | O | H | H | —$CH_3$ |
| 2.72 | H | H | O | O | H | H | —$CH_3$ |
| 2.73 | H | H | O | O | H | H | —$CH_3$ |
| 2.74 | H | H | N | O | H | H | 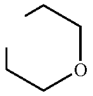 |
| 2.75 | H | H | N | O | H | H | 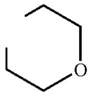 |
| 2.76 | 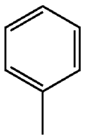 | 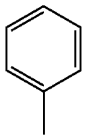 | O | O | 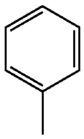 | 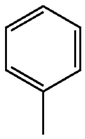 | —$CH_3$ |
| 2.78 | 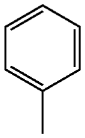 | 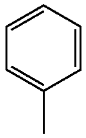 | O | O | 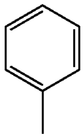 | 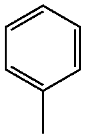 | —$CH_3$ |
| 2.79 | 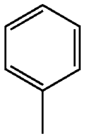 | 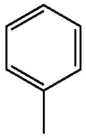 | O | O | 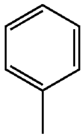 | 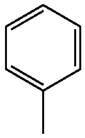 | —$CH_3$ |

TABLE 2-continued
| 2,5-diamino-3,6-dihydroterephthalic acid derivatives | | |
|---|---|---|
| Substance | $R^6$ | $R^7$ |
| 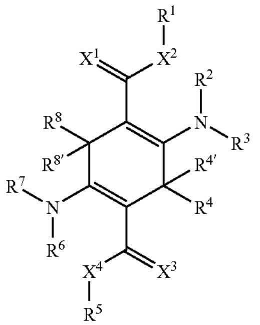 2.0 | | |
| 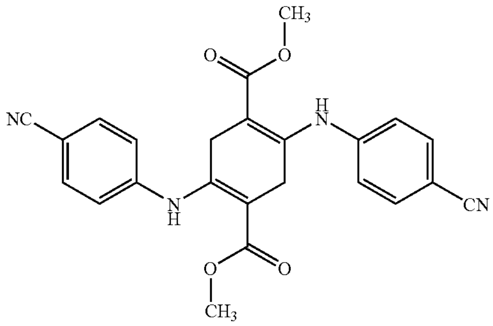 2.1 | H | 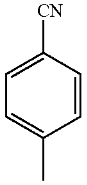 |
| 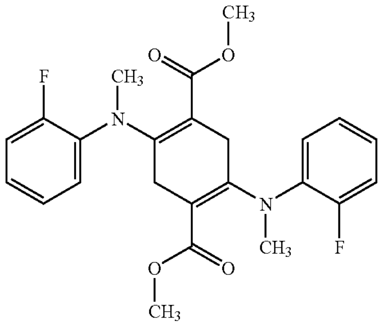 2.2 | —$CH_3$ | 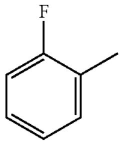 |
| 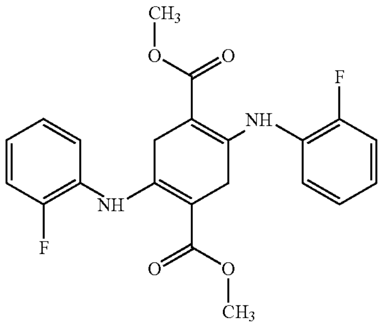 2.3 | H | 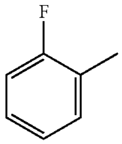 |

TABLE 2-continued
| 2,5-diamino-3,6-dihydroterephthalic acid derivatives | | |
|---|---|---|
| 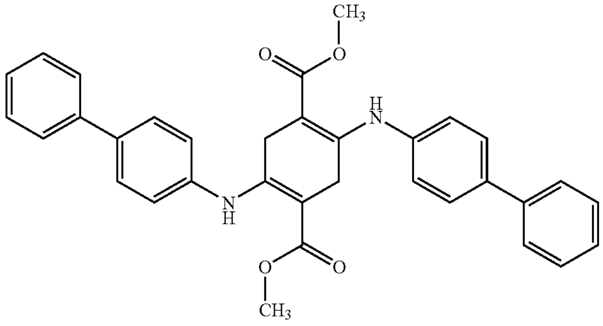<br>2.4 | H | 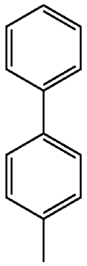 |
| 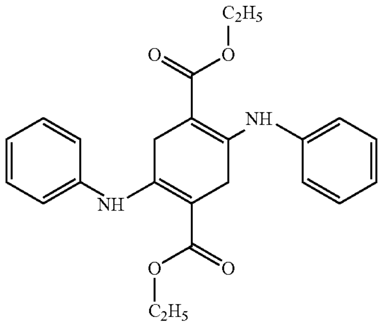<br>2.5 | H | 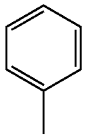 |
| 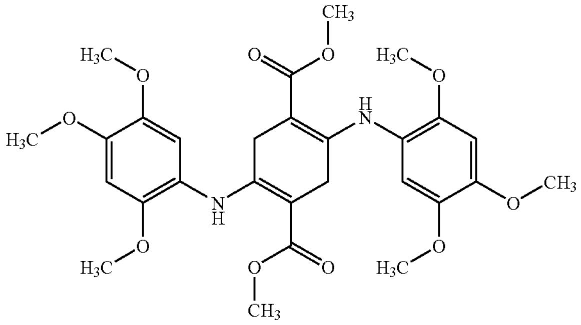<br>2.6 | H | 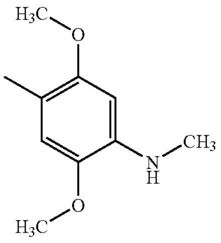 |
| 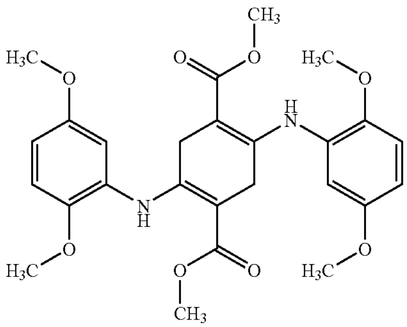<br>2.7 | H | 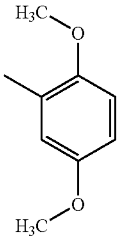 |

TABLE 2-continued
| 2,5-diamino-3,6-dihydroterephthalic acid derivatives | | |
|---|---|---|
| 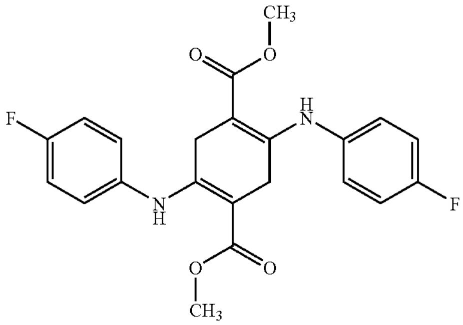 2.8 | H | 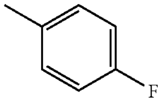 |
| 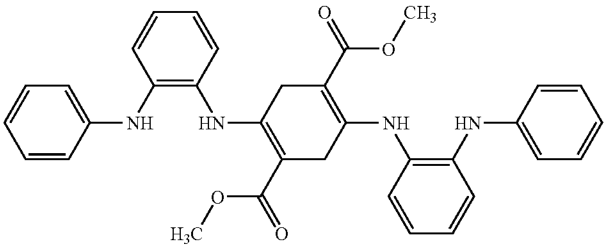 2.9 | H | 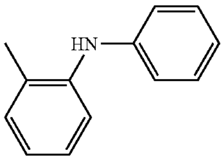 |
| 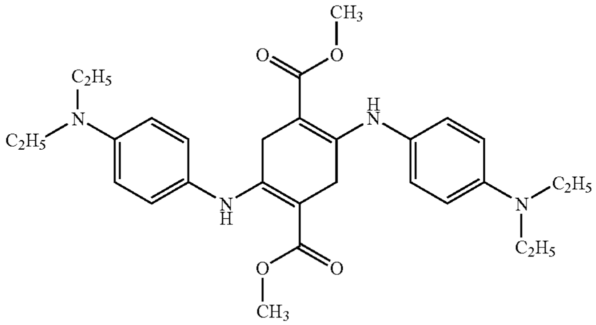 2.10 | H | 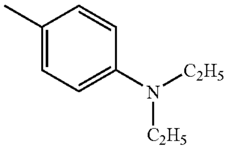 |
| 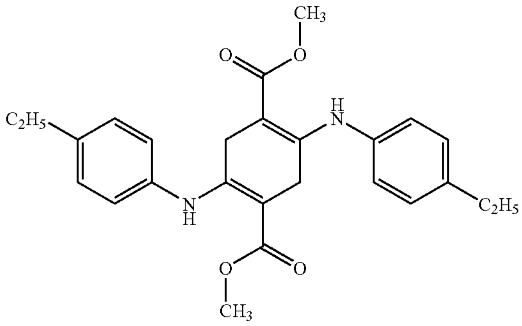 2.11 | H | 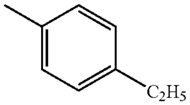 |

TABLE 2-continued
| 2,5-diamino-3,6-dihydroterephthalic acid derivatives | | |
|---|---|---|
| 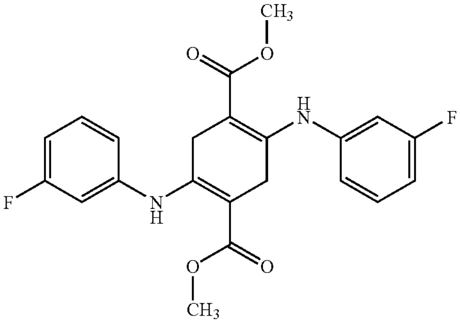 2.12 | H | 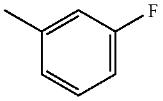 |
| 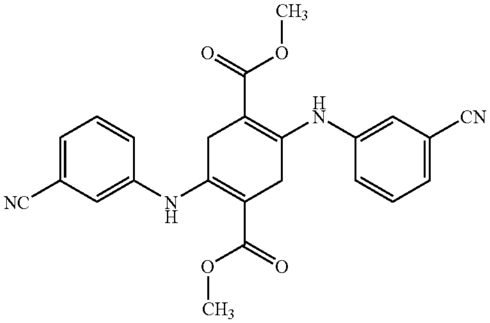 2.13 | H | 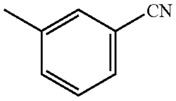 |
| 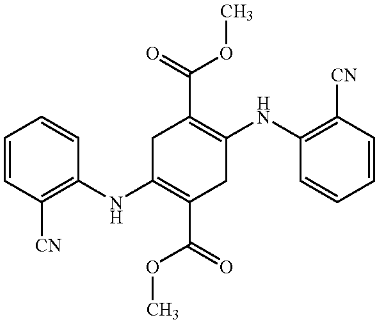 2.14 | H | 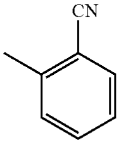 |
| 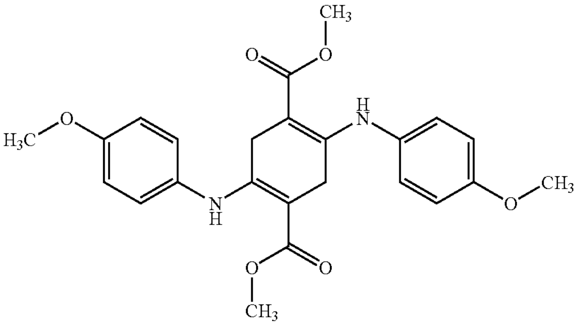 2.15 | H | 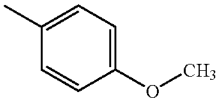 |

TABLE 2-continued
2,5-diamino-3,6-dihydroterephthalic acid derivatives
| | | |
|---|---|---|
| 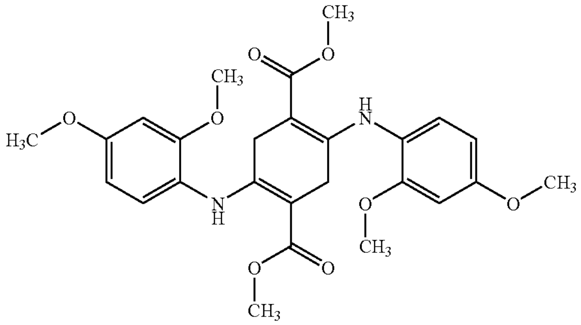<br>2.16 | H | 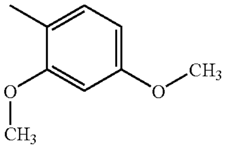 |
| 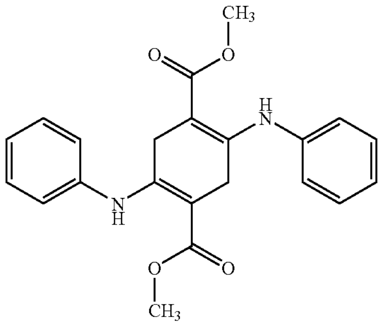<br>2.17 | H | 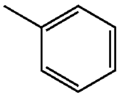 |
| 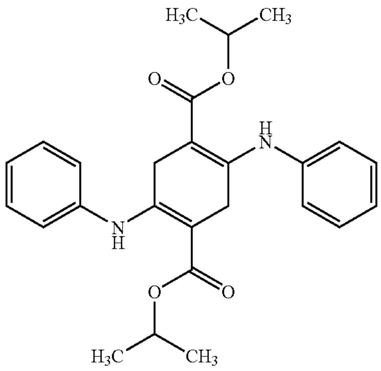<br>2.18 | H | 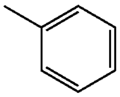 |
| 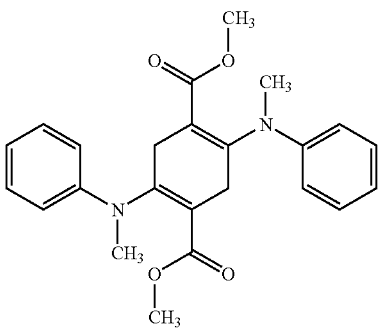<br>2.19 | —$CH_3$ | 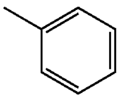 |

TABLE 2-continued
| 2,5-diamino-3,6-dihydroterephthalic acid derivatives | | |
|---|---|---|
| 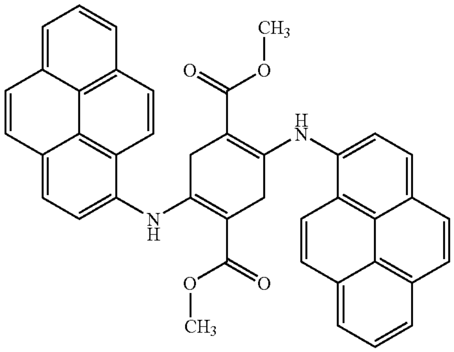 2.20 | H | 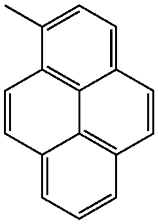 |
| 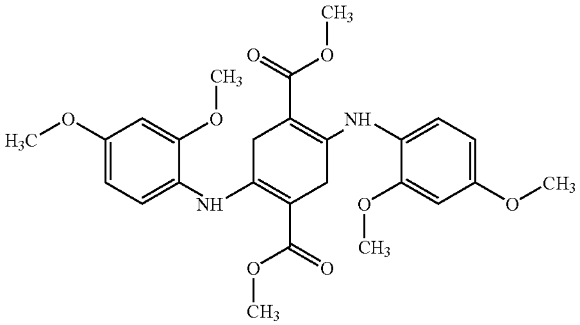 2.21 | H | 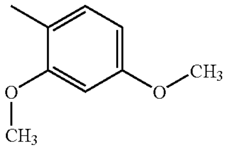 |
| 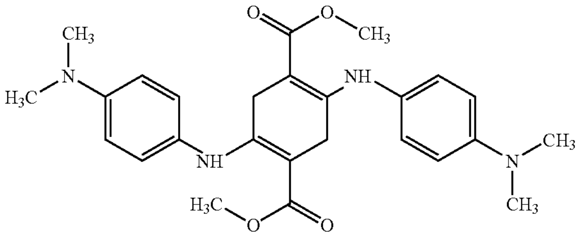 2.22 | H | 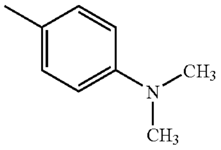 |
| 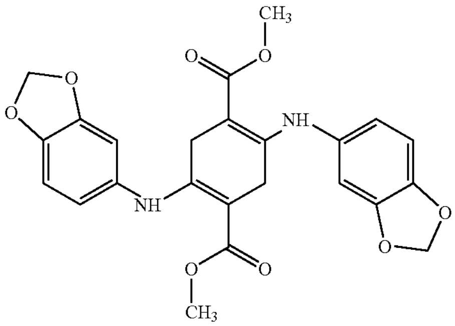 2.24 | H | 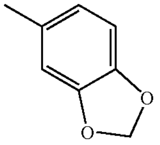 |

TABLE 2-continued
| 2,5-diamino-3,6-dihydroterephthalic acid derivatives | | |
|---|---|---|
| 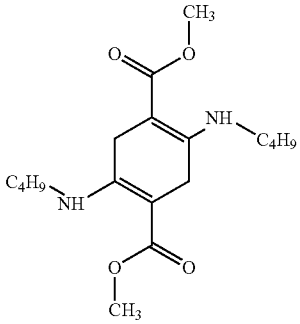 2.25 | H | —$C_4H_9$ |
| 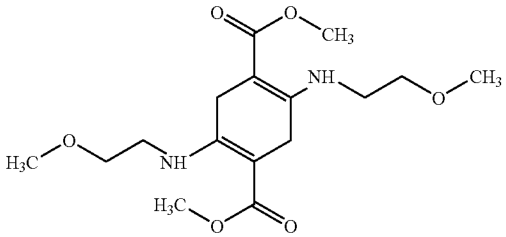 2.26 | H | 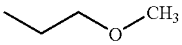 |
| 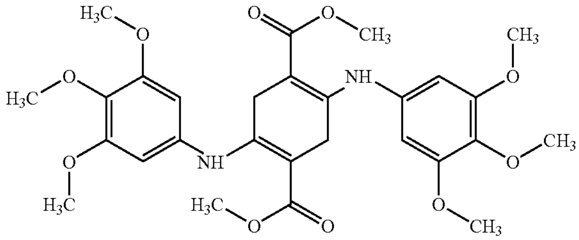 2.27 | H | 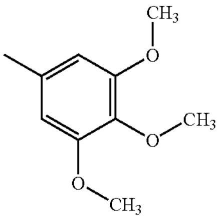 |
| 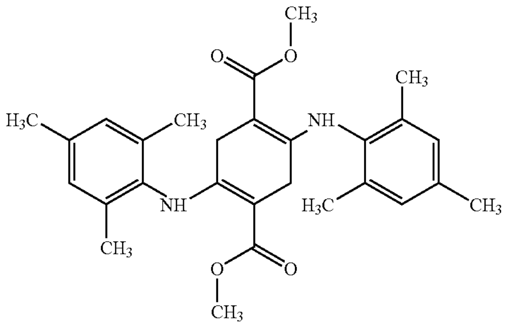 2.28 | H | 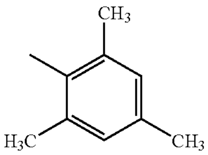 |

TABLE 2-continued
| 2,5-diamino-3,6-dihydroterephthalic acid derivatives | | |
|---|---|---|
| 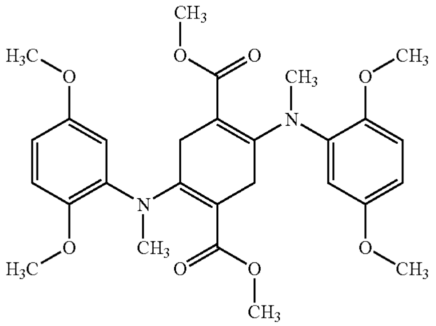<br>2.29 | $-CH_3$ | 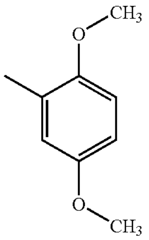 |
| 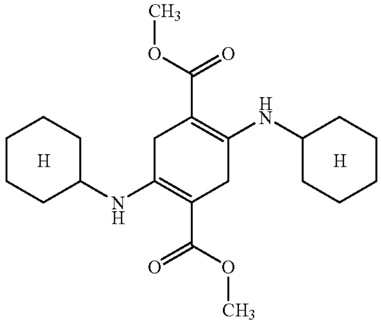<br>2.30 | H | 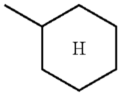 |
| 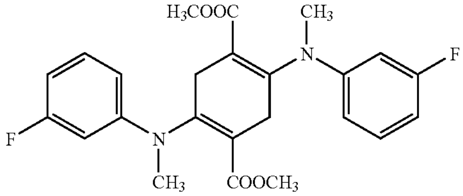<br>2.31 | $-CH_3$ | 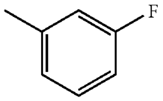 |
| 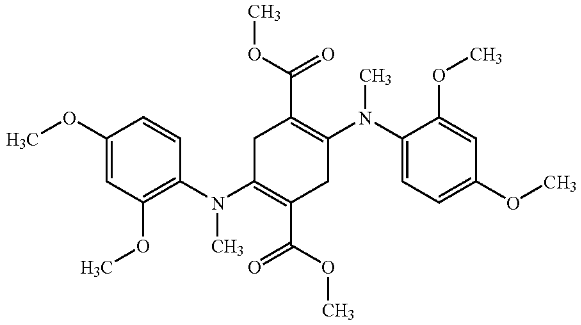<br>2.32 | $-CH_3$ | 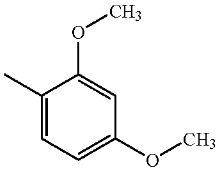 |
| 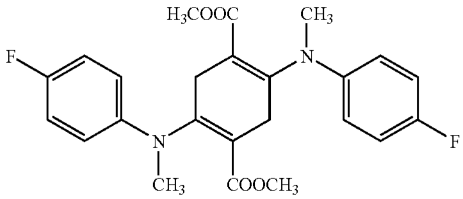<br>2.33 | $-CH_3$ | 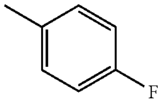 |

TABLE 2-continued
| 2,5-diamino-3,6-dihydroterephthalic acid derivatives | | |
|---|---|---|
| 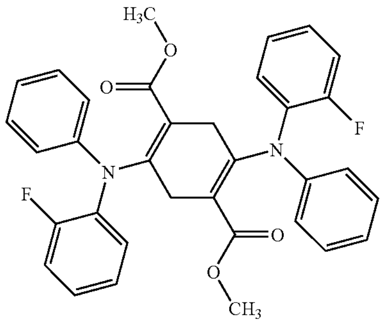 2.34 | 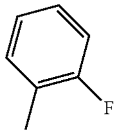 | 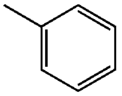 |
| 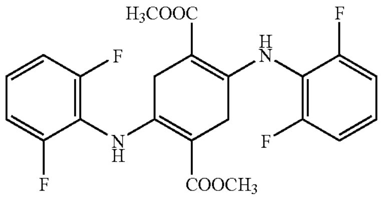 2.35 | H | 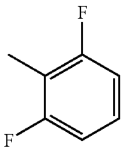 |
| 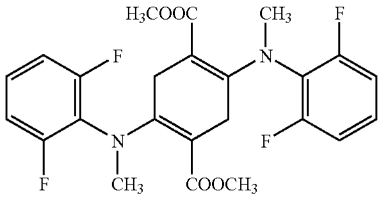 2.36 | $-CH_3$ | 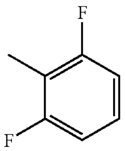 |
| 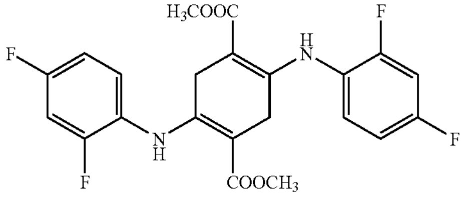 2.37 | H | 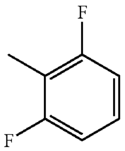 |
| 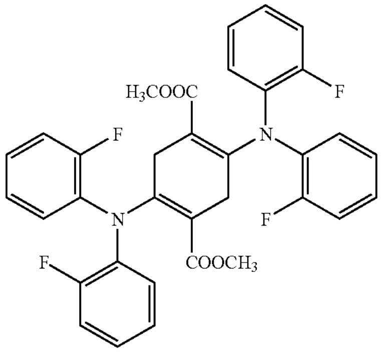 2.38 | 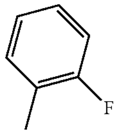 | 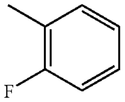 |

TABLE 2-continued
| 2,5-diamino-3,6-dihydroterephthalic acid derivatives | | |
|---|---|---|
| 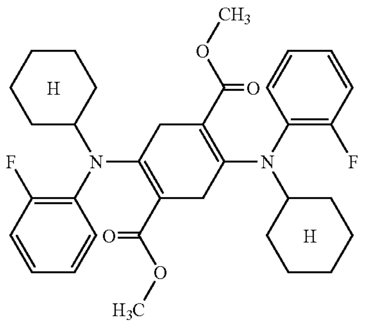 2.39 | 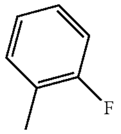 | 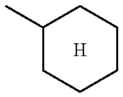 |
| 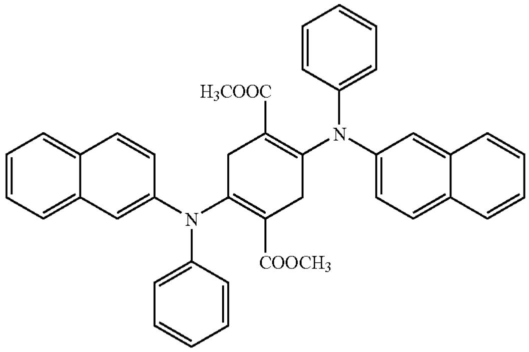 2.40 | 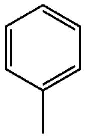 | 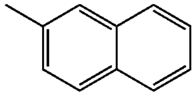 |
| 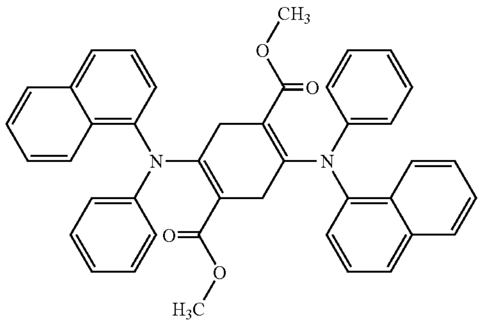 2.41 | 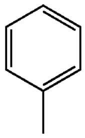 | 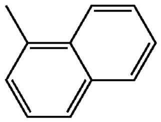 |
| 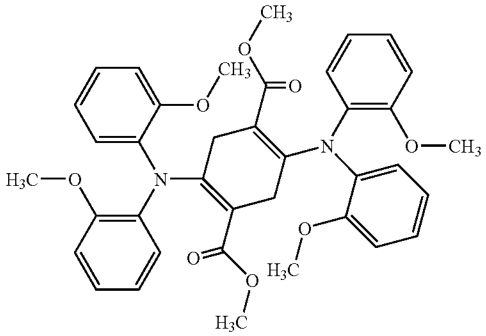 2.42 | 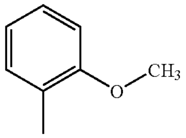 | 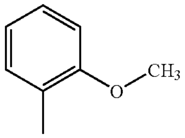 |

TABLE 2-continued
| 2,5-diamino-3,6-dihydroterephthalic acid derivatives | | | |
|---|---|---|---|
| 2.43 | 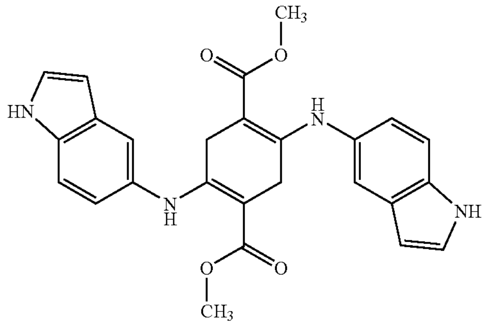 | H | 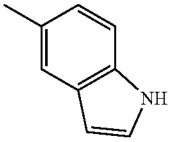 |
| 2.44 | | —$CH_3$ | 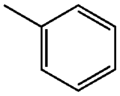 |
| 2.45 | | —$CH_3$ | 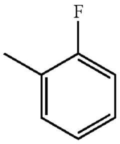 |
| 2.46 | | 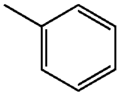 | 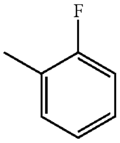 |
| 2.47 | | 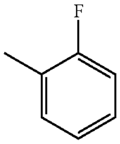 | 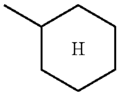 |
| 2.48 | | —$CH_3$ | 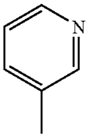 |
| 2.49 | | —$CH_3$ | 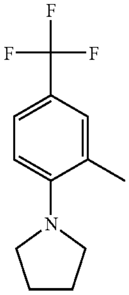 |
| 2.50 | | —$CH_3$ | 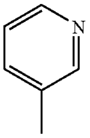 |

TABLE 2-continued
| 2,5-diamino-3,6-dihydroterephthalic acid derivatives | | |
|---|---|---|
| 2.51 | $-CH_3$ | 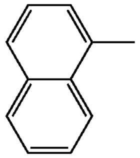 |
| 2.52 | $-CH_3$ | 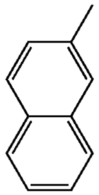 |
| 2.53 | $-CH_3$ | 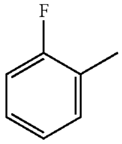 |
| 2.54 | $-CF_3$ | 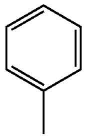 |
| 2.55 | $-CF_3$ | 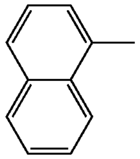 |
| 2.56 | $-CF_3$ | 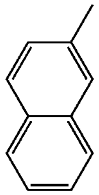 |
| 2.57 | $-CF_3$ | 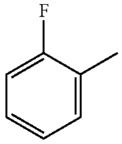 |
| 2.58 | $-CF_3$ | 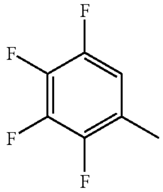 |
| 2.59 | $-CF_3$ | 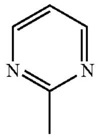 |

TABLE 2-continued
2,5-diamino-3,6-dihydroterephthalic acid derivatives
| | | |
|---|---|---|
| 2.60 | 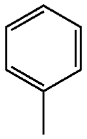 | 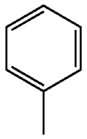 |
| 2.61 | 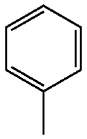 | 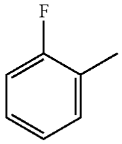 |
| 2.62 | 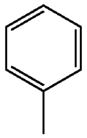 | 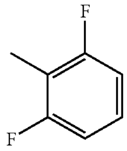 |
| 2.63 | 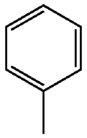 | 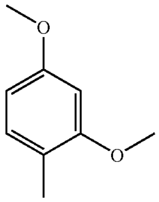 |
| 2.64 | 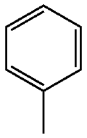 | 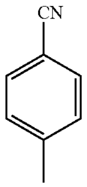 |
| 2.65 | 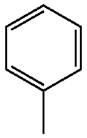 | 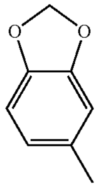 |
| 2.66 | 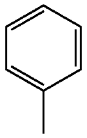 | 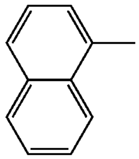 |
| 2.67 | 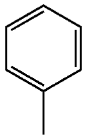 | 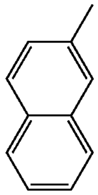 |

TABLE 2-continued
| 2,5-diamino-3,6-dihydroterephthalic acid derivatives | | |
|---|---|---|
| 2.68 | 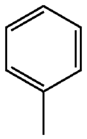 | 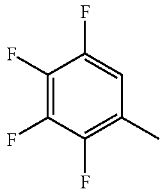 |
| 2.69 | —$CH_3$ | 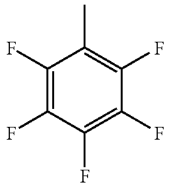 |
| 2.70 | 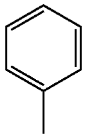 | 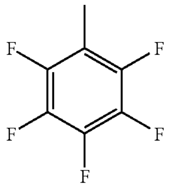 |
| 2.71 | 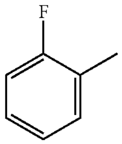 | 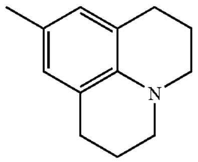 |
| 2.72 | 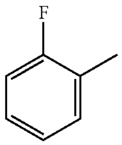 | 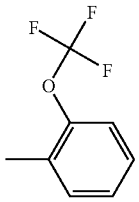 |
| 2.73 | 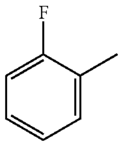 | 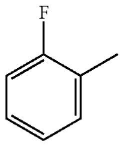 |
| 2.74 | H | 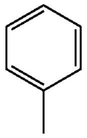 |
| 2.75 | 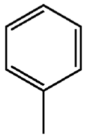 | 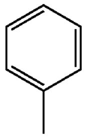 |

TABLE 2-continued
2,5-diamino-3,6-dihydroterephthalic acid derivatives
| | | |
|---|---|---|
| 2.76 | $-CH_3$ | 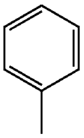 |
| 2.78 | 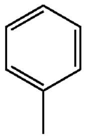 | 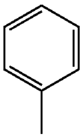 |
| 2.79 | 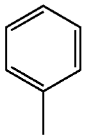 | 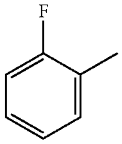 |
| Substance | $X^1$ | $X^2$ | $R^3$ | $R^1$ | $R^2$ | $R^4$ |
|---|---|---|---|---|---|---|
| 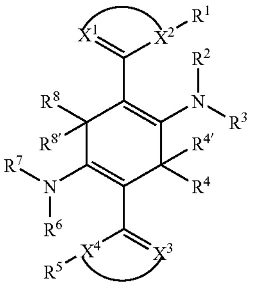 37.0 | | | | | | |
| 37.1 | 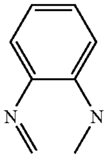 | | 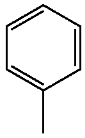 | $-CH_3$ | $-CH_3$ | H |
| 37.2 | 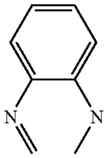 | | 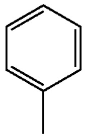 | 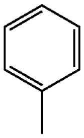 | $-CH_3$ | H |
| 37.3 | 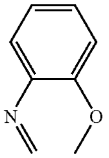 | | 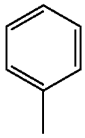 | — | $-CH_3$ | H |
| 37.4 | 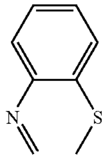 | | 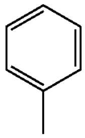 | — | $-CH_3$ | H |

TABLE 2-continued
| 2,5-diamino-3,6-dihydroterephthalic acid derivatives | | | | | | |
|---|---|---|---|---|---|---|
| 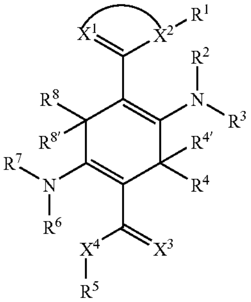 23.0 | | | | | | |
| 23.1 | | 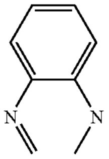 | 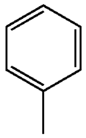 | 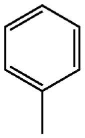 | —$CH_3$ | H |
| 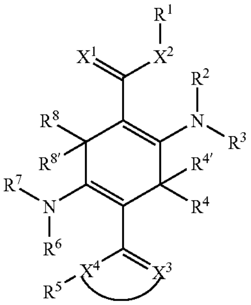 30.0 | | | | | | |
| 30.1 | O | O | 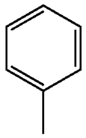 | —$CH_3$ | —$CH_3$ | H |
| Substance | $X^4$ | $X^3$ | $R^8$ | $R^5$ | $R^6$ | $R^7$ | $R^{4'}$ | $R^{8'}$ |
|---|---|---|---|---|---|---|---|---|
| 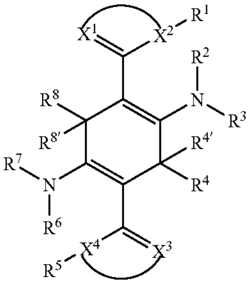 37.0 | | | | | | | | |
| 37.1 | | 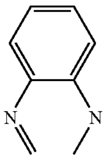 | H | —$CH_3$ | —$CH_3$ | 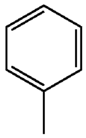 | H | H |

TABLE 2-continued
2,5-diamino-3,6-dihydroterephthalic acid derivatives
| | | | | | | | | |
|---|---|---|---|---|---|---|---|---|
| 37.2 | 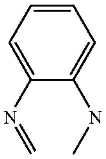 | | H | 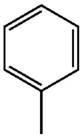 | —$CH_3$ | 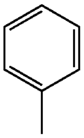 | H | H |
| 37.3 | 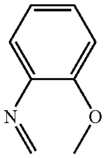 | | H | — | —$CH_3$ | 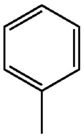 | H | H |
| 37.4 | 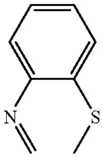 | | H | — | —$CH_3$ | 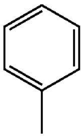 | H | H |
| 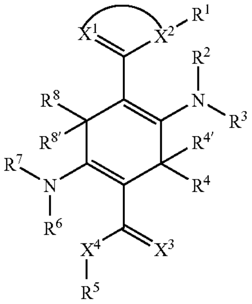 23.0 | | | | | | | | |
| 23.1 | O | O | H | —$CH_3$ | —$CH_3$ | 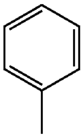 | H | H |
| 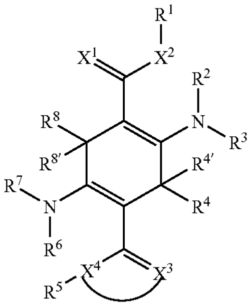 30.0 | | | | | | | | |
| 30.1 | 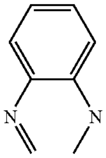 | | 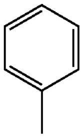 | —$CH_3$ | —$CH_3$ | 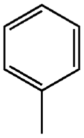 | H | 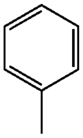 |

TABLE 2-continued
2,5-diamino-3,6-dihydroterephthalic acid derivatives
| Substance | $X^1$ | $X^2$ | $R^3$ | $R^2$ | $R^1$ | $R^4$ | $X^4$ | $X^3$ |
|---|---|---|---|---|---|---|---|---|
| 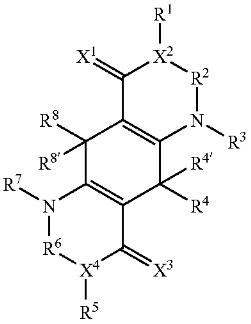 39.0 | | | | | | | | |
| 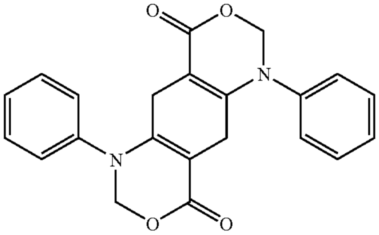 39.1 | O | O | 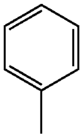 | —$CH_2$— | — | H | O | O |
| 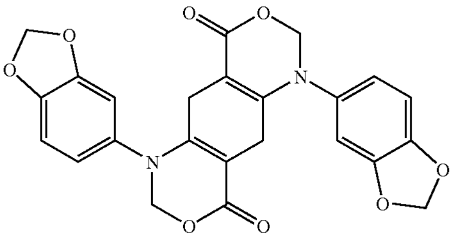 39.2 | O | O | 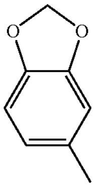 | —$CH_2$— | — | H | O | O |
| 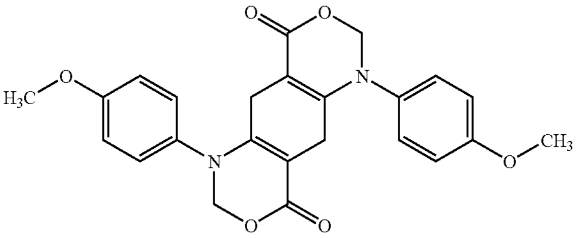 39.3 | O | O | 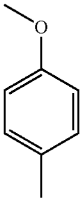 | —$CH_2$— | — | H | O | O |
| 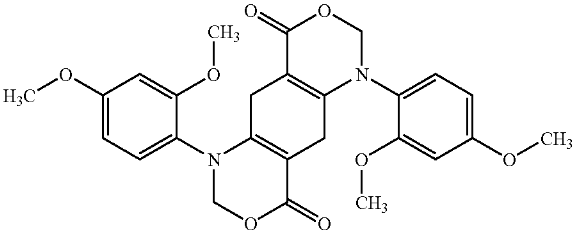 39.4 | O | O | 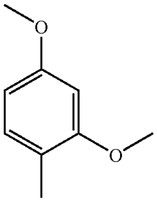 | —$CH_2$— | — | H | O | O |

TABLE 2-continued
2,5-diamino-3,6-dihydroterephthalic acid derivatives
| | | | | | | | | | |
|---|---|---|---|---|---|---|---|---|---|
| 39.5 | 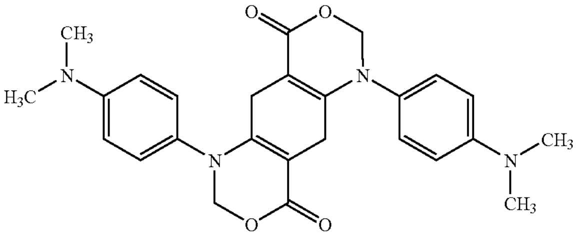 | O | O | 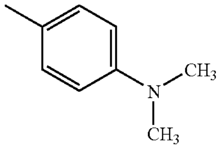 | $—CH_2—$ | — | H | O | O |
| 39.6 | 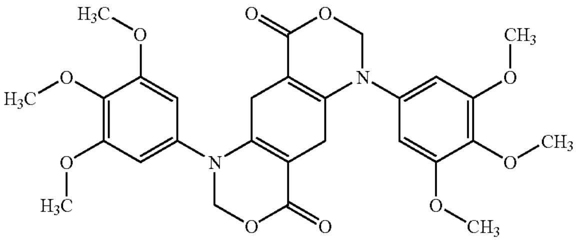 | O | O | 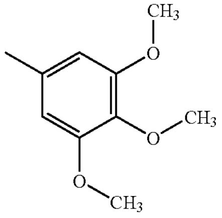 | $—CH_2—$ | — | H | O | O |
| 39.7 | 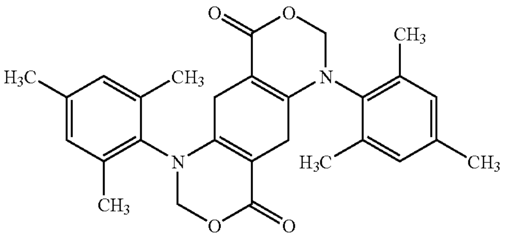 | O | O | 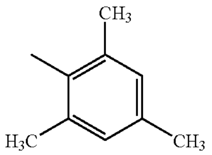 | $—CH_2—$ | — | H | O | O |
| 39.8 | 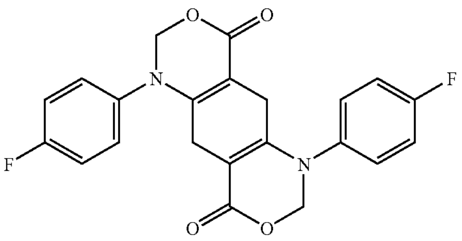 | O | O | 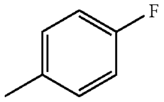 | $—CH_2—$ | — | H | O | O |
| 39.9 | 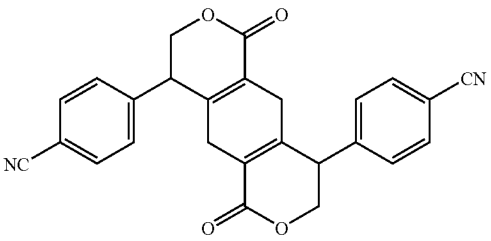 | O | O | 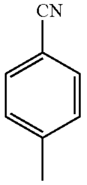 | $—CH_2—$ | — | H | O | O |

TABLE 2-continued
| 2,5-diamino-3,6-dihydroterephthalic acid derivatives | | | | | | | | |
|---|---|---|---|---|---|---|---|---|
| 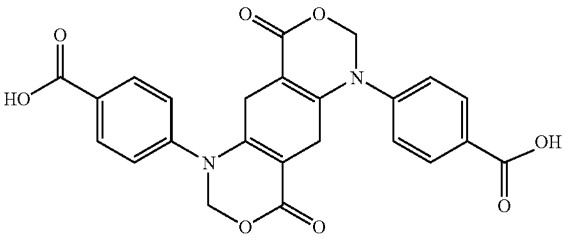 39.10 | O | O | 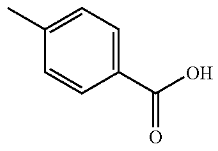 | —$CH_2$— | — | H | O | O |
| 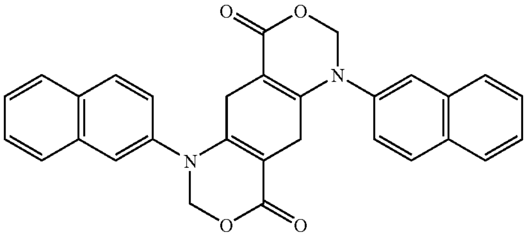 39.11 | O | O | 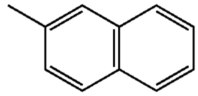 | —$CH_2$— | — | H | O | O |
| 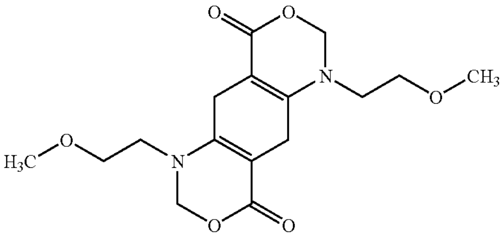 39.12 | O | O | 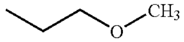 | —$CH_3$— | — | H | O | O |
| 39.13 | O | O | 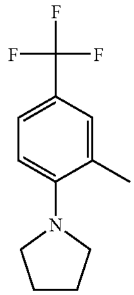 | —$CH_2$— | — | H | O | O |
| 39.14 | O | O | 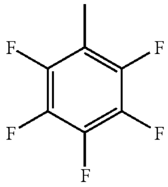 | —$CH_2$— | — | H | O | O |
| 39.15 | O | O | 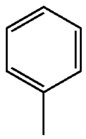 | —$CF_2$— | — | H | O | O |

TABLE 2-continued
2,5-diamino-3,6-dihydroterephthalic acid derivatives
| | | | | | | | | |
|---|---|---|---|---|---|---|---|---|
| 39.16 | O | O | 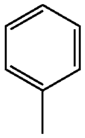 | 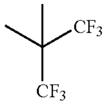 | — | H | O | O |
| 39.17 | O | O | 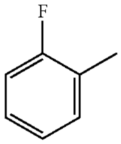 | 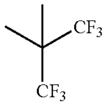 | — | H | O | O |
| 39.18 | O | O | 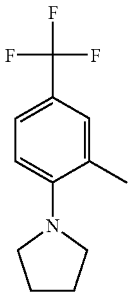 | —$CH_2$— | — | H | O | O |
| 39.19 | O | O | 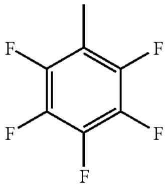 | —$CH_2$— | — | H | O | O |
| 39.20 | O | O | 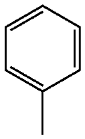 | —$CF_2$— | — | H | O | O |
| 39.21 | O | O | 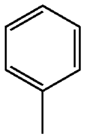 | 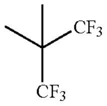 | — | H | O | O |
| 39.22 | O | O | 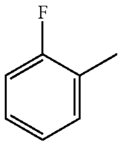 | 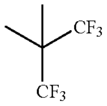 | — | H | O | O |

TABLE 2-continued
2,5-diamino-3,6-dihydroterephthalic acid derivatives
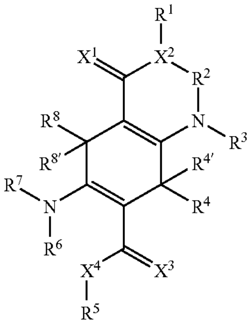
25.0
| | | | | | | | | |
|---|---|---|---|---|---|---|---|---|
| 25.1 | O | O | 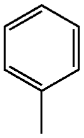 | —CH2— | | H | O | O |
| 25.2 | O | O | 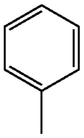 | —CH2— | | H | N | O |
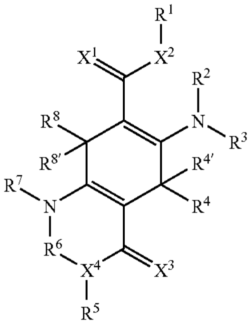
32.0
| | | | | | | | | |
|---|---|---|---|---|---|---|---|---|
| 32.1 | O | O | 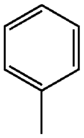 | 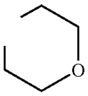 | $—CH_3$ | H | N | O |
| 32.2 | O | O | 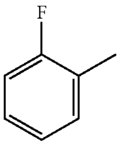 | 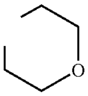 | $—CH_3$ | H | N | O |

TABLE 2-continued
2,5-diamino-3,6-dihydroterephthalic acid derivatives
| Substance | $R^8$ | $R^6$ | $R^5$ | $R^7$ | $R^{4'}$ | $R^{8'}$ |
|---|---|---|---|---|---|---|
| 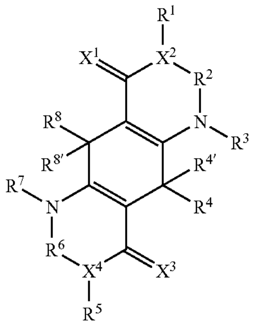 39.0 | | | | | | |
| 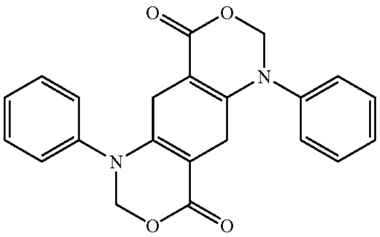 39.1 | H | —$CH_2$— | — | 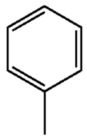 | H | H |
| 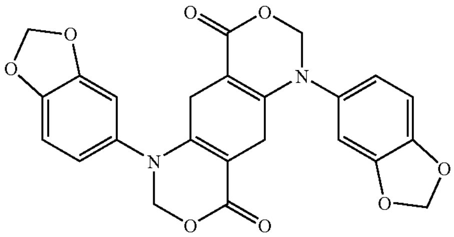 39.2 | H | —$CH_2$— | — | 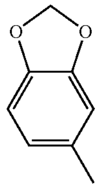 | H | H |
| 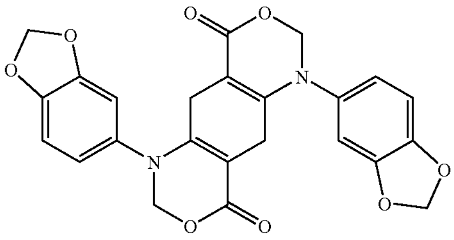 39.3 | H | —$CH_2$— | — | 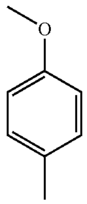 | H | H |
| 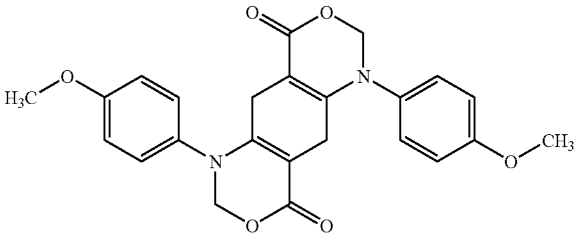 39.4 | H | —$CH_2$— | — | 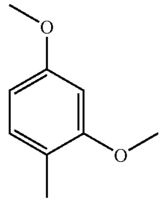 | H | H |

TABLE 2-continued
| 2,5-diamino-3,6-dihydroterephthalic acid derivatives | | | | | | |
|---|---|---|---|---|---|---|
| 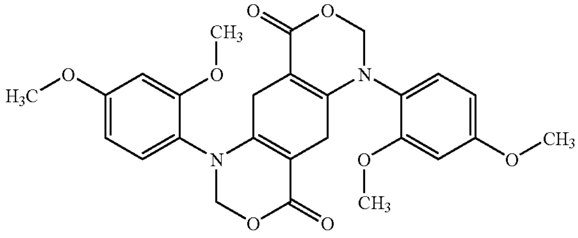 39.5 | H | —$CH_2$— | — | 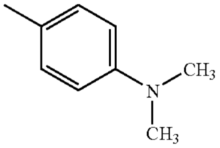 | H | H |
| 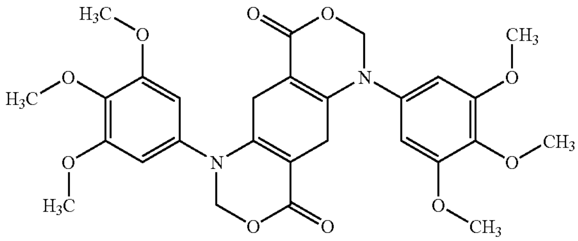 39.6 | H | —$CH_2$— | — | 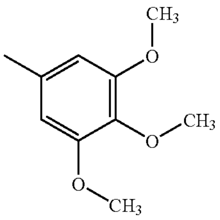 | H | H |
| 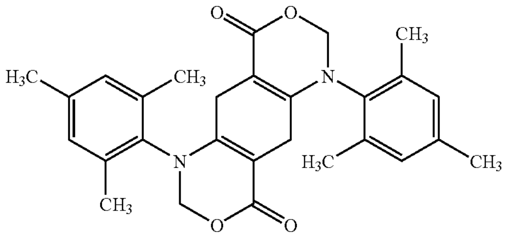 39.7 | H | —$CH_2$— | — | 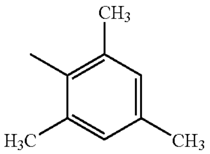 | H | H |
| 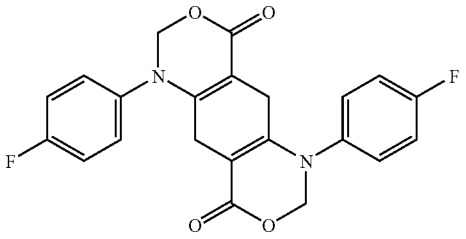 39.8 | H | —$CH_2$— | — | 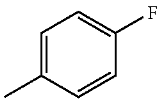 | H | H |
| 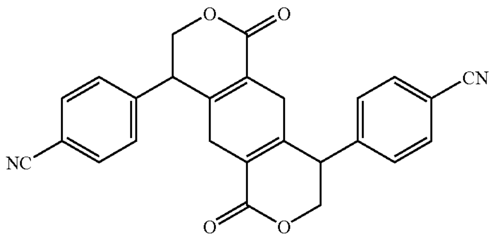 39.9 | H | —$CH_2$— | — | 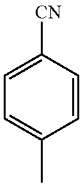 | H | H |

TABLE 2-continued
2,5-diamino-3,6-dihydroterephthalic acid derivatives
| | | | | | | | |
|---|---|---|---|---|---|---|---|
| 39.10 | 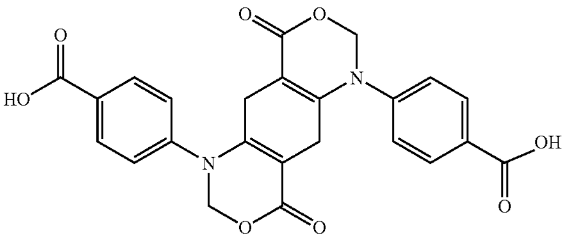 | H | —$CH_2$— | — | 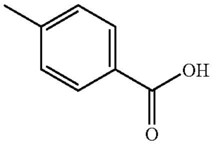 | H | H |
| 39.11 | 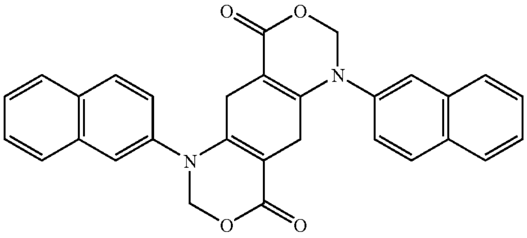 | H | —$CH_2$— | — | 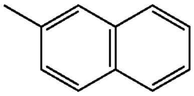 | H | H |
| 39.12 | 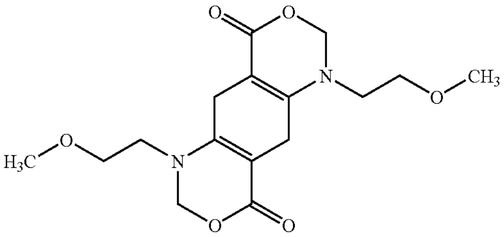 | H | —$CH_2$— | — | 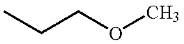 | H | H |
| 39.13 | | H | —$CH_2$— | — | 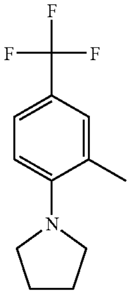 | H | H |
| 39.14 | | H | —$CH_2$— | — | 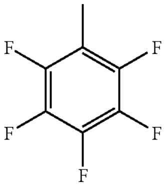 | H | H |
| 39.15 | | H | —$CF_2$— | — | 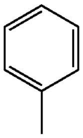 | H | H |

TABLE 2-continued
| 2,5-diamino-3,6-dihydroterephthalic acid derivatives | | | | | | |
|---|---|---|---|---|---|---|
| 39.16 | H | 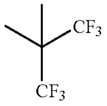 | — | 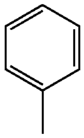 | H | H |
| 39.17 | H | 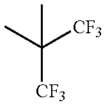 | — | 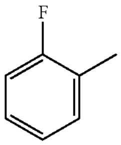 | H | H |
| 39.18 | H | $—CH_2—$ | — | 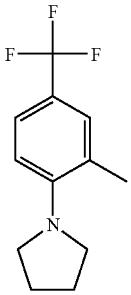 | H | H |
| 39.19 | H | $—CH_2—$ | — | 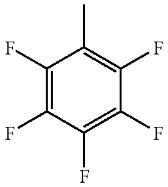 | H | H |
| 39.20 | H | $—CF_2—$ | — | 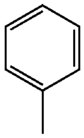 | H | H |
| 39.21 | H | 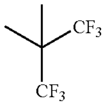 | — | 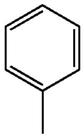 | H | H |
| 39.22 | H | 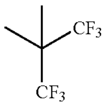 | — | 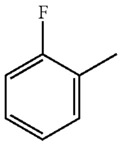 | H | H |

TABLE 2-continued
2,5-diamino-3,6-dihydroterephthalic acid derivatives
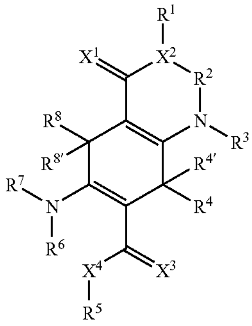
25.0
| | | | | | | |
|---|---|---|---|---|---|---|
| 25.1 | H | $—CH_3$ | $—CH_3$ | 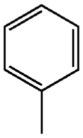 | H | H |
| 25.2 | H | 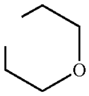 | $—CH_3$ | 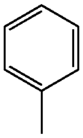 | H | H |
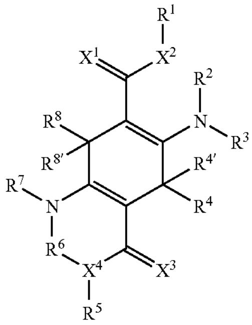
32.0
| | | | | | | |
|---|---|---|---|---|---|---|
| 32.1 | H | $—CH_2—$ | | 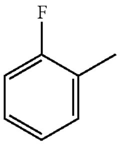 | H | H |
| 32.2 | H | $—CH_2—$ | | 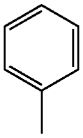 | H | H |

TABLE 2-continued
| 2,5-diamino-3,6-dihydroterephthalic acid derivatives | | | | | | | | | | | | |
|---|---|---|---|---|---|---|---|---|---|---|---|---|
| Substance | $X^1$ | $R^1$ | $X^2$ | $R^2$ | $R^3$ | $R^4$ | $R^5$ | $X^3$ | $X^4$ | $R^6$ | $R^7$ | $R^8$ |
| 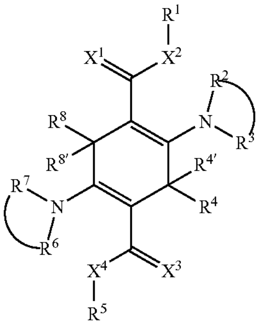 40.0 | | | | | | | | | | | | |
| 40.1 | O | —$CH_3$ | O | | 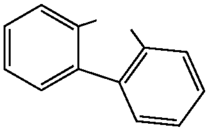 | H | —$CH_3$ | O | O | | 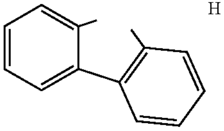 | H |
| 40.2 | O | —$CH_3$ | O | | 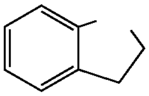 | H | —$CH_3$ | O | O | | 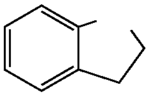 | H |
| 40.3 | O | —$CH_3$ | O | | 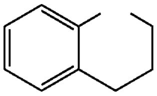 | H | —$CH_3$ | O | O | | 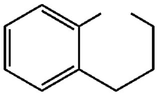 | H |
| 40.4 | O | —$CH_3$ | O | | 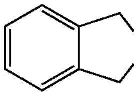 | H | —$CH_3$ | O | O | | 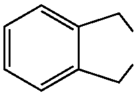 | H |
| 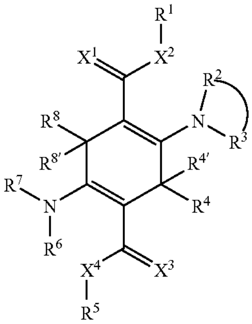 26.0 | | | | | | | | | | | | |
| 26.1 | O | —$CH_3$ | O | | 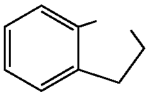 | H | —$CH_3$ | O | O | —$CH_3$ | 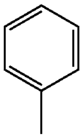 | H |
| 26.2 | O | —$CH_3$ | O | | 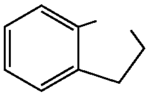 | H | —$CH_3$ | O | O | 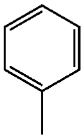 | 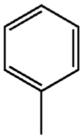 | H |

TABLE 2-continued
2,5-diamino-3,6-dihydroterephthalic acid derivatives
| | | | | | | | | | | | |
|---|---|---|---|---|---|---|---|---|---|---|---|
| 26.3 | O | —$CH_3$ | O | 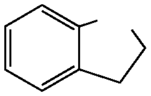 | 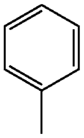 | —$CH_3$ | O | O | 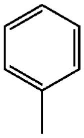 | 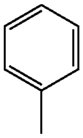 | H |
| Substance | $R^{4'}$ | $R^{8'}$ |
|---|---|---|
| 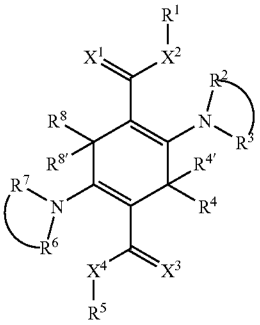 | | |
| 40.0 | | |
| 40.1 | H | H |
| 40.2 | H | H |
| 40.3 | H | H |
| 40.4 | H | H |
| 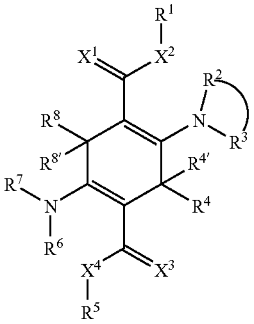 | | |
| 26.0 | | |
| 26.1 | H | H |
| 26.2 | H | H |
| 26.3 | 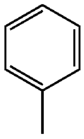 | H |

TABLE 2-continued
2,5-diamino-3,6-dihydroterephthalic acid derivatives
| Substance | $X^1$ | $R^1$ | $X^2$ | $R^4$ | $R^2$ | $R^3$ | $R^5$ | $X^3$ | $X^4$ | $R^6$ | $R^7$ | $R^8$ | $R^{4'}$ | $R^{8'}$ |
|---|---|---|---|---|---|---|---|---|---|---|---|---|---|---|
| 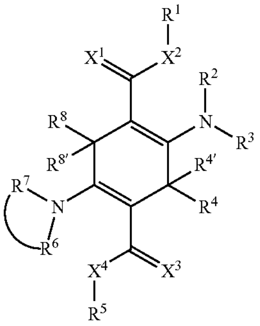 33.0 | | | | | | | | | | | | | | |
| 33.1 | O | $—CH_3$ | O | $—CH_3$ | 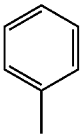 | 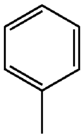 | $—CH_3$ | O | O | 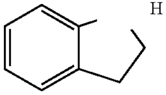 | | H | $—CH_3$ | H |
| 33.2 | O | $—CH_3$ | O | 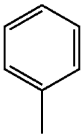 | 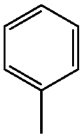 | 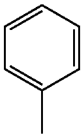 | $—CH_3$ | O | O | 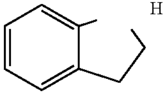 | | H | 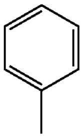 | H |
| Substance | $R^1$ | $X^2$ | $X^1$ | $R^4$ | $R^3$ | $R^2$ | $R^5$ | $X^4$ | $X^3$ | $R^8$ | $R^7$ | $R^6$ | $R^{4'}$ | $R^{8'}$ |
|---|---|---|---|---|---|---|---|---|---|---|---|---|---|---|
| 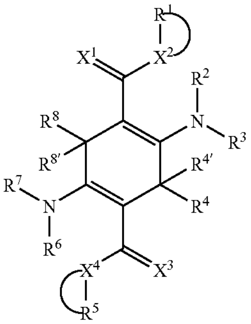 38.0 | | | | | | | | | | | | | | |
| 38.1 | 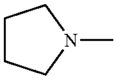 | | O | H | 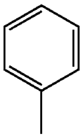 | $—CH_3$ | 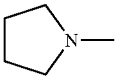 | | O | H | 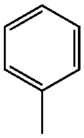 | $—CH_3$ | H | H |
| 38.2 | 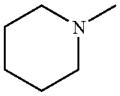 | | O | H | 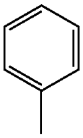 | $—CH_3$ | 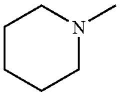 | | O | H | 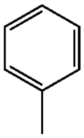 | $—CH_3$ | H | H |
| 38.3 | 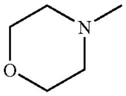 | | O | H | 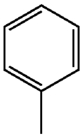 | $—CH_3$ | 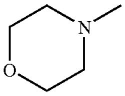 | | O | H | 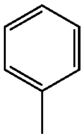 | $—CH_3$ | H | H |

TABLE 2-continued
2,5-diamino-3,6-dihydroterephthalic acid derivatives
| | | | | | | | | | | | | | | |
|---|---|---|---|---|---|---|---|---|---|---|---|---|---|---|
| 38.4 | 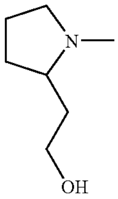 | | O | H | 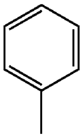 | —$CH_3$ | 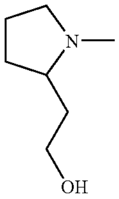 | | O | H | 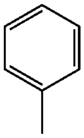 | —$CH_3$ | H | H |
| 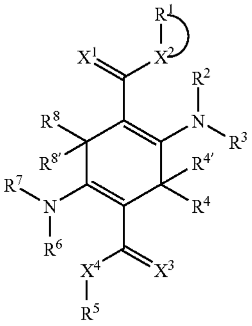 24.0 | | | | | | | | | | | | | | |
| 24.1 | 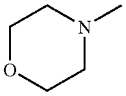 | | O | H | 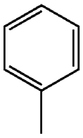 | —$CH_3$ | —$CH_3$ | O | O | H | 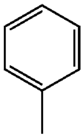 | —$CH_3$ | H | H |
| 24.2 | 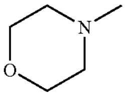 | | O | H | 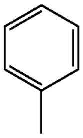 | 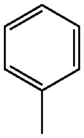 | —$CH_3$ | O | O | H | 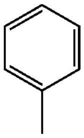 | 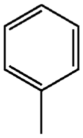 | H | H |
| 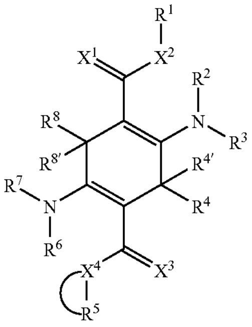 31.0 | | | | | | | | | | | | | | |
| 31.1 | —$CH_3$ | O | O | H | 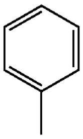 | —$CH_3$ | 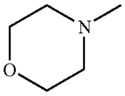 | | O | H | 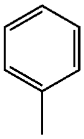 | H | H | H |
| 31.2 | —$CH_3$ | O | O | H | 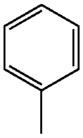 | 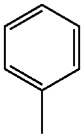 | 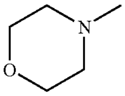 | | O | H | 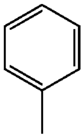 | —$CH_3$ | H | H |

TABLE 2-continued
2,5-diamino-3,6-dihydroterephthalic acid derivatives
| Substance | $R^1$ | $X^2$ | $X^1$ | $R^{4'}$ | $R^3$ | $R^2$ | $R^5$ | $X^4$ | $X^3$ | $R^{8'}$ | $R^7$ | $R^6$ | $R^4$ | $R^8$ |
|---|---|---|---|---|---|---|---|---|---|---|---|---|---|---|
| 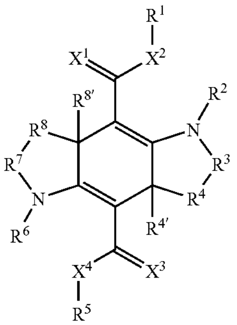 41.0 | | | | | | | | | | | | | | |
| 41.1 | —$CH_3$ | O | O | | 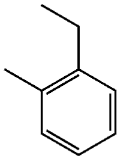 | 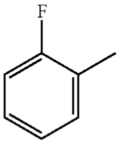 | —$CH_3$ | O | O | | 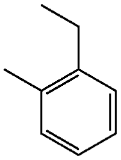 | 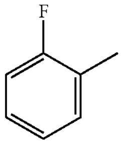 | H | H |
| 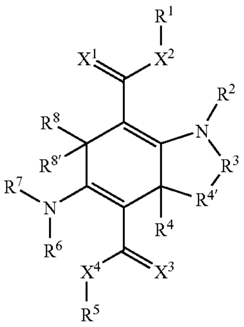 27.0 | | | | | | | | | | | | | | |
| 27.1 | —$CH_3$ | O | O | | 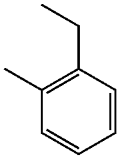 | 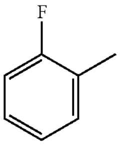 | —$CH_3$ | O | O | H | 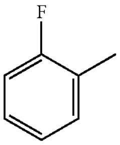 | 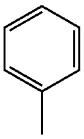 | H | H |
| 27.2 | —$CH_3$ | O | O | | 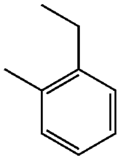 | 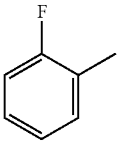 | 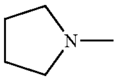 | | O | H | 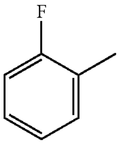 | 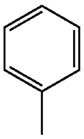 | H | H |

TABLE 2-continued
2,5-diamino-3,6-dihydroterephthalic acid derivatives
| Substance | $R^1$ | $X^2$ | $X^1$ | $R^4$ | $R^3$ | $R^2$ | $R^5$ | $X^4$ | $X^3$ | $R^5$ | $R^7$ | $R^{8'}$ | $R^{4'}$ | $R^8$ |
|---|---|---|---|---|---|---|---|---|---|---|---|---|---|---|
| 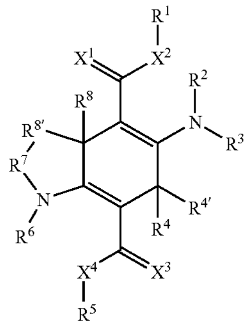 34.0 | | | | | | | | | | | | | | |
| 34.1 | 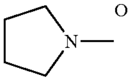 | | O | H | 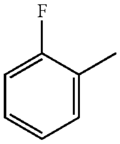 | $—CH_3$ | $—CH_3$ | O | O | 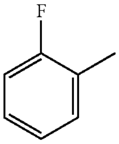 | 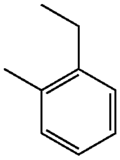 | | H | H |
| Substance | $X^2$ | $R^2$ | $R^3$ | $R^4$ | $X^3$ | $R^5$ | $R^6$ | $X^4$ | $R^7$ | $R^8$ | $X^1$ | $R^1$ |
|---|---|---|---|---|---|---|---|---|---|---|---|---|
| 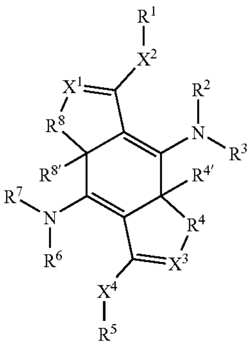 43.0 | | | | | | | | | | | | |
| 43.1 | O | $—CH_3$ | 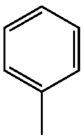 | 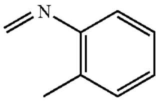 | | $—CH_3$ | $—CH_3$ | O | 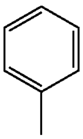 | 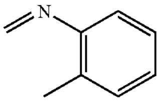 | | $—CH_3$ |
| 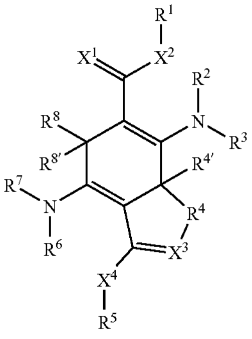 29.0 | | | | | | | | | | | | |

TABLE 2-continued
2,5-diamino-3,6-dihydroterephthalic acid derivatives
| | | | | | | | | | | | |
|---|---|---|---|---|---|---|---|---|---|---|---|
| 29.1 | O | —CH$_3$ | 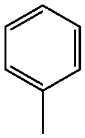 | 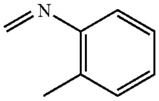 | —CH$_3$ | —CH$_3$ | O | 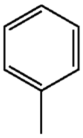 | H | O | —CH$_3$ |
| 29.2 | O | | 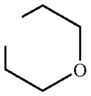 | 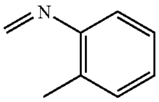 | —CH$_3$ | —CH$_3$ | O | | H | O | —CH$_3$ |
| 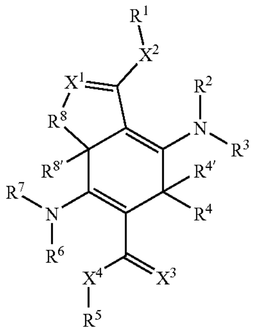 36.0 | | | | | | | | | | | |
| 36.1 | O | | 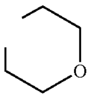 | H | O | —CH$_3$ | —CH$_3$ | O | 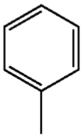 | 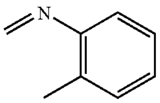 | —CH$_3$ |
| Substance | R$^{4'}$ | R$^{8'}$ |
|---|---|---|
| 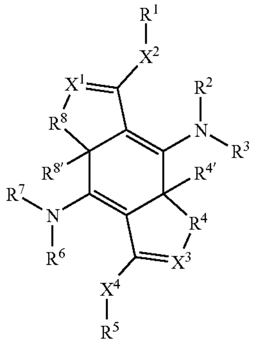 43.0 | | |
| 43.1 | —CH$_3$ | —CH$_3$ |

TABLE 2-continued
| 2,5-diamino-3,6-dihydroterephthalic acid derivatives | | |
|---|---|---|
| 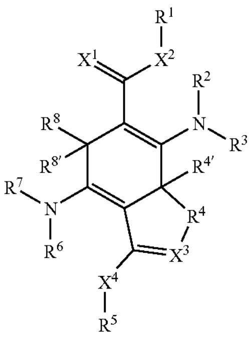 | | |
| 29.0 | | |
| 29.1 | —$CH_3$ | —$CH_3$ |
| 29.2 | H | H |
| 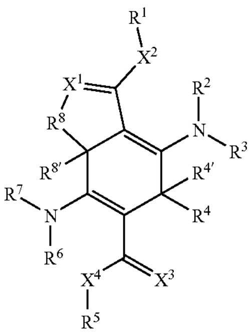 | | |
| 36.0 | | |
| 36.1 | H | H |

TABLE 3
| Substituted 2,5-diaminoterephthalic acid dinitriles | | | | | | | |
|---|---|---|---|---|---|---|---|
| Substance | | $R^3$ | $R^2$ | $R^4$ | $R^8$ | $R^6$ | $R^7$ |
| 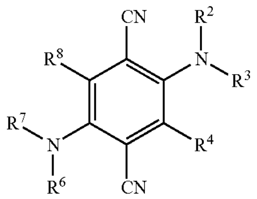 | 3.0 | | | | | | |
| 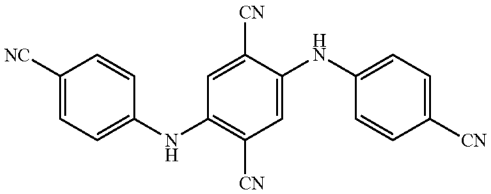 | 3.1 | 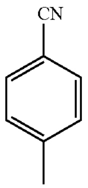 | H | H | H | H | 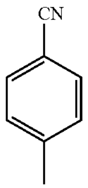 |
| 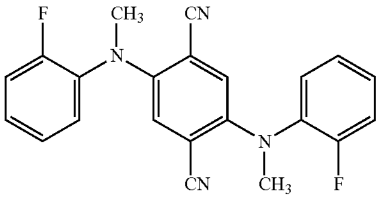 | 3.2 | 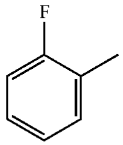 | $—CH_3$ | H | H | $—CH_3$ | 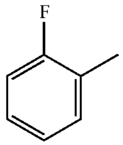 |
| 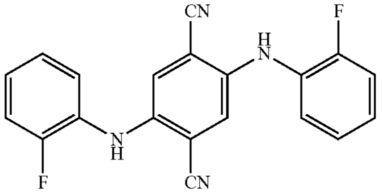 | 3.3 | 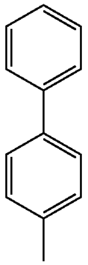 | H | H | H | H | 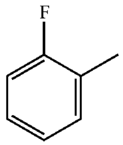 |

TABLE 3-continued
| Substituted 2,5-diaminoterephthalic acid dinitriles | | | | | | | |
|---|---|---|---|---|---|---|---|
| 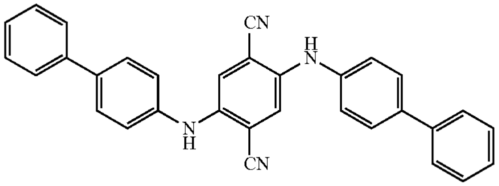 | 3.4 | 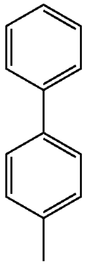 | H | H | H | H | 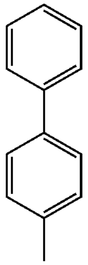 |
| 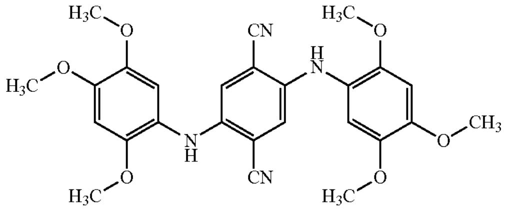 | 3.5 | 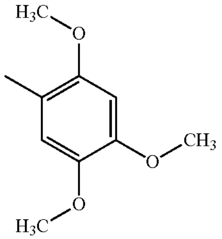 | H | H | H | H | 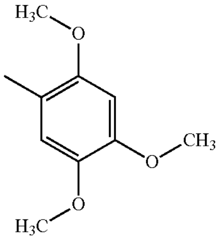 |
| 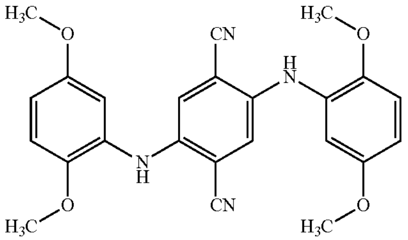 | 3.6 | 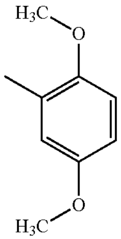 | H | H | H | H | 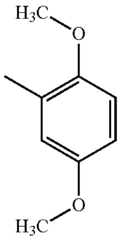 |
| 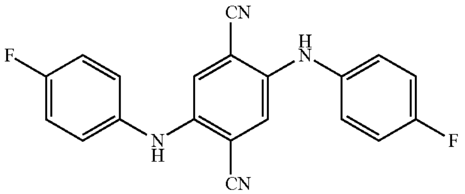 | 3.7 | 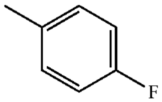 | H | H | H | H | 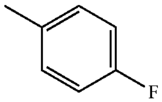 |

TABLE 3-continued
| Substituted 2,5-diaminoterephthalic acid dinitriles | | | | | | | |
|---|---|---|---|---|---|---|---|
| 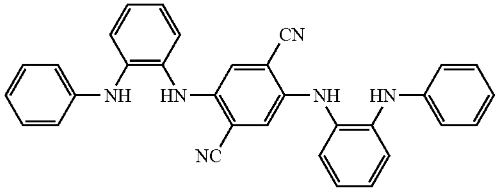 | 3.8 | 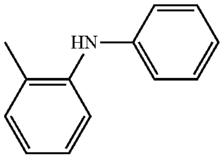 | H | H | H | H | 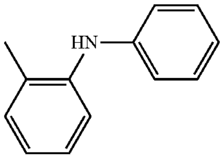 |
| 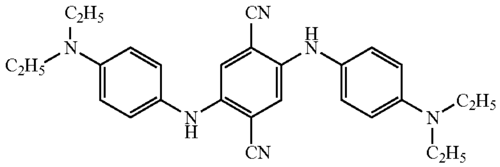 | 3.9 | 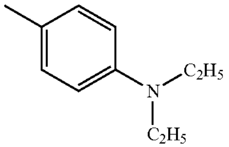 | H | H | H | H | 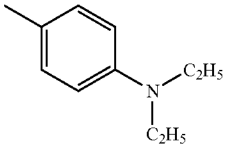 |
| 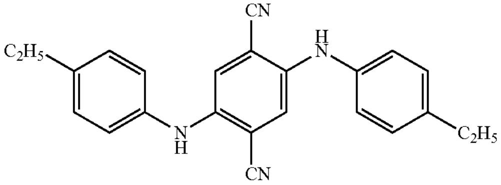 | 3.10 | 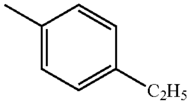 | H | H | H | H | 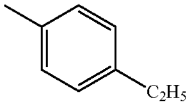 |
| 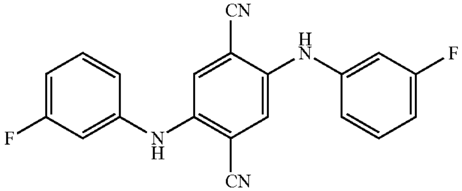 | 3.11 | 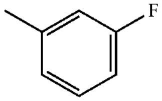 | H | H | H | H | 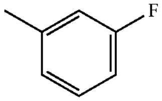 |
| 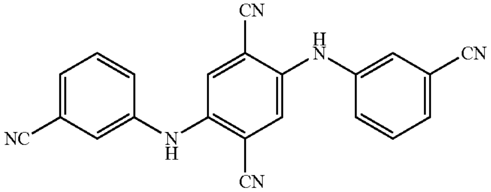 | 3.12 | 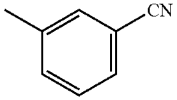 | H | H | H | H | 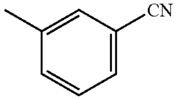 |

TABLE 3-continued
Substituted 2,5-diaminoterephthalic acid dinitriles
| | | | | | | | |
|---|---|---|---|---|---|---|---|
| 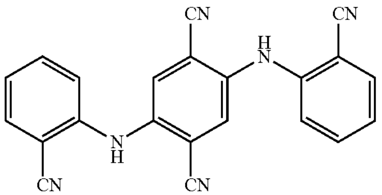 | 3.13 | 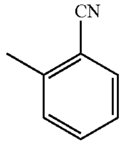 | H | H | H | H | 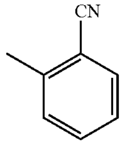 |
| 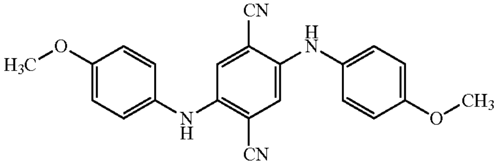 | 3.14 | 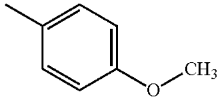 | H | H | H | H | 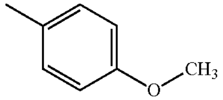 |
| 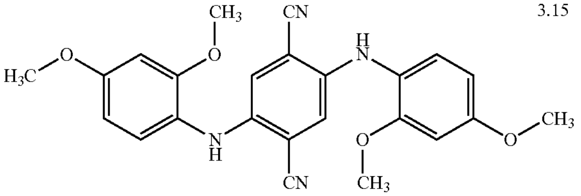 | 3.15 | 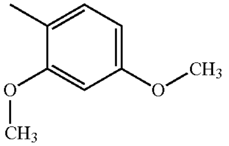 | H | H | H | H | 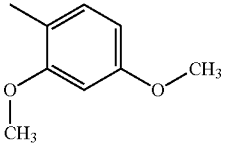 |
| 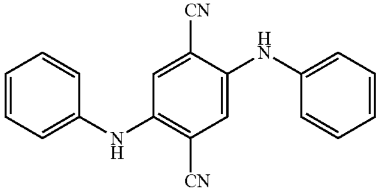 | 3.16 | 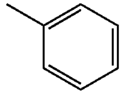 | H | H | H | H | 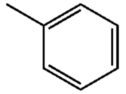 |
| 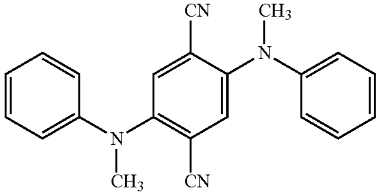 | 3.17 | 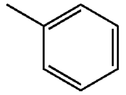 | —CH$_3$ | H | H | —CH$_3$ | 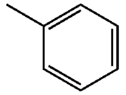 |

TABLE 3-continued
Substituted 2,5-diaminoterephthalic acid dinitriles
| | | | | | | | |
|---|---|---|---|---|---|---|---|
| 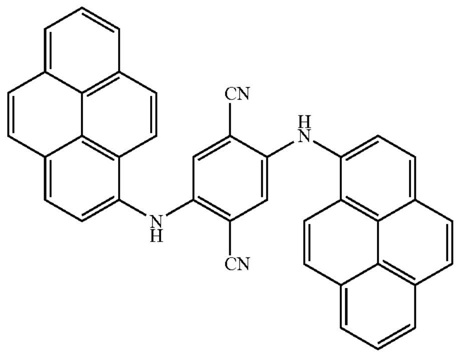 | 3.18 | 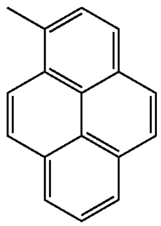 | H | H | H | H | 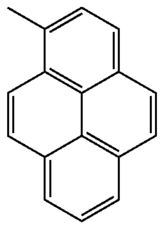 |
| 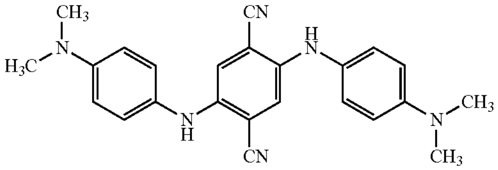 | 3.19 | 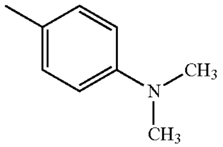 | H | H | H | H | 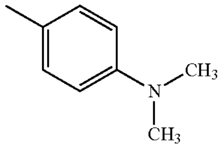 |
| 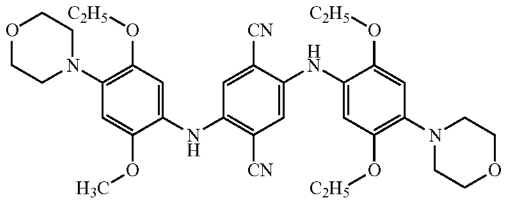 | 3.20 | 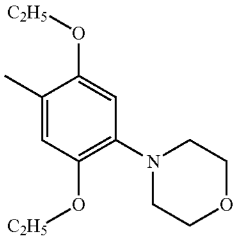 | H | H | H | H | 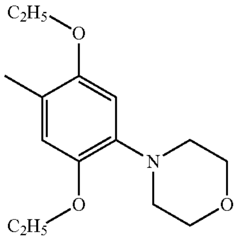 |
| 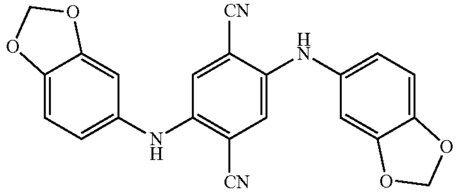 | 3.21 | 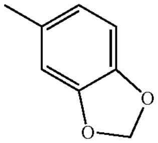 | H | H | H | H | 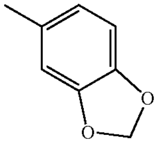 |

TABLE 3-continued
Substituted 2,5-diaminoterephthalic acid dinitriles
| | | | | | | | |
|---|---|---|---|---|---|---|---|
| 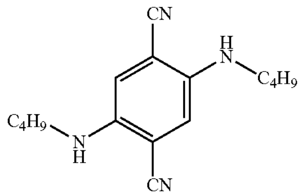 | 3.22 | $—C_4H_9$ | H | H | H | H | $—C_4H_9$ |
| 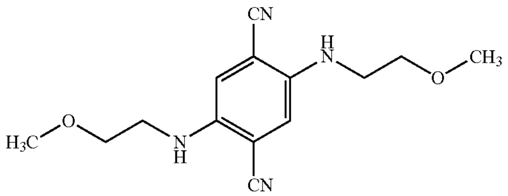 | 3.23 | 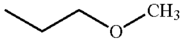 | H | H | H | H | 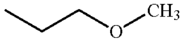 |
| 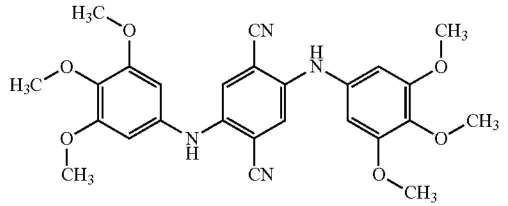 | 3.24 | 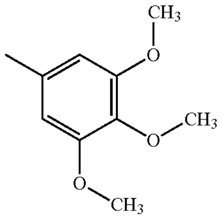 | H | H | H | H | 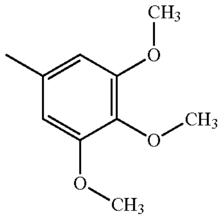 |
| 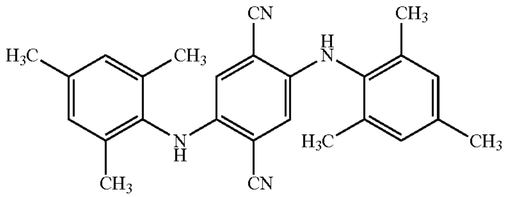 | 3.25 | 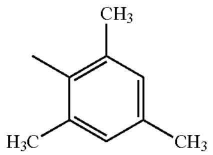 | H | H | H | H | 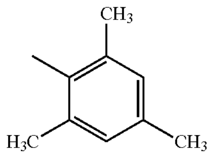 |

TABLE 3-continued
| Substituted 2,5-diaminoterephthalic acid dinitriles | | | | | | | |
|---|---|---|---|---|---|---|---|
| 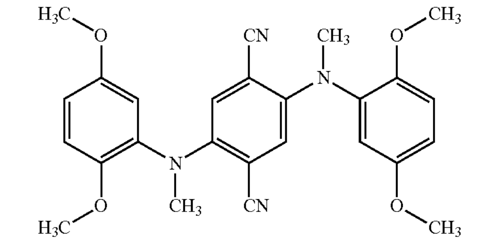 | 3.26 | 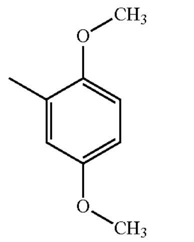 | —$CH_3$ | H | H | —$CH_3$ | 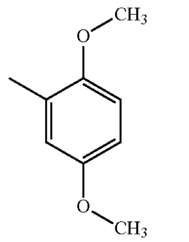 |
| 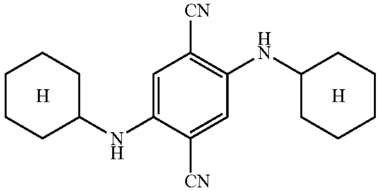 | 3.27 | 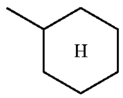 | H | H | H | H | 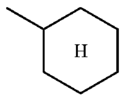 |
| 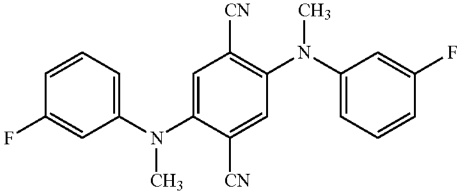 | 3.28 | 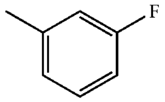 | —$CH_3$ | H | H | —$CH_3$ | 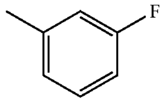 |
| 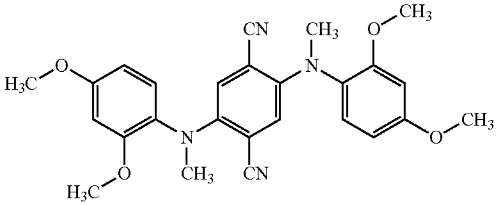 | 3.29 | 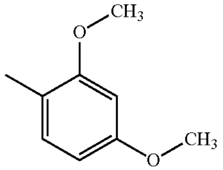 | —$CH_3$ | H | H | —$CH_3$ | 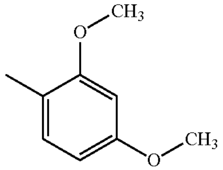 |

TABLE 3-continued
Substituted 2,5-diaminoterephthalic acid dinitriles
| | | | | | | | |
|---|---|---|---|---|---|---|---|
| 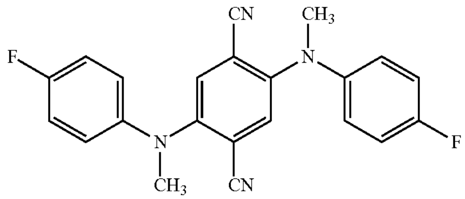 | 3.30 | 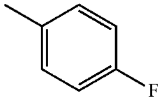 | $—CH_3$ | H | H | $—CH_3$ | 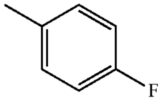 |
| 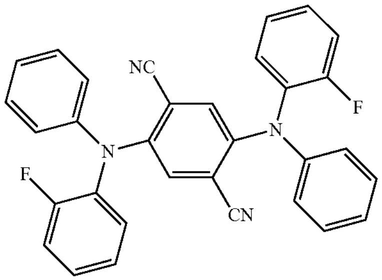 | 3.31 | 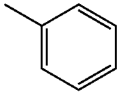 | 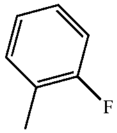 | H | H | 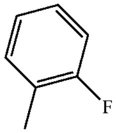 | 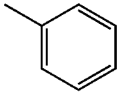 |
| 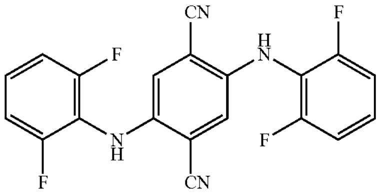 | 3.32 | 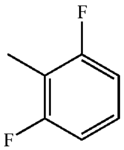 | H | H | H | H | 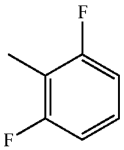 |
| 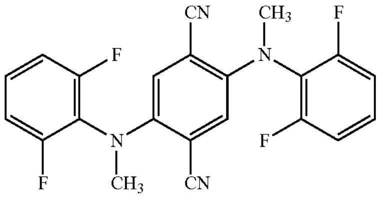 | 3.33 | 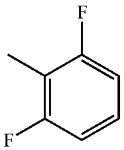 | $—CH_3$ | H | H | $—CH_3$ | 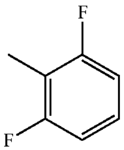 |

TABLE 3-continued
| Substituted 2,5-diaminoterephthalic acid dinitriles | | | | | | | |
|---|---|---|---|---|---|---|---|
| 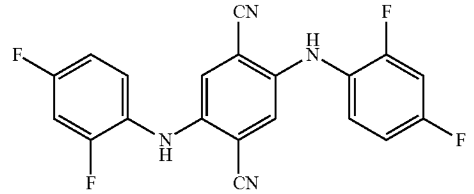 | 3.34 | 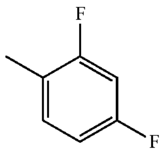 | H | H | H | H | 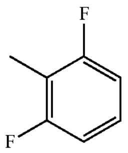 |
| 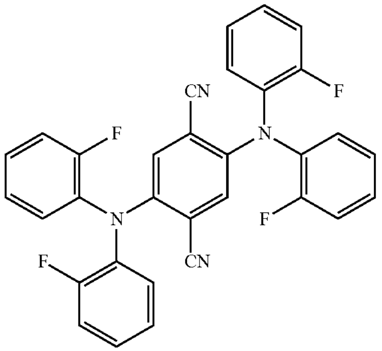 | 3.35 | 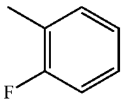 | 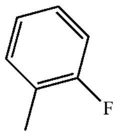 | H | H | 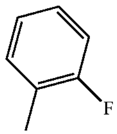 | 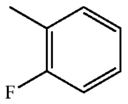 |
| 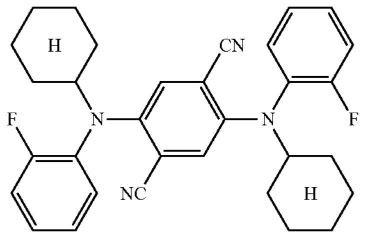 | 3.36 | 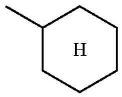 | 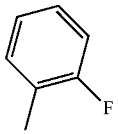 | H | H | 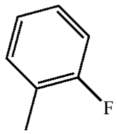 | 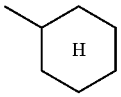 |

TABLE 3-continued
| Substituted 2,5-diaminoterephthalic acid dinitriles | | | | | | | |
|---|---|---|---|---|---|---|---|
| 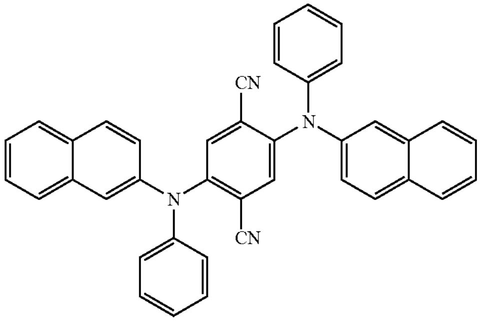 | 3.37 | 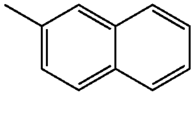 | 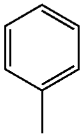 | H | H | 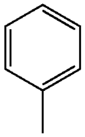 | 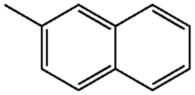 |
| 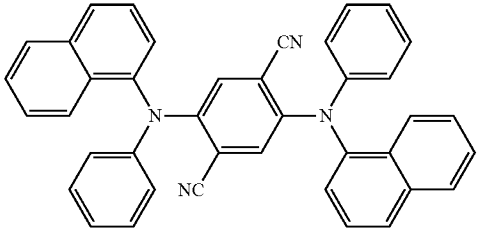 | 3.38 | 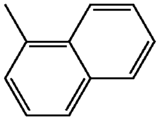 | 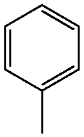 | H | H | 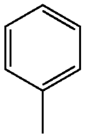 | 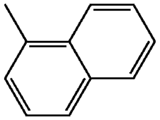 |
| 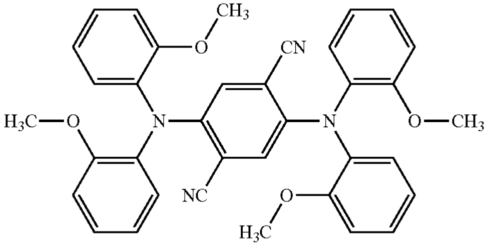 | 3.39 | 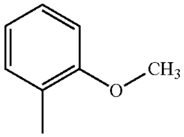 | 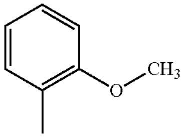 | H | H | 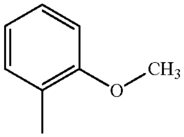 | 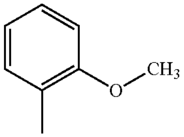 |
| 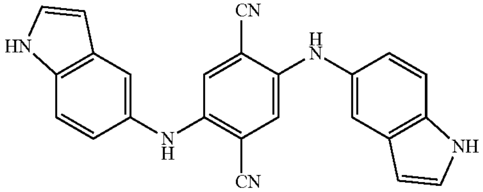 | 3.40 | 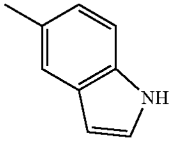 | H | H | H | H | 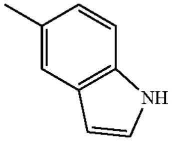 |

TABLE 3-continued
| Substituted 2,5-diaminoterephthalic acid dinitriles | | | | | | |
|---|---|---|---|---|---|---|
| 3.41 | 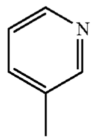 | —$CH_3$ | H | H | —$CH_3$ | 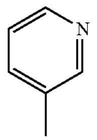 |
| 3.42 | 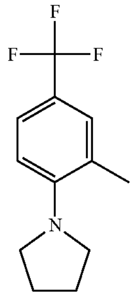 | —$CH_3$ | H | H | —$CH_3$ | 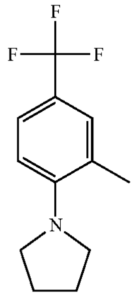 |
| 3.43 | 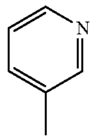 | —$CH_3$ | H | H | —$CH_3$ | 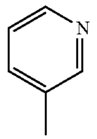 |
| 3.44 | 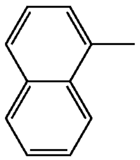 | —$CH_3$ | H | H | —$CH_3$ | 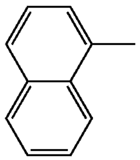 |
| 3.45 | 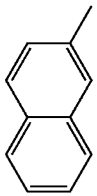 | —$CH_3$ | H | H | —$CH_3$ | 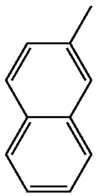 |

TABLE 3-continued
| Substituted 2,5-diaminoterephthalic acid dinitriles | | | | | | |
|---|---|---|---|---|---|---|
| 3.46 | 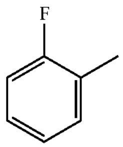 | —$CH_3$ | H | H | —$CH_3$ | 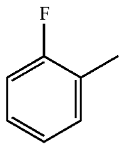 |
| 3.47 | 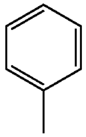 | —$CF_3$ | H | H | —$CF_3$ | 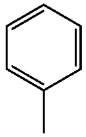 |
| 3.48 | 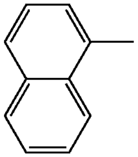 | —$CF_3$ | H | H | —$CF_3$ | 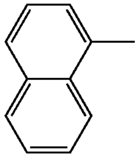 |
| 3.49 | 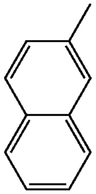 | —$CF_3$ | H | H | —$CF_3$ | 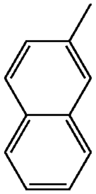 |
| 3.50 | 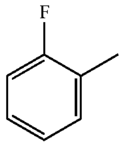 | —$CF_3$ | H | H | —$CF_3$ | 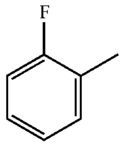 |

TABLE 3-continued
| Substituted 2,5-diaminoterephthalic acid dinitriles | | | | | | |
|---|---|---|---|---|---|---|
| 3.51 | 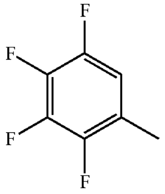 | —$CF_3$ | H | H | —$CF_3$ | 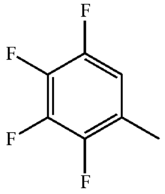 |
| 3.52 | 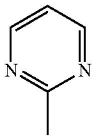 | —$CF_3$ | H | H | —$CF_3$ | 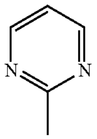 |
| 3.53 | 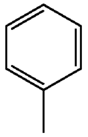 | 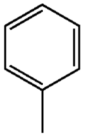 | H | H | 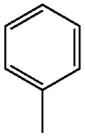 | 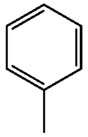 |
| 3.54 | 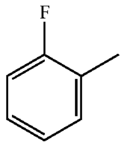 | 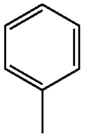 | H | H | 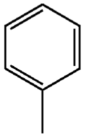 | 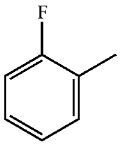 |
| 3.55 | 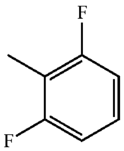 | 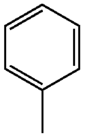 | H | H | 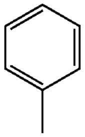 | 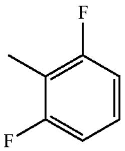 |
| 3.56 | 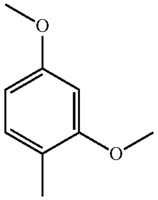 | 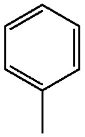 | H | H | 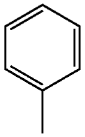 | 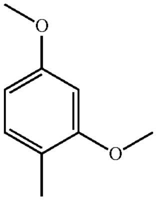 |

TABLE 3-continued
Substituted 2,5-diaminoterephthalic acid dinitriles
| | | | | | | |
|---|---|---|---|---|---|---|
| 3.57 | 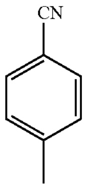 | 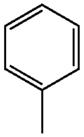 | H | H | 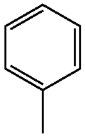 | 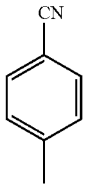 |
| 3.58 | 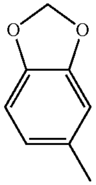 | 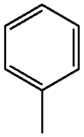 | H | H | 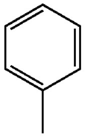 | 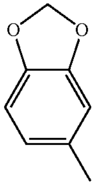 |
| 3.59 | 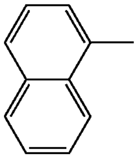 | 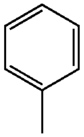 | H | H | 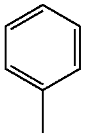 | 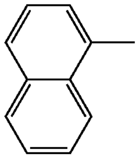 |
| 3.60 | 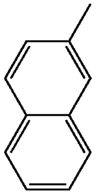 | 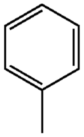 | H | H | 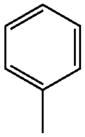 | 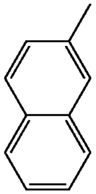 |
| 3.61 | 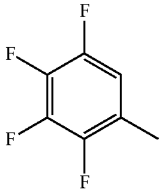 | 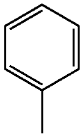 | H | H | 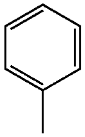 | 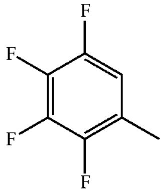 |

TABLE 3-continued
| Substituted 2,5-diaminoterephthalic acid dinitriles | | | | | | |
|---|---|---|---|---|---|---|
| 3.62 | 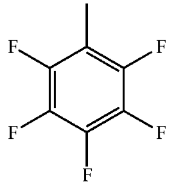 | —$CH_3$ | H | H | —$CH_3$ | 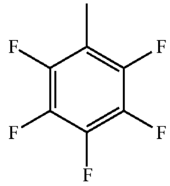 |
| 3.63 | 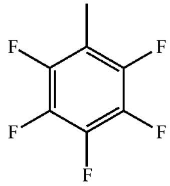 | 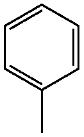 | H | H | 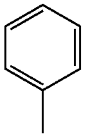 | 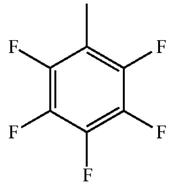 |
| 3.64 | 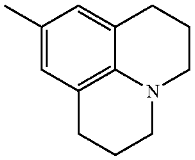 | 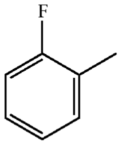 | H | H | 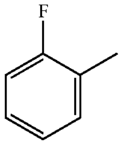 | 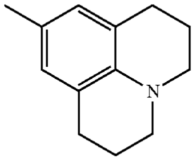 |
| 3.65 | 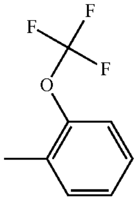 | 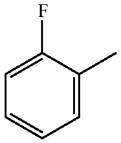 | H | H | 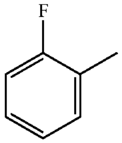 | 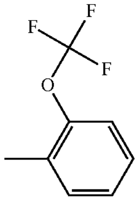 |
| 3.66 | 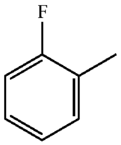 | 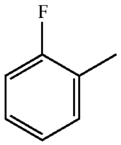 | H | H | 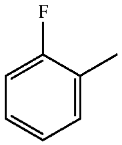 | 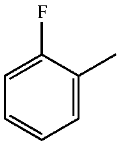 |

TABLE 3-continued
Substituted 2,5-diaminoterephthalic acid dinitriles
| | | | | | | |
|---|---|---|---|---|---|---|
| 3.67 | 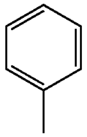 | H | H | H | H | 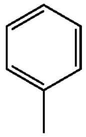 |
| 3.68 | 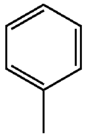 | 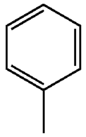 | H | H | 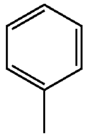 | 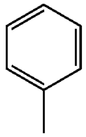 |
| 3.69 | 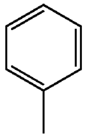 | $—CH_3$ | 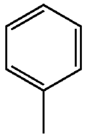 | 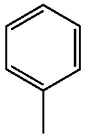 | $—CH_3$ | 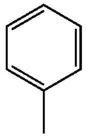 |
| 3.70 | 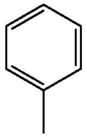 | 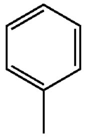 | 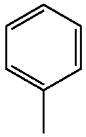 | 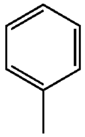 | 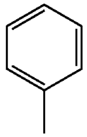 | 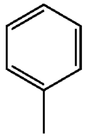 |
| 3.71 | 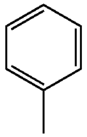 | 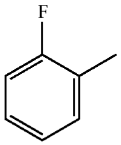 | 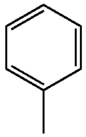 | 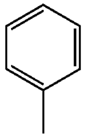 | 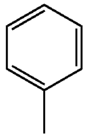 | 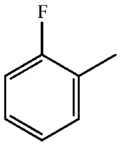 |

TABLE 3-continued
| Substituted 2,5-diaminoterephthalic acid dinitriles | | | | | | | |
|---|---|---|---|---|---|---|---|
| Substance | | $R^2$ | $R^3$ | $R^4$ | $R^6$ | $R^7$ | $R^8$ |
| 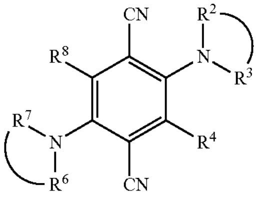 | 48.0 | | | | | | |
| | 48.1 | 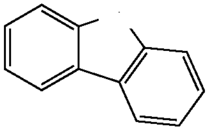 | | H | 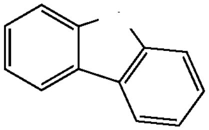 | | H |
| | 48.2 | 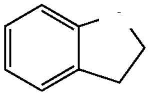 | | H | 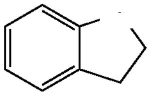 | | H |
| | 48.3 | 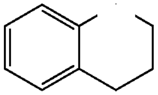 | | H | 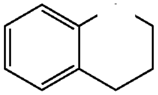 | | H |
| | 48.4 | 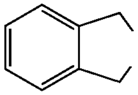 | | H | 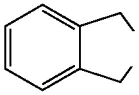 | | H |
| 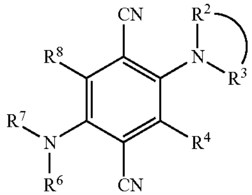 | 44.0 | | | | | | |

TABLE 3-continued
Substituted 2,5-diaminoterephthalic acid dinitriles
| Substance | | $R^8$ | $R^2$ | $R^3$ | $R^6$ | $R^7$ | $R^4$ |
|---|---|---|---|---|---|---|---|
| | 44.1 | 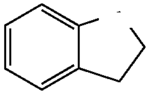 | | H | —$CH_3$ | 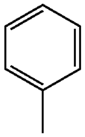 | H |
| | 44.2 | 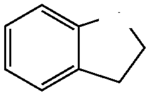 | | H | 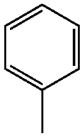 | 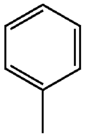 | H |
| | 44.3 | 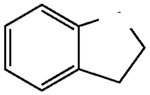 | | 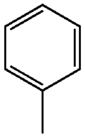 | 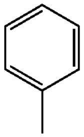 | 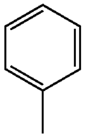 | H |
| 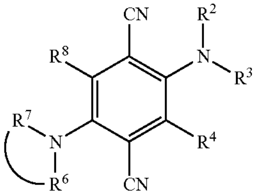 | 46.0 | | | | | | |
| | 46.1 | H | —$CH_3$ | 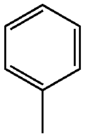 | 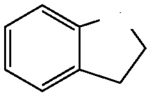 | | H |
| | 46.2 | H | 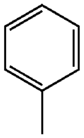 | 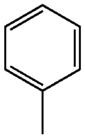 | 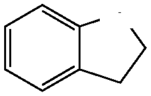 | | H |

TABLE 3-continued
| Substituted 2,5-diaminoterephthalic acid dinitriles | | | | | | | |
|---|---|---|---|---|---|---|---|
| Substance | | $R^4$ | $R^3$ | $R^2$ | $R^8$ | $R^7$ | $R^6$ |
| 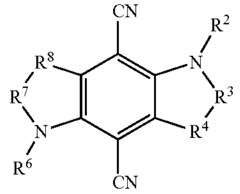 | 49.0 | | | | | | |
| | 49.1 | | 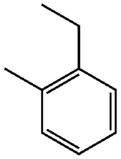 | 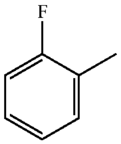 | | 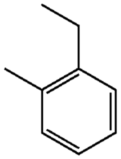 | 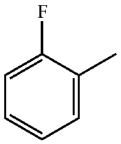 |
| 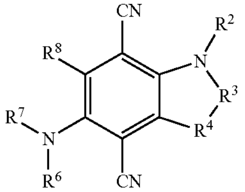 | 45.0 | | | | | | |
| | 45.1 | | 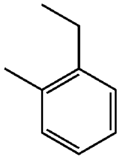 | 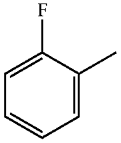 | H | 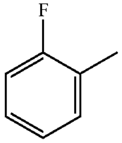 | 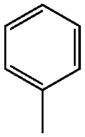 |

TABLE 3-continued
| Substituted 2,5-diaminoterephthalic acid dinitriles | | | | | |
|---|---|---|---|---|---|
| 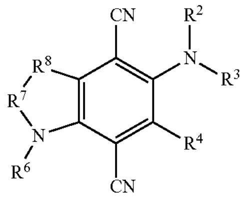 | 47.0 | | | | |
| | 47.1 | H | 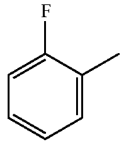 | 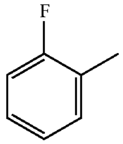 | 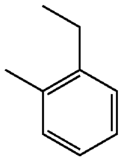 |

TABLE 4
| Substituted 2,5-diamino-3,6-dihydroterephthalic acid dinitriles | | | | | | | | | |
|---|---|---|---|---|---|---|---|---|---|
| Substance | | $R^3$ | $R^2$ | $R^4$ | $R^{4'}$ | $R^8$ | $R^{8'}$ | $R^6$ | $R^7$ |
| 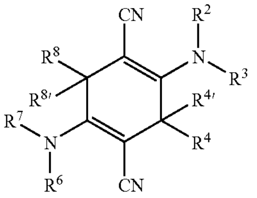 | 4.0 | | | $-CH_3$ | $-CH_3$ | $-CH_3$ | $-CH_3$ | | |
| 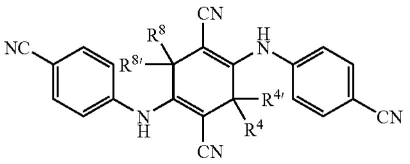 | 4.1 | 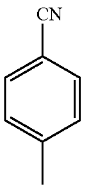 | H | $-CH_3$ | $-CH_3$ | $-CH_3$ | $-CH_3$ | H | 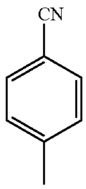 |
| 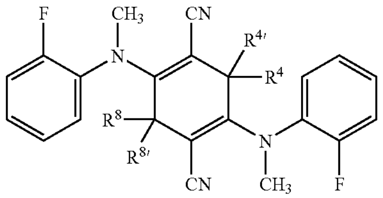 | 4.2 | 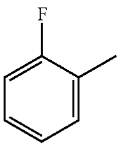 | $-CH_3$ | $-CH_3$ | $-CH_3$ | $-CH_3$ | $-CH_3$ | $-CH_3$ | 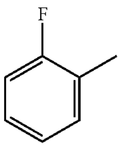 |
| 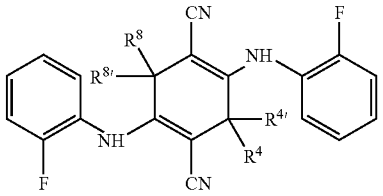 | 4.3 | 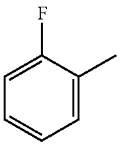 | H | $-CH_3$ | $-CH_3$ | $-CH_3$ | $-CH_3$ | H | 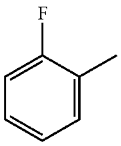 |
| Substance | | $R^3$ | $R^2$ |
|---|---|---|---|
| 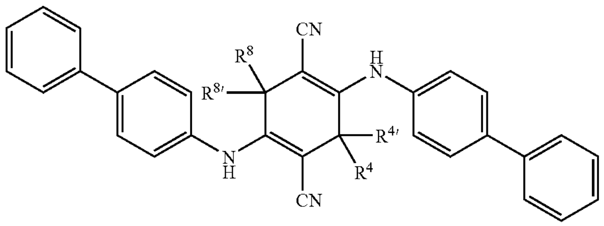 | 4.4 | 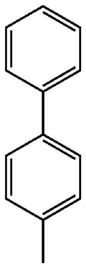 | H |
| 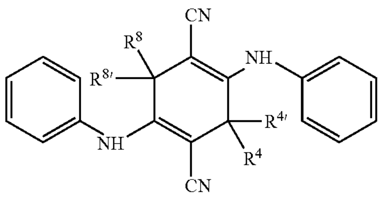 | 4.5 | 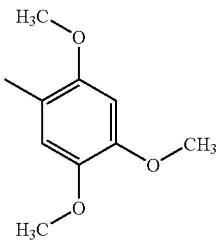 | H |

TABLE 4-continued
| Substituted 2,5-diamino-3,6-dihydroterephthalic acid dinitriles | | | |
|---|---|---|---|
| 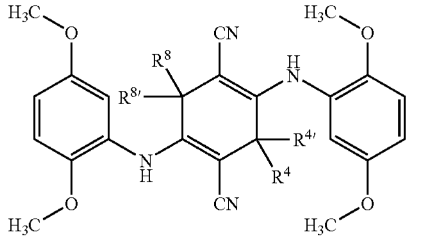 | 4.6 | 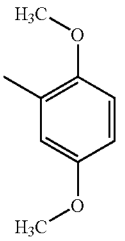 | H |
| 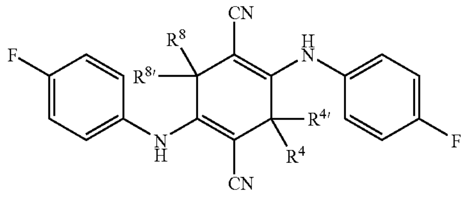 | 4.7 | 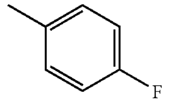 | H |
| 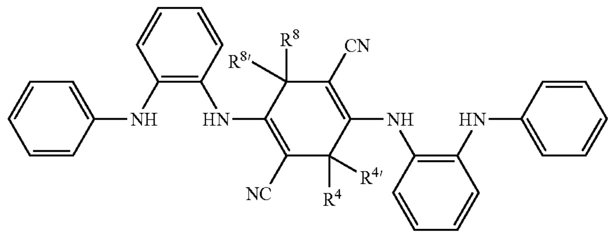 | 4.8 | 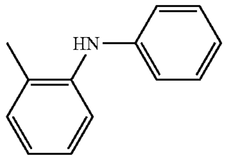 | H |
| 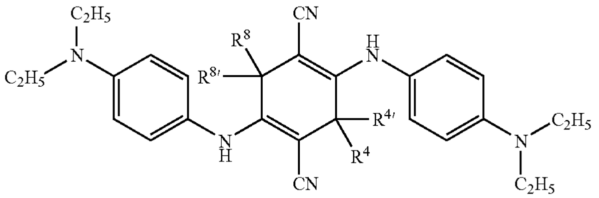 | 4.9 | 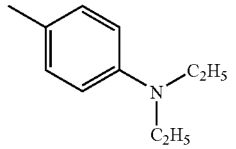 | H |
| 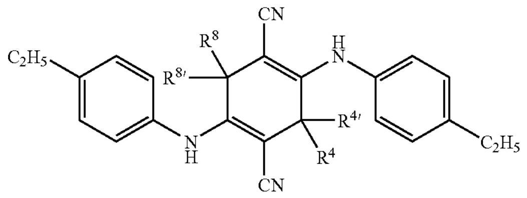 | 4.10 | 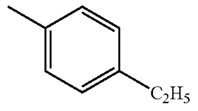 | H |
| 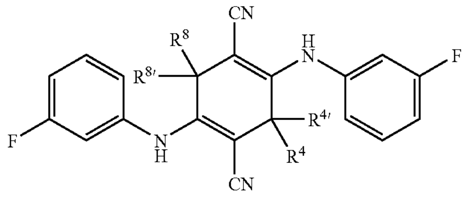 | 4.11 | 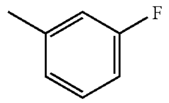 | H |
| 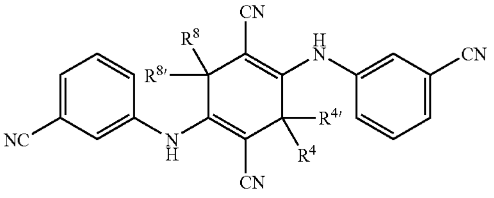 | 4.12 | 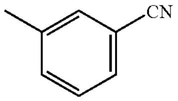 | H |

TABLE 4-continued
| Substituted 2,5-diamino-3,6-dihydroterephthalic acid dinitriles | | | |
|---|---|---|---|
| 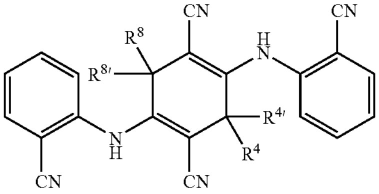 | 4.13 | 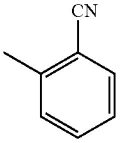 | H |
| 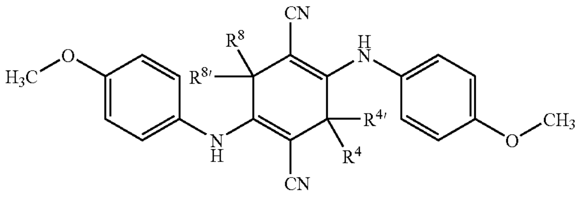 | 4.14 | 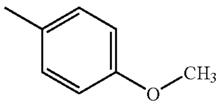 | H |
| 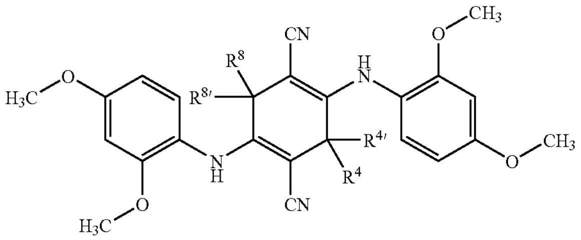 | 4.15 | 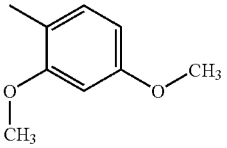 | H |
| 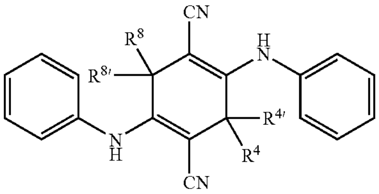 | 4.16 | 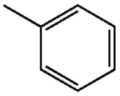 | H |
| 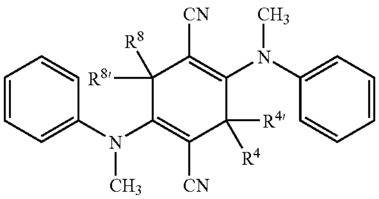 | 4.17 | 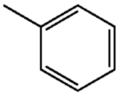 | —$CH_3$ |
| 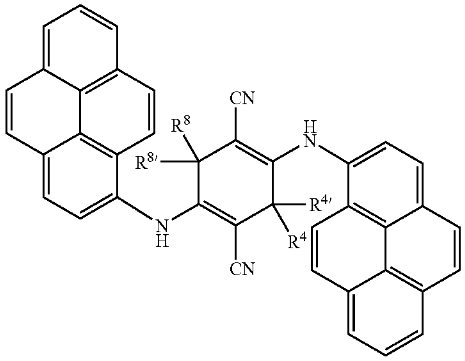 | 4.18 | 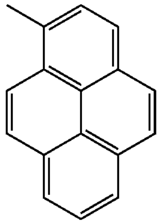 | H |

TABLE 4-continued
Substituted 2,5-diamino-3,6-dihydroterephthalic acid dinitriles
| | | | |
|---|---|---|---|
| 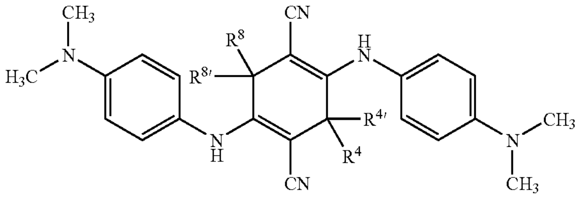 | 4.19 | 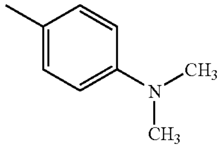 | H |
| 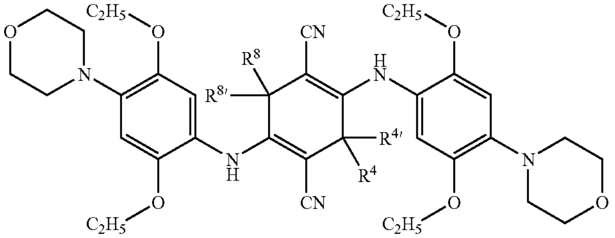 | 4.20 | 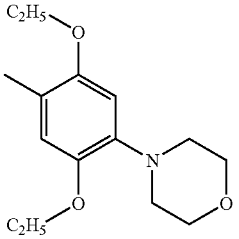 | H |
| 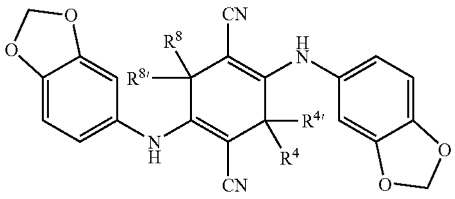 | 4.21 | 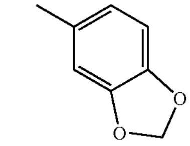 | H |
| 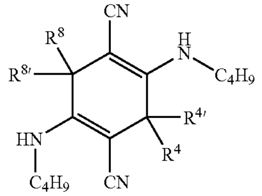 | 4.22 | $-C_4H_9$ | H |
| 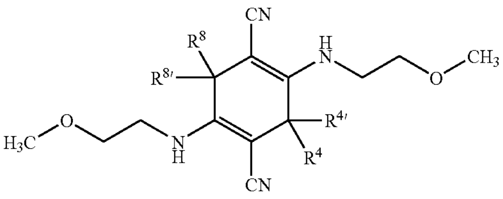 | 4.23 | 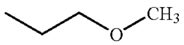 | H |
| 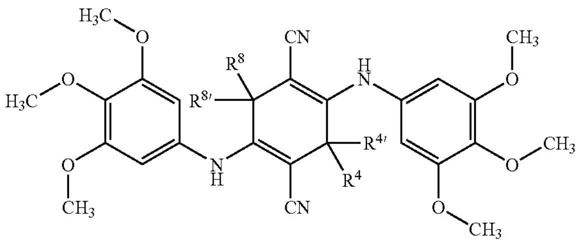 | 4.24 | 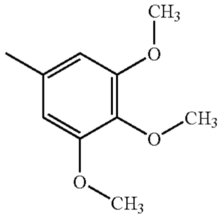 | H |
| 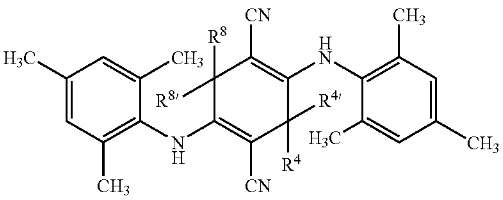 | 4.25 | 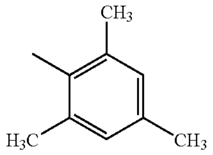 | H |

TABLE 4-continued
| Substituted 2,5-diamino-3,6-dihydroterephthalic acid dinitriles | | | |
|---|---|---|---|
| 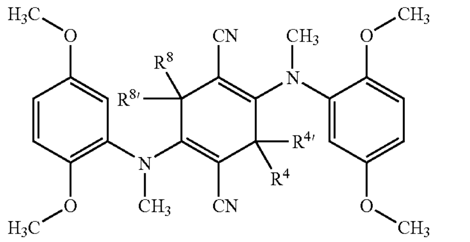 | 4.26 | 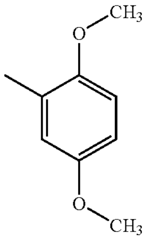 | —$CH_3$ |
| 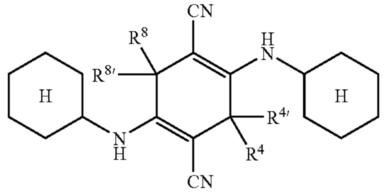 | 4.27 | 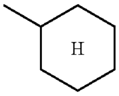 | H |
| 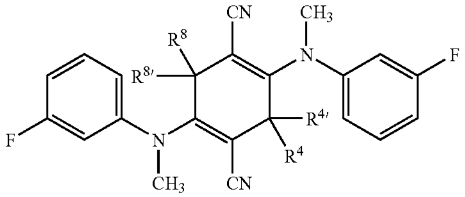 | 4.28 | 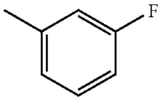 | —$CH_3$ |
| 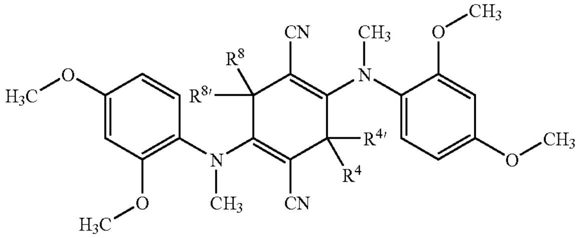 | 4.29 | 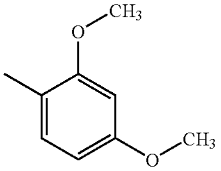 | —$CH_3$ |
| 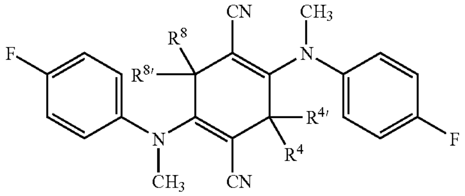 | 4.30 | 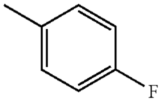 | —$CH_3$ |
| 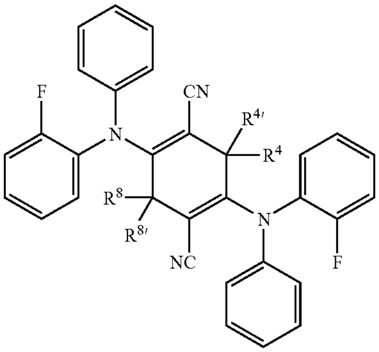 | 4.31 | 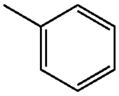 | 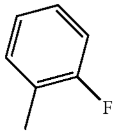 |

TABLE 4-continued
Substituted 2,5-diamino-3,6-dihydroterephthalic acid dinitriles
| | | | |
|---|---|---|---|
| 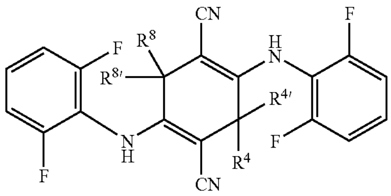 | | 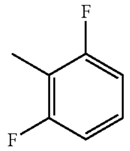 | H |
| 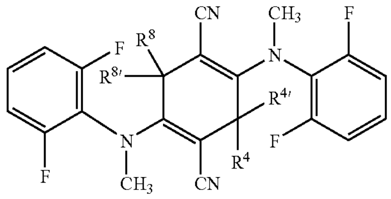 | 4.32 | 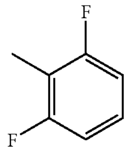 | —$CH_3$ |
| 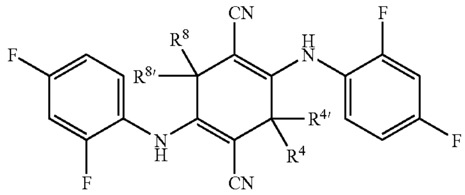 | 4.33 | 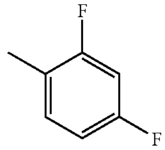 | H |
| 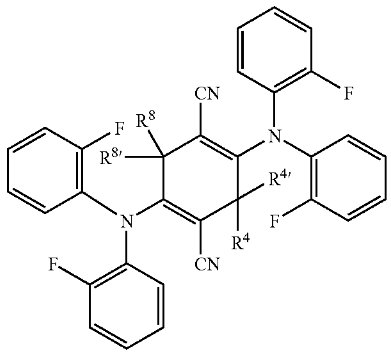 | 4.34 | 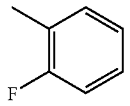 | 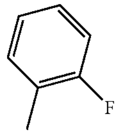 |
| 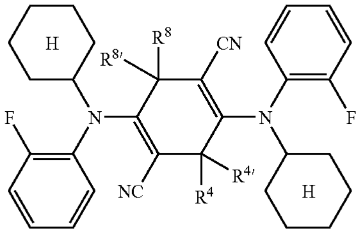 | 4.35 | 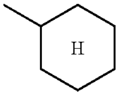 | 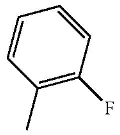 |
| 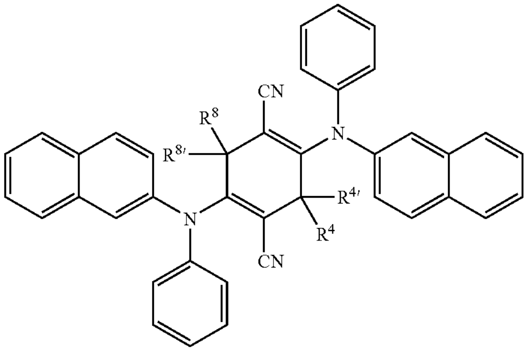 | 4.36 | 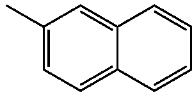 | 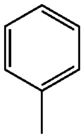 |

TABLE 4-continued
Substituted 2,5-diamino-3,6-dihydroterephthalic acid dinitriles
| | | | |
|---|---|---|---|
| 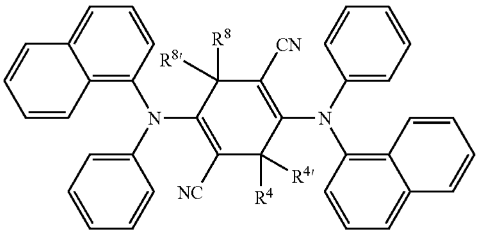 | 4.37 | 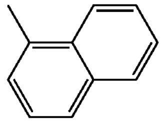 | 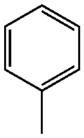 |
| 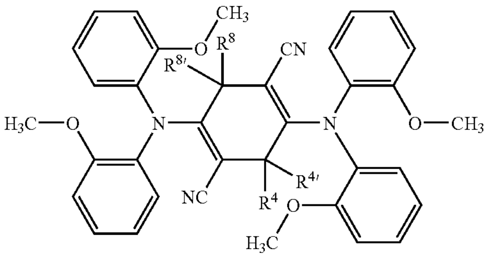 | 4.38 | 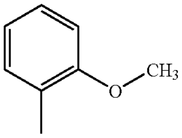 | 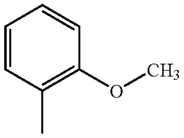 |
| 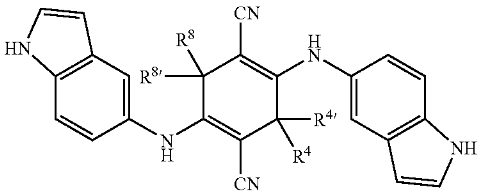 | 4.39 | 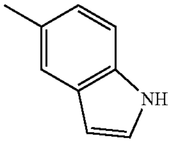 | H |
| | 4.40 | 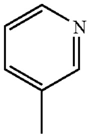 | $—CH_3$ |
| | 4.41 | 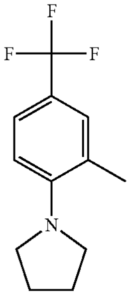 | $—CH_3$ |
| | 4.42 | 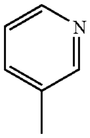 | $—CH_3$ |
| | 4.43 | 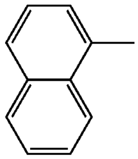 | $—CH_3$ |

TABLE 4-continued
| Substituted 2,5-diamino-3,6-dihydroterephthalic acid dinitriles | | | |
|---|---|---|---|
| | 4.44 | 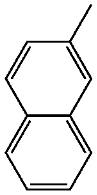 | —$CH_3$ |
| | 4.45 | 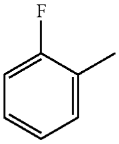 | —$CH_3$ |
| | 4.46 | 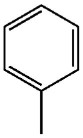 | —$CF_3$ |
| | 4.47 | 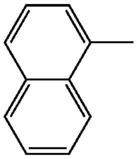 | —$CF_3$ |
| | 4.48 | 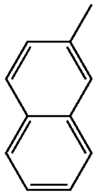 | —$CF_3$ |
| | 4.49 | 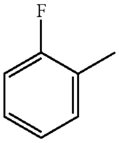 | —$CF_3$ |
| | 4.50 | 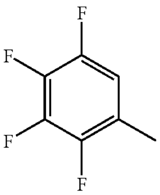 | —$CF_3$ |
| | 4.51 | 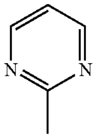 | —$CF_3$ |
| | 4.52 | 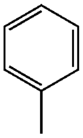 | 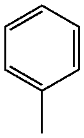 |

TABLE 4-continued
| Substituted 2,5-diamino-3,6-dihydroterephthalic acid dinitriles | | |
|---|---|---|
| 4.53 | 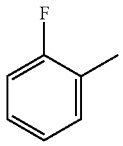 | 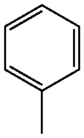 |
| 4.54 | 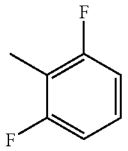 | 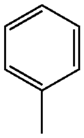 |
| 4.55 | 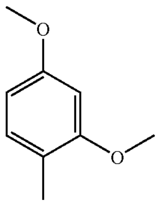 | 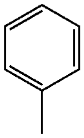 |
| 4.56 | 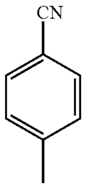 | 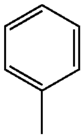 |
| 4.57 | 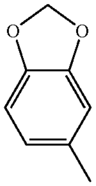 | 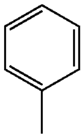 |
| 4.58 | 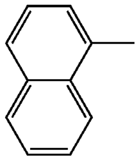 | 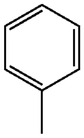 |
| 4.59 | 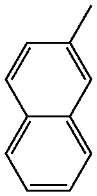 | 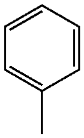 |
| 4.60 | 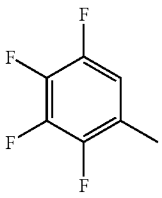 | 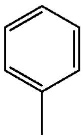 |

TABLE 4-continued
| Substituted 2,5-diamino-3,6-dihydroterephthalic acid dinitriles | | |
|---|---|---|
| 4.61 | 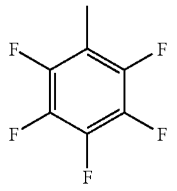 | $—CH_3$ |
| 4.62 | 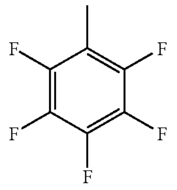 | 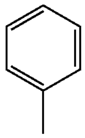 |
| 4.63 | 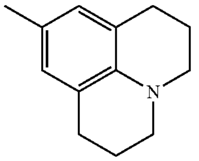 | 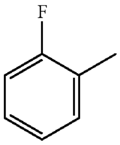 |
| 4.64 | 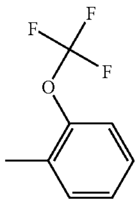 | 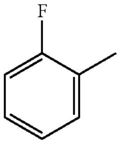 |
| 4.65 | 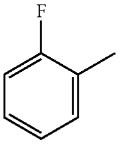 | 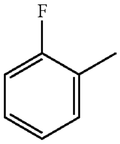 |
| 4.66 | 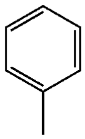 | H |
| 4.67 | 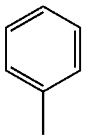 | 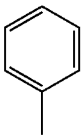 |
| 4.68 | 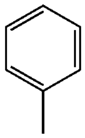 | $—CH_3$ |
| 4.69 | 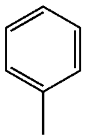 | 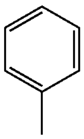 |

TABLE 4-continued
| Substituted 2,5-diamino-3,6-dihydroterephthalic acid dinitriles | | | | |
|---|---|---|---|---|
| | 4.70 | 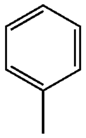 | | 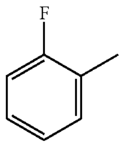 |
| Substance | | $R^4$ | $R^8$ | $R^6$ |
| 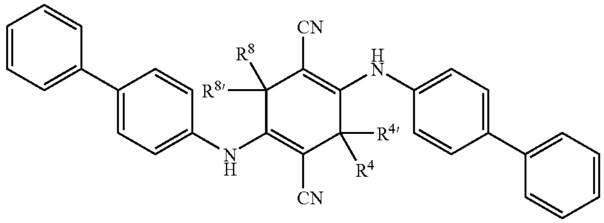 | 4.4 | $-CH_3$ | $-CH_3$ | H |
| 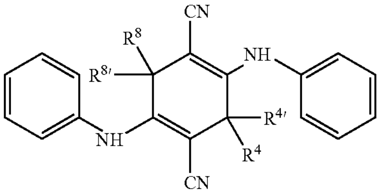 | 4.5 | $-CH_3$ | $-CH_3$ | H |
| 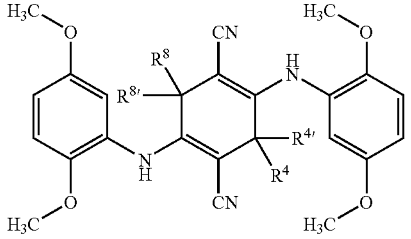 | 4.6 | $-CH_3$ | $-CH_3$ | H |
| 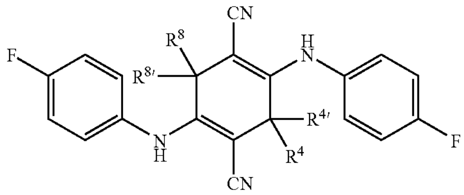 | 4.7 | $-CH_3$ | $-CH_3$ | H |
| 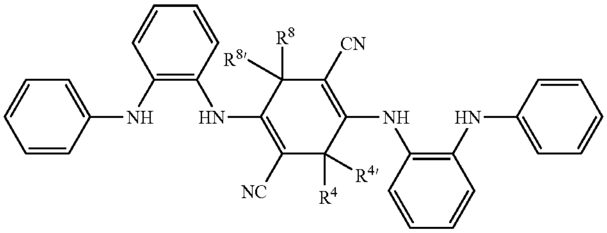 | 4.8 | $-CH_3$ | $-CH_3$ | H |
| 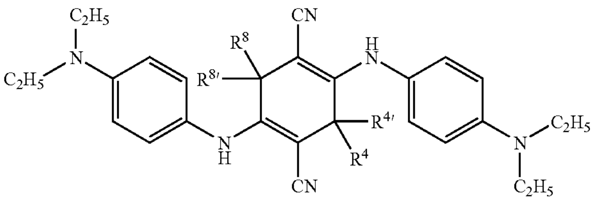 | 4.9 | $-CH_3$ | $-CH_3$ | H |

TABLE 4-continued
| Substituted 2,5-diamino-3,6-dihydroterephthalic acid dinitriles | | | | |
|---|---|---|---|---|
| 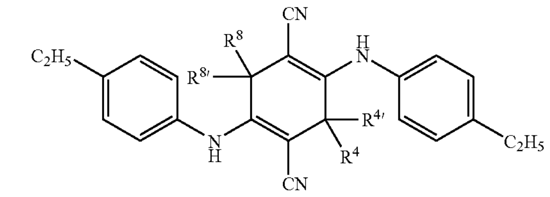 | 4.10 | $-CH_3$ | $-CH_3$ | H |
| 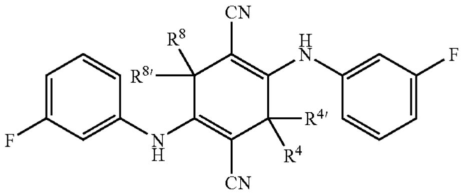 | 4.11 | $-CH_3$ | $-CH_3$ | H |
| 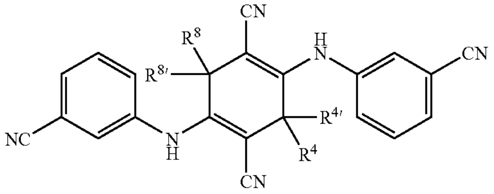 | 4.12 | $-CH_3$ | $-CH_3$ | H |
| 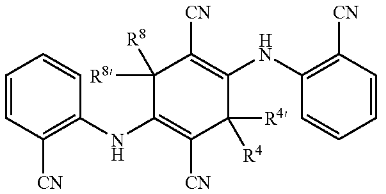 | 4.13 | $-CH_3$ | $-CH_3$ | H |
| 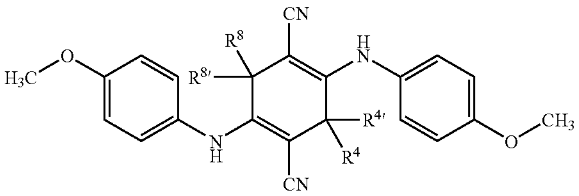 | 4.14 | $-CH_3$ | $-CH_3$ | H |
| 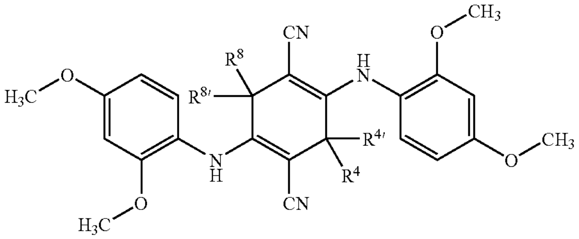 | 4.15 | $-CH_3$ | $-CH_3$ | H |
| 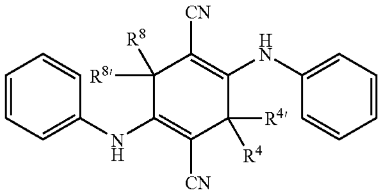 | 4.16 | $-CH_3$ | $-CH_3$ | H |

TABLE 4-continued
| Substituted 2,5-diamino-3,6-dihydroterephthalic acid dinitriles | | | | |
|---|---|---|---|---|
| 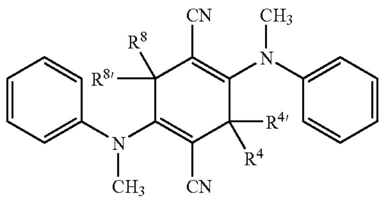 | 4.17 | —$CH_3$ | —$CH_3$ | —$CH_3$ |
| 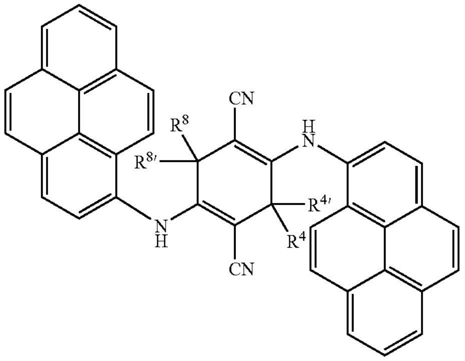 | 4.18 | —$CH_3$ | —$CH_3$ | H |
| 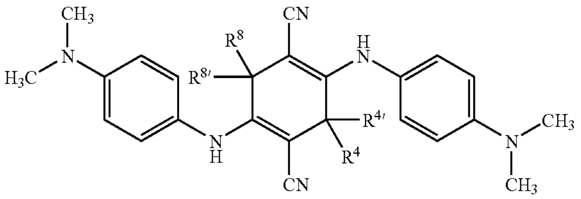 | 4.19 | —$CH_3$ | —$CH_3$ | H |
| 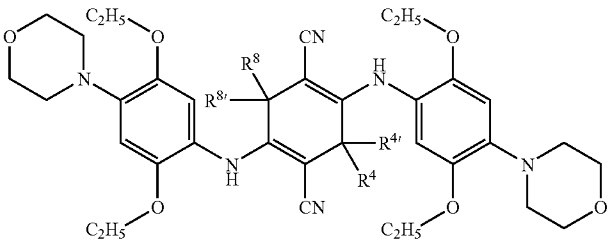 | 4.20 | —$CH_3$ | —$CH_3$ | H |
| 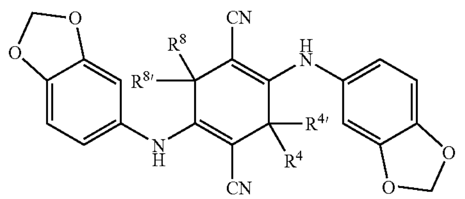 | 4.21 | —$CH_3$ | —$CH_3$ | H |
| 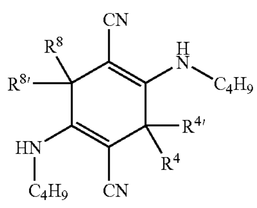 | 4.22 | —$CH_3$ | —$CH_3$ | H |

TABLE 4-continued
Substituted 2,5-diamino-3,6-dihydroterephthalic acid dinitriles
| | | | | |
|---|---|---|---|---|
| 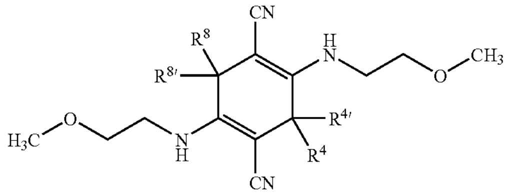 | 4.23 | —$CH_3$ | —$CH_3$ | H |
| 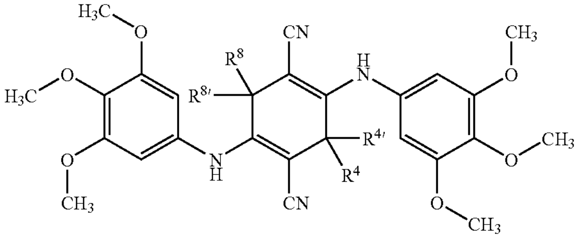 | 4.24 | —$CH_3$ | —$CH_3$ | H |
| 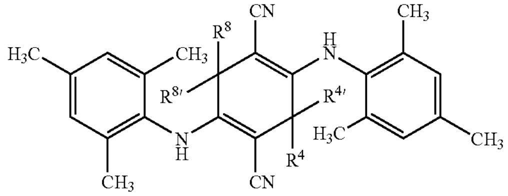 | 4.25 | —$CH_3$ | —$CH_3$ | H |
| 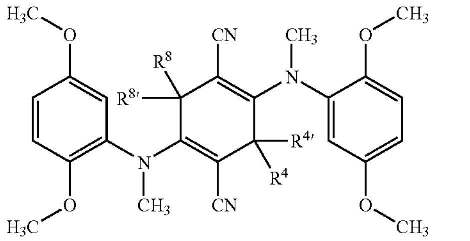 | 4.26 | —$CH_3$ | —$CH_3$ | —$CH_3$ |
| 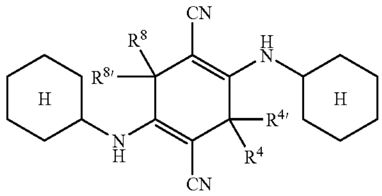 | 4.27 | —$CH_3$ | —$CH_3$ | H |
| 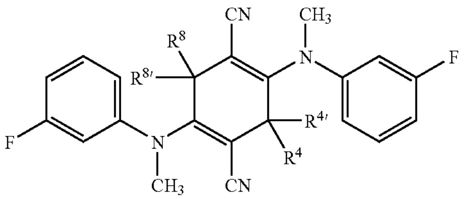 | 4.28 | —$CH_3$ | —$CH_3$ | —$CH_3$ |
| 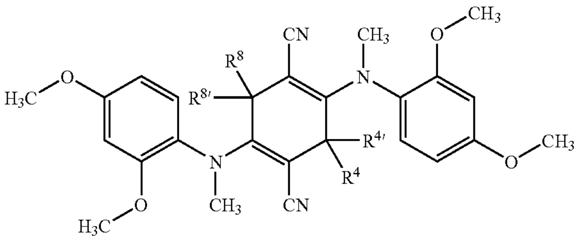 | 4.29 | —$CH_3$ | —$CH_3$ | —$CH_3$ |

TABLE 4-continued
Substituted 2,5-diamino-3,6-dihydroterephthalic acid dinitriles
| | | | | |
|---|---|---|---|---|
| 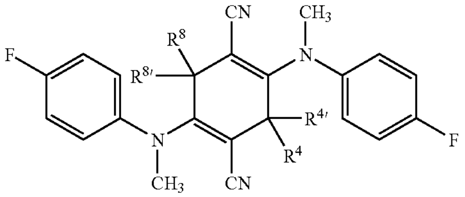 | 4.30 | —$CH_3$ | —$CH_3$ | —$CH_3$ |
| 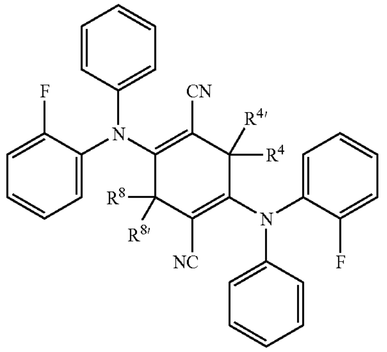 | 4.31 | —$CH_3$ | —$CH_3$ | 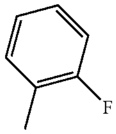 |
| 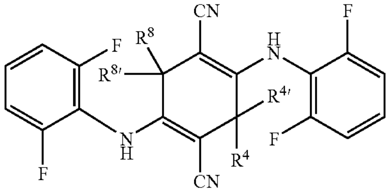 | | —$CH_3$ | —$CH_3$ | H |
| 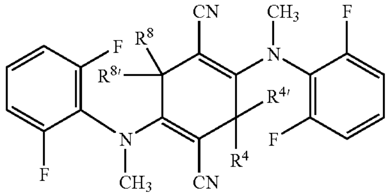 | 4.32 | —$CH_3$ | —$CH_3$ | —$CH_3$ |
| 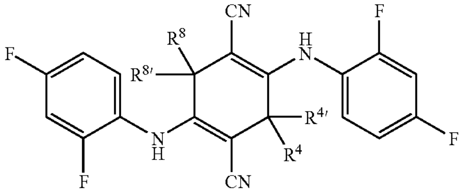 | 4.33 | —$CH_3$ | —$CH_3$ | H |
| 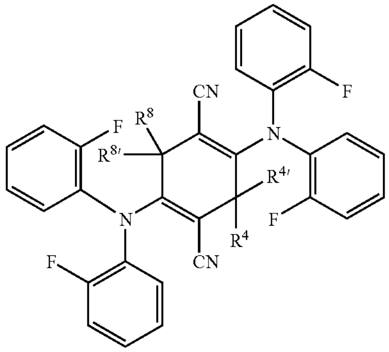 | 4.34 | —$CH_3$ | —$CH_3$ | 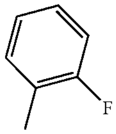 |

TABLE 4-continued
| Substituted 2,5-diamino-3,6-dihydroterephthalic acid dinitriles | | | | |
|---|---|---|---|---|
| 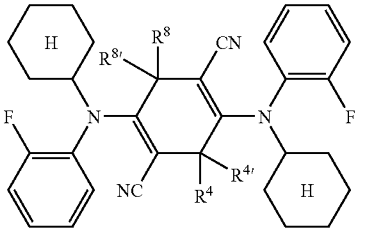 | 4.35 | —$CH_3$ | —$CH_3$ | 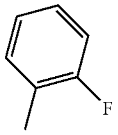 |
| 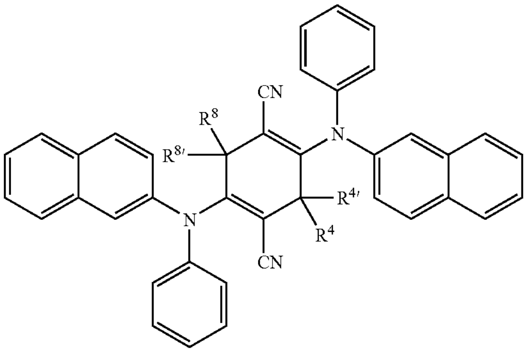 | 4.36 | —$CH_3$ | —$CH_3$ | 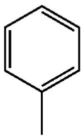 |
| 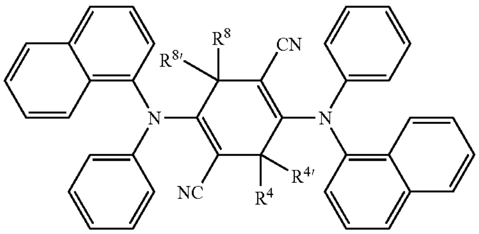 | 4.37 | —$CH_3$ | —$CH_3$ | 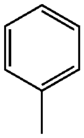 |
| 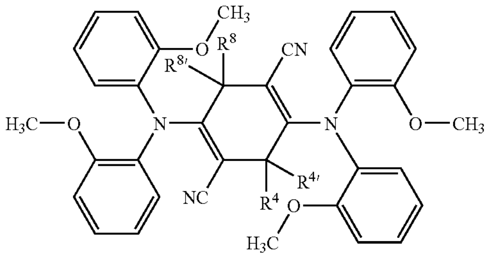 | 4.38 | —$CH_3$ | —$CH_3$ | 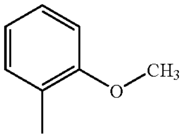 |
| 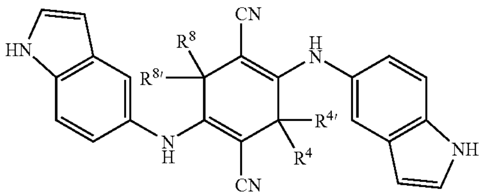 | 4.39 | —$CH_3$ | —$CH_3$ | H |
| | 4.40 | —$CH_3$ | —$CH_3$ | —$CH_3$ |
| | 4.41 | —$CH_3$ | —$CH_3$ | —$CH_3$ |
| | 4.42 | —$CH_3$ | —$CH_3$ | —$CH_3$ |
| | 4.43 | —$CH_3$ | —$CH_3$ | —$CH_3$ |
| | 4.44 | —$CH_3$ | —$CH_3$ | —$CH_3$ |
| | 4.45 | —$CH_3$ | —$CH_3$ | —$CH_3$ |
| | 4.46 | —$CH_3$ | —$CH_3$ | —$CF_3$ |
| | 4.47 | —$CH_3$ | —$CH_3$ | —$CF_3$ |
| | 4.48 | —$CH_3$ | —$CH_3$ | —$CF_3$ |
| | 4.49 | —$CH_3$ | —$CH_3$ | —$CF_3$ |
| | 4.50 | —$CH_3$ | —$CH_3$ | —$CF_3$ |
| | 4.51 | —$CH_3$ | —$CH_3$ | —$CF_3$ |

TABLE 4-continued
Substituted 2,5-diamino-3,6-dihydroterephthalic acid dinitriles
| | | | |
|---|---|---|---|
| 4.52 | $—CH_3$ | $—CH_3$ | 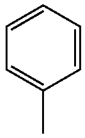 |
| 4.53 | $—CH_3$ | $—CH_3$ | 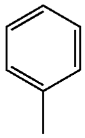 |
| 4.54 | $—CH_3$ | $—CH_3$ | 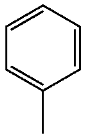 |
| 4.55 | $—CH_3$ | $—CH_3$ | 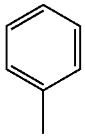 |
| 4.56 | $—CH_3$ | $—CH_3$ | 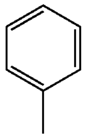 |
| 4.57 | $—CH_3$ | $—CH_3$ | 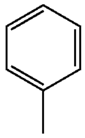 |
| 4.58 | $—CH_3$ | $—CH_3$ | 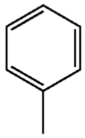 |
| 4.59 | $—CH_3$ | $—CH_3$ | 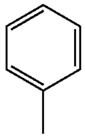 |
| 4.60 | $—CH_3$ | $—CH_3$ | 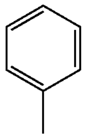 |
| 4.61 | $—CH_3$ | H | $—CH_3$ |
| 4.62 | $—CH_3$ | H | 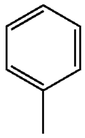 |

TABLE 4-continued
| Substituted 2,5-diamino-3,6-dihydroterephthalic acid dinitriles | | | | |
|---|---|---|---|---|
| | 4.63 | —$CH_3$ | H | 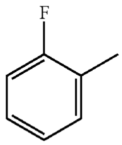 |
| | 4.64 | —$CH_3$ | H | 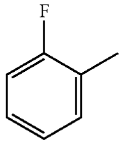 |
| | 4.65 | —$CH_3$ | H | 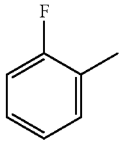 |
| | 4.66 | —$CH_3$ | H | H |
| | 4.67 | —$CH_3$ | H | 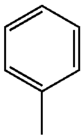 |
| | 4.68 | 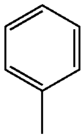 | 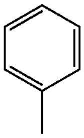 | —$CH_3$ |
| | 4.69 | 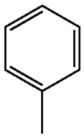 | 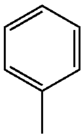 | 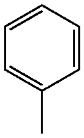 |
| | 4.70 | 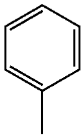 | 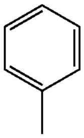 | 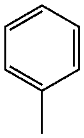 |
| Substance | | $R^7$ | $R^{4'}$ | $R^{8'}$ |
|---|---|---|---|---|
| 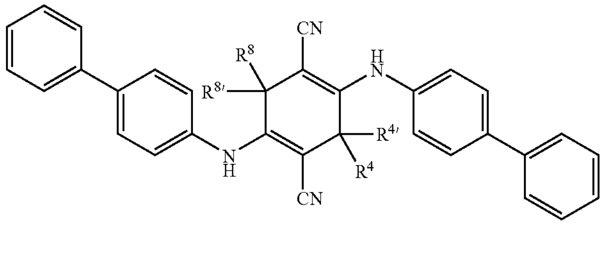 | 4.4 | 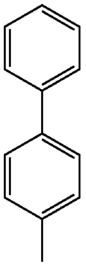 | —$CH_3$ | —$CH_3$ |

TABLE 4-continued
Substituted 2,5-diamino-3,6-dihydroterephthalic acid dinitriles
| | | | | |
|---|---|---|---|---|
| 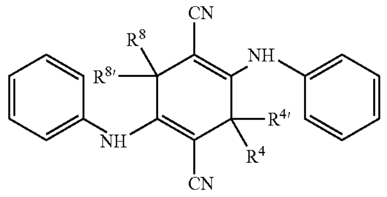 | 4.5 | 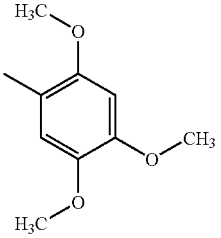 | $—CH_3$ | $—CH_3$ |
| 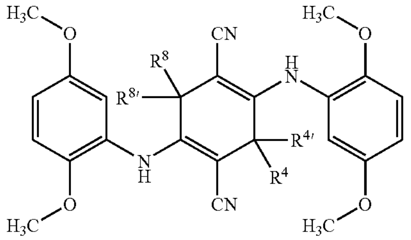 | 4.6 | 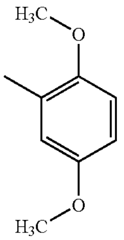 | $—CH_3$ | $—CH_3$ |
| 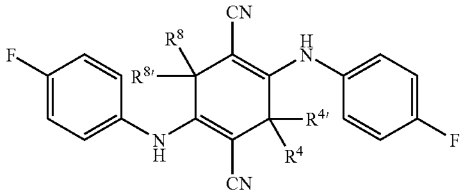 | 4.7 | 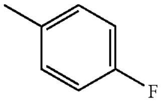 | $—CH_3$ | $—CH_3$ |
| 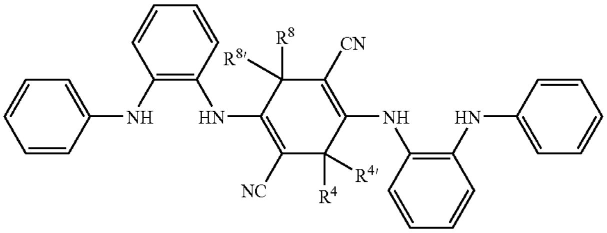 | 4.8 | 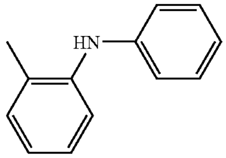 | $—CH_3$ | $—CH_3$ |
| 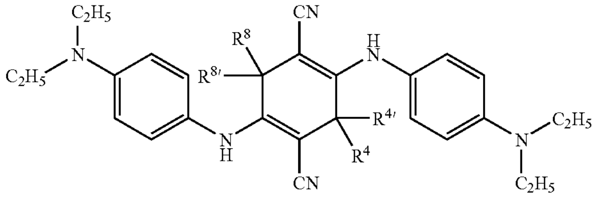 | 4.9 | 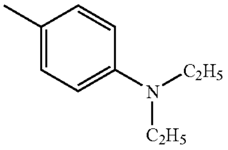 | $—CH_3$ | $—CH_3$ |
| 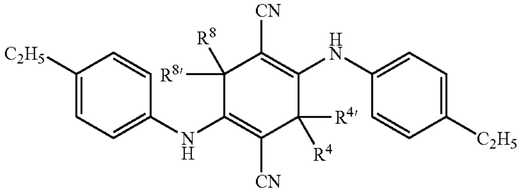 | 4.10 | 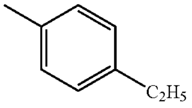 | $—CH_3$ | $—CH_3$ |
| 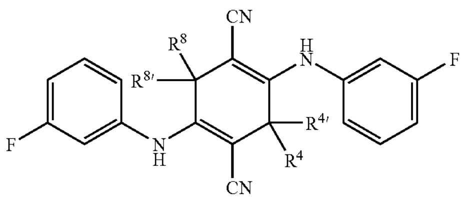 | 4.11 | 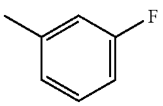 | $—CH_3$ | $—CH_3$ |

TABLE 4-continued
Substituted 2,5-diamino-3,6-dihydroterephthalic acid dinitriles
| | | | | |
|---|---|---|---|---|
| 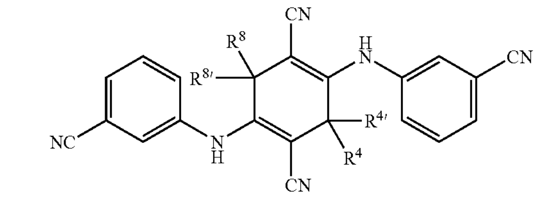 | 4.12 | 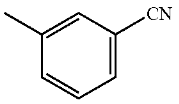 | —$CH_3$ | —$CH_3$ |
| 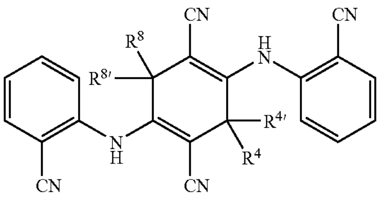 | 4.13 | 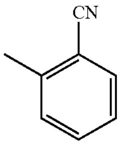 | —$CH_3$ | —$CH_3$ |
| 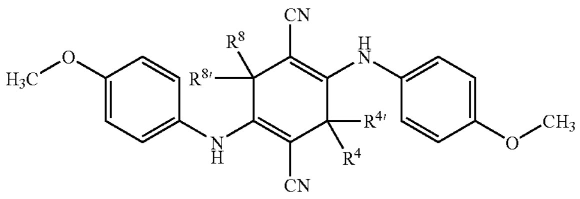 | 4.14 | 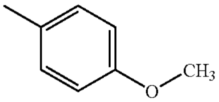 | —$CH_3$ | —$CH_3$ |
| 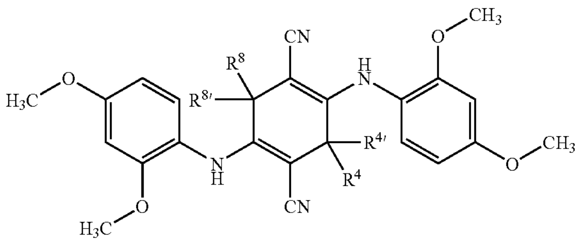 | 4.15 | 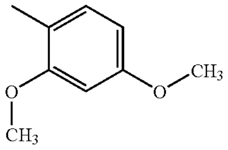 | —$CH_3$ | —$CH_3$ |
| 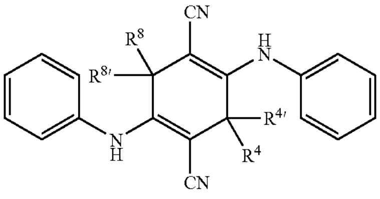 | 4.16 | 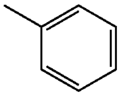 | —$CH_3$ | —$CH_3$ |
| 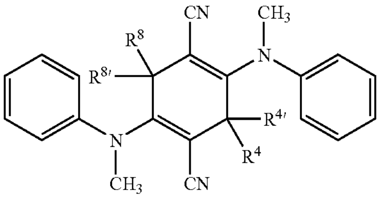 | 4.17 | 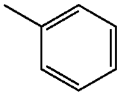 | —$CH_3$ | —$CH_3$ |

TABLE 4-continued
Substituted 2,5-diamino-3,6-dihydroterephthalic acid dinitriles
| | | | | |
|---|---|---|---|---|
| 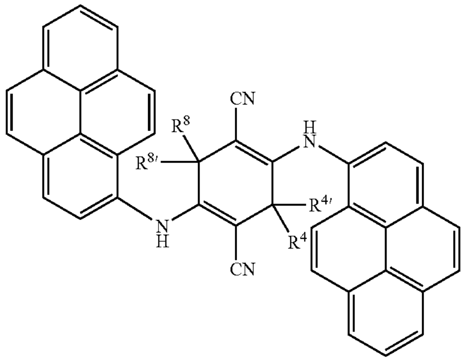 | 4.18 | 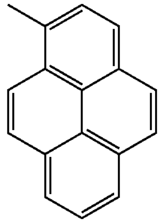 | —$CH_3$ | —$CH_3$ |
| 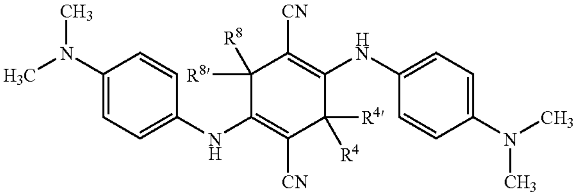 | 4.19 | 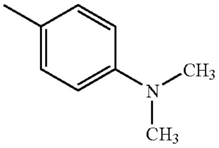 | —$CH_3$ | —$CH_3$ |
| 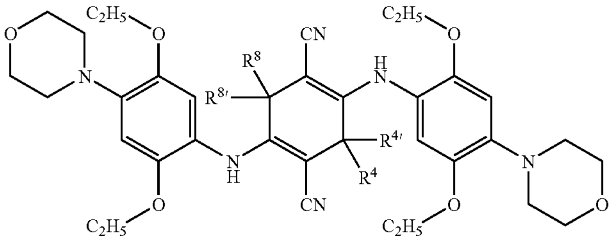 | 4.20 | 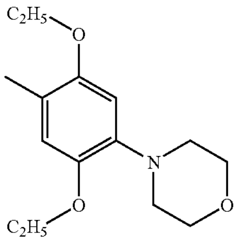 | —$CH_3$ | —$CH_3$ |
| 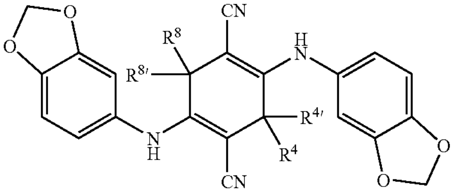 | 4.21 | 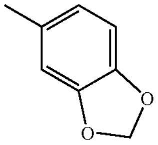 | —$CH_3$ | —$CH_3$ |
| 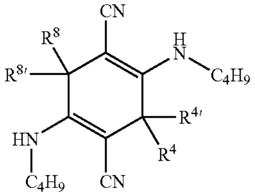 | 4.22 | —$C_4H_9$ | —$CH_3$ | —$CH_3$ |
| 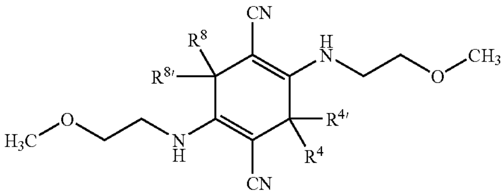 | 4.23 | 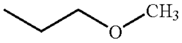 | —$CH_3$ | —$CH_3$ |

TABLE 4-continued
| Substituted 2,5-diamino-3,6-dihydroterephthalic acid dinitriles | | | | |
|---|---|---|---|---|
| 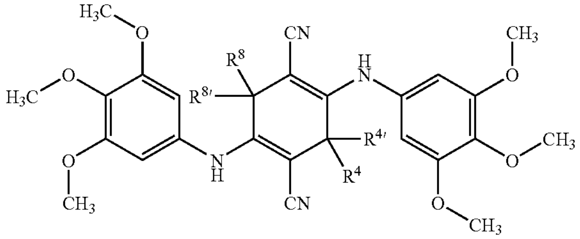 | 4.24 | 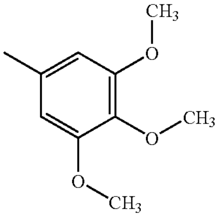 | —CH$_3$ | —CH$_3$ |
| 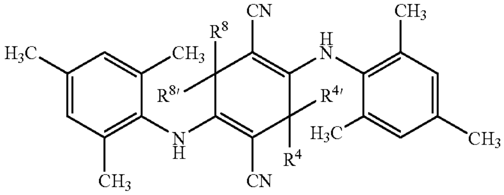 | 4.25 | 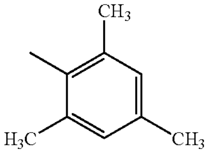 | —CH$_3$ | —CH$_3$ |
| 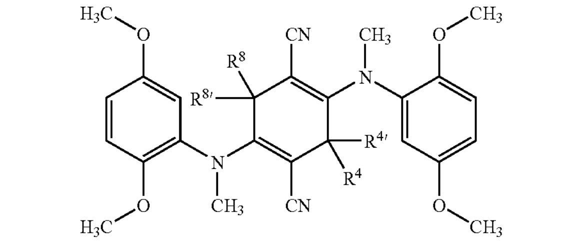 | 4.26 | 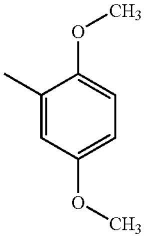 | —CH$_3$ | —CH$_3$ |
| 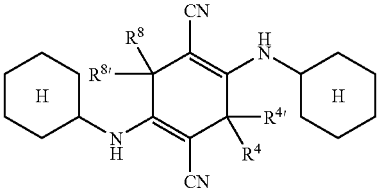 | 4.27 | 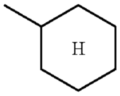 | —CH$_3$ | —CH$_3$ |
| 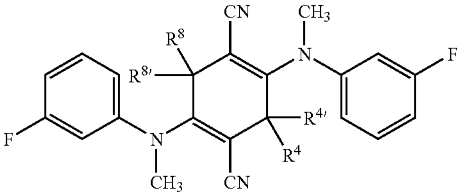 | 4.28 | 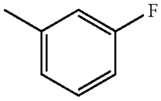 | —CH$_3$ | —CH$_3$ |
| 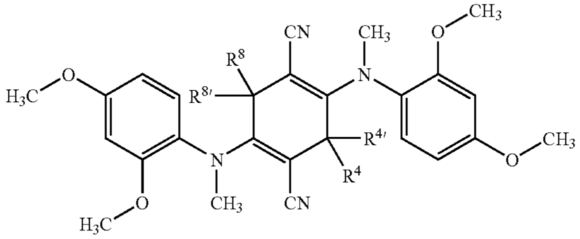 | 4.29 | 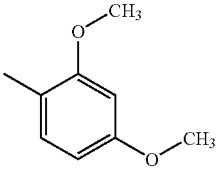 | —CH$_3$ | —CH$_3$ |
| 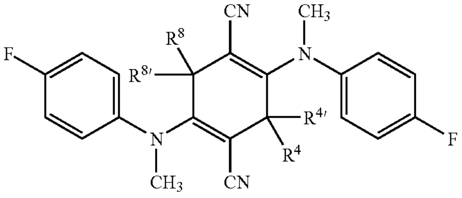 | 4.30 | 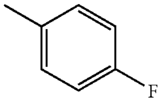 | —CH$_3$ | —CH$_3$ |

TABLE 4-continued
Substituted 2,5-diamino-3,6-dihydroterephthalic acid dinitriles
| | | | | |
|---|---|---|---|---|
| 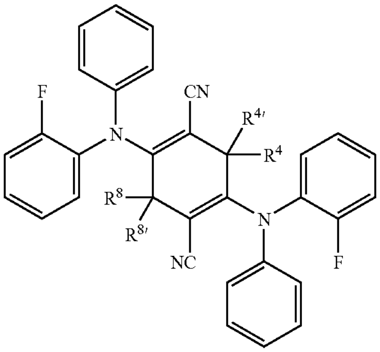 | 4.31 | 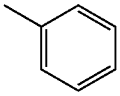 | —$CH_3$ | —$CH_3$ |
| 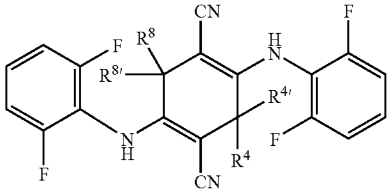 | | 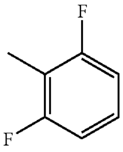 | —$CH_3$ | —$CH_3$ |
| 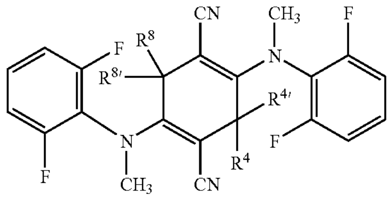 | 4.32 | 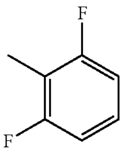 | —$CH_3$ | —$CH_3$ |
| 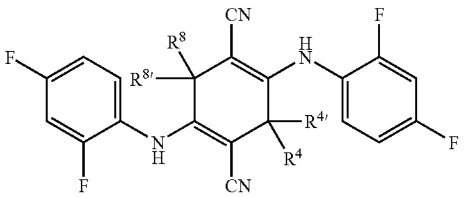 | 4.33 | 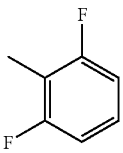 | —$CH_3$ | —$CH_3$ |
| 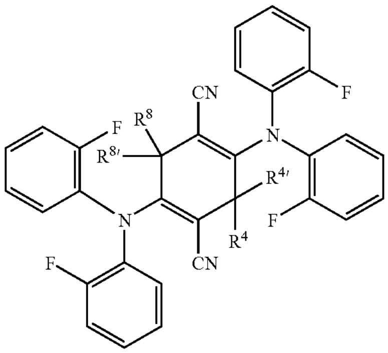 | 4.34 | 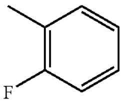 | —$CH_3$ | —$CH_3$ |

TABLE 4-continued
| Substituted 2,5-diamino-3,6-dihydroterephthalic acid dinitriles | | | | |
|---|---|---|---|---|
| 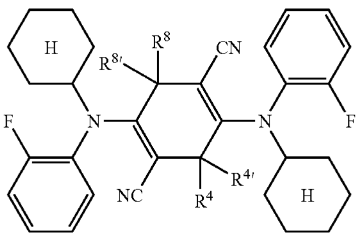 | 4.35 | 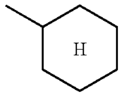 | —$CH_3$ | —$CH_3$ |
| 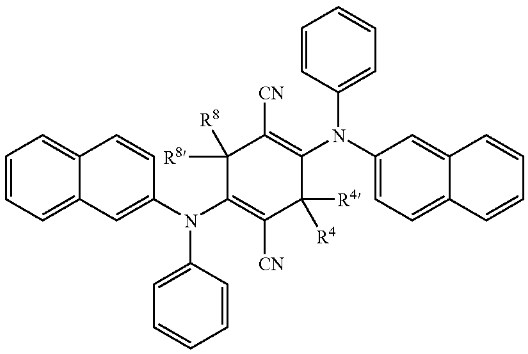 | 4.36 | 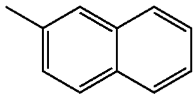 | —$CH_3$ | —$CH_3$ |
| 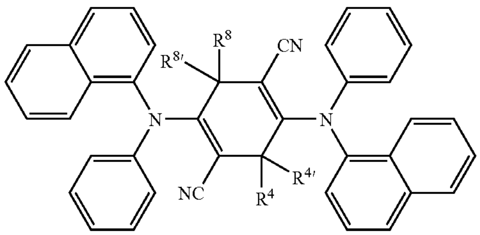 | 4.37 | 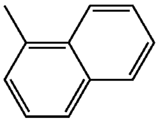 | —$CH_3$ | —$CH_3$ |
| 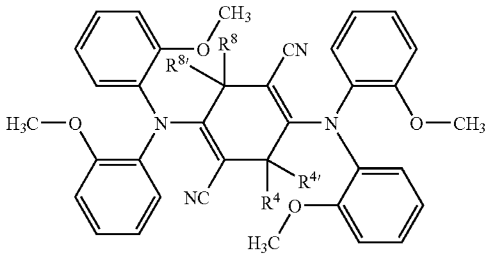 | 4.38 | 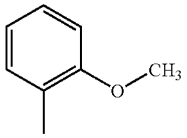 | —$CH_3$ | —$CH_3$ |
| 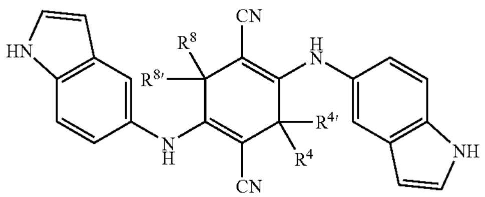 | 4.39 | 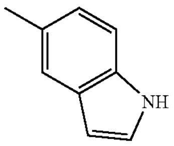 | —$CH_3$ | —$CH_3$ |
| | 4.40 | 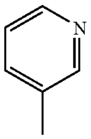 | —$CH_3$ | —$CH_3$ |

TABLE 4-continued
| Substituted 2,5-diamino-3,6-dihydroterephthalic acid dinitriles | | | |
|---|---|---|---|
| 4.41 | 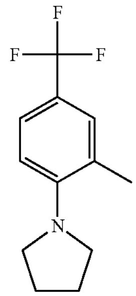 | —$CH_3$ | —$CH_3$ |
| 4.42 | 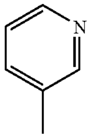 | —$CH_3$ | —$CH_3$ |
| 4.43 | 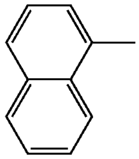 | —$CH_3$ | —$CH_3$ |
| 4.44 | 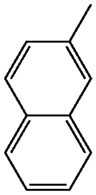 | —$CH_3$ | —$CH_3$ |
| 4.45 | 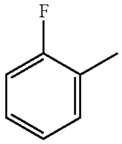 | —$CH_3$ | —$CH_3$ |
| 4.46 | 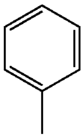 | —$CH_3$ | —$CH_3$ |
| 4.47 | 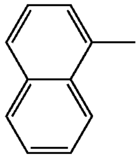 | —$CH_3$ | —$CH_3$ |
| 4.48 | 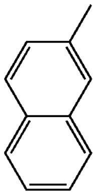 | —$CH_3$ | —$CH_3$ |

TABLE 4-continued
| Substituted 2,5-diamino-3,6-dihydroterephthalic acid dinitriles | | | |
|---|---|---|---|
| 4.49 | 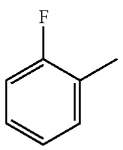 | —$CH_3$ | —$CH_3$ |
| 4.50 | 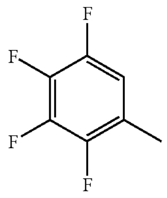 | —$CH_3$ | —$CH_3$ |
| 4.51 | 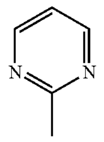 | —$CH_3$ | —$CH_3$ |
| 4.52 | 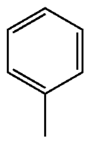 | —$CH_3$ | —$CH_3$ |
| 4.53 | 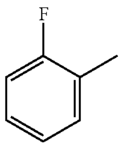 | —$CH_3$ | —$CH_3$ |
| 4.54 | 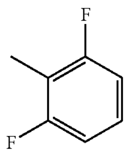 | —$CH_3$ | —$CH_3$ |
| 4.55 | 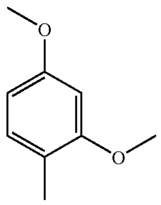 | —$CH_3$ | —$CH_3$ |
| 4.56 | 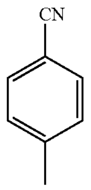 | —$CH_3$ | —$CH_3$ |
| 4.57 | 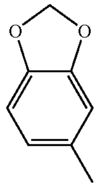 | —$CH_3$ | —$CH_3$ |

TABLE 4-continued
| Substituted 2,5-diamino-3,6-dihydroterephthalic acid dinitriles | | | |
|---|---|---|---|
| 4.58 | 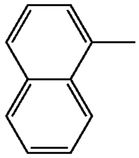 | $-CH_3$ | $-CH_3$ |
| 4.59 | 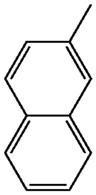 | $-CH_3$ | $-CH_3$ |
| 4.60 | 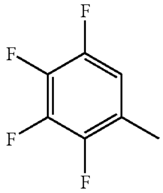 | $-CH_3$ | $-CH_3$ |
| 4.61 | 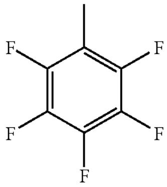 | $-CH_3$ | $-CH_3$ |
| 4.62 | 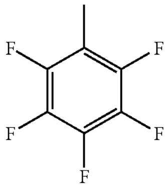 | $-CH_3$ | $-CH_3$ |
| 4.63 | 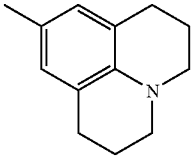 | $-CH_3$ | $-CH_3$ |
| 4.64 | 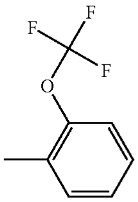 | $-CH_3$ | $-CH_3$ |
| 4.65 | 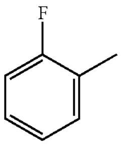 | $-CH_3$ | $-CH_3$ |

TABLE 4-continued
Substituted 2,5-diamino-3,6-dihydroterephthalic acid dinitriles
| | | | |
|---|---|---|---|
| 4.66 | 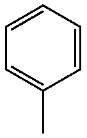 | $—CH_3$ | $—CH_3$ |
| 4.67 | 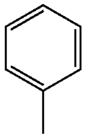 | $—CH_3$ | $—CH_3$ |
| 4.68 | 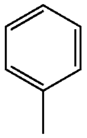 | $—CH_3$ | $—CH_3$ |
| 4.69 | 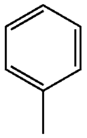 | $—CH_3$ | $—CH_3$ |
| 4.70 | 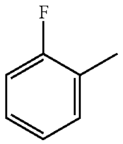 | $—CH_3$ | $—CH_3$ |
| Substance | | $R^2$ | $R^3$ | $R^4$ | $R^6$ | $R^7$ | $R^8$ | $R^{8'}$ | $R^{4'}$ |
|---|---|---|---|---|---|---|---|---|---|
| 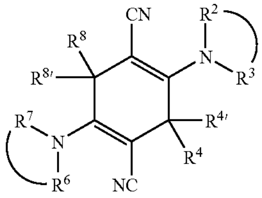 | 56.0 | | | | | | | | |
| | 56.1 | 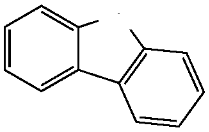 | | $—CH_3$ | 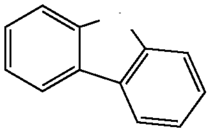 | | $—CH_3$ | $—CH_3$ | $—CH_3$ |
| | 56.2 | 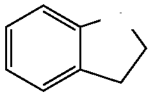 | | $—CH_3$ | 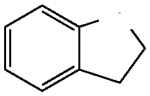 | | $—CH_3$ | $—CH_3$ | $—CH_3$ |
| | 56.3 | 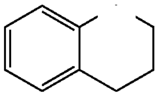 | | $—CH_3$ | 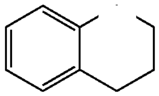 | | $—CH_3$ | $—CH_3$ | $—CH_3$ |
| | 56.4 | 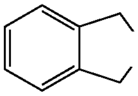 | | $—CH_3$ | 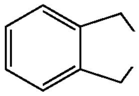 | | $—CH_3$ | $—CH_3$ | $—CH_3$ |

TABLE 4-continued
Substituted 2,5-diamino-3,6-dihydroterephthalic acid dinitriles
| Substance | | $R^2$ | $R^3$ | $R^6$ | $R^7$ | $R^8$ | $R^{8'}$ | $R^4$ | $R^{4'}$ |
|---|---|---|---|---|---|---|---|---|---|
| 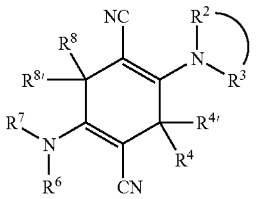 | 50.0 | | | | | | | | |
| | 50.1 | 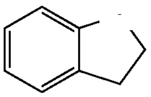 | | —$CH_3$ | 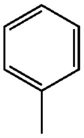 | —$CH_3$ | —$CH_3$ | —$CH_3$ | —$CH_3$ |
| | 50.2 | 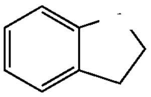 | | 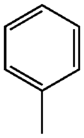 | 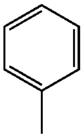 | —$CH_3$ | —$CH_3$ | —$CH_3$ | —$CH_3$ |
| | 50.3 | 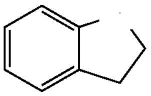 | | 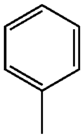 | 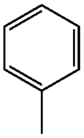 | 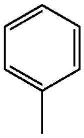 | —$CH_3$ | 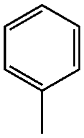 | —$CH_3$ |
| Substance | | $R^8$ | $R^{8'}$ | $R^3$ | $R^6$ | $R^7$ | $R^4$ | $R^{4'}$ | $R^2$ |
|---|---|---|---|---|---|---|---|---|---|
| 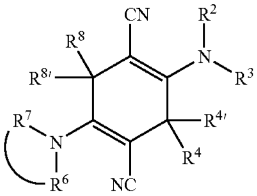 | 53.0 | | | | | | | | |
| | 53.1 | —$CH_3$ | —$CH_3$ | 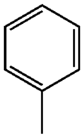 | 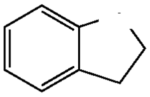 | | —$CH_3$ | —$CH_3$ | —$CH_3$ |
| | 53.2 | —$CH_3$ | —$CH_3$ | 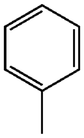 | 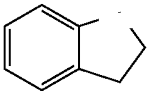 | | —$CH_3$ | —$CH_3$ | 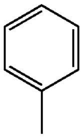 |

TABLE 4-continued
Substituted 2,5-diamino-3,6-dihydroterephthalic acid dinitriles
| Substance | | $R^{4'}$ | $R^3$ | $R^2$ | $R^{8'}$ | $R^7$ | $R^6$ | $R^4$ | $R^8$ |
|---|---|---|---|---|---|---|---|---|---|
| 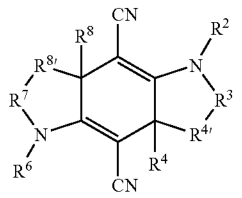 | 57.0 | | | | | | | | |
| | 57.1 | 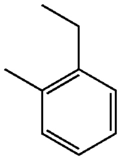 | | 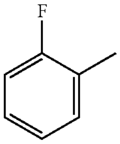 | 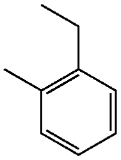 | | 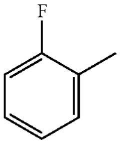 | —$CH_3$ | —$CH_3$ |
| 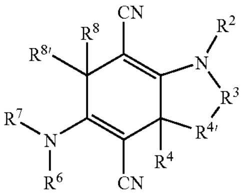 | 51.0 | | | | | | | | |
| | 51.1 | 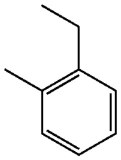 | | 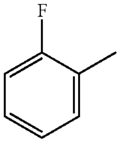 | H | 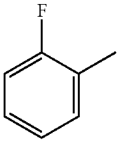 | 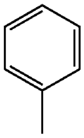 | —$CH_3$ | —$CH_3$ |
| Substance | | $R^4$ | $R^{4'}$ | $R^3$ | $R^2$ | $R^6$ | $R^7$ | $R^{8'}$ | $R^8$ |
|---|---|---|---|---|---|---|---|---|---|
| 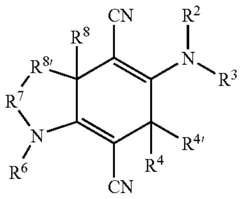 | 54.0 | | | | | | | | |
| | 54.1 | —$CH_3$ | —$CH_3$ | 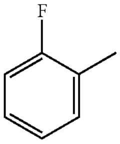 | 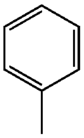 | 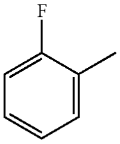 | 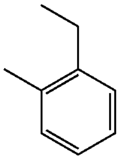 | | —$CH_3$ |

TABLE 4-continued
Substituted 2,5-diamino-3,6-dihydroterephthalic acid dinitriles
| Substance | | $R^4$ | $R^{4'}$ | $R^3$ | $R^2$ | $R^6$ | $R^7$ | $R^{8'}$ | $R^{8'}$ |
|---|---|---|---|---|---|---|---|---|---|
| 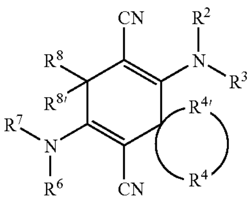 | 52.0 | | | | | | | | |
| 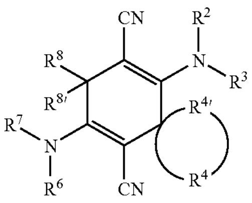 | 52.1 | 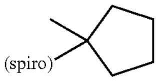 | | 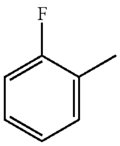 | 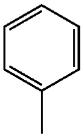 | 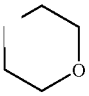 | | —$CH_3$ | —$CH_3$ |
| 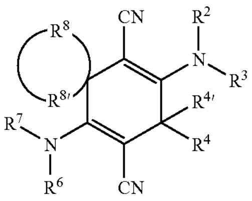 | 55.0 | | | | | | | | |
| 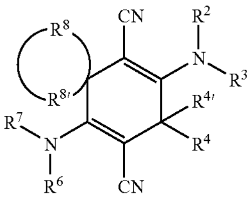 | 55.1 | —$CH_3$ | —$CH_3$ | 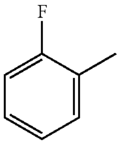 | 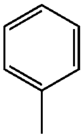 | 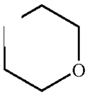 | | 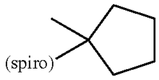 | |
| 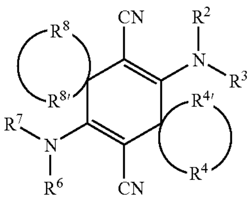 | 58.0 | | | | | | | | |
| 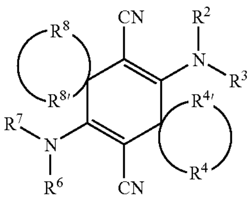 | 58.1 | 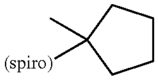 | | 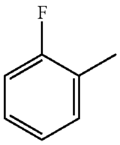 | 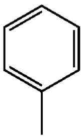 | 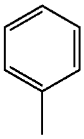 | 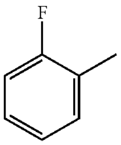 | 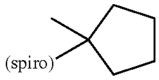 | |

The new emitters are used in a device comprising or not comprising an electron transport layer, wherein the layers in a device can be arranged as shown in FIG. 2:

1. The substrate consists of a transparent material, e.g. glass;
2. The anode consists of ITO which injects the holes into the hole transport layer;
3./4. The hole conductor mainly consists of triphenylamine derivatives; several hole conductor layers can be provided whose characteristics are adapted to the device;
5. Between the hole conductor and the electron conductor, one or more emitter layers are arranged;
6. The electron conductor can e.g. consist of Alq3 and conducts the electrons from the cathode to the emitting layer or the hole conductor inside the device;
7. The buffer layer consists of certain metal salts or the oxides thereof, e.g. LiF, and improves the electron injection into the layer 6;
8. The cathode consists of a base metal or an alloy (e.g. aluminium or calcium).

Typically, the emitter layers are 3–10 nm thick, preferably 4–6 nm. The emission wavelengths depend on the chemical structure in a characteristic manner, i.e. electronic and steric factors of the molecules obviously influence the wavelength of the emitted light and the performance achieved. The wavelengths of the examples listed in Table 2 range between 538 nm and 618 nm.

In order to achieve mixed colours, the new emitters of formulas 1.0–58.0 can be arranged on top of one another, either in the form of several layers each of which consists of an emitter material in its pure form (FIG. 2) or in the form of one or several layer(s) in which the emitter materials are provided in a mixed form.

The layers comprising the new emitters of formulas 1.0–58.0 can be doped with known emitter materials, as shown in FIG. 1.

The new emitters of formulas 1.0–58.0 can be used in devices comprising hole conductors known per se (59 and 60) and other components. Typical examples are shown in FIGS. 1 and 2.

59

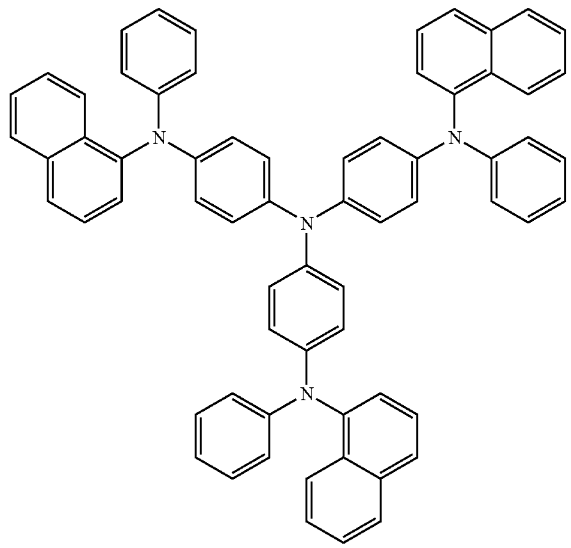

4,4',4"-tris(N-(α-naphthyl)-N-phenylamino)-triphenylamine (1-NAPHDATA)

60

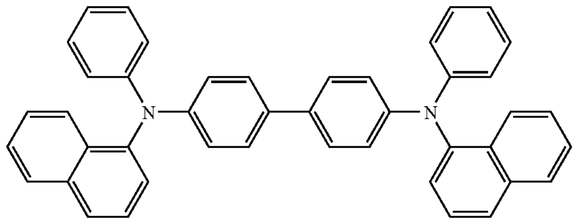

N,N'-di(α-naphthyl)-N,N'-diphenylbenzidine (α-NPD)

The devices based on the new emitters can be produced in a manner known per se, i.e. by vacuum deposition at between 1 and $10^{-9}$ torrs.

Alternatively, the devices can be produced by solution coating, e.g. web coating or spin coating. Here, the new emitters of formulas 1.0–58.0 can be applied either as the pure substance or as a dopant contained in a suitable polymer.

Surprisingly, it has been found that particularly efficient devices can be produced using substances of the formula 1.0 which have been substituted with fluorine. A remarkably high photometric efficiency is observed in these cases. Using the substance 1.2, a device emitting a spectrally nearly pure green is obtained.

EXPERIMENTAL PART

The following examples are intended to illustrate the invention in more detail, but do by no means limit the same.

Example 1 (Substances 2.1, 2.3–2.5)

2.3

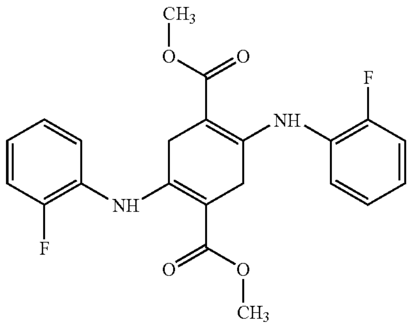

0.06 mol cyclohexane-2,5-dione-1,4-dicarboxylic acid diester is suspended in a mixture of 200 ml glacial acetic acid and 200 ml alcohol (corresponding to the ester component). In a nitrogen atmosphere, 0.135 mol of a primary amine or aniline is speedily added. The reaction mixture is refluxed for 5–8 hours while stirring thoroughly. Anilines which have been substituted with an acceptor require longer reaction times.

In the case of anilines, the crude product can be isolated by sucking off the cooled-down reaction mixture, thoroughly washing it with methanol and drying.

Aliphatic amines form highly soluble products, i.e. the solvent must be separated almost completely using a rotary evaporator. The crude product is added into methanol, thoroughly cooled, sucked off and dried.

Example 2 (Substances 1.1, 1.31.5)

1.3

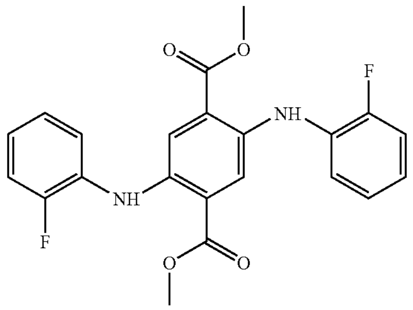

The esters of dihydroterephthalic acid obtained in Example 1 are oxidized. Yields of up to 95% are achieved during isolation. In order to purify the separated crude product, it can be recrystallized from DMF, toluene, chloroform or methanol. The substances obtained are sublimable.

Example 3 (Substances 19.1–19.4)

The esters obtained according to Example 2 are saponified in mixtures of n-propanol and water. 0.01 mol terephthalic acid diester is suspended in approx. 50 ml n-propanol, and 50 ml water containing 0.03 mol potassium hydroxide is added. The suspension is refluxed until a clear solution is obtained. Once another 2 hours have passed, the liquid is sucked off. In order to neutralize the solution, approx. 5 ml glacial acetic acid is added dropwise. The acid obtained is washed with methanol and dried.

In order to produce the substances 19.1–19.4, 0.01 mol of the terephthalic acid obtained is refluxed for 2 hours in 100 ml glacial acetic acid to which 15 ml formaldehyde solution (37%) has been added.

The reaction products are separated and washed with methanol. They are recrystallized from acetonitrile or chloroform. The substances obtained can be purified by sublimation.

Example 4 (Substance 1.2)

In order to obtain compounds of this type, the respective terephthalic acid ester (Example 2) can be alkylated. 0.05 mol terephthalic acid ester is suspended in 350 ml anhydrous DMSO, and 18.63 g (0.131 mol) methyl iodide is added. 6.1 g (0.152 mol) 60% sodium hydride in paraffin is added in portions at a temperature ranging between 20 and 23° C. and while stirring throrougly. Once a reaction time of approx. 5 hours has passed, the colour of the solid constitutents has changed from orange to pure yellow. Now, approx. 200 ml methanol is added to the mixture, thereby considerably improving filterability.

The separated yellow reaction product is thoroughly washed with methanol and dried. A pure product is obtained by recrystallization from toluene.

Example 5 (Device: Substance 19.4)

A 55 nm thick layer of 4,4',4"-tris(N-(α-naphthyl)-N-phenylamino)-triphenylamine and another 5 nm thick layer of N,N'-di(α-naphthyl)-N,N'-diphenylbenzidine were deposited onto a structured ITO glass substrate measuring 50×50 $mm^2$. Onto these hole transport layers, 5 nm 1,6-bis(2,4-dimethoxyphenyl)-benzo[1,2-d;4,5-d']-1,2,6,7-tetrahydro-bis[1,3]oxazine-4,9-dione (19.4) is deposited.

In addition, a 30 nm thick layer of tris-(8-hydroxychinolinato)-aluminium is now applied onto this emitter layer, followed by a very thin buffer layer (0.5 nm) of lithium fluoride and finally aluminium.

The arrangement was tested applying an adjustable voltage between 0 and 15 V. The device emits a wavelength of 578 nm (yellow). A luminance (emission intensity) of 100 $cd/m^2$ was achieved at 5.0 V. The maximum luminance (emission intensity) achieved was 11,400 $cd/m^2$.

Example 6 (Device: Substance 1.21)

A device was produced according to Example 5, into which a 5 nm thick layer of 2,5-bis-(N-(2,4-dimethoxyphenyl)amino)terephthalic acid diethyl ester was incorporated as emitter substance between the hole conductor and the electron conductor.

The device was also tested applying an adjustable voltage between 0 and 15 V. The device emits a wavelength of 618 nm (red). A luminance (emission intensity) of 100 $cd/m^2$ was achieved at 9.5 V. The maximum luminance (emission intensity) achieved was 644 $cd/m^2$.

Example 7 (Device: Substance 1.5)

The device has the same structure as those of Examples 5 and 6. The emitter substance used was 2,5-bis-(N-phenylamino)-terephthalic acid diethyl ester.

Once again, the device was tested applying an adjustable voltage between 0 and 15 V. The device emits a yellow light (578 mm). A luminance (emission intensity) of 100 $cd/m^2$ was achieved at 5.6 V. The maximum luminance (emission intensity) recorded was 5,300 $cd/m^2$.

Example 8 (Device: Substance 1.2)

Analogously to Examples 5–7 and according to the same structural principle, a 5 nm thick layer of N,N'-dimethyl-2,5-bis-(N-(2-fluorophenyl)-amino)terephthalic acid dimethyl ester was deposited onto the hole transport layers.

The arrangement (FIG. 2) was tested applying an adjustable voltage between 0 and 15 V. The device emits a green light ($\lambda_{max}$=547 nm). A luminance (emission intensity) of 100 $cd/m^2$ was achieved at 5.4 V. The maximum luminance (emission intensity) achieved was 17,700 $cd/m^2$.

1. The substrate consists of glass;
2. The anode consists of ITO;
3. 1-Naphdata is applied as hole conductor;
4. Another hole conductor layer consists of α-NPD;
5. One or several emitter layers are arranged between the hole conductor and the electron conductor;
6. The electron conductor can e.g. consist of Alq3;
7. The buffer layer consists of LiF;
8. The cathode consists of a base metal or an alloy (e.g. aluminium or calcium).

Typically, the emitter layers are 3–10 nm thick, preferably 4–6 nm.

Photometric Parameters of Selected Emitter Substances

TABLE 2

| # | [1]V | [2]nm | Colour | [3]cd/m² | [4]cd/A | [5]lm/W |
|---|---|---|---|---|---|---|
| 1.21 | 9.2 | 629 | red-white | 1980 | 0.12 | 0.07 |
| 1.16*) | 9.3 | 634 | red-white | 3990 | 0.14 | 0.10 |
| 1.16 | 14.0 | 618 | red | 144 | 0.09 | 0.07 |
| 1.30 | 5.6 | 612 | orange-red | 12100 | 2.17 | 2.27 |
| 19.4 | 5.0 | 578 | yellow | 11400 | 2.04 | 1.72 |
| 1.5 | 5.6 | 578 | yellow | 5300 | 1.59 | 1.42 |
| 1.4 | 8.0 | 577 | yellow | 1410 | 0.81 | 0.37 |
| 19.3 | 6.5 | 565 | yellow-green | 4530 | 0.72 | 0.49 |
| 1.3 | 8.1 | 577 | yellow-green | 4330 | 2.77 | 1.52 |
| 19.7 | 10.2 | | yellow-green | 474 | 0.26 | 0.10 |
| 1.34 | 3.5 | 550 | green | 36500 | 1.00 | 9.21 |
| 1.36 | 5.7 | 546 | green | 18100 | 6.60 | 4.34 |
| 1.2 | 5.4 | 547 | green | 17700 | 7.70 | 4.93 |
| 1.38 | 6.4 | 546 | green | 11300 | 4.62 | 2.47 |
| 19.2 | 6.6 | 564 | green | 6010 | 0.89 | 0.66 |
| 19.1 | 6.7 | 540 | green | 4680 | 3.05 | 1.70 |
| 19.6 | 8.6 | 545 | green | 2610 | 0.52 | 0.36 |
| 1.29 | 11.1 | 564 | green | 1330 | 1.59 | 0.47 |
| 1.1 | 7.1 | 538 | green | 1300 | 0.48 | 0.22 |
| 1.33 | 10.3 | 563 | green | 1100 | 1.53 | 0.54 |
| 1.31 | 10.8 | 566 | green | 754 | 1.60 | 0.53 |
| 19.8 | 13.4 | | green | 273 | 1.20 | 0.70 |
| 19.11 | 14.4 | 532 | green | 144 | 0.03 | 0.01 |
| 19.5 | >20.0 | 540 | green | 8 | 0.30 | 0.28 |
| 19.9 | >15.0 | 544 | green | 64 | 0.58 | 0.13 |

[1]voltage at 100 cd/m²
[2]$\lambda_{max}$ of electroluminescence
[3]max. luminance (emission intensity)
[4]max. photometric efficiency
[5]max. performance efficiency

TABLE 3

| Table 3# | $\lambda_{max}$ (solid) | $\lambda_{em}$ (solid) |
|---|---|---|
| 1.6 | | 614 |
| 1.7 | | 597 |
| 1.8 | | 604 |
| 1.10 | | 626 |
| 1.11 | | 596 |
| 1.12 | | 586 |
| 1.1 | | 547 |
| 1.13 | | 559 |
| 1.14 | | 543 |
| 1.15 | | 605 |
| 1.16 | 500 | 635 |
| 1.17 | | 596 |
| 1.18 | | 617 |
| 1.19 | 435 | 531 |
| 1.4 | | 599 |
| 1.20 | | 596 |
| 19.1 | 475 | 564 |
| 19.4 | 460 | 598 |
| 1.5 | 465 | 582 |
| 1.21 | 495 | 625 |
| 19.5 | | 612 |
| 1.23 | | 573 |
| 1.24 | | 564 |
| 1.25 | | 605 |
| 1.26 | | 602 |
| 19.3 | | 582 |
| 1.6 | | 623 |
| 19.6 | | 592 |
| 1.28 | | 588 |
| 1.3 | | 595 |
| 1.24 | | 612 |
| 19.8 | 453 | 583 |
| 1.2 | | 558 |
| 1.5 | 496 | 622 |

$\lambda_{max}$: absorption maximum
$\lambda_{em}$: emission maximum
$\lambda_{ell}$: maximum of electroluminescence

TABLE 4

Absorbance coefficients ε of selected emitter substances

| # | $\lambda_{max}$ (nm) | ε ($l \cdot mol^{-1} cm^{-1}$) | Solvent |
|---|---|---|---|
| 1.16 | 489 | 6000 | $CHCl_3$ |
| 1.5 | 469 | 6640 | $CHCl_3$ |
| 1.34 | 403 | 4744 | NMP |
| 19.6 | 452 | 5250 | $CHCl_3$ |
| 19.5 | 474 | 4670 | $CHCl_3$ |
| 19.7 | 433 | 5450 | NMP |
| 1.17 | 472 | 6410 | $CHCl_3$ |
| 1.15 | 486 | 5930 | $CHCl_3$ |
| 1.12 | 460 | 5930 | $CHCl_3$ |
| 1.11 | 481 | 6840 | $CHCl_3$ |
| 1.8 | 472 | 6450 | $CHCl_3$ |
| 1.7 | 474 | 6550 | $CHCl_3$ |
| 19.1 | 434 | 4700 | NMP |
| 1.30 | 493 | 5450 | NMP |
| 1.27 | 482 | 6800 | $CHCl_3$ |

TABLE 5

| Absorption maxima of selected emitter substances in solution# | $\lambda_{max}$ (NMP) |
|---|---|
| 1.6 | 482 |
| 1.7 | 476 |
| 1.8 | 463 |
| 1.9 | 652 |
| 1.10 | 509 |
| 1.11 | 475 |
| 1.12 | 445 |
| 1.1 | 413 |
| 1.13 | 427 |
| 1.14 | 428 |
| 1.15 | 482 |
| 1.16 | 494 |
| 1.17 | 464 |
| 1.18 | 464 |
| 1.19 | 417 |
| 1.4 | 468 |
| 1.20 | 461 |
| 19.1 | 435 |
| 19.4 | 458 |
| 1.5 | 451 |
| 1.21 | 479 |
| 1.22 | 505 |
| 19.5 | 472 |
| 1.23 | 432 |
| 1.24 | 446 |
| 1.25 | 487 |
| 1.26 | 482 |
| 19.3 | 447 |
| 1.6 | 481 |
| 19.6 | 452 |
| 1.28 | 473 |
| 1.3 | 451 |
| 1.24 | 480 |
| 1.30 | 493 |
| 1.34 | 403 |
| 1.5 | 461 |
| 1.43 | 496 |

TABLE 6

| DSC values of selected emitter substances# | DSC peak in ° C. |
|---|---|
| 19.3 | 260.0 |
| 1.6 | 269.1 |
| 1.7 | 171.3 |
| 1.8 | 227.8 |
| 1.11 | 192.1 |
| 1.12 | 172.2 |

TABLE 6-continued

| DSC values of selected emitter substances# | DSC peak in ° C. |
|---|---|
| 1.15 | 232.0 |
| 1.17 | 166.5 |
| 19.1 | 325.7 |
| 1.16 | 183.3 |
| 1.34 | 254.7 |
| 19.1 | 325.7 |
| 1.27 | 182.5 |

Preparation and Measuring Conditions a) Substrate: 125 nm ITO, approx. 13 Ω/sq and 85% tranmission, 50×50 $mm^2$ glass substrate (1.1 mm thick polished soda-lime float glass with $SiO_2$ layer and 8 individual ITO anodes (active surface area: 2×2 $mm^2$))

Purified 2×20 min in an ultrasonic bath with Aceton selectopur and Methanol selectopur, 3× snow jet cleaning ($CO_2$ ice crystals)

$O_2$ plasma treatment (5 min at 450 W and 0.12 mbar)

b) Pressure (2–4)×$10^{-5}$ mbar during deposition

Aluminium oxide ceramic crucible

Deposition rate: 0.06 nm/s

Layer thickness checked using a piezoelectric microbalance measuring device

Change of mask and intermediate aeration of the deposition chamber, first with nitrogen and then with air Cathodes, 0.5 nm lithium fluoride (insulating) and 100 nm aluminium each c) The device according to FIG. 2 was introduced in a glove box, the active OLED suface was positioned above calibrated $V_\lambda$ silicon photodiodes in a darkened measuring device, and the anode (ITO-) and cathode (A1-) contacts were brought in contact with gilded spring electrodes Programmable voltage supply (SMU) and digital multimeter for recording and processing the OLED curve in a PC via GPIB-BUS and LabView program Voltage pulse operation (pulses lasting 1 s) between −10 V and +15 V (0.5 V increments): current density-voltage curve and luminance (emission intensity)-voltage curve as well as the calculated photometric efficiency values (in cd/A) and performance efficiency values (in 1 m/W) as a function of U d) Wavelength of maximum by recording the electroluminescence spectrum using an Xdap diode array spectrometer

The invention claimed is:

1. A 2,5-diaminoterephthalic acid derivative of formula 19,

19

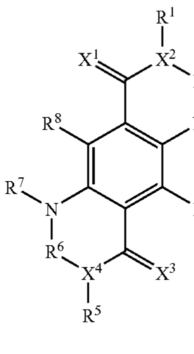

wherein $X^1$ and $X^3$ are O, $X^2$ and $X^4$, which can be the same or different, are O or N; $R^2$ and $R^6$ are methylene (—$CH_2$—), which can be substituted with trifluoromethyl, $R^3$ and $R^7$ are the same or different, H, $C_1$–$C_8$ alkyl, aryl, or heteroaryl, and $R^4$ and $R^8$ are the same or different, H, alkyl, aryl or trifluoromethyl, and $R^1$ and $R^5$, which can be the same or different and are H, $C_1$–$C_4$ alkyl or phenyl with the proviso that $R^1$ is absent if $X^2$ is O and $R^5$ is absent if $X^4$ is O.

2. The derivative of claim 1, wherein alkyl is $C_1$–$C_4$ alkyl, aryl is phenyl or naphthyl, and heteroaryl is pyridyl, thienyl or furyl.

3. The derivative of claim 1, wherein alkyl is $C_1$–$C_8$ alkyl, aryl is phenyl or naphthyl, and heteroaryl is cumaryl, pyridyl, chinolyl, indolyl, carbazolyl, imidazolyl, thienyl, thiazolyl, furyl or oxazolyl.

4. The derivative of claim 1, wherein $R^4$ and $R^8$ are trifluoromethyl, 2-fluorophenyl, 3-fluorophenyl, 4-flurophenyl, 2,4,-difluorophenyl, 2,6-difluorophenyl, 2,3,4,5-tetrafluorophenyl or pentafluorophenyl.

5. The derivitive of claim 1, wherein $R^4$ and $R^8$ are the same or different and are hydrogen, $C_1$–$C_8$ alkyl or phenyl.

6. The derivative of claim 1, wherein $R^4$ and $R^8$ are the same or different and are hydrogen, $C_1$–$C_4$ alkyl or phenyl.

7. The derivative of claim 6, wherein $R^1$ and $R^8$ *are H.*

8. The derivative of claim 1, wherein $R^1$ and $R^5$ are $C_1$–$C_4$ alkyl or phenyl, and $X^2$ and $X^4$ are nitrogen.

9. The derivative of claim 1, wherein $X^2$ is N.

10. The derivative of claim 1, wherein $X^2$ is O.

11. The derivative of claim 1, wherein $R^3$ and $R^7$ are 2-fluorophenyl, 3-fluorophenyl, 4-flurophenyl, 2,4,-difluorophenyl, 2,6-difluorophenyl, 2,3,4,5-tetrafluorophenyl or pentafluorophenyl.

12. The derivative of claim 1, wherein $R^3$ and $R^7$ are the same or different and are substituted or unsubstituted phenyl, said substituted phenyl being substituted singly or multiply with halogen, CN, $C_1$–$C_4$ alkyl, $C_1$–$C_4$ alkoxy, amino or phenyl.

13. The derivative of claim 12, wherein $R^3$ and $R^7$ are N,N-dimethyl-4-aminophenyl, and $R^4$ and $R^8$ are H.

14. The derivative of claim 12, wherein $X^2$ and $X^4$ are O, $R^3$ and $R^7$ are 4-cyanophenyl, and $R^4$ and $R^8$ are H.

15. The derivative of claim 1, wherein $R^3$ and $R^7$ are the same or different and are substituted or unsubstituted phenyl, said substituted phenyl being substituted singly or multiply with fluoro, chloro, CN, methyl, methoxy, trifluoromethyl, or phenyl.

16. The derivative of claim 1, wherein $X^2$ and $X^4$ are O, $R^3$ and $R^7$ are phenyl, and $R^4$ and $R^8$ are H.

17. The derivative of claim 1, wherein $X^2$ and $X^4$ are O, and $R^4$ and $R^8$ are H.

18. The derivative of claim 17, wherein $R^3$ and $R^7$ are substituted or unsubstituted α-naphthyl.

19. The derivative of claim 17, wherein $R^3$ and $R^7$ are substituted or unsubstituted β-naphthyl.

20. The derivative of claim 17, wherein $R^3$ and $R^7$ are substituted or unsubstituted phenyl.

21. The derivative of claim 20, wherein $R^3$ and $R^7$ are the same or different and are substituted phenyl, said phenyl substituted singly or multiply with $C_1$–$C_4$ alkyl, $C_1$–$C_4$ alkoxy or a combination thereof.

22. The derivative of claim 21, wherein $R^3$ and $R^7$ are 2,4-dimethylphenyl.

23. The derivative of claim 1, wherein $X^2$ and $X^4$ are N.

24. The derivative of claim 23, wherein $R^1$ and $R^5$ are phenyl.

25. The derivative of claim 23, wherein $R^1$ and $R^5$ are $C_1$–$C_4$ alkyl.

26. The derivative of claim 23, wherein $R^3$ and $R^7$ are substituted or unsubstituted α-naphthyl.

27. The derivative of claim 23, wherein $R^3$ and $R^7$ are substituted or unsubstituted β-naphthyl.

28. The derivative of claim 23, wherein $R^3$ and $R^7$ are substituted or unsubstituted phenyl.

29. The derivative of claim 28, wherein $R^3$ and $R^7$ are the same or different and are substituted phenyl, said phenyl substituted singly or multiply with $C_1$–$C_4$ alkyl, $C_1$–$C_4$ alkoxy or a combination thereof.

30. The derivative of claim 28, wherein $R^3$ and $R^7$ are 2,4-dimethylphenyl.

31. The derivative of claim 28, wherein $R^3$ and $R^7$ are the same or different and are substituted phenyl, said phenyl substituted singly or multiply with halogen, nitro, cyano, amino, $C_1$–$C_8$ alkyl or phenyl.

32. The derivative of claim 28, wherein $R^3$ and $R^7$ are the same or different and are substituted phenyl, said phenyl substituted singly or multiply with halogen, $C_1$–$C_4$ alkyl, trifluoromethyl, $C_1$–$C_4$ alkoxy or a combination thereof.

33. The derivative of claim 1, wherein $R^3$ and $R^7$ are the same or different and are $C_1$–$C_4$ alkyl, unsubstituted phenyl, or substituted phenyl.

* * * * *